United States Patent
Iwato et al.

(10) Patent No.: US 9,140,981 B2
(45) Date of Patent: Sep. 22, 2015

(54) ACTINIC-RAY-SENSITIVE OR RADIATION-SENSITIVE RESIN COMPOSITION, AND RESIST FILM USING THE SAME, PATTERN FORMING METHOD, ELECTRONIC DEVICE MANUFACTURING METHOD, AND ELECTRONIC DEVICE, EACH USING THE SAME

(75) Inventors: Kaoru Iwato, Haibara-gun (JP); Hidenori Takahashi, Haibara-gun (JP); Michihiro Shirakawa, Haibara-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/614,797

(22) Filed: Sep. 13, 2012

(65) Prior Publication Data

US 2013/0078433 A1     Mar. 28, 2013

(30) Foreign Application Priority Data

Sep. 22, 2011  (JP) .................................. 2011-207018

(51) Int. Cl.

| | | |
|---|---|---|
| G03F 7/004 | (2006.01) | |
| G03F 7/38 | (2006.01) | |
| C07D 327/10 | (2006.01) | |
| C07C 303/32 | (2006.01) | |
| C07C 309/04 | (2006.01) | |
| C07C 309/06 | (2006.01) | |
| C07C 309/12 | (2006.01) | |
| C07C 309/17 | (2006.01) | |
| C07C 309/19 | (2006.01) | |
| C07C 309/24 | (2006.01) | |
| G03F 7/038 | (2006.01) | |
| G03F 7/039 | (2006.01) | |
| B32B 3/10 | (2006.01) | |
| G03F 7/20 | (2006.01) | |

(52) U.S. Cl.
CPC ............... G03F 7/0045 (2013.01); B32B 3/10 (2013.01); C07C 303/32 (2013.01); C07C 309/04 (2013.01); C07C 309/06 (2013.01); C07C 309/12 (2013.01); C07C 309/17 (2013.01); C07C 309/19 (2013.01); C07C 309/24 (2013.01); C07D 327/10 (2013.01); G03F 7/038 (2013.01); G03F 7/0382 (2013.01); G03F 7/0397 (2013.01); G03F 7/20 (2013.01); G03F 7/38 (2013.01); *Y10T 428/24802* (2015.01)

(58) Field of Classification Search
CPC ... G03F 7/0045; G03F 7/0397; G03F 7/0382; G03F 7/38; C07C 303/32; C07C 309/04; C07C 309/06; C07C 309/12; C07C 309/17; C07C 309/19; C07C 309/24; C07D 327/10
USPC ......... 430/270.1, 910, 921, 922, 325; 549/10; 560/149; 562/100, 109, 113
See application file for complete search history.

(56) References Cited

U.S. PATENT DOCUMENTS

| | | | | |
|---|---|---|---|---|
| 6,908,722 | B2 * | 6/2005 | Ebata et al. | ................. 430/270.1 |
| 2003/0113658 | A1 * | 6/2003 | Ebata et al. | ................. 430/270.1 |
| 2009/0023097 | A1 | 1/2009 | Dazai et al. | |
| 2010/0121077 | A1 | 5/2010 | Seshimo et al. | |
| 2010/0221659 | A1 | 9/2010 | Ebata et al. | |
| 2010/0285405 | A1 | 11/2010 | Shimokawa et al. | |
| 2010/0304303 | A1 * | 12/2010 | Maeda et al. | ............... 430/286.1 |
| 2012/0028188 | A1 * | 2/2012 | Ichikawa et al. | ........... 430/281.1 |
| 2012/0295198 | A1 | 11/2012 | Matsuda et al. | |
| 2012/0322007 | A1 | 12/2012 | Kato et al. | |

FOREIGN PATENT DOCUMENTS

| | | |
|---|---|---|
| JP | 04-039665 A | 10/1992 |
| JP | 2009-025619 A | 2/2009 |
| JP | 2010-100595 A | 5/2010 |
| JP | 2010-164958 A | 7/2010 |
| JP | 2010282189 A | 12/2010 |
| JP | 2011-079778 A | 4/2011 |
| JP | 2011-081045 A | 4/2011 |
| WO | 2009-051088 A1 | 4/2009 |
| WO | 2011-093280 A1 | 8/2011 |
| WO | 2011102546 A1 | 8/2011 |
| WO | 2012169620 A1 | 12/2012 |

OTHER PUBLICATIONS

Notice of Reasons for Rejection, mailed Aug. 27, 2013, issued in corresponding JP Application No. 2011-207018, 13 pages in English and Japanese.

* cited by examiner

*Primary Examiner* — John Chu
(74) *Attorney, Agent, or Firm* — Sughrue Mion, PLLC

(57) ABSTRACT

Provided are an actinic-ray-sensitive or a radiation-sensitive resin composition with greater residual film ratio and capable of suppressing pattern collapse and an occurrence of bridge defects after development, and a resist film, a pattern forming method, an electronic device manufacturing method, and an electronic device, each using the same. An actinic-ray-sensitive or radiation-sensitive resin composition includes a resin (P) having a repeating unit (a) represented by following General Formula (I), a compound (B) represented by any of following General Formulae (B-1) to (B-3), and a solvent,

[Chem. 1]

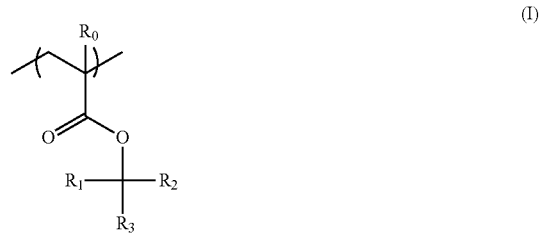

in General Formula (I), $R_0$ represents a hydrogen atom or a methyl group, and $R_1$, $R_2$ and $R_3$ each independently represent a straight chain or branched alkyl group.

42 Claims, No Drawings

ACTINIC-RAY-SENSITIVE OR RADIATION-SENSITIVE RESIN COMPOSITION, AND RESIST FILM USING THE SAME, PATTERN FORMING METHOD, ELECTRONIC DEVICE MANUFACTURING METHOD, AND ELECTRONIC DEVICE, EACH USING THE SAME

BACKGROUND OF THE INVENTION

1. Field of the Invention

The present invention relates to a pattern forming method, an actinic-ray-sensitive or a radiation-sensitive resin composition and a resist film. In more detail, the present invention relates to a pattern forming method, an actinic-ray-sensitive or a radiation-sensitive resin composition, and a resist film suitably used for a manufacturing process of semiconductor such as an IC, a manufacturing process of circuit board such as a liquid crystal and thermal head, and also a lithography process of photofabrication in addition to these. In particular, the present invention relates to a pattern forming method, an actinic-ray-sensitive or a radiation-sensitive resin composition, and a resist film suitably used for exposures in an ArF an exposure apparatus, an ArF liquid immersion type projection exposure apparatus, and an EUV exposure apparatus of which a light source is far ultraviolet light with a wavelength of 300 nm or less.

2. Description of the Related Art

After resists for a KrF excimer laser (248 nm) were developed, an image forming method using chemical amplification has been used in order to compensate for sensitivity decrease due to light absorption. For example, in a positive type image forming method of chemical amplification, an acid generator included in an exposed area generates acid by being decomposed by light irradiation. Then, in a post exposure bake (PEB) process after exposure and the like, an alkali-insoluble group included in a light sensitive composition is changed to an alkali-soluble group by a catalytic reaction of the acid generated. After that, for example, development is carried out using the alkali solution. As a result, the exposed area is removed and a desirable pattern is obtained.

In the method described above, a variety of alkaline developers have been proposed. For example, an aqueous alkaline developer such as an aqueous solution of 2.38% by mass TMAH (tetramethylammonium hydroxide) is generally used as the alkaline developer.

For microfabrication of semiconductor devices, shorter wavelength of exposure light source and higher numerical aperture of projection lens (high NA) have been progressed, and now, an exposure apparatus with an ArF excimer laser having a wavelength of 193 nm as light source is being developed. As a technology which further enhances resolution, a method in which liquid with a high refractive index (hereinafter, also referred to as "immersion liquid") is filled between a projection lens and a sample (that is, an immersion method) has been proposed. An EUV lithography in which an exposure is carried out using ultraviolet light of shorter wavelength (13.5 nm) has also been proposed.

In addition, a variety of compounds have been developed for use as a photoacid generator, which is a major component of a chemical amplification type resist composition (see, for example, WO 2009/051088, WO 2011/093280, JP2009-25619A, JP2011-81045A, JP2011-79778A, and JP2010-100595A). In each patent document, photoacid generators having characteristic structures in the anion part are described.

However, practically, it is extremely difficult to find a suitable combination of resist composition, developer, rinsing solution and the like required to form a pattern of which performance is comprehensively satisfactory, and further improvements are required.

Recently, a negative-type pattern forming method using a developer including an organic solvent has been developed (see, for example, JP2010-164958A and JP1992-39665A (JP-H-04-39665A)). In JP2010-164958A, a pattern forming method having a step in which a resist composition containing a resin, which has a relatively high content of repeating unit having a group generating a polar group by being decomposed by an action of acid, is developed using a developer containing an organic solvent is disclosed. It is described that a micro pattern with satisfactory line width roughness (LWR), exposure latitude (EL), depth of focus (DOF) and the like, may be formed according to these methods.

In addition, in JP1992-39665A (JP-H-04-39665A), a patterning by an organic solvent (xylene) using a resist composition made of a copolymer of adamantyl methacrylate and t-butyl methacrylate is disclosed.

However, further improvements are required in the formation of a negative-type pattern by organic solvent development with regard to a suppression of pattern collapse and bridge defect generation after development, and an improvement of residual film ratio (suppression of a film reduction).

SUMMARY OF THE INVENTION

The object of the present invention is, in the formation of a negative-type pattern by an organic solvent development, to provide an actinic-ray-sensitive or a radiation-sensitive resin composition with greater residual film ratio and capable of suppressing pattern collapse and an occurrence of bridge defects after development, and a resist film, a pattern forming method, an electronic device manufacturing method, and an electronic device, each using the same.

The present invention has configurations of the following, and the object of the present invention is achieved by these configurations.

[1] An actinic-ray-sensitive or radiation-sensitive resin composition includes a resin (P) having a repeating unit (a) represented by a following General Formula (I), a compound (B) represented by any of following General Formulae (B-1) to (B-3), and a solvent.

[Chem. 1]

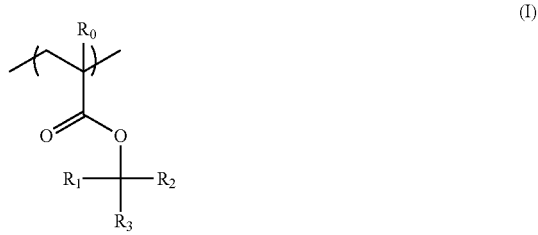

(I)

In General Formula (I), $R_0$ represents a hydrogen atom or a methyl group.

$R_1$, $R_2$, and $R_3$ each independently represent a straight chain or branched alkyl group.

[Chem. 2]

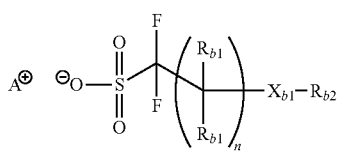

(B-1)

In General Formula (B-1), A' represents a sulfonium cation or an iodonium cation.

$R_{b1}$s, each independently, represent a hydrogen atom, a fluorine atom, or a trifluoromethyl group.

n represents an integer of 1 to 4.

$X_{b1}$ represents a single bond, an ether bond, an ester bond (—OCO— or —COO—) or a sulfonate bond (—OSO$_2$— or —SO$_3$—).

$R_{b2}$ represents a substituent having 6 or more carbon atoms.

[Chem. 3]

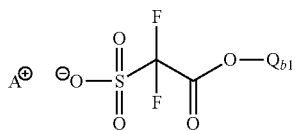

(B-2)

In General Formula (B-2), A$^+$ represents a sulfonium cation or an iodonium cation.

$Q_{b1}$ represents a group having a lactone structure, a group having a sultone structure, or a group having a cyclic carbonate structure.

[Chem. 4]

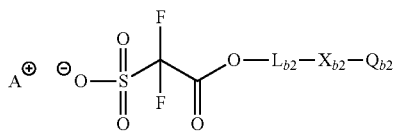

(B-3)

In General Formula (B-3), A$^+$ represents a sulfonium cation or an iodonium cation.

$L_{b2}$ represents an alkylene group having 1 to 6 carbon atoms.

$X_{b2}$ represents an ether bond or an ester bond (—OCO— or —COO—).

$Q_{b2}$ represents an alicyclic group or a group having an aromatic ring.

[2] The actinic-ray-sensitive or radiation-sensitive resin composition according to [1], wherein the resin (P) is a resin containing 45 mol % or more of the repeating unit (a) with regard to all repeating units in the resin (P).

[3] The actinic-ray-sensitive or radiation-sensitive resin composition according to [1] or [2], wherein a weight-average molecular weight of the resin (P) is 10,000 or more.

[4] The actinic-ray-sensitive or radiation-sensitive resin composition according to any one of [1] to [3], further includes a basic compound or an ammonium salt compound (C) of which basicity is decreased by irradiation of actinic ray or radiation.

[5] The actinic-ray-sensitive or radiation-sensitive resin composition according to any one of [1] to [4], wherein the straight chain or branched alkyl group of $R_1$, $R_2$, and $R_3$ in General Formula (I) is an alkyl group having 1 to 4 carbon atoms.

[6] The actinic-ray-sensitive or radiation-sensitive resin composition according to any one of [1] to [5], wherein the resin (P) is a resin having an alicyclic hydrocarbon structure.

[7] The actinic-ray-sensitive or radiation-sensitive resin composition according to any one of [1] to [6], further including a hydrophobic resin having at least one of a fluorine atom and a silicon atom.

[8] A resist film which is formed by the actinic-ray-sensitive or radiation-sensitive resin composition according to any one of [1] to [7].

[9] A pattern forming method including, (a) forming a film by the actinic-ray-sensitive or radiation-sensitive resin composition according to any one of [1] to [7], (b) exposing the film, and (c) developing the film after the exposure using a developer including an organic solvent to form a negative-type pattern.

[10] The pattern forming method according to [9], wherein the developer is a developer containing at least one organic solvent selected from the group consisting of ketone-based solvents, ester-based solvents, alcohol-based solvents, amide-based solvents and ether-based solvents.

[11] The pattern forming method according to any one of [9] to [10], further includes cleaning using a rinsing solution containing an organic solvent.

[12] An electronic device manufacturing method including the pattern forming method according to any one of [9] to [11].

[13] An electronic device, which is manufactured by the electronic device manufacturing method according to [12].

The present invention preferably has further configurations of the following.

[14] The actinic-ray-sensitive or radiation-sensitive resin composition according to any one of [1] to [7], wherein the resin (P) further includes a repeating unit having a lactone structure or a sultone structure.

[15] The actinic-ray-sensitive or radiation-sensitive resin composition according to any one of [1] to [7], and [14], wherein the resin (P) further includes a repeating unit having a hydroxyadamantyl group or dihydroxyadamantyl group.

[16] The actinic-ray-sensitive or radiation-sensitive resin composition according to any one of [1] to [7], [14] and [15], which is a chemical amplification type resist composition for organic solvent development.

[17] The actinic-ray-sensitive or radiation-sensitive resin composition according to any one of [1] to [7] and [14] to [16], which is for liquid immersion exposure.

[18] The pattern forming method according to any one of [9] to [11], wherein the exposure in the step for exposing the resist film is liquid immersion exposure.

According to the present invention, an actinic-ray-sensitive or a radiation-sensitive resin composition with greater residual film ratio due to suppressing pattern collapse and an occurrence of bridge defects after development, and a resist film using the same, a pattern forming method, an electronic device manufacturing method, and an electronic device, may be provided.

DESCRIPTION OF THE PREFERRED EMBODIMENTS

Hereinafter, the embodiments of the present invention will be described in detail.

In the notation of a group (an atomic group) in the present specification, a notation in which substituted and unsubstituted are not specified includes not only a group (an atomic group) having no substituents, but also a group (an atomic group) having a substituent. For example, an "alkyl group" includes not only an alkyl group having no substituents (an unsubstituted alkyl group), but also an alkyl group having a substituent (a substituted alkyl group).

"Actinic rays" or "radiation" means, for example, a bright line spectrum of a mercury lamp, far ultraviolet rays represented by an excimer laser, extreme ultraviolet rays (EUV light), X-rays, an electron beam (EB) and the like. In addition, in the present invention, light means actinic rays or radiation.

In addition, "exposure" in the present specification includes, unless otherwise specified, not only an exposure by a mercury lamp, far ultraviolet rays represented by an excimer laser, extreme ultraviolet rays, X-rays, EUV light and the like, but also a drawing by particle rays such as an electron beam or an ion beam.

An actinic-ray-sensitive or radiation-sensitive resin composition of the present invention contains, a resin (P) having a repeating unit (a) represented by following General Formula (I), a compound (B) represented by any of following General Formulae (B-1) to (B-3), and a solvent.

[Chem. 5]

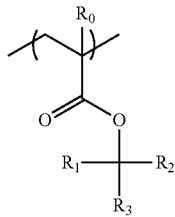

(I)

In General Formula (I), $R_0$ represents a hydrogen atom or a methyl group.

$R_1$, $R_2$, and $R_3$, each independently, represent a straight chain or branched alkyl group.

[Chem. 6]

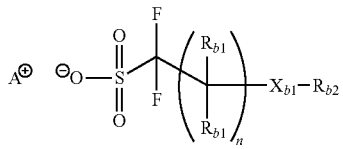

(B-1)

In General Formula (B-1), $A^+$ represents a sulfonium cation or an iodonium cation.

$R_{b1}$s, each independently, represent a hydrogen atom, a fluorine atom, or a trifluoromethyl group.

n represents an integer of 1 to 4.

$X_{b1}$ represents a single bond, an ether bond, an ester bond (—OCO— or —COO—) or a sulfonate bond (—OSO$_2$— or —SO$_3$—).

$R_{b2}$ represents a substituent having 6 or more carbon atoms.

[Chem. 7]

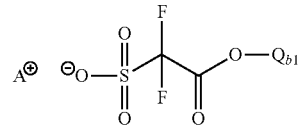

(B-2)

In General Formula (B-2), $A^+$ represents a sulfonium cation or an iodonium cation.

$Q_{b1}$ represents a group having a lactone structure, a group having a sultone structure, or a group having a cyclic carbonate structure.

[Chem. 8]

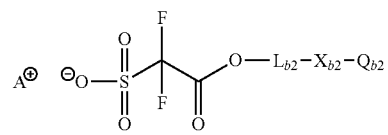

(B-3)

In General Formula (B-3), $A^+$ represents a sulfonium cation or an iodonium cation.

$L_{b2}$ represents an alkylene group having 1 to 6 carbon atoms.

$X_{b2}$ represents an ether bond or an ester bond (—OCO— or —COO—).

$Q_{b2}$ represents an alicyclic group or a group having an aromatic ring.

The reason that the actinic-ray-sensitive or radiation-sensitive resin composition of the present invention containing a resin (P) having a repeating unit (a) represented by following General Formula (I) and a compound (B) represented by any of following General Formulae (B-1) to (B-3) has greater residual film ratio and suppresses pattern collapse and an occurrence of bridge defects after development is not clear in forming a negative-type pattern by developing with an organic solvent, however, is postulated to be as follows.

If development is carried out using a developer including an organic solvent, acid generated from an acid generator tends to diffuse toward a resist film surface layer in a resist film when heated after development, therefore, pattern collapse and an occurrence of bridge defects after development easily occur. In addition, pattern collapse and an occurrence of bridge defects after development also easily occur from the generation of acid being attenuated toward the bottom side of the resist film since light is attenuated as the light progresses in the resist film due to optical transparency of the resist film. In addition, partial dissolution of the pattern boundary occurring when dissolution contrast is low in the resist film also causes pattern collapse and an occurrence of bridge defects after development.

In contrast, dissolution contrast for an organic solvent between an exposed area and an unexposed area in the resist film may be made to be large by using the resin (P) having a repeating unit represented by General Formula (I). In addition, it is postulated that diffusion of the acid generated toward the surface layer in the resist film is suppressed by the compound (B) having a structure represented by any of (B-1) to (B-3), therefore, pattern collapse and an occurrence of bridge defects after development is suppressed, although the reason is not clear. In addition, a molecular weight of detached substance generated by the acid decomposable group having a repeating unit represented by General Formula (I) being decomposed at the time of exposure tends to be small, therefore, film thickness reduction of a patterned area formed by exposure is suppressed and residual film ratio is improved.

The actinic-ray-sensitive or radiation-sensitive resin composition of the present invention may be used in a negative-type development (a development in which an exposed area remains as a pattern by its solubility being decreased for a developer when exposed, therefore, an unexposed area is removed). In other words, the actinic-ray-sensitive or radiation-sensitive resin composition of the present invention can be an actinic-ray-sensitive or radiation-sensitive resin composition for organic solvent development used in the development using the developer including an organic solvent. Here, for organic solvent development means, at least, an application is provided with a step in which a substance is developed using a developer including an organic solvent.

The actinic-ray-sensitive or radiation-sensitive resin composition of the present invention is typically a resist composition, and is particularly preferably a negative-type resist composition (that is, a resist composition for organic solvent development) from the viewpoint of obtaining high effects. The composition relating to the present invention is typically a chemical amplification type resist composition.

[1] Resin (P) Having a Repeating Unit (a) Represented by Following General Formula (I)

[Chem. 9]

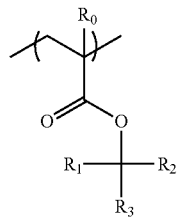

(I)

In General Formula (I), $R_0$ represents a hydrogen atom or a methyl group.

$R_1$, $R_2$, and $R_3$, each independently, represent a straight chain or branched alkyl group.

As the straight chain or branched alkyl group of $R_1$, $R_2$, and $R_3$, an alkyl group having 1 to 4 carbon atoms is preferable, a methyl group, an ethyl group, an n-propyl group, an isopropyl group, an n-butyl group, an isobutyl group or a tert-butyl group may be included.

As $R_1$, a methyl group, an ethyl group, an n-propyl group or an n-butyl group is preferable, a methyl group or an ethyl group is more preferable, and a methyl group is particularly preferable.

As $R_2$, a methyl group, an ethyl group, an n-propyl group, an isopropyl group or an n-butyl group is preferable, a methyl group or an ethyl group is more preferable, and a methyl group is particularly preferable.

As $R_3$, a methyl group, an ethyl group, an n-propyl group, an isopropyl group, an n-butyl group, an isobutyl group or a tert-butyl group is preferable, a methyl group, an ethyl group, an isopropyl group or an isobutyl group is more preferable, and a methyl group, an ethyl group or an isopropyl group is particularly preferable.

The repeating unit (a) represented by General Formula (I) is a repeating unit having a group generating a polar group (a carboxyl group) by being decomposed by an action of acid (hereinafter, also referred to as an "acid decomposable group").

The resin having the repeating unit (a) represented by General Formula (I) used for the actinic-ray-sensitive or radiation-sensitive resin composition relating to the present invention (hereinafter, also referred to as a "resin (P)") is a resin having the acid decomposable group (hereinafter, also referred to as an "acid decomposable resin"), and is a resin of which solubility is decreased for a developer including an organic solvent since polarity is increased due to an action of acid.

In addition, the resin (P) is a resin of which solubility is increased for an alkaline developer since polarity is increased due to an action of acid.

In the resin (P) of the present invention, the content of the repeating unit (a) represented by General Formula (I) (the total content when containing one, two or more types) is not particularly limited, however, 45 mol % or more with regard to all repeating units in the resin (P) is preferable from the viewpoint of achieving the effects of the present invention more reliably, 50 mol % or more is more preferable from the viewpoint of particularly improving dissolution contrast, and 55 mol % or more is particularly preferable. In addition, as the upper limit, 90 mol % or less is preferable from the viewpoint of forming satisfactory patterns, and 85 mol % or less is more preferable.

Specific examples of the repeating unit (a) represented by General Formula (I) are exemplified below, however, the present invention is not limited to these.

[Chem. 10]

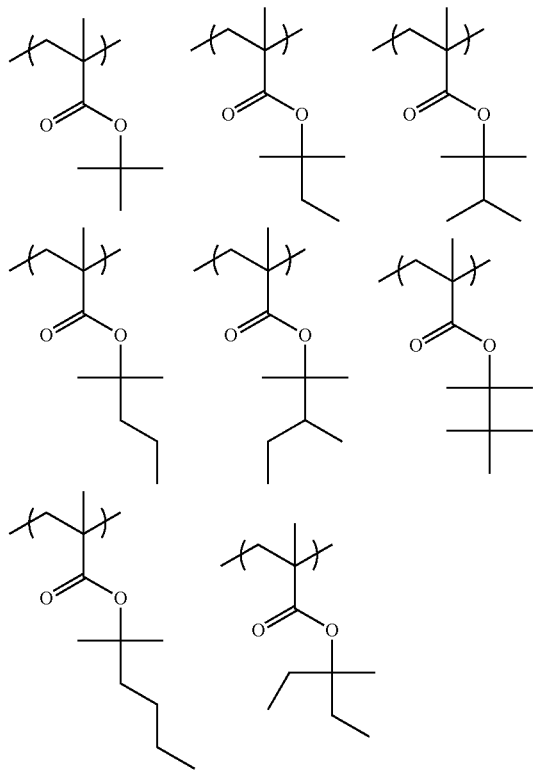

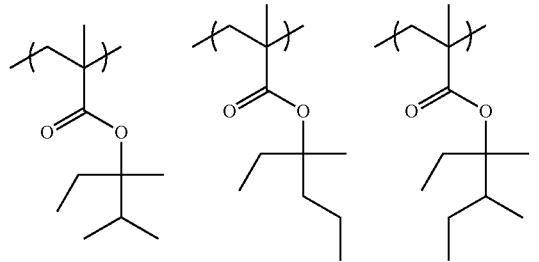
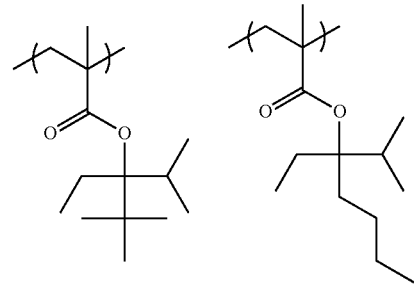
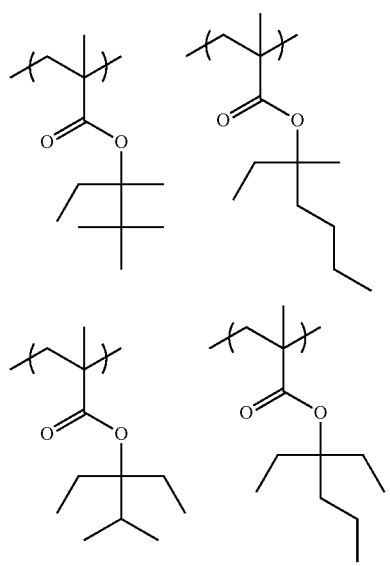
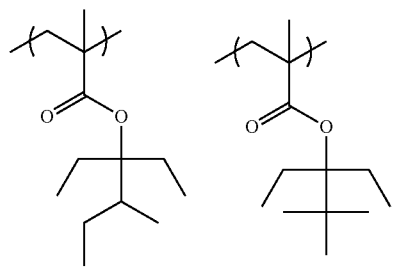
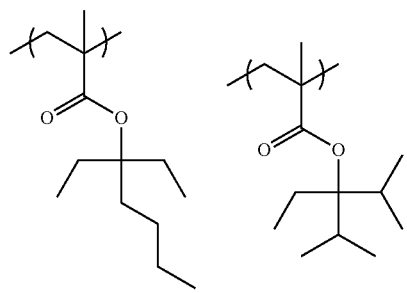
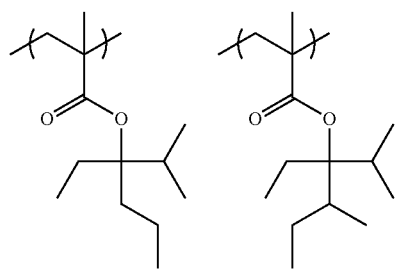
In the present invention, the resin (P) may have a repeating unit (b) which has an acid decomposable group different from that of the repeating unit (a).

The acid decomposable group different from that of the repeating unit (a) preferably has a structure protected by a group in which a polar group is decomposed by an action of acid and detached.

The polar group is not particularly limited as long as it is a group sparingly soluble or insoluble in the developer including an organic solvent, however, an acidic group such as a carboxyl group, a sulfonate group (a group which dissociates in an aqueous solution of 2.38% by mass tetramethylammonium hydroxide, which is used as a conventional developer or resist), an alcoholic hydroxyl group, or the like, may be included.

The alcoholic hydroxyl group is a hydroxyl group bonded directly to a hydrocarbon group and refers to a hydroxyl group other than a hydroxyl group bonded on an aromatic ring (a phenolic hydroxyl group) and excludes aliphatic alcohols of which α-position is substituted with an electron withdrawing group such as a fluorine atom as an acid group (for example, a fluorinated alcohol group (hexafluoroisopropanol group or the like)). As the alcoholic hydroxyl group, a hydroxyl group of which pKa is greater than or equal to 12 and less than or equal to 20 is preferable.

The group preferable as the acid decomposable group is a group substituted with a group in which a hydrogen atom of the group such as this is detached by acid.

As the group detached by acid, for example, —C($R_{36}$)($R_{37}$)($R_{38}$), —C($R_{36}$)($R_{37}$)(O$R_{39}$), —C($R_{01}$)($R_{02}$)(O$R_{39}$), or the like, may be included.

In the above General Formula, $R_{36}$ to $R_{39}$, each independently, represent an alkyl group, a cycloalkyl group, an aryl group, an aralkyl group, or an alkenyl group. $R_{36}$ and $R_{37}$ may be bonded to each other and form a ring.

$R_{01}$ and $R_{02}$, each independently, represent a hydrogen atom, an alkyl group, a cycloalkyl group, an aryl group, an aralkyl group, or an alkenyl group.

The alkyl group of $R_{36}$ to $R_{39}$, $R_{01}$ and $R_{02}$ is preferably an alkyl group having 1 to 8 carbon atoms and, for example, a methyl group, an ethyl group, a propyl group, an n-butyl group, a sec-butyl group, a hexyl group, an octyl group, or the like, may be included.

The cycloalkyl group of $R_{36}$ to $R_{39}$, $R_{01}$ and $R_{02}$ may be monocyclic or polycyclic. As the monocyclic, a cycloalkyl group having 3 to 8 carbon atoms is preferable and, for example, a cyclopropyl group, a cyclobutyl group, a cyclopentyl group, a cyclohexyl group, a cyclooctyl group, or the like, may be included. As the polycyclic, a cycloalkyl group having 6 to 20 carbon atoms is preferable and, for example, an adamantyl group, a norbornyl group, an isobornyl group, a camphanyl group, a dicyclopentyl group, an α-pinel group, a tricyclodecanyl group, a tetracyclododecyl group, an androstanyl group, or the like, may be included. In addition, at least one of the carbon atoms in the cycloalkyl group may be substituted with a heteroatom such as an oxygen atom.

The aryl group of $R_{36}$ to $R_{39}$, $R_{01}$ and $R_{02}$ is preferably an aryl group having 6 to 10 carbon atoms and, for example, a phenyl group, a naphthyl group, an anthryl group, or the like may be included.

The aralkyl group of $R_{36}$ to $R_{39}$, $R_{01}$ and $R_{02}$ is preferably an aralkyl group having 7 to 12 carbon atoms and, for example, a benzyl group, a phenethyl group, a naphthylmethyl group, or the like, may be included.

The alkenyl group of $R_{36}$ to $R_{39}$, $R_{01}$ and $R_{02}$ is preferably an alkenyl group having 2 to 8 carbon atoms and, for example, a vinyl group, an allyl group, a butenyl group, a cyclohexenyl group, or the like, may be included.

As the ring formed by $R_{36}$ and $R_{37}$ being bonded, a cycloalkyl group (monocyclic or polycyclic) is preferable. As the cycloalkyl group, a monocyclic cycloalkyl group such as a cyclopentyl group or a cyclohexyl group, or a polycyclic cycloalkyl group such as a norbornyl group, a tetracyclodecanyl group, a tetracyclododecanyl group or an adamantyl group is preferable. A monocylic cycloalkyl group having 5 to 6 carbon atoms is more preferable, and a monocylic cycloalkyl group having 5 carbon atoms is particularly preferable.

As the repeating unit (b) which has an acid decomposable group different from that of the repeating unit (a) the resin (P) may contain, a repeating unit represented by following General Formula (AI) is preferable.

[Chem. 11]

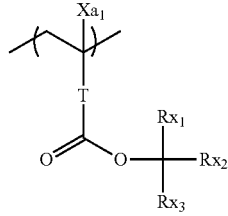

(AI)

In General Formula (AI), $Xa_1$ represents a hydrogen atom, a methyl group which may have a substituent, or a group expressed by —$CH_2$—$R_9$. $R_9$ represents a hydroxyl group or a monovalent organic group, and the monovalent organic group includes, for example, an alkyl group having 5 or less carbon atoms, an acyl group having 5 or less carbon atoms, is preferably an alkyl group having 3 or less carbon atoms, is more preferably a methyl group. $Xa_1$ preferably represents a hydrogen atom, a methyl group, a trifluoromethyl group or a hydroxymethyl group.

T represents a single bond or a divalent linking group.

$Rx_1$ to $Rx_3$, each independently, represent an alkyl group (straight chain or branched) or a cycloalkyl group (monocyclic or polycyclic).

Two of $Rx_1$ to $Rx_3$ may be bonded and form a cycloalkyl group (monocyclic or polycyclic).

However, all of $Rx_1$ to $Rx_3$ do not represent an alkyl group when T represents a single bond.

As the divalent linking group of T, an alkylene group, a —COO-Rt- group, a —O—Rt- group, a phenylene group, or the like, may be included. Rt in the above Formula represents an alkylene group or a cycloalkylene group.

T is preferably a single bond or a —COO-Rt- group. Rt is preferably an alkylene group having 1 to 5 carbon atoms and more preferably a —$CH_2$— group, a —$(CH_2)_2$— group, a —$(CH_2)_3$— group.

The alkyl group of $Rx_1$ to $Rx_3$ is preferably an alkyl group having 1 to 4 carbon atoms such as a methyl group, an ethyl group, an n-propyl group, an isopropyl group, an n-butyl group, an isobutyl group or a t-butyl group.

The cycloalkyl group of $Rx_1$ to $Rx_3$ is preferably a monocyclic cycloalkyl group such as a cyclopentyl group or a cyclohexyl group, or a polycyclic cycloalkyl group such as a norbornyl group, a tetracyclodecanyl group, a tetracyclododecanyl group or an adamantyl group.

As the cycloalkyl group formed by two of $Rx_1$ to $Rx_3$ being bonded, a monocyclic cycloalkyl group such as a cyclopentyl group or a cyclohexyl group, or a polycyclic cycloalkyl group such as a norbornyl group, a tetracyclodecanyl group, a tetracyclododecanyl group or an adamantyl group is preferable.

A monocylic cycloalkyl group having 5 to 6 carbon atoms is particularly preferable.

An aspect in which $Rx_1$ is a methyl group or an ethyl group, and the cycloalkyl group described above is formed by $Rx_2$ and $Rx_3$ being bonded is preferable.

Each of the above groups may have a substituent, and as the substituent, for example, an alkyl group (1 to 4 carbon atoms), a cycloalkyl group (3 to 8 carbon atoms), a halogen atom, an alkoxy group (1 to 4 carbon atoms), a carboxyl group, an alkoxycarbonyl group (2 to 6 carbon atoms) or the like may be included, and having 8 or less carbon atoms is preferable. Among these, a substituent which does not have a heteroatom such as an oxygen atom, a nitrogen atom or a sulfur atom is more preferable (for example, a group which is not an alkyl group substituted with a hydroxyl group or the like is more preferable) from the viewpoint of further improving dissolution contrast for a developer including an organic solvent before and after acid decomposition, a group formed only from hydrogen atoms and carbon atoms is even more preferable and a straight chain or branched alkyl group, or a cycloalkyl group is particularly preferable.

Preferable specific examples of the repeating unit (b) which has an acid decomposable group different from that of the repeating unit (a) are shown below, however, the present invention is not limited to these.

In the specific examples, Rx and $Xa_1$ represent a hydrogen atom, $CH_3$, $CF_3$, or $CH_2OH$. Each of Rxa and Rxb represents an alkyl group having 1 to 4 carbon atoms. Z represents a substituent and if present in plural numbers, plural numbers of Z may be the same as or different from each other. p represents 0 or a positive integer. Specific examples and preferable examples of Z is the same as the specific examples and preferable examples of the substituents each group such as $Rx_1$ to $Rx_3$ may have.

[Chem. 12]

1

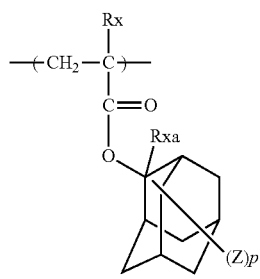

2

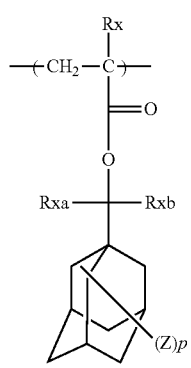

3

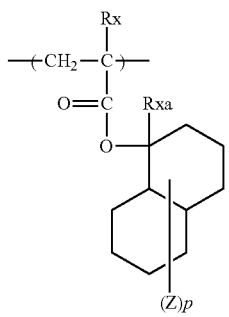

4

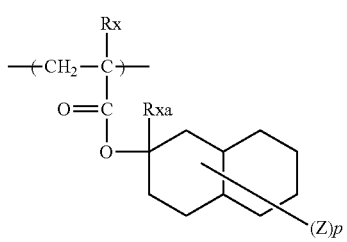

5

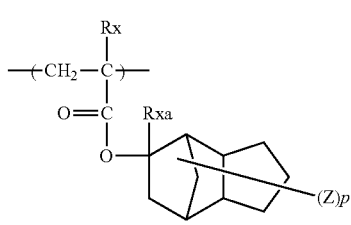

6

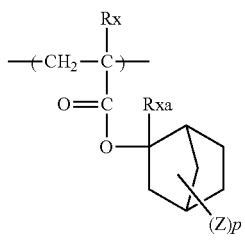

7

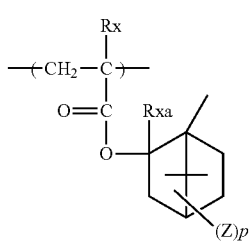

8

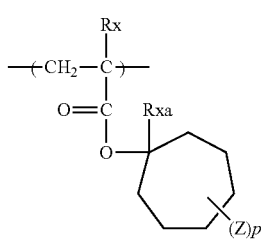

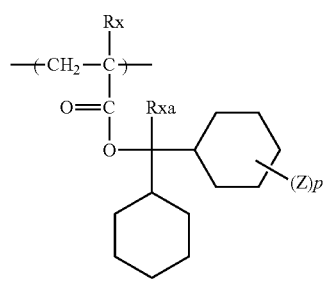
8
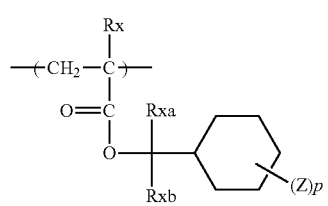
9
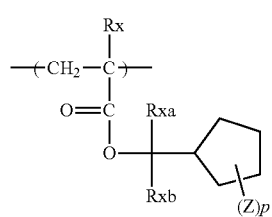
10
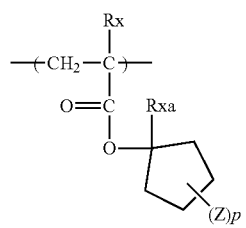
11
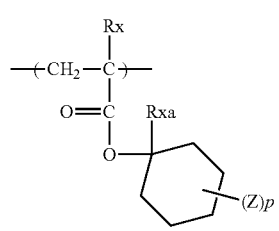
12
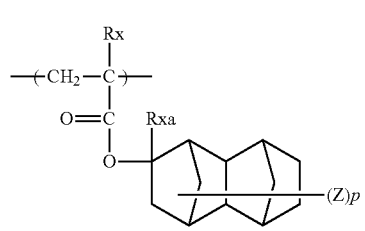
13
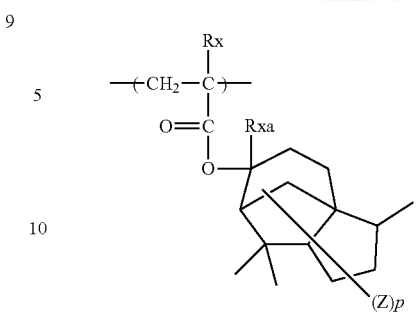
14
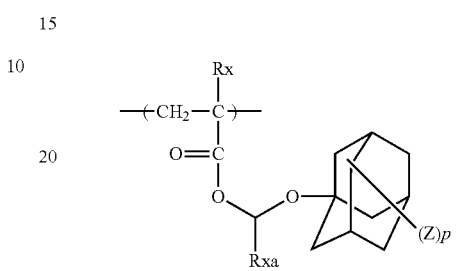
15
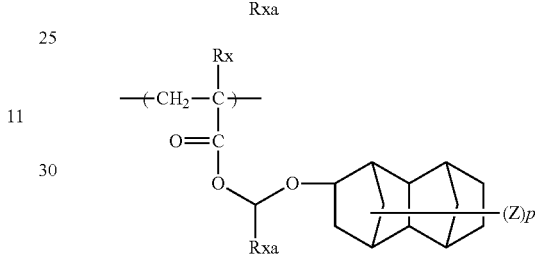
16
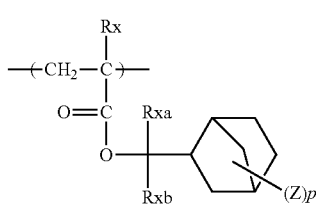
17
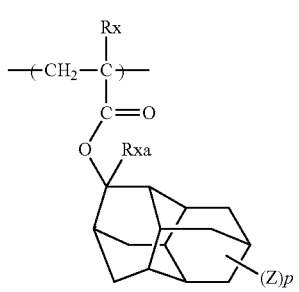
18
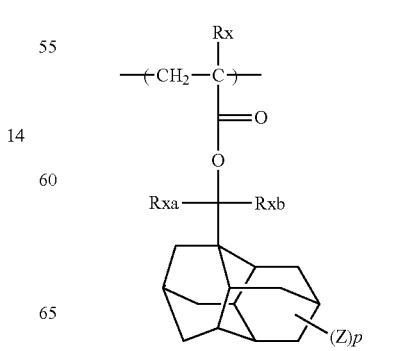
19

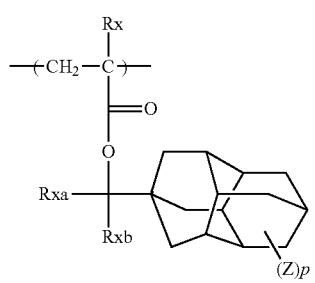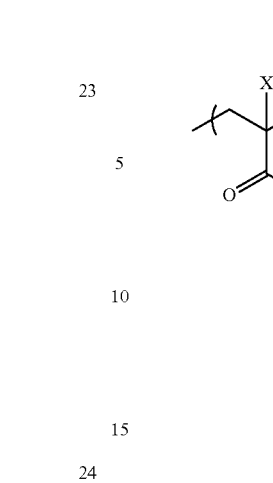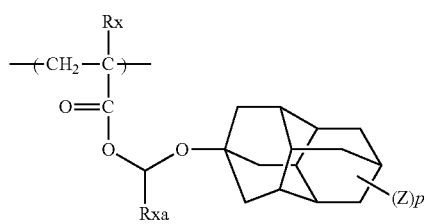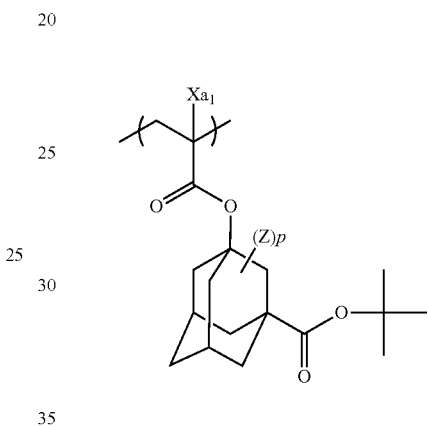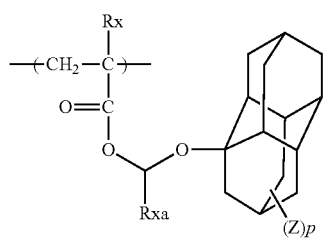
[Chem. 13]
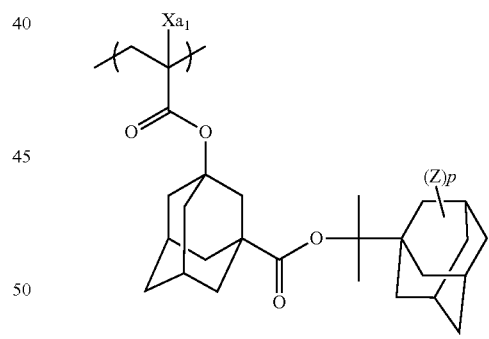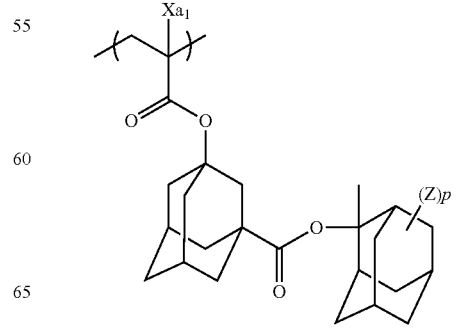

-continued
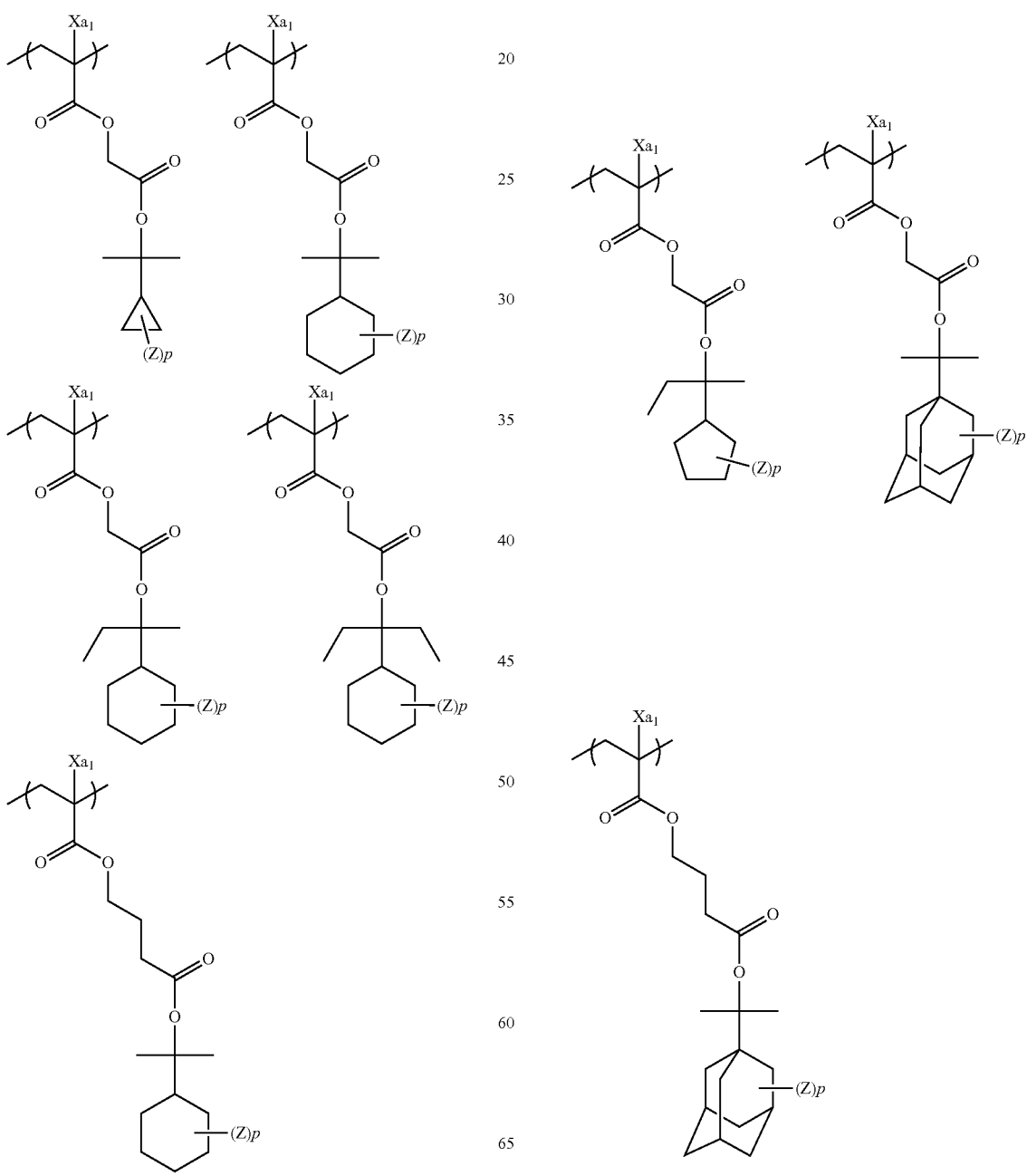

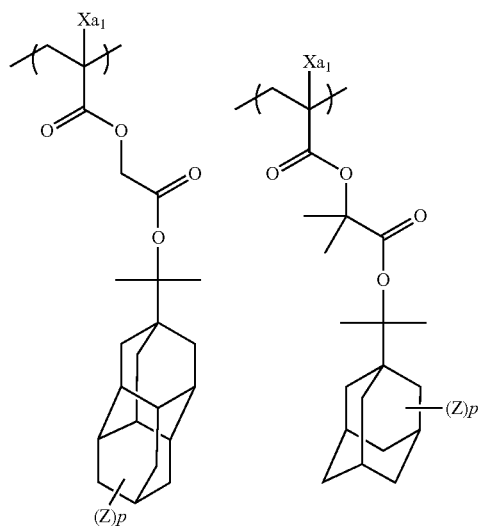
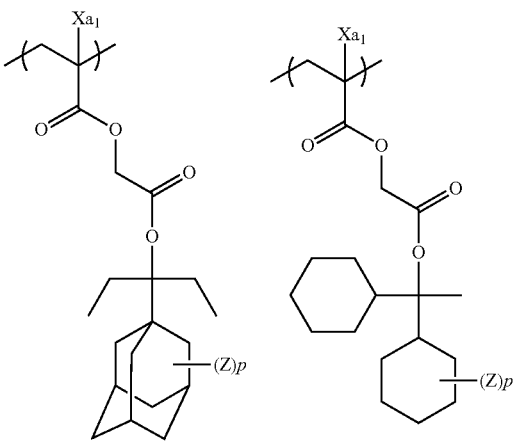
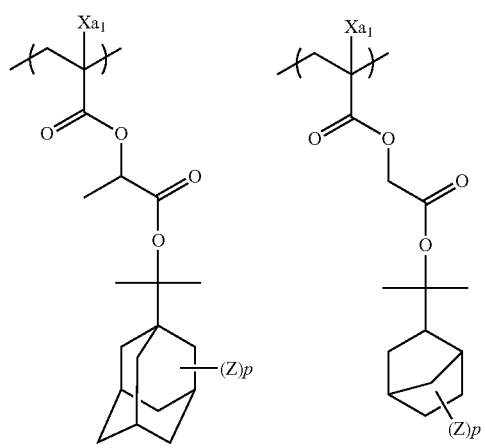
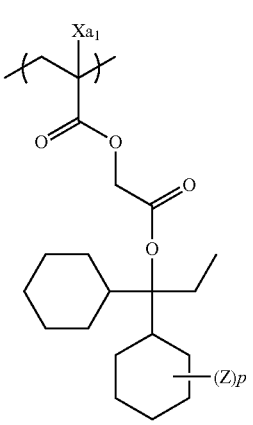
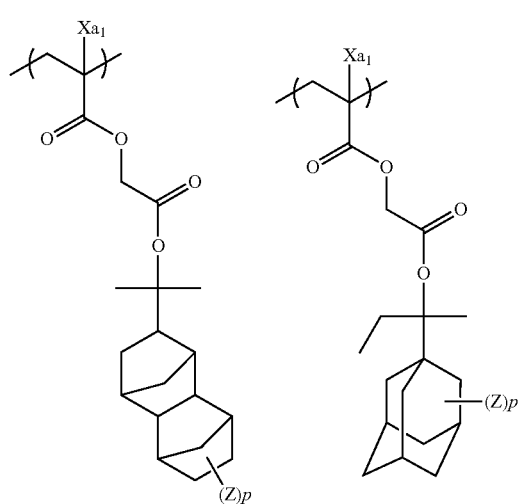
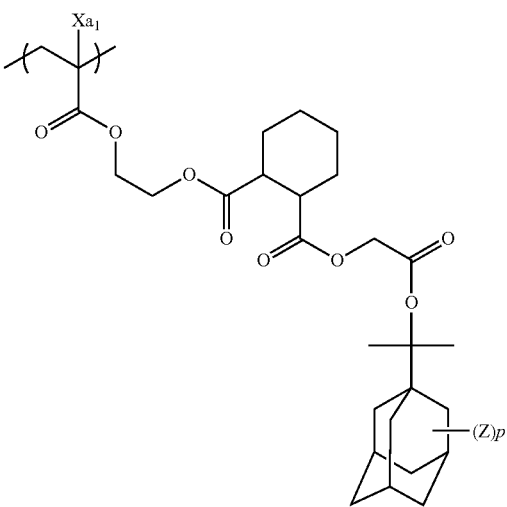

[Chem. 15]
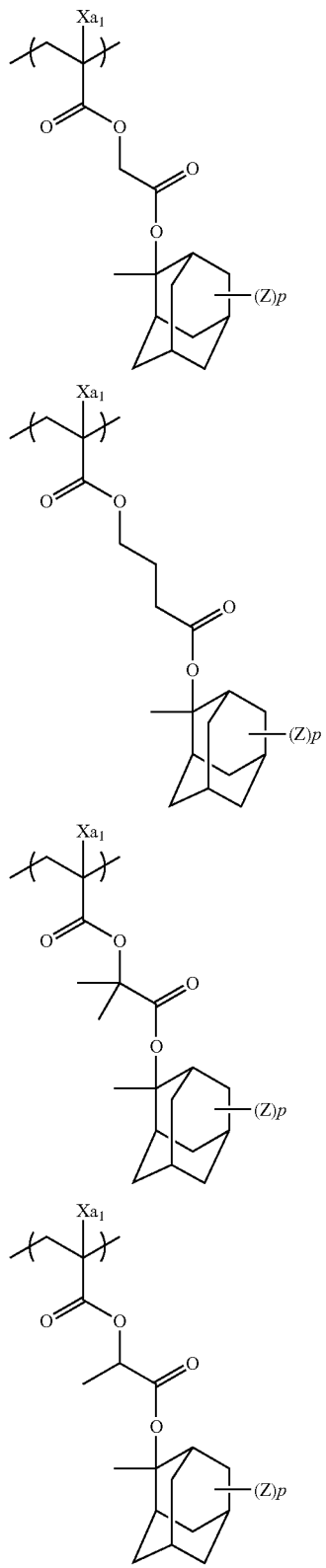
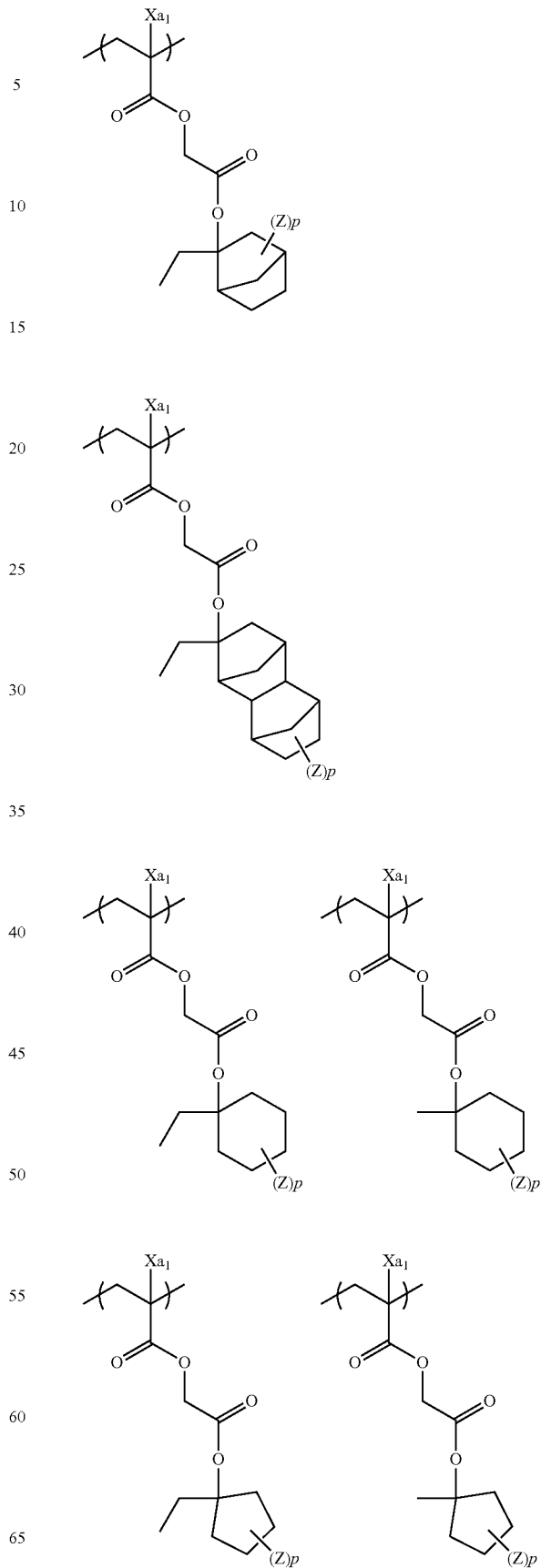

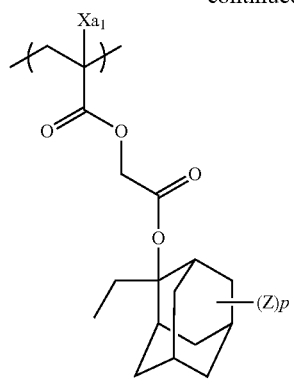
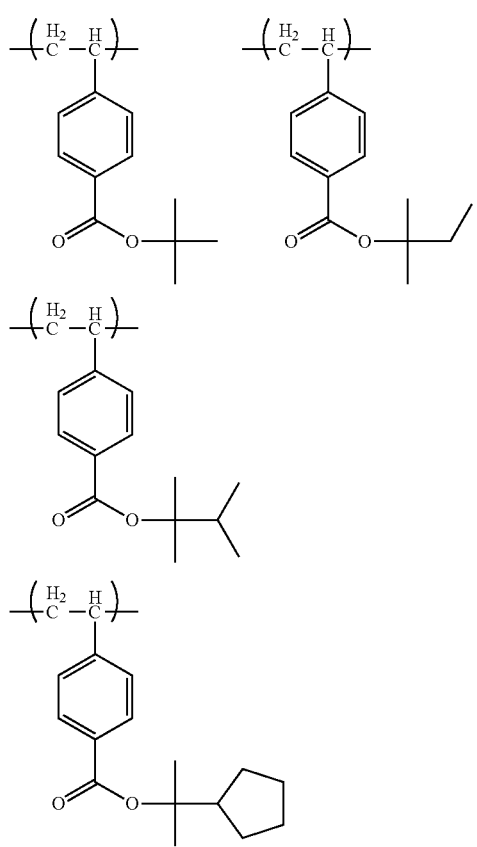
[Chem. 16]
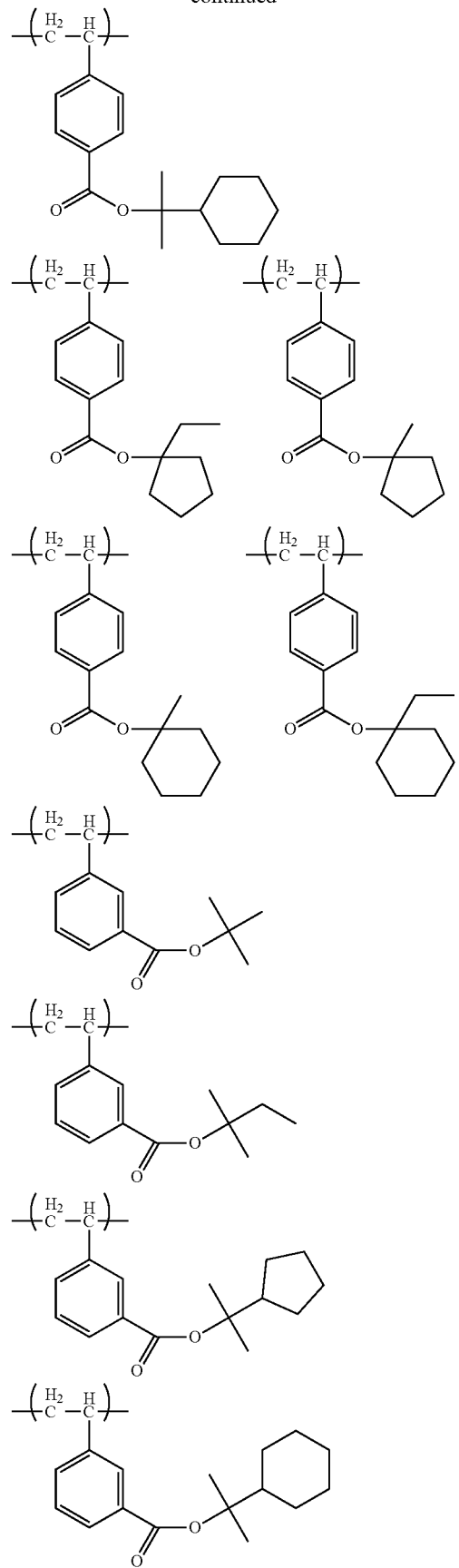

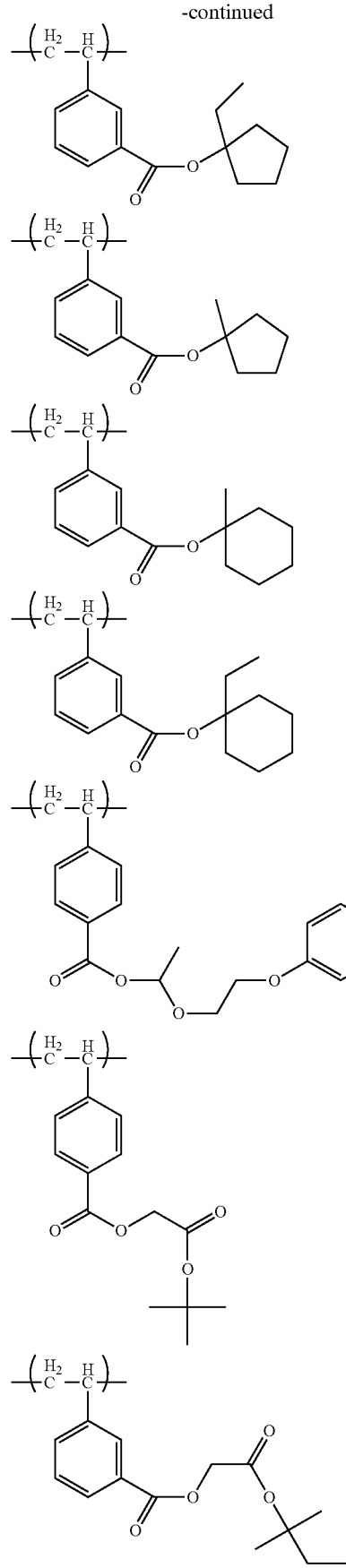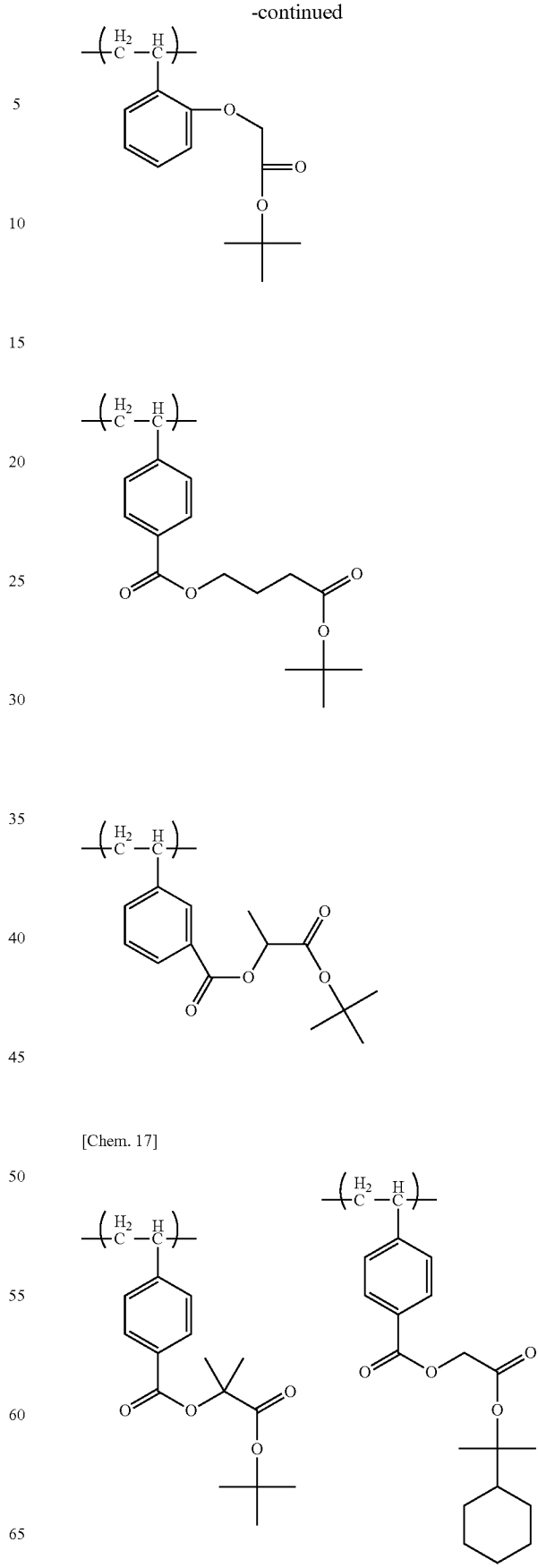

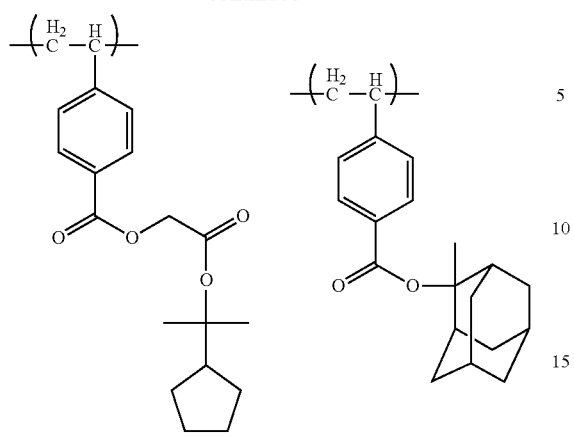
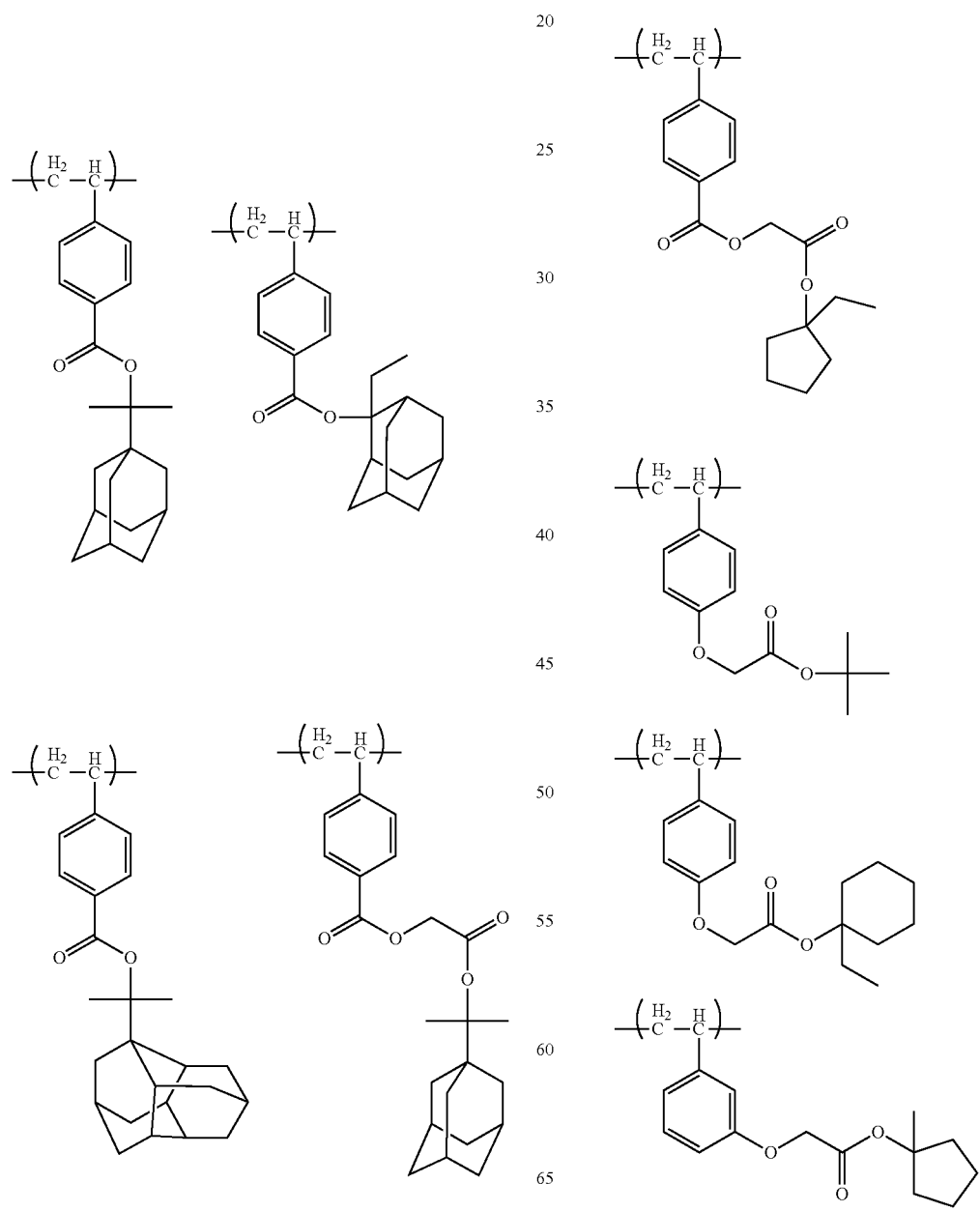

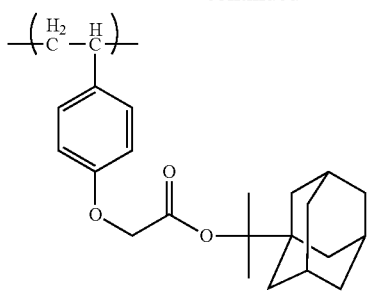
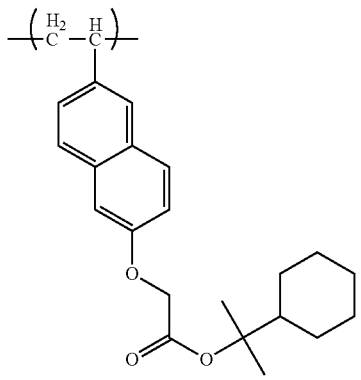
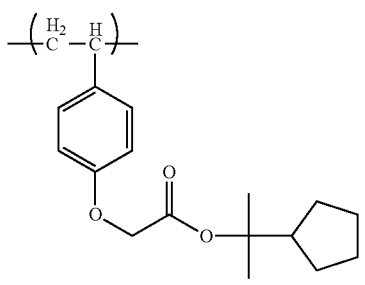
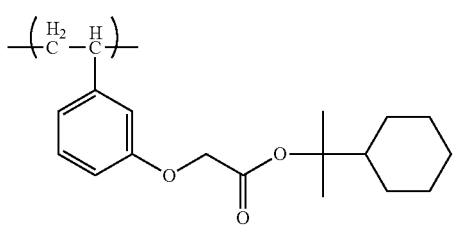
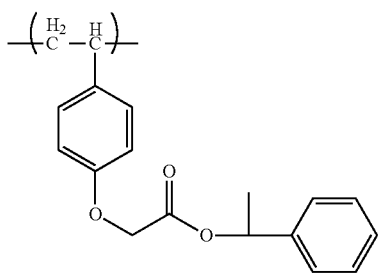
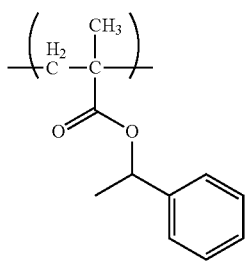

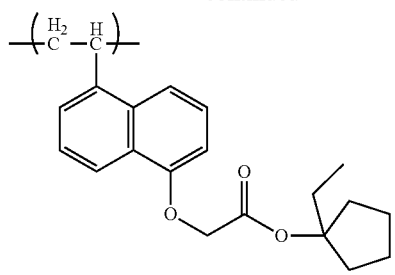

In addition, the resin (P) may include a repeating unit represented by following General Formula (VI) as the repeating unit (b), and particularly, it is preferable when exposed by KrF, an electron beam or EUV.

[Chem. 18]

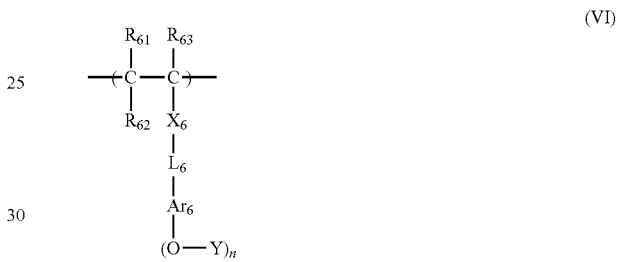

(VI)

In General Formula (VI), $R_{61}$, $R_{62}$, and $R_{63}$, each independently, represent a hydrogen atom, an alkyl group, a cycloalkyl group, a halogen atom, a cyano group or an alkoxycarbonyl group. $R_{62}$ may be bonded to $Ar_6$ and form a ring (preferably a 5-membered or 6-membered ring), and $R_{62}$ represents an alkylene group in that case.

$X_6$ represents a single bond, —COO— or —CONR$_{64}$— ($R_{64}$ represents a hydrogen atom or an alkyl group). $L_6$ represents a single bond or an alkylene group. $Ar_6$ represents a divalent aromatic ring group. Y, each independently when present in plural numbers, represents a hydrogen atom or a group detached by an action of acid. However, at least one of Y represents a group detached by an action of acid. n represents an integer of 1 to 4.

As the repeating unit (b), the following repeating unit represented by General Formula (1) or the following repeating unit represented by General Formula (2) is preferable.

[Chem. 19]

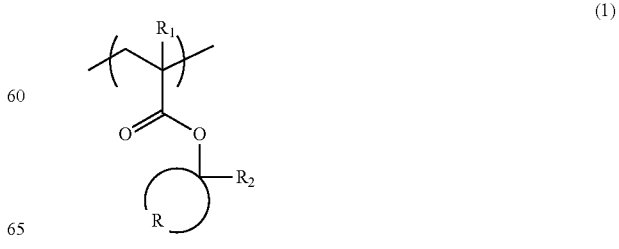

(1)

-continued (2)

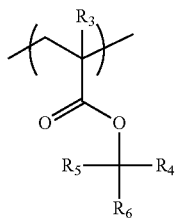

In General Formulae (1) and (2), $R_1$ and $R_3$, each independently, represent a hydrogen atom, a methyl group which may have a substituent, or a group expressed by —$CH_2$—$R_9$. $R_9$ represents a hydroxyl group or a monovalent organic group.

$R_2$ represents an alkyl group or a cycloalkyl group.

$R_4$, $R_5$, and $R_6$, each independently, represent an alkyl group or a cycloalkyl group and at least one of $R_4$, $R_5$, and $R_6$ represents a cycloalkyl group.

R represents an atomic group necessary for forming an alicyclic structure with a carbon atom.

$R_1$ and $R_3$ preferably represent a hydrogen atom, a methyl group, a trifluoromethyl group or a hydroxymethyl group. Specific examples and preferable examples of the monovalent organic group in $R_9$ is the same as described in $R_9$ of General Formula (AI).

The alkyl group in $R_2$ may be straight chain or branched, or have a substituent.

The alkyl group in $R_2$ may be monocyclic or polycyclic, or have a substituent.

$R_2$ is preferably an alkyl group, more preferably an alkyl group having 1 to 10 carbon atoms, even more preferably an alkyl group having 1 to 5 carbon atoms, and for example, a methyl group or an ethyl group may be included.

R represents an atomic group necessary for forming an alicyclic structure with a carbon atom. The alicyclic structure formed by R with the carbon atom is preferably a monocyclic alicyclic structure, the number of carbons is preferably 3 to 7, and more preferably 5 or 6.

The alkyl group in $R_4$, $R_5$, and $R_6$ may be straight chain or branched, or have a substituent. As the alkyl group, an alkyl group having 1 to 4 carbon atoms such as a methyl group, an ethyl group, an n-propyl group, an isopropyl group, an n-butyl group, an isobutyl, group or a t-butyl group is preferable.

The cycloalkyl group in $R_4$, $R_5$, and $R_6$ may be monocyclic or polycyclic, or have a substituent. As the cycloalkyl group, a monocyclic cycloalkyl group such as a cyclopentyl group or a cyclohexyl group, or a polycyclic cycloalkyl group such as a norbornyl group, a tetracyclodecanyl group, a tetracyclododecanyl group or an adamantyl group is preferable.

In addition, as the repeating unit (b), an aspect of a repeating unit generating an alcoholic hydroxyl group as shown below may be used as an aspect different from the repeating unit exemplified above.

In the following specific examples, $X_{a1}$ represents a hydrogen atom, $CH_3$, $CF_3$, or $CH_2OH$.

[Chem. 20]

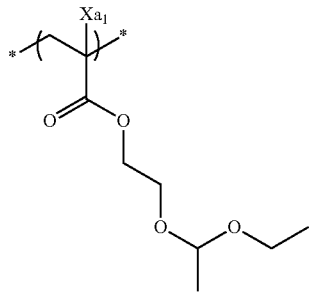

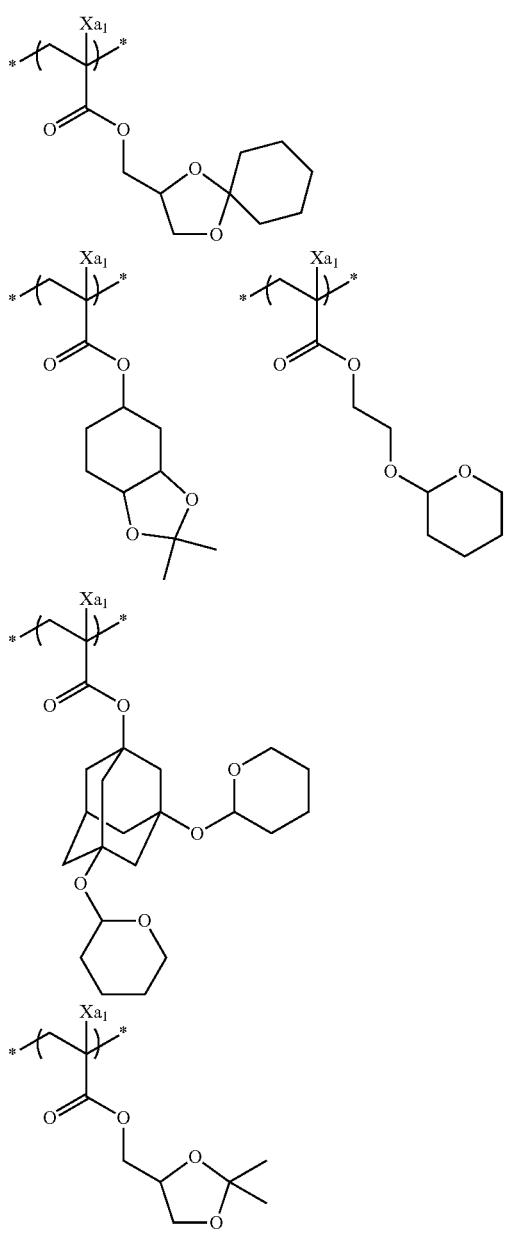

35
-continued
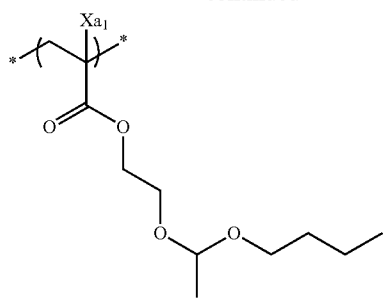
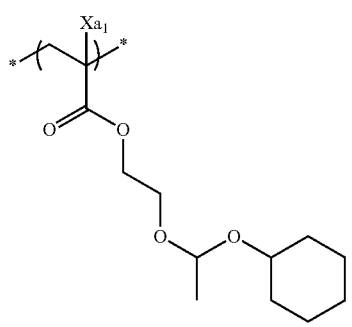
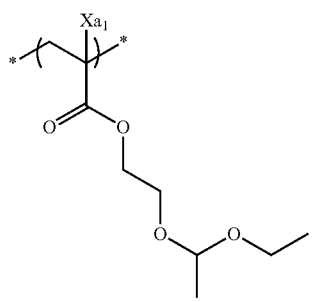
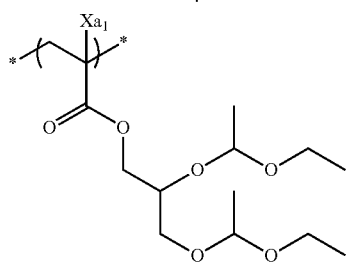
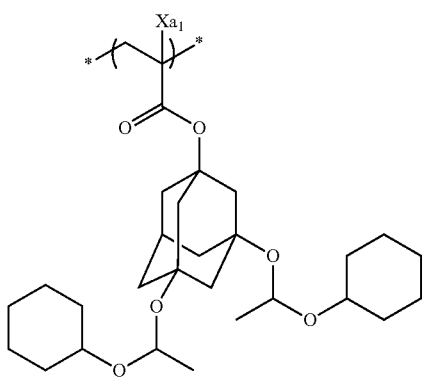
36
-continued
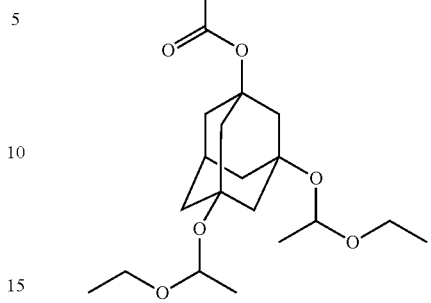
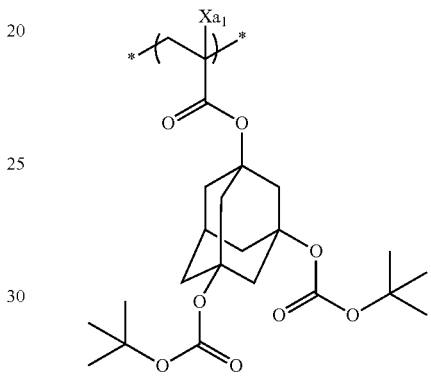
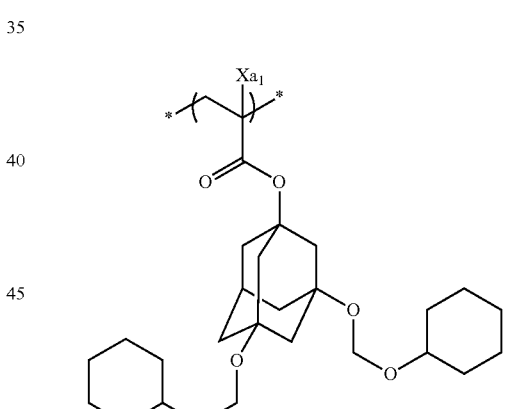
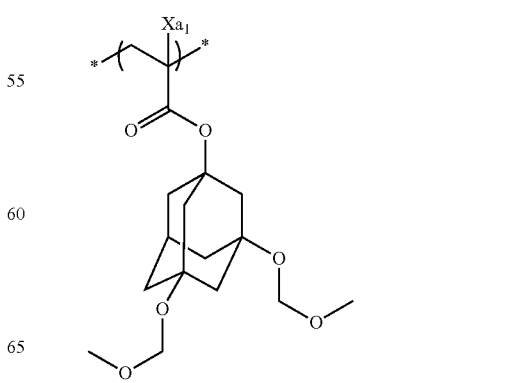

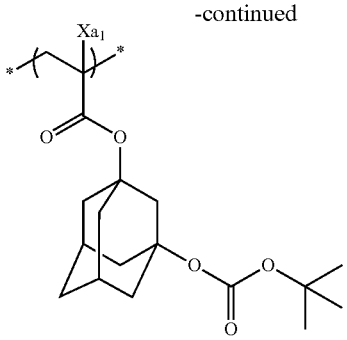

The resin (P) may or may not contain the repeating unit (b) which has an acid decomposable group different from that of the repeating unit (a), however, when the resin (P) contains the repeating unit (b), the content of the repeating unit (b) is preferably 1 to 30 mol %, more preferably 1 to 20 mol %, and even more preferably 1 to 15 mol % with regard to all repeating units in the resin (P).

In the present invention, a molecular weight (a weighted average value of the molecular weight by a mole fraction when two or more types of detached substances are generated (hereinafter, also referred to as an average mole value)) of the detached substance generated by the acid decomposable group being decomposed in the repeating unit (a) or (b) is preferably 140 or less. Thus, reduction of the film thickness of a patterned area may be prevented by making the molecular weight of the detached substance smaller since the exposed area remains as a pattern particularly when a negative-type image is formed.

In the present invention, "the detached substance generated by the acid decomposable group being decomposed" is the one detached by being decomposed by an action of acid, corresponding to a group detached by being decomposed by an action of acid. For example, it refers to alkene ($H_2C=C(CH_3)_2$) generated by the t-butyl part being decomposed when $R_1$ to $R_3$ in General Formula (I) of the repeating unit (a) are all methyl groups and form a t-butyl group.

The resin (P) preferably contains a repeating unit having a polar group. By containing the repeating unit having a polar group, dissolution rate of the resin (composition) for the developer including an organic solvent can be easily controlled to be in a suitable range.

The repeating unit having a polar group is not particularly limited, however, specifically, a repeating unit (c) having a lactone structure or a sultone structure, a repeating unit (d) having an acid group, a repeating unit (e) having a hydroxyl group or a cyano group, or the like, may be included.

As the repeating unit (c) having a lactone structure or a sultone structure, a repeating unit represented by following General Formula (AII) is more preferable.

[Chem. 21]

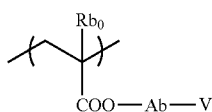

(AII)

In General Formula (AII), $Rb_0$ represents a hydrogen atom, a halogen atom, or an alkyl group which may have a substituent (preferably 1 to 4 carbon atoms).

As the preferable substituent the alkyl group of $Rb_0$ may have, a hydroxyl group or a halogen atom may be included. As the halogen atom of $Rb_0$, a fluorine atom, a chlorine atom, a bromine atom, or an iodine atom, may be included. As $Rb_0$, a hydrogen atom, a methyl group, a hydroxymethyl group or a trifluoromethyl group is preferable, and a hydrogen atom or a methyl group is particularly preferable.

Ab represents a single bond, an alkylene group, a divalent linking group having a monocyclic or polycyclic cycloalkyl structure, an ether bond, an ester bond, a carbonyl group, or a divalent linking group combining these. Ab is preferably a single bond or a divalent linking group represented by $-Ab_1-CO_2-$.

$Ab_1$ is a straight chain or branched alkylene group, a monocyclic or polycyclic cycloalkylene group, and preferably, a methylene group, an ethylene group, a cyclohexylene group, an adamantylene group, or a norbornylene group.

V represents a group having a lactone structure or a sultone structure.

As the group having a lactone structure or a sultone structure, any group may be used as long as it has a lactone structure or a sultone structure, however, a lactone structure having a 5- to 7-membered ring is preferable, and a structure in which other ring structure is condensed to a lactone structure having a 5- to 7-membered ring to form a bicycle structure or a Spiro structure is preferable. Containing a repeating structure having a lactone structure represented by any of following General Formulae (LC1-1) to (LC1-17) or a sultone structure represented by any of following General Formulae (SL1-1) to (SL1-3) is more preferable. In addition, the lactone structure or the sultone structure may be bonded directly to a main chain. The preferable lactone structures are (LC1-1), (LC1-4), (LC1-5), (LC1-6), (LC1-8), (LC1-13), and (LC1-14).

[Chem. 22]

LC1-1

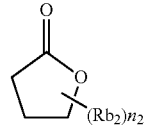

LC1-2

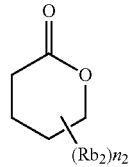

LC1-3

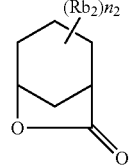

LC1-4

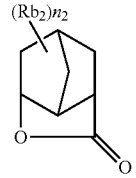

-continued

LC1-5 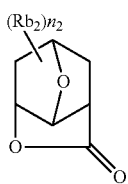

LC1-6 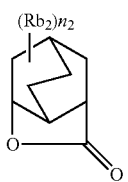

LC1-7 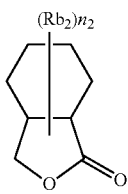

LC1-8 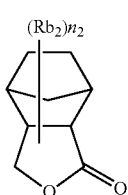

LC1-9 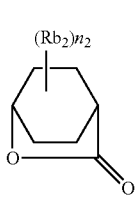

LC1-10 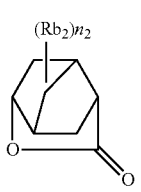

LC1-11 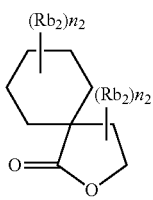

LC1-12 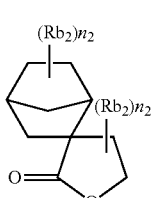

LC1-13 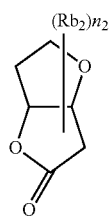

LC1-14 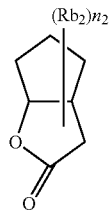

LC1-15 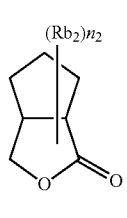

LC1-16 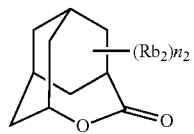

LC1-17 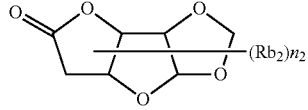

SL1-1 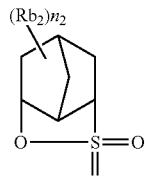

SL1-2 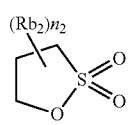

SL1-3 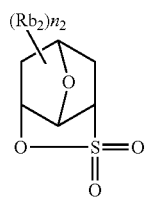

The lactone structure or the sultone structure part may or may not have a substituent ($Rb_2$). As the preferable substituent ($Rb_2$), an alkyl group having 1 to 8 carbon atoms, a monovalent cycloalkyl group having 4 to 7 carbon atoms, an alkoxy group having 1 to 8 carbon atoms, an alkoxycarbonyl group having 2 to 8 carbon atoms, a carboxyl group, a halogen atom, a hydroxyl group, a cyano group, an acid-decomposable group, or the like, may be included. An alkyl group having 1 to 4 carbon atoms, a cyano group or an acid-decomposable group is more preferable. $n_2$ represents an integer of 0 to 4. If $n_2$ is 2 or more, the substituents ($Rb_2$) present in plural numbers may be the same as or different from each other, and the substituents ($Rb_2$) present in plural numbers may be bonded to each other and form a ring.

The repeating unit having a lactone structure or a sultone structure typically includes optical isomers, however, any optical isomer may be used. In addition, one optical isomer may be used alone or a plurality of optical isomers may be mixed and used. If one optical isomer is mainly used, optical purity (ee) thereof is preferably 90% or more, and more preferably 95% or more.

When the resin (P) contains the repeating unit (c), the content of the repeating unit (c) in the resin (P) is preferably the range of 1 to 70 mol %, more preferably the range of 3 to 60 mol %, and even more preferably the range of 5 to 55 mol % with regard to all repeating units. The repeating unit (c) may be used either alone or as a combination of two or more. By using a specific lactone structure, a pattern collapse suppression performance and a bridge defect suppression performance becomes satisfactory.

Specific examples of the repeating unit (c) in the resin (P) are shown below, however, the present invention is not limited to these.

[Chem. 23]

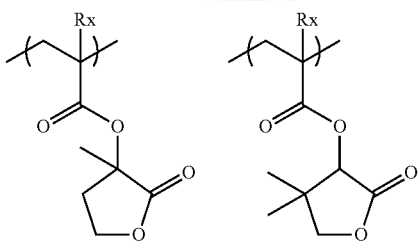

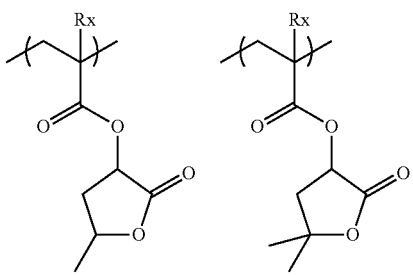

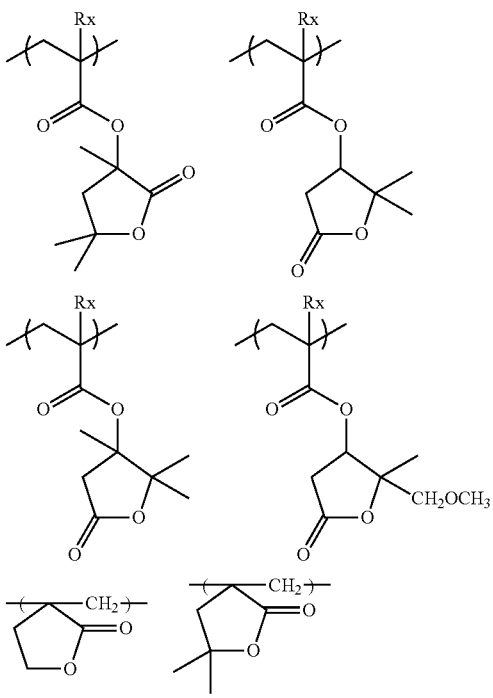

[Chem. 24]

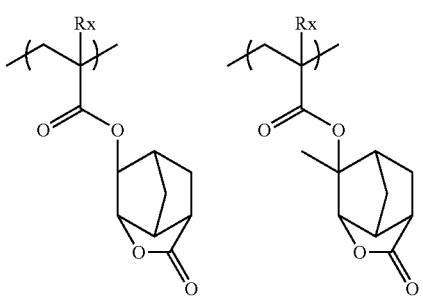

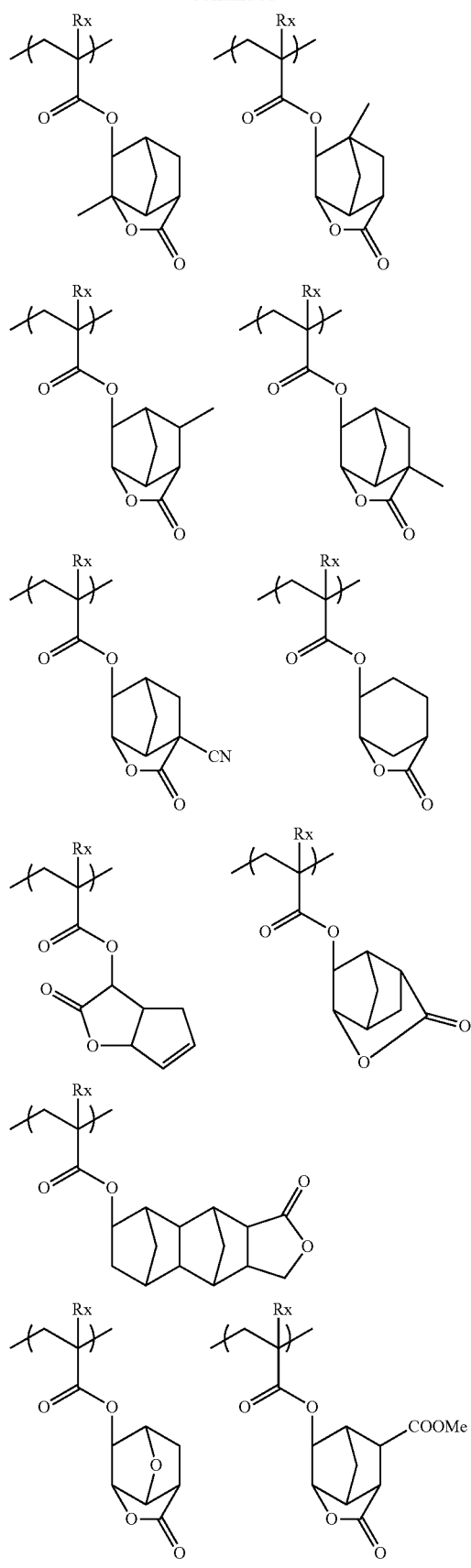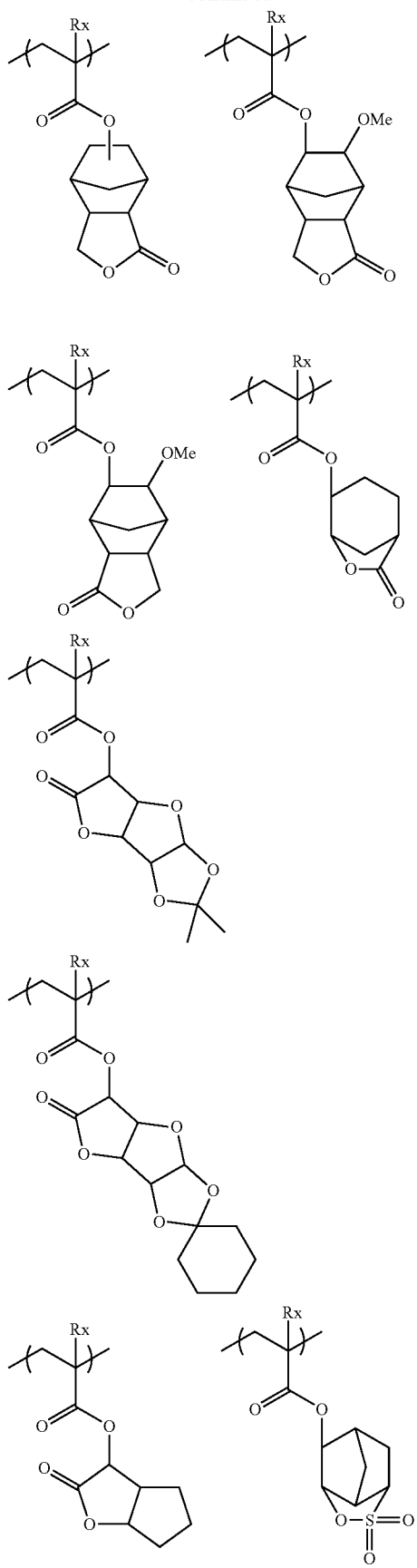

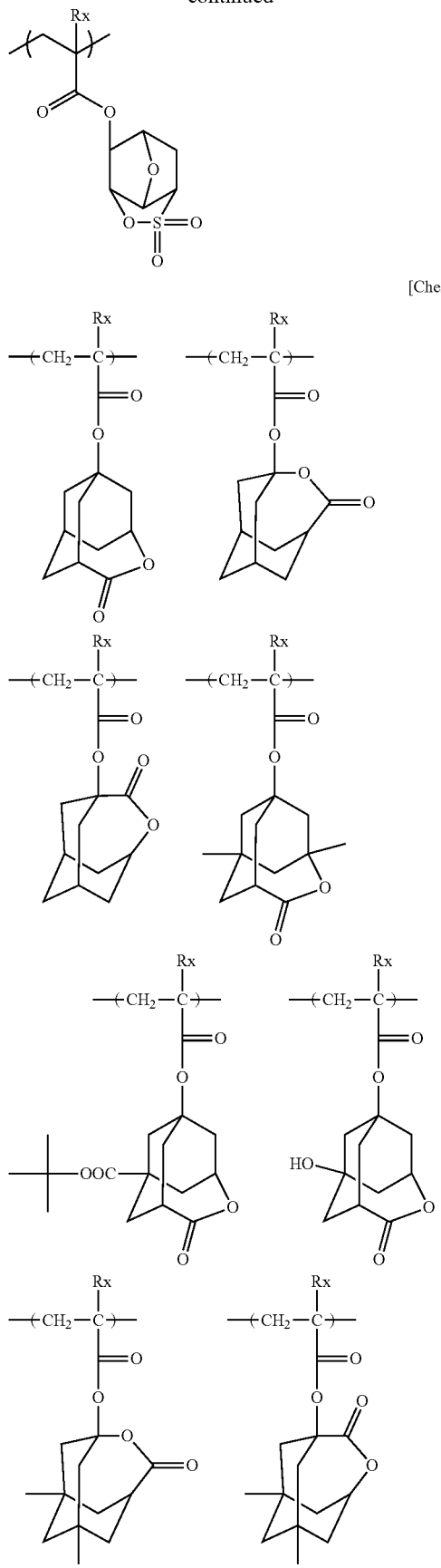
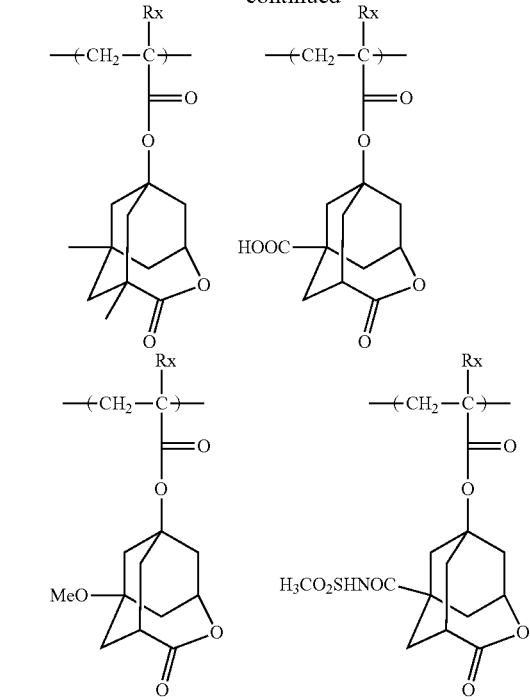
(In the formula, Rx is H, CH₃, CH₂OH, or CF₃.)
In the specific examples below, R represents a hydrogen atom, an alkyl group which may have a substituent or a halogen atom, and preferably represents a hydrogen atom, a methyl group, a hydroxymethyl group or an acetoxymethyl group.
[Chem. 26]
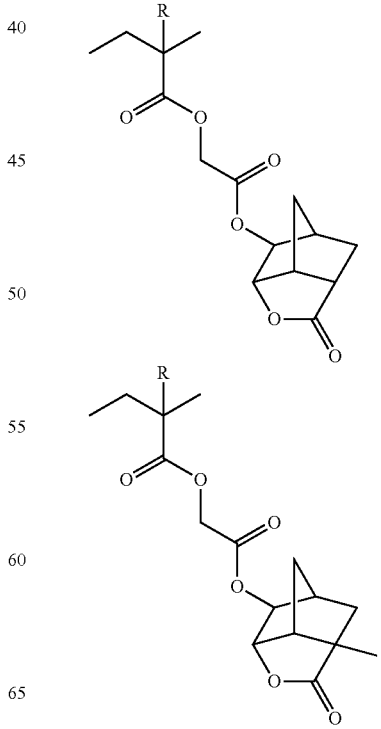

47
-continued
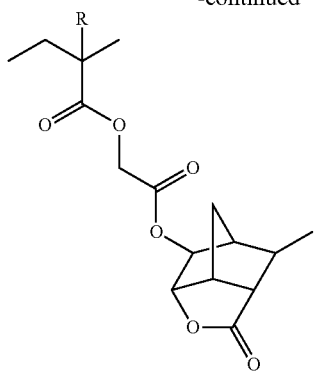
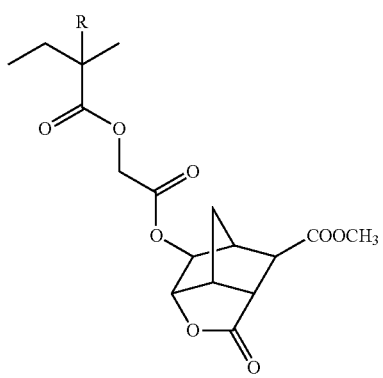
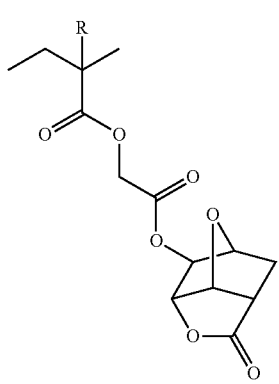
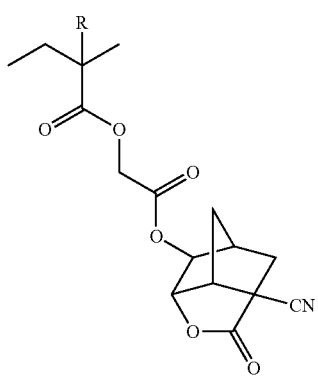
48
-continued
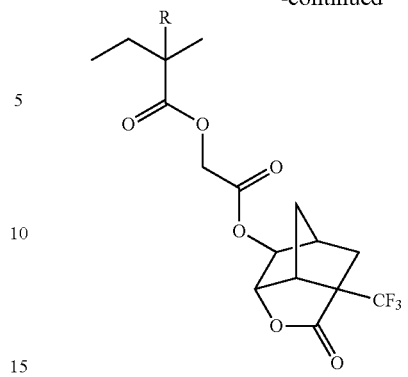
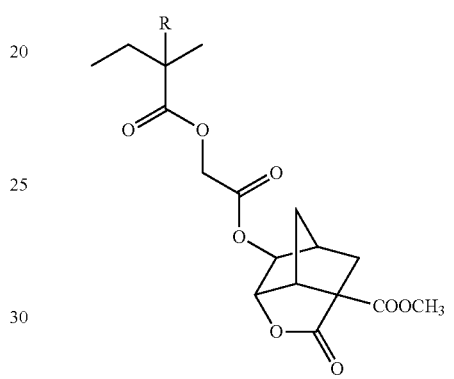
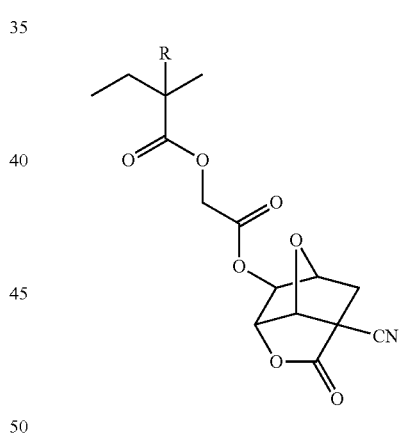
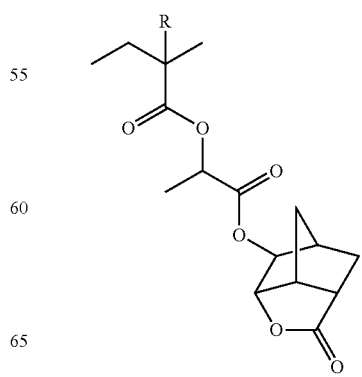

49
-continued
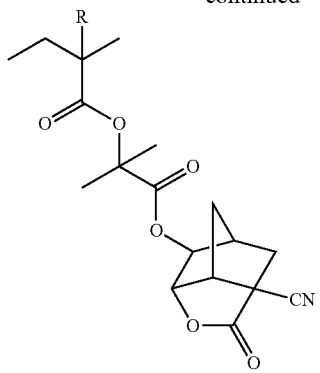
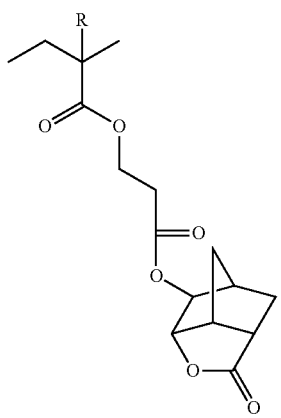
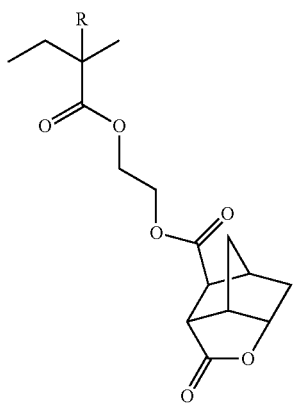
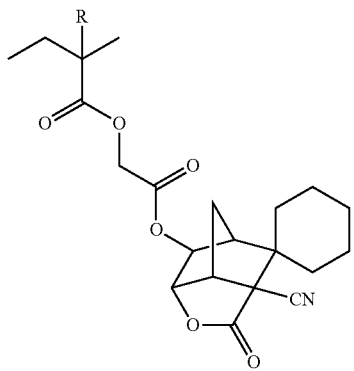
50
-continued
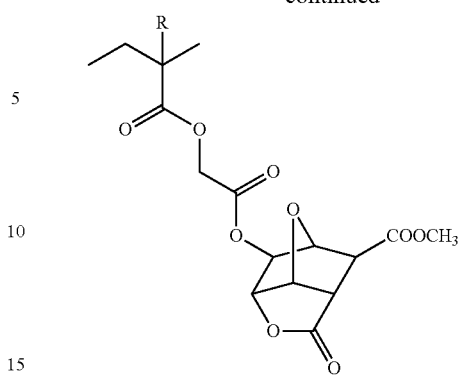
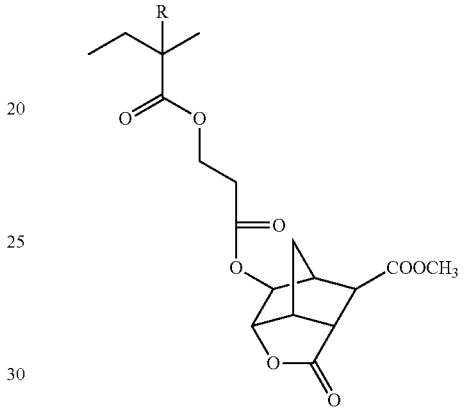
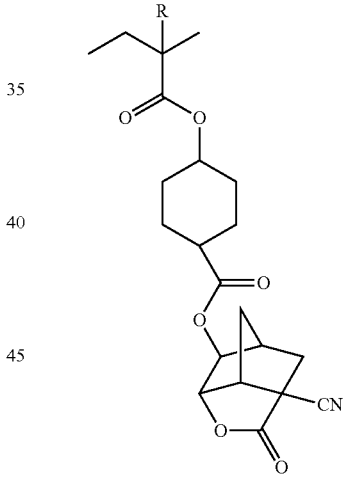
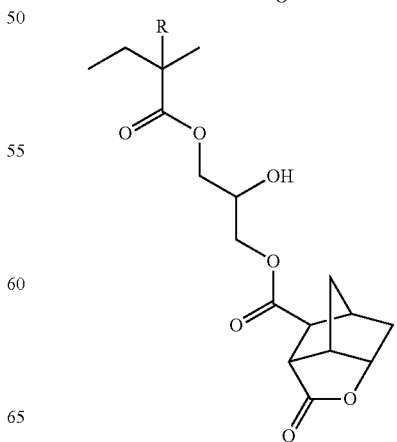

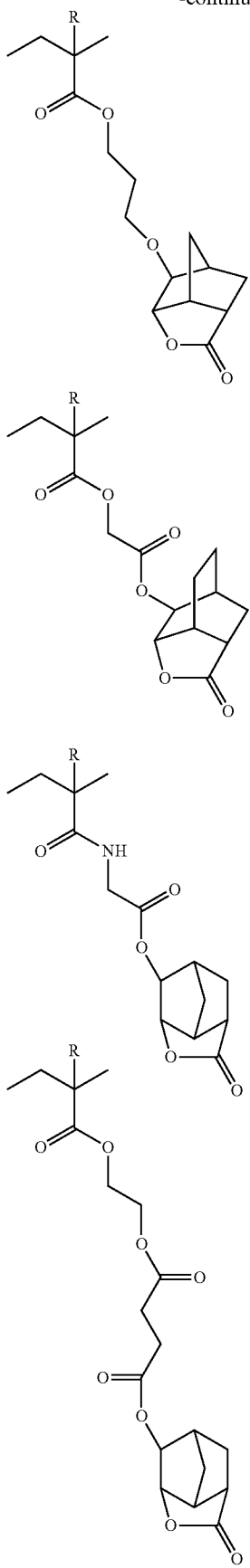

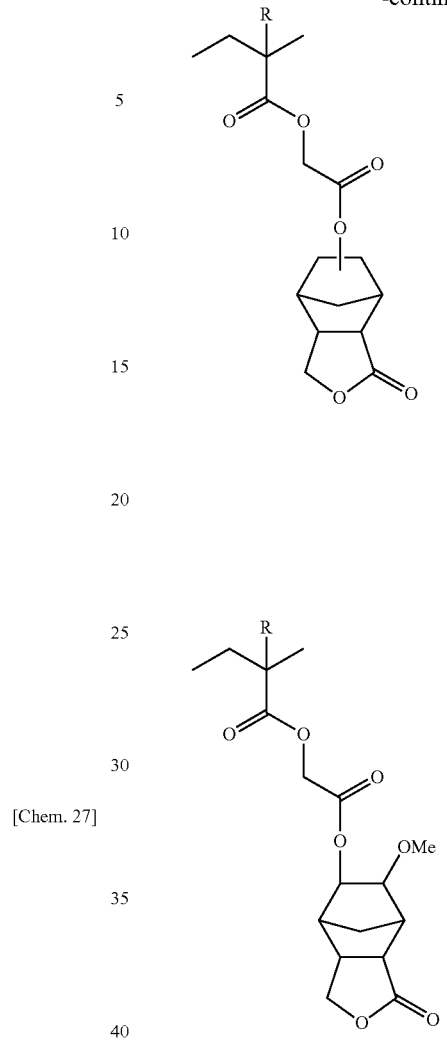

[Chem. 27]

As the acid group in the repeating unit (d) having an acid group, a carboxyl group, a sulfonate group, a sulfonamide group, a sulfonylimide group, a bissulfonylimide group, an aliphatic alcoholic hydroxyl group of which α-position is substituted with an electron withdrawing group (for example, a hexafluoroisopropanol group) or the like may be included, and containing a repeating unit having a carboxyl group is more preferable.

By the resin (P) containing the repeating unit having an acid group, resolution in a contact hole application increases. As the repeating unit having an acid group, any of repeating units in which the acid group is bonded directly to the main chain of the resin such as a repeating unit by acrylic acid or methacrylic acid, or a repeating unit in which the acid group is bonded to the main chain of the resin through a linking group may be included. The linking group may have a monocyclic or polycyclic cyclic hydrocarbon structure. A repeating structure by acrylic acid or methacrylic acid is particularly preferable. In addition, the acid group may also be introduced to the resin (P) by introducing the acid group at the end of the polymer chain using a polymerization initiator or a chain transfer agent having an acid group when polymerized.

The repeating unit (d) having an acid group is preferably a repeating unit (d1) represented by following General Formula (II).

[Chem. 28]

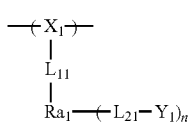

(II)

In General Formula (II), $X_1$s, each independently represent a polymerization unit structure constituting a polymer main chain.

$Ra_1$ represents an alicyclic hydrocarbon group of (n+1) valence.

$L_{11}$ and $L_{21}$, each independently, represent a single bond or a divalent linking group.

n represents an integer of 1 or more.

$Y_1$ represents an acid group.

In General Formula (II), the acid group of $Y_1$ includes a carboxyl group, a sulfonate group, an alcoholic hydroxyl group of which α-position is substituted with an electron withdrawing group (for example, a hexafluoroisopropanol group) or the like, and a carboxyl group is preferable.

As the alicyclic hydrocarbon group of (n+1) valence $Ra_1$, a monocyclic hydrocarbon ring group such as a cyclopentane ring group, a cyclohexane ring group may be used, however, a polycyclic hydrocarbon group is preferable and a polycyclic hydrocarbon group having 7 or more carbon atoms (preferably 7 to 30 carbon atoms) is more preferable.

As the monocyclic hydrocarbon group for the alicyclic hydrocarbon group $Ra_1$, a group in which any (n+1) numbers of hydrogen atoms are removed from the monocyclic hydrocarbon ring.

As the polycyclic hydrocarbon group for the alicyclic hydrocarbon group $Ra_1$, a ring-assembled hydrocarbon ring group or a crosslinked cyclic hydrocarbon ring group is included, and respectively, a group in which any (n+1) numbers of hydrogen atoms are removed from the ring-assembled hydrocarbon ring group, or a group in which any (n+1) numbers of hydrogen atoms are removed from the crosslinked cyclic hydrocarbon ring group may be included.

Examples of the ring-assembled hydrocarbon ring group include a bicyclohexane ring group or a perhydronaphthalene ring group. As the crosslinked cyclic hydrocarbon ring group, for example, a dicyclic hydrocarbon ring group such as a pinane ring group, a bornane ring group, a norpinane ring group, a norbornane ring group, a bicyclo octane ring group (a bicyclo[2.2.2] octane ring group or a bicyclo[3.2.1] octane ring group) or a bicyclononane ring group, a tricyclic hydrocarbon ring groups such as a homobredane ring group, an adamantane ring group, a tricyclo[5.2.1.0$^{2,6}$] decane ring group or a tricyclo[4.3.1.1.$^{2,5}$]undecane ring group, a tetracyclic hydrocarbon ring group such as tetracyclo[4.4.0.1$^{2,5}$.1$^{7,10}$]dodecane ring group or a perhydro-1,4-methano-5,8-methanonaphthalene ring group, or the like, may be included. In addition, as the crosslinked cyclic hydrocarbon ring group, a condensed cyclic hydrocarbon ring, for example, a condensed cyclic group in which a plurality of 5- to 8-membered cycloalkane ring groups such as a perhydronaphthalene (decaline) ring group, a perhydroanthracene ring group, a perhydrophenanthrene ring group, a perhydroacenaphthene ring group, a perhydrofluorene ring group, a perhydroindene ring group, a perhydrophenalene ring group are condensed.

As the preferable crosslinked cyclic hydrocarbon ring group, a norbornane ring group, an adamantane ring group, a bicyclo octane ring group, a tricyclo[5.2.1.0.$^{2,6}$] decane ring group, or the like, may be included. As the more preferable crosslinked cyclic hydrocarbon ring group, a norbornane ring group or an adamantane ring group may be included.

The alicyclic hydrocarbon group $Ra_1$ may have a substituent. As the substituent $Ra_1$ may have, for example, a substituent such as an alkyl group or a cycloalkyl group may be included.

The alkyl group or the cycloalkyl group, as the substituent $Ra_1$ may have, may have further substituents and the substituent such as this may include a halogen atom (preferably a fluorine atom).

In the alicyclic hydrocarbon group $Ra_1$, carbon constituting the ring (carbon contributing to the ring formation) may also be carbonyl carbon. In addition, a polycycle thereof, as described above, may have a hetero atom such as an oxygen atom, sulfur atom, or the like as a ring member. However, $Ra_1$ do not contain an ester bond as the atomic group constituting the ring group.

As the linking group represented by $L_{11}$ and $L_{21}$, —COO—, —OCO—, —CONH—, —NHCO—, —CO—, —O—, —S—, —SO—, —SO$_2$—, an alkylene group (preferably 1 to 6 carbon atoms), a cycloalkylene group (preferably 3 to 10 carbon atoms), an alkenylene group (preferably 2 to 6 carbon atoms), a linking group combining a plurality of these or the like may be included, and a linking group having 12 or less total carbon atoms is preferable. An alkylene group, a cycloalkylene group, and a alkenylene group in the alkylene group, the cycloalkylene group, the alkenylene group, and the linking group combining these may have a substituent, and an alkyl group (preferably 1 to 4 carbon atoms) or the like may be included as the substituent.

$L_{11}$ is a single bond, an alkylene group, —COO—, —OCO—, —CONH—, —NHCO—, -alkylene group-COO—, -alkylene group-OCO—, -alkylene group-CONH—, -alkylene group- NHCO—, —CO—, —O—, —SO$_2$— or -alkylene group-O— is preferable, and a single bond, an alkylene group, -alkylene group-COO— or -alkylene group-O— is more preferable.

$L_{21}$ is a single bond, an alkylene group, —COO—, —OCO—, —CONH—, —NHCO—, —COO-alkylene group-, —OCO-alkylene group-, —CONH-alkylene group-, —NHCO-alkylene group-, —CO—, —O—, —SO$_2$—, —O-alkylene group- or —O-cyclo alkylene group- is preferable, and a single bond, an alkylene groups, —COO-alkylene group-, —O-alkylene group- or —O-cyclo alkylene group- is more preferable.

In the above description method, a leftmost linking arm "-" means connecting to $X_1$ of the main chain side in $L_{11}$ and to $Ra_1$ in $L_{21}$, a rightmost linking arm "-" means connecting to $Ra_1$ of the main chain side in $L_{11}$ and to $Y_1$ in $L_{21}$.

In addition, $L_{11}$ may be bonded to the same atom constituting the ring in $Ra_1$.

n is preferably an integer of 1 to 3, more preferably 1 or 2, and even more preferably 1.

A polymerization unit structure constituting the polymer main chain for X1 is preferably a repeating unit derived from a polymerizable monomer. As the polymerization unit structure constituting the polymer main chain X1, for example, a polymerization unit structure represented by following General Formula (a) derived from (meth)acrylate which is a polymerizable monomer, a polymerization unit structure represented by following General Formula (b) derived from a styrene monomer, a polymerization unit structure represented by following General Formula (c) derived from a vinyl monomer, or the like, may be included.

[Chem. 29]

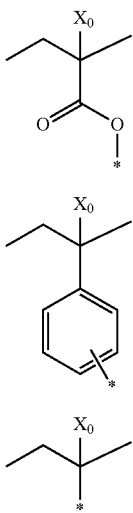

In the above General Formulae, * represents a bonding position with $L_{11}$ in General Formula (II).

$X_0$ represents a hydrogen atom, an alkyl group, a cyano group or a halogen atom.

The alkyl group of $X_0$ may have a substituent, and as the substituent, for example, a hydroxyl group or a halogen atom (preferably, a fluorine atom) may be included.

The alkyl group of $X_0$ is preferably an alkyl group having 1 to 4 carbon atoms, and a methyl group, an ethyl group, a propyl group, a hydroxymethyl group, a trifluoromethyl group or the like may be included, however, a methyl group is preferable.

$X_0$ is preferably a hydrogen atom or a methyl group.

In the present invention, $X_1$ in General Formula (II) is preferably a polymerization unit structure derived from (meth)acrylate. If $X_1$ is a polymerization unit structure derived from (meth)acrylate, the repeating unit (d1) represented by General Formula (II) may be represented by following General Formula (II').

[Chem. 30]

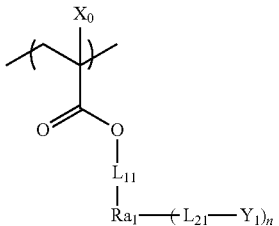
(II')

In General Formula (II'), $X_0$ is synonymous with $X_0$ in General Formula (a).

$Ra_1, L_{11}, L_{21}, n,$ and $Y_1$ are synonymous with $Ra_1, L_{11}, L_{21}, n,$ and $Y_1$ in General Formula (II).

Specific examples of the repeating unit (d) having an acid group are shown below, however, the present invention is not limited to these.

In the specific examples, Rx represents H, $CH_3$, $CH_2OH$, or $CF_3$. Xa represents a hydrogen atom, $CH_3$, $CF_3$, or $CH_2OH$.

[Chem. 31]

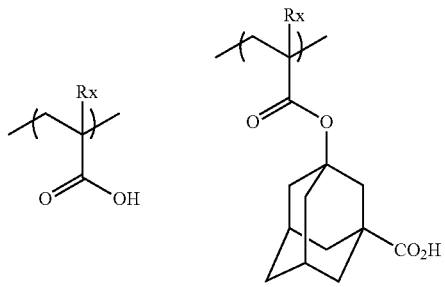

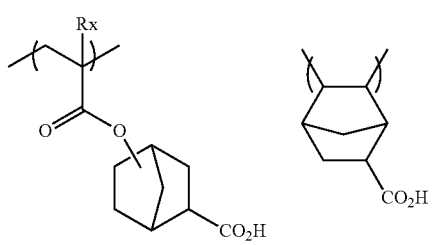

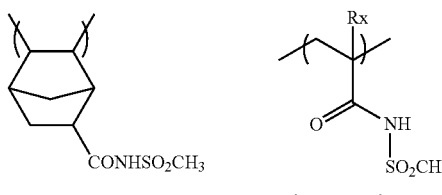

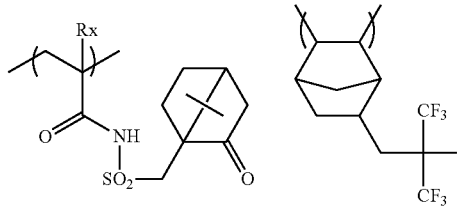

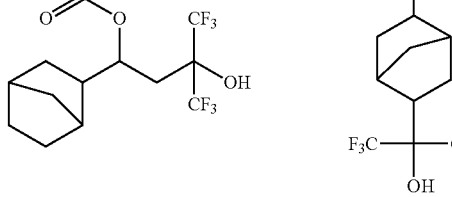

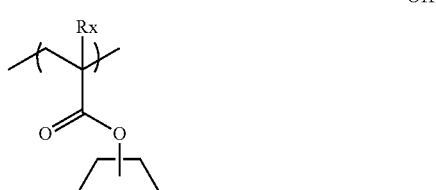

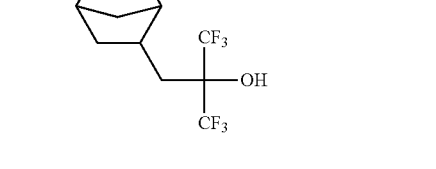

57
-continued
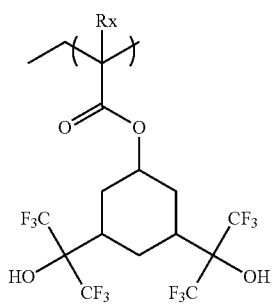
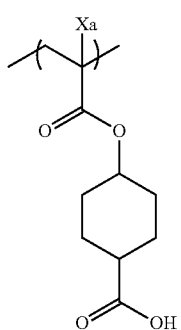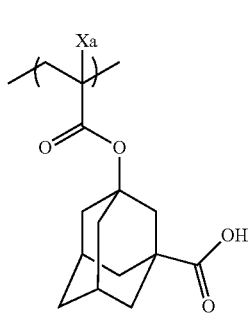
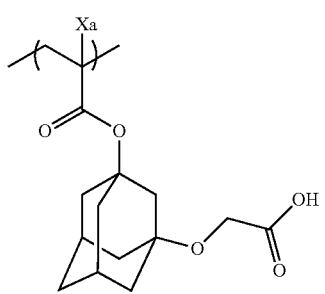
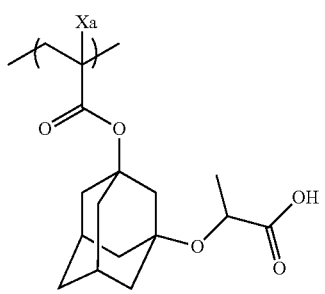
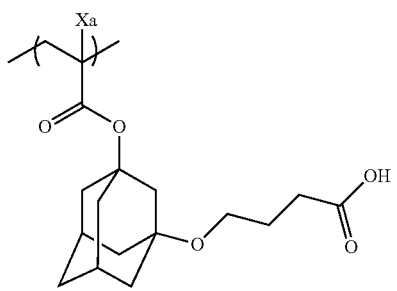
58
-continued
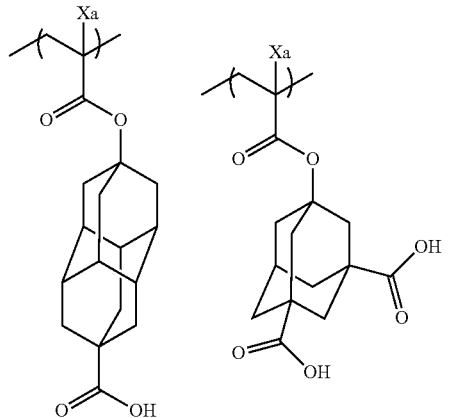
[Chem. 32]
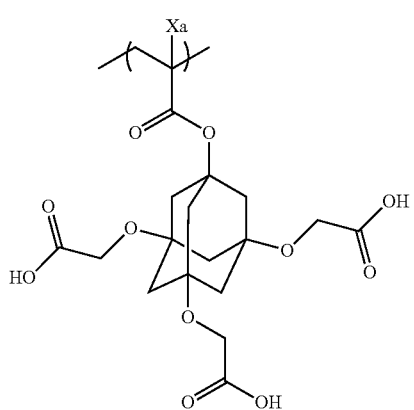
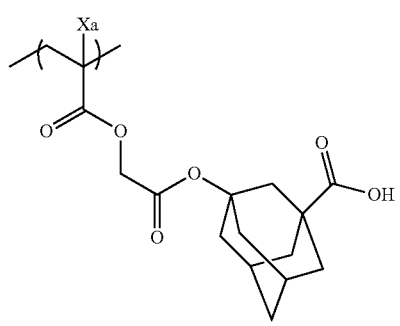
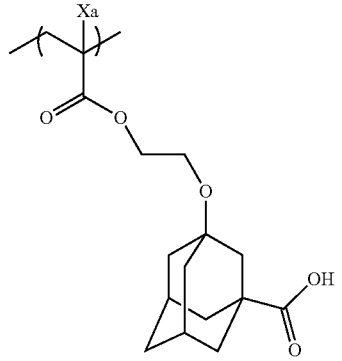

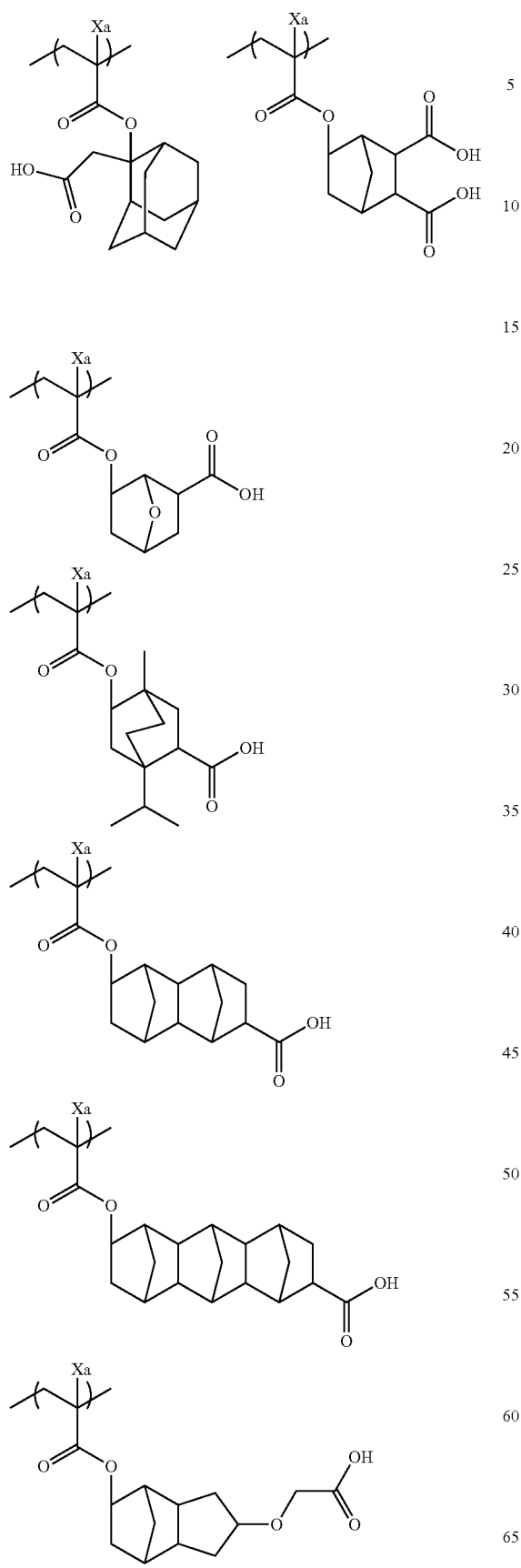
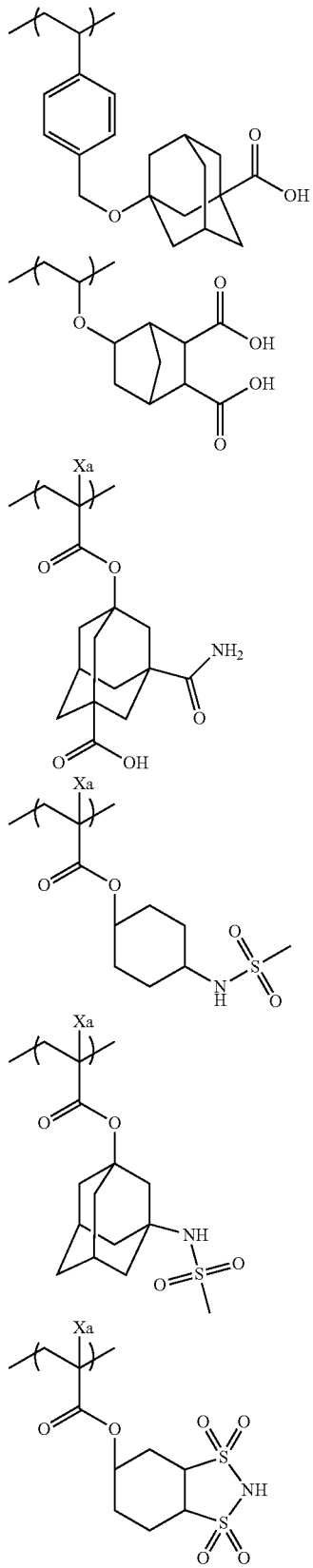
In the repeating unit (d) having an acid group, the acid group preferably has an aromatic ring group when exposed by KrF excimer laser light, an electron beam, X-rays, a light beam of high energy with the wavelength of 50 nm or less (EUV or the like) or the like.

The repeating unit having an acid group may be used either alone or as a combination of two or more.

The resin (P) may not contain the repeating unit (d) having an acid group, however, when the resin (P) contains the repeating unit (d), the content of the repeating unit (d) having an acid group is preferably 1 to 50 mol %, more preferably 5 to 45 mol %, even more preferably 5 to 40 mol %, and particularly preferably 10 to 40 mol % with regards to all repeating units in the resin (P).

In particular, when the resin (P) contains the repeating unit (d1) represented by General Formula (II), the content of the repeating unit (d1) is also preferably 1 to 50 mol %, more preferably 5 to 45 mol %, even more preferably 5 to 40 mol %, and particularly preferably 10 to 40 mol % with regard to all repeating units in the resin (P).

The resin (P) may further contain the repeating unit (e) having a hydroxyl group or a cyano group, which is a repeating unit other than the repeating units described above. As a result, substrate adhesion, developer affinity may be improved. The repeating unit (e) having a hydroxyl group or a cyano group is preferably a repeating unit having an alicyclic hydrocarbon structure substituted with a hydroxyl group or a cyano group, and preferably a repeating unit having no acid decomposable groups. As the alicyclic hydrocarbon structure in the alicyclic hydrocarbon structure substituted with a hydroxyl group or a cyano group, an adamantyl group, a diamantyl group or a norbornane group is preferable, and an adamantyl group is more preferable. In addition, substituting with a hydroxyl group is preferable, and containing a repeating unit having an adamantyl group substituted with at least one hydroxyl group is more preferable.

In particular, the resin (P) containing a repeating unit having a hydroxyadamantyl group or a dihydroxyadamantyl group is the most preferable from the viewpoint of suppressing the diffusion of acid generated.

As the alicyclic hydrocarbon structure substituted with a hydroxyl group or a cyano group, a partial structure represented by following General Formulae (VIIa) to (VIId) is preferable, and a partial structure represented by following General Formula (VIIa) is more preferable.

[Chem. 33]

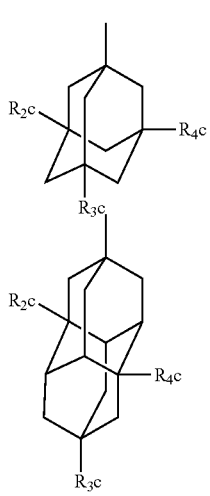

(VIIa)

(VIIb)

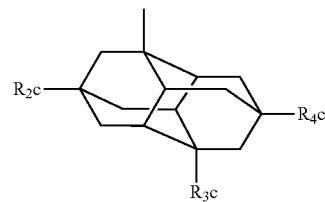

(VIIc)

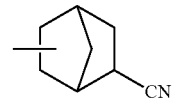

(VIId)

In General Formulae (VIIa) to (VIIc), $R_{2c}$ to $R_{4c}$, each independently represent a hydrogen atom, a hydroxyl group, or a cyano group. However, at least one of $R_{2c}$ to $R_{cc}$ represents a hydroxyl group, or a cyano group. Preferably, one or two of $R_{2c}$ to $R_{4c}$ is a hydroxyl group, and the rest is a hydrogen atom. In General Formula (VIIa), two of $R_{2c}$ to $R_{4c}$ are hydroxyl groups and the rest are a hydrogen atom.

As the repeating unit having a partial structure represented by General Formulae (VIIa) to (VIId), a repeating structure represented by following General Formulae (AIIa) to (AIId) may be included.

[Chem. 34]

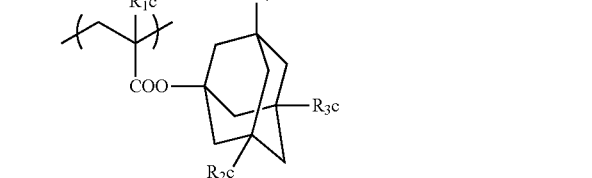

(AIIa)

(AIIb)

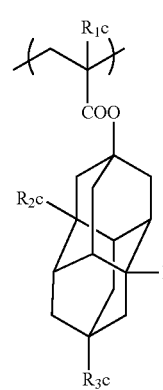

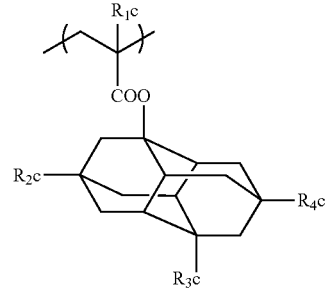

(AIIc)

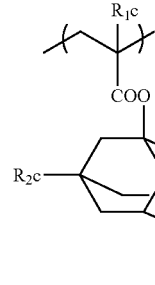

-continued (AIId)

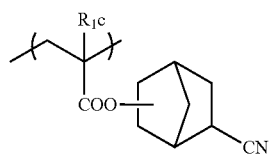

In General Formulae (AIIa) to (AIId), $R_{1c}$ represents a hydrogen atom, a methyl group, a trifluoromethyl group or a hydroxymethyl group.

$R_{2c}$ to $R_{4c}$ are synonymous with $R_{2c}$ to $R_{4c}$ in General Formulae (VIIa) to (VIIc).

Specific examples of the repeating unit (e) having a hydroxyl group, or a cyano group are shown below, however, the present invention is not limited to these.

[Chem. 35]

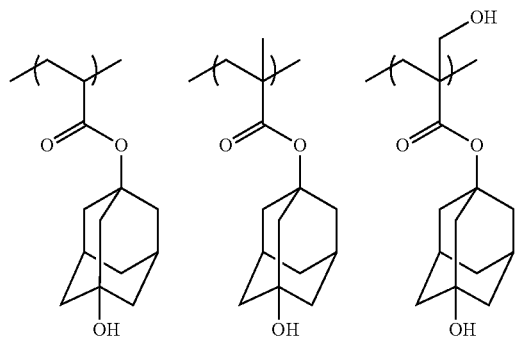

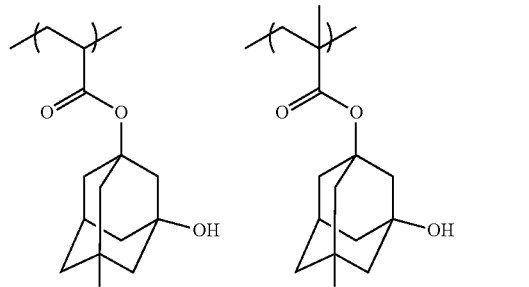

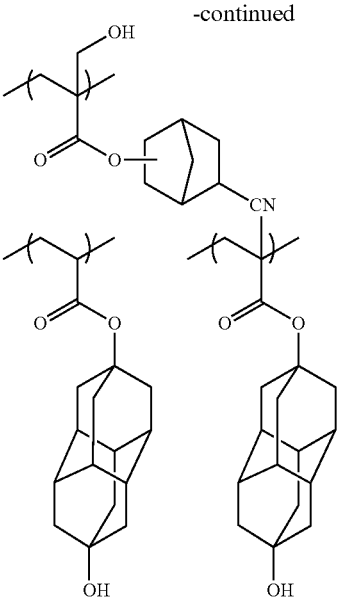

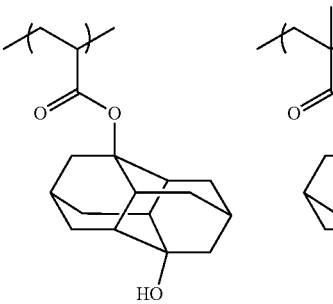

The resin (P) may or may not contain the repeating unit having a hydroxyl group or a cyano group, however, when the resin (P) contains the repeating unit (e), the content of the repeating unit (e) having a hydroxyl group or a cyano group is preferably 1 to 50 mol %, more preferably 5 to 45 mol %, even more preferably 5 to 40 mol %, and particularly preferably 10 to 40 mol % with regard to all repeating units in the resin (P).

The resin (P) in the present invention may further contain a repeating unit which has an alicyclic hydrocarbon structure having no polar groups (for example, the acid group, the hydroxyl group or a cyano group) and does not show acid decomposability. Thereby, elution of low molecular weight components from the resist film to immersion liquid during the immersion exposure may be reduced, and solubility of the resin may be properly adjusted during the development using the developer including an organic solvent. As the repeating unit such as this, a repeating unit represented by the General Formula (IV) may be included.

[Chem. 36]

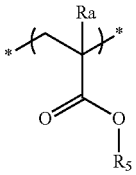

(IV)

In General Formula (IV), $R_5$ represents a hydrocarbon group which has at least one cyclic structure and do not have a polar group.

Ra represents a hydrogen atom, an alkyl group or —$CH_2$—O—$Ra_2$. In the formula, $Ra_2$ represents a hydrogen atom, an alkyl group or an acyl group. Ra is preferably a hydrogen atom, a methyl group, a hydroxymethyl group or a trifluoromethyl group, and a hydrogen atom or a methyl group is particularly preferable.

The cyclic structure $R_5$ has includes a monocyclic hydrocarbon group and a polycyclic hydrocarbon group. As the monocyclic hydrocarbon group, for example, a cycloalkyl group having 3 to 12 carbon atoms such as a cyclopentyl group, a cyclohexyl group, a cycloheptyl group or a cyclooctyl group, or a cycloalkenyl group having 3 to 12 carbon atoms such as a cyclohexenyl group. The preferable monocyclic hydrocarbon group is a monocyclic hydrocarbon group having 3 to 7 carbon atoms and more preferably includes a cyclopentyl group or a cyclohexyl group.

The polycyclic hydrocarbon group includes a ring-assembled hydrocarbon group and a crosslinked cyclic hydrocarbon group, and examples of the ring-assembled hydrocarbon group include a bicyclohexyl group or a perhydronaphthalenyl group. As the crosslinked cyclic hydrocarbon ring, for example, a dicyclic hydrocarbon ring such as pinane, bornane, norpinane, norbornane or a bicyclo octane ring (a bicyclo[2.2.2] octane ring or a bicyclo[3.2.1] octane ring), a tricyclic hydrocarbon ring such as homobredane, adamantane, a tricyclo[5.2.1.0.$^{2,6}$] decane ring or a tricyclo[4.3.1.1.$^{2,5}$] undecane ring, a tetracyclic hydrocarbon ring such as a tetracyclo[4.4.0.1$^{2,5}$.1$^{7,10}$] dodecane ring or a perhydro-1,4-methano-5,8-methanonaphthalene ring, or the like, may be included. In addition, as the crosslinked cyclic hydrocarbon ring, a condensed cyclic hydrocarbon ring, for example, a condensed cyclic ring in which a plurality of 5- to 8-membered cycloalkane rings such as perhydronaphthalene (decaline), perhydroanthracene, perhydrophenanthrene, perhydroacenaphthene, perhydrofluorene, perhydroindene, perhydrophenalene are condensed.

As the preferable crosslinked cyclic hydrocarbon ring, a norbornyl group, an adamantyl group, a bicyclo octanyl group, a tricyclo[5.2.1.0.$^{2,6}$] decanyl group, or the like, may be included. As the more preferable crosslinked cyclic hydrocarbon ring, a norbornyl group or an adamantyl group may be included.

These alicyclic hydrocarbon group may have a substituent, and as the preferable substituent, a halogen atom, an alkyl group, a hydroxyl group of which hydrogen atom is substituted, an amino group of which hydrogen atom is substituted or the like may be included. As the preferable halogen atom, a bromine atom, a chlorine atom or a fluorine atom may be included, and as the preferable alkyl group, a methyl group, an ethyl group, a butyl group or a t-butyl group may be included. The above alkyl group may have further substituents, and as the substituent the alkyl group may further has include a halogen atom, an alkyl group, a hydroxyl group of which hydrogen atom is substituted, an amino group of which hydrogen atom is substituted may be included.

As the substituent of the hydrogen atom, for example, an alkyl group, a cycloalkyl group, an aralkyl group, a substituted methyl group, a substituted ethyl group, an alkoxycarbonyl group, an aralkyloxycarbonyl group, or the like. As the preferable alkyl groups, an alkyl group having 1 to 4 carbon atoms, as the preferable substituted methyl group, a methoxymethyl group, a methoxythiomethyl group, a benzyloxymethyl group, a t-butoxymethyl group or a 2-methoxyethoxymethyl group, as the preferable substituted ethyl group, a 1-ethoxyethyl group or a 1-methyl-1-methoxyethyl group, as the preferable acyl group, an aliphatic acyl group having 1 to 6 carbon atoms such as a formyl group, an acetyl group, a propionyl group, a butyryl group, an isobutyryl group, a valeryl group or a pivaloyl group, and as the alkoxycarbonyl group, an alkoxycarbonyl group having 1 to 4 carbon atoms or the like, may be included.

The resin (P) may not contain the repeating unit which has an alicyclic hydrocarbon structure having no polar group and does not show acid decomposability, however, when the resin contains the repeating unit (f) which has an alicyclic hydrocarbon structure having no polar group and does not show acid decomposability, the content of the repeating unit (f) is preferably 1 to 30 mol % and more preferably 3 to 20 mol % with regard to all repeating units in the resin (P).

Specific examples of the repeating unit (f) are shown below, however, the present invention is not limited to these. In the formula, Ra represents H, $CH_3$, $CH_2OH$, or $CF_3$.

[Chem. 37]

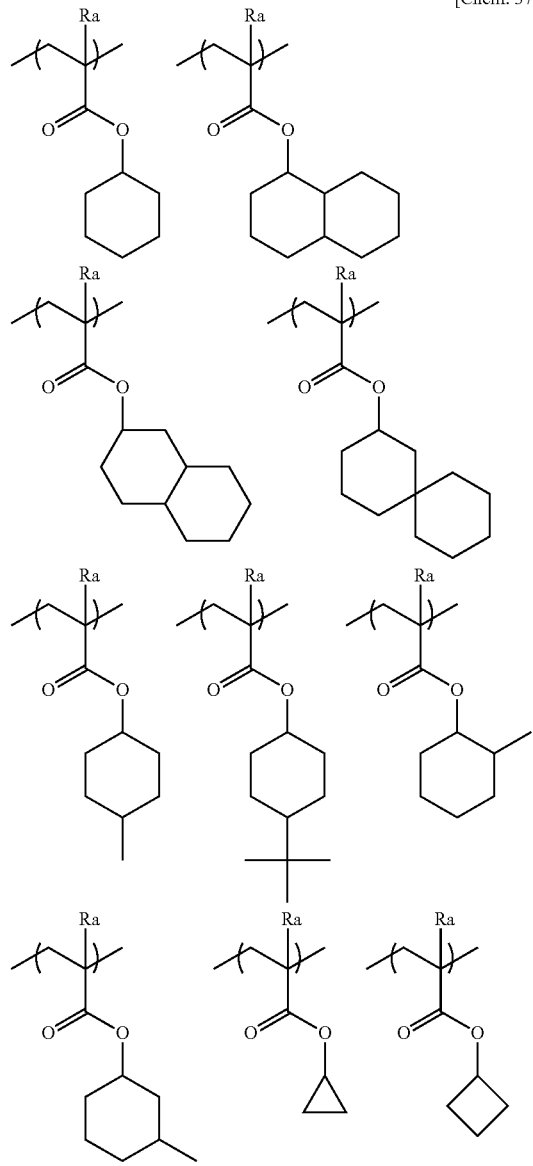

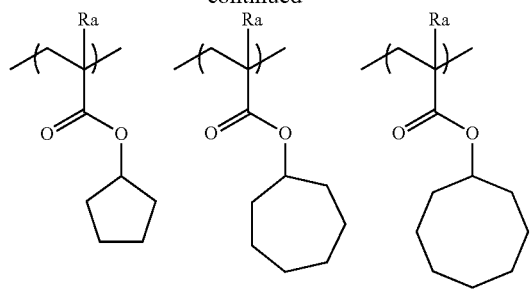
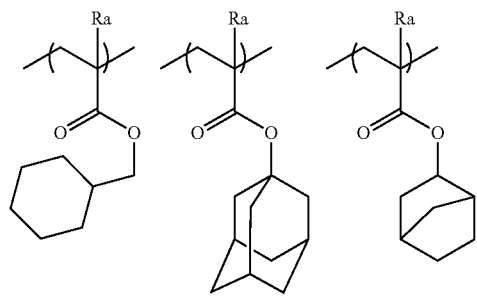
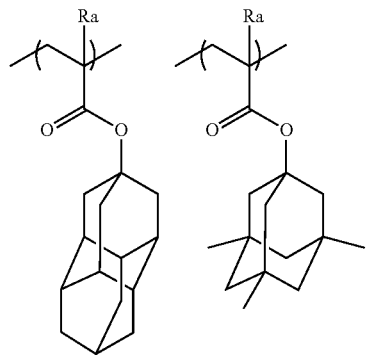
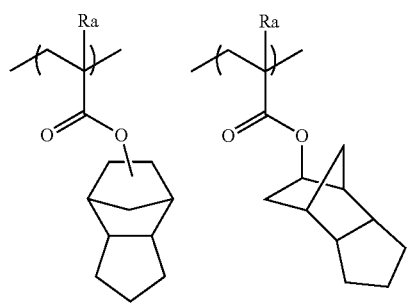

[Chem. 38]

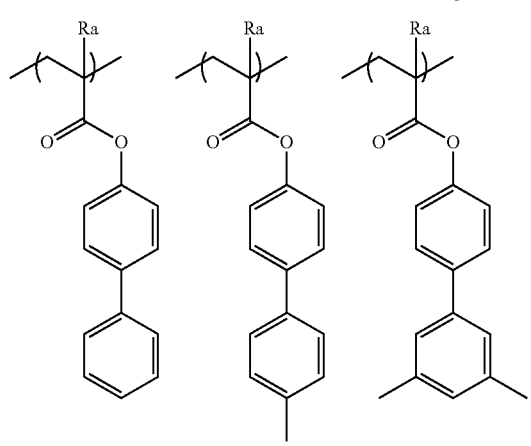

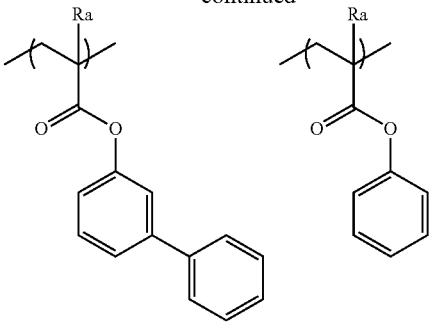
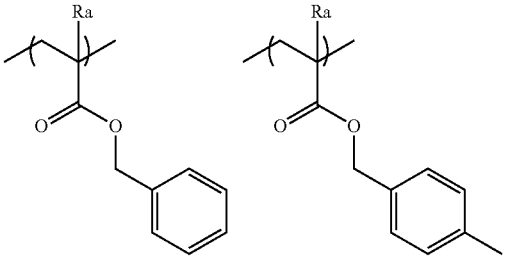
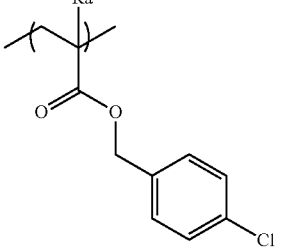
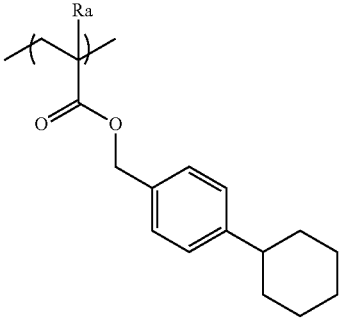
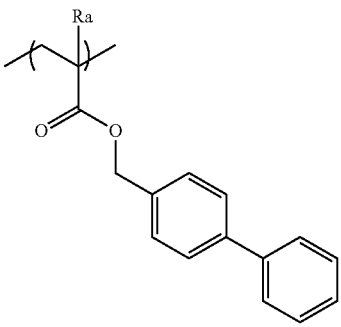

The resin (P) used in the composition of the present invention may have a variety of repeating structural units in addition to the above repeating structural units for the purpose of adjusting dry etching resistance or standard developer suitability, substrate adhesion, resist profile, or characteristics generally needed for the actinic-ray-sensitive or radiation-sensitive resin composition such as resolution, heat resistance and a sensitivity.

The repeating unit structures such as this may include repeating unit structures corresponding to the following monomers, however, are not limited to these.

As a result, fine tuning of the performances required for a resin used in the composition of the present invention, particularly, such as,
(1) solubility for a coating solvent,
(2) film formability (glass transition point),
(3) alkali developability,
(4) film reduction (hydrophobicity, alkali-soluble group selection),
(5) adhesion of the unexposed area to the substrate,
(6) dry etching resistance
becomes possible.

The monomer such as this may include, for example, a compound having one addition-polymerizable unsaturated bond selected from acrylates, methacrylates, acrylamides, methacrylamides, allyl compounds, vinyl ethers, vinyl esters, styrenes, crotonates and the like, or the like.

In addition to these, addition-polymerizable unsaturated compounds, which are copolymerizable with monomers corresponding to a variety of repeating structural units described above, may be copolymerized.

In the resin (P) used in the composition of the present invention, molar ratio of the content of each repeating structural unit is appropriately determined in order to adjust dry etching resistance of the actinic-ray-sensitive or radiation-sensitive resin composition, standard developer suitability, adhesion to a substrate, a resist profile, and generally required performances of a resist such as resolution, heat resistance, and sensitivity.

A shape of the resin (P) in the present invention may be any shape of a random shape, a block shape, a comb shape, or a star shape. The resin (P) may be synthesized by, for example, a radical, cationic, or anionic polymerization of an unsaturated monomer corresponding to each structure. A target resin may also be obtained from a polymerization reaction after polymerization using an unsaturated monomers corresponding to the precursors of each structure.

Practically, the resin (P) used in the composition of the present invention preferably does not have an aromatic ring (specifically, in the resin, the ratio of the repeating unit having an aromatic group is preferably 5 mol % or less, more preferably 3 mol % or less, and ideally 0 mol %, that is, an aromatic group is not present) when the composition of the present invention is for ArF exposure in terms of transparency to ArF light.

In addition, the resin (P) preferably has an alicyclic hydrocarbon structure. The alicyclic hydrocarbon structure may be either monocyclic or polycyclic, the alicyclic hydrocarbon structure may be included in any part of the resin (P), and for example, included in a plurality of repeating units described above (except for the repeating unit (a) represented by General Formula (I)) or included in other repeating units.

In addition, the resin (P) preferably does not contain a fluorine atom or a silicon atom since the compositions of the present invention contains a resin (E) described later from the viewpoint of compatibility with the resin (E).

In addition, the resin (P) preferably does not contain a fluorine atom or a silicon atom or if it does, contains a small amount. More specifically, in all repeating units of the resin (P), a repeating unit having a fluorine atom or silicon atom is preferably 0 to 20 mol %, more preferably 0 to 10 mol %, particularly preferably 0 to 5 mol %, and ideally does not contain a repeating unit having a fluorine atom or a silicon atom. As a result, suitable solubility of the resin (P) for a developer including an organic solvent can be ensured, and localization of a hydrophobic resin on the surface of the resist film can be improved when a hydrophobic resin described later is included.

The main repeating unit of the resin (P) is preferably a (meth)acrylate-based repeating unit. More specifically, the (meth)acrylate-based repeating unit is preferably 50 mol % or more, more preferably 70 mol %, even more preferably 90 mol % or more in all repeating units of the resin (P), and it is particularly preferable that all repeating units are (meth)acrylate-based repeating units.

In the resin (P) used in the composition of the present invention, it is preferable that all repeating units are composed of (meth)acrylate-based repeating units. In this case, any of the repeating units in which all repeating units are methacrylate-based repeating units, all repeating units are acrylate-based repeating units, and all repeating units are methacrylate-based repeating units and acrylate-based repeating units may be used, however, the acrylate-based repeating unit being 50 mol % or less of the all repeating units is preferable. In addition, a copolymer, including 20 to 50 mol % of the (meth)acrylate repeating unit having an acid decomposable group, 20 to 50 mol % of the (meth)acrylate repeating unit having a lactone group, 5 to 30 mol % of the (meth)acrylate repeating unit having an alicyclic hydrocarbon structure substituted with a hydroxyl group or a cyano group, and further including 0 to 20 mol % of other (meth)acrylate repeating units, is also preferable.

When KrF excimer laser light, an electron beam, X-rays, and high-energy light beam with the wavelength of 50 nm or less (EUV, and the like) are irradiated on the composition of the present invention, the resin (P) preferably further has a hydroxystyrene-based repeating unit. More preferably, including a hydroxystyrene-based repeating unit, a hydroxystyrene-based repeating unit protected by an acid decomposable group and an acid decomposable repeating unit such as tertiary alkyl(meth)acrylate is preferable.

Examples of the repeating unit having a preferable hydroxystyrene-based acid decomposable group may include a repeating unit by t-butoxycarbonyloxy styrene, 1-alkoxyethoxy styrene, tertiary alkyl(meth)acrylate or the like, and a repeating unit by 2-alkyl-2-adamantyl(meth)acrylate and dialkyl(1-adamantyl)methyl(meth)acrylate is more preferable.

The resin (P) in the present invention can be synthesized in accordance with conventional methods (for example, radical polymerization). For example, as the general synthesis method, a bulk polymerization method in which polymerization is carried out by dissolving monomer species and an initiator in a solvent and heating the solution, a dropwise adding polymerization method in which a solution of monomer species and an initiator is added dropwise to a heating solvent over 1 to 10 hours, or the like may be included, and a dropwise adding polymerization method is preferable. Examples of the reaction solvent may include a solvent which dissolves the composition of the present invention such as ethers such as tetrahydrofuran, 1,4-dioxane or diisopropyl ether, ketones such as methylethyl ketone or methyl isobutyl ketone, ester solvents such as ethyl acetate, amide solvents such as dimethyl formamide or dimethyl acetamide, propylene glycol monomethyl ether acetate described later, propylene glycol monomethyl ether or cyclohexanone. Polymerization using the same solvent as the solvent used in the actinic-ray-sensitive or radiation-sensitive resin composition of the present invention is more preferable. This suppresses generation of the particles during storage.

It is preferable that the polymerization reaction be carried out under an inert gas atmosphere such as nitrogen or argon.

As the polymerization initiator, commercially available radical initiators (an azo-based initiator, peroxide, or the like) may used. As the radical initiator, an azo initiator is preferable, and the azo initiator having an ester group, a cyano group or a carboxyl group is preferable. Preferable initiators may include azobisisobutyronitrile, azobisdimethylvaleronitrile, dimethyl 2,2'-azobis(2-methyl propionate), or the like. The initiator is added or added in installments, when necessary, and the target polymer is recovered after the reaction is complete by being added to a solvent using a method such as powder or solid recovery. The concentration of the reaction is 5 to 50% by mass and preferably 10 to 30% by mass. The reaction temperature is normally 10° C. to 150° C., preferably 30° C. to 120° C., and more preferably 60° C. to 100° C.

After the reaction is complete, the resultant is allowed to cool to room temperature and purified. Purification may be carried out using common methods such as a liquid-liquid extraction method in which residual monomers and oligomer components are removed by washing with water or combining appropriate solvents, a purification method in a solution state such as ultrafiltration in which those with less than or equal to specific molecular weight is extracted and removed, a re-precipitation method in which residual monomers and the like are removed by coagulating the resin in a poor solvent through a dropwise addition of the resin solution to a poor solvent, and a purification method in a solid state in which separated resin slurry is washed with a poor solvent. For example, the resin is precipitated as solids by contacting the resin with a sparingly soluble or insoluble solvent (a poor solvent) in 10 times or less volume amount of the reaction solution, and preferably 5 to 10 times volume amount.

The solvent used during precipitation or reprecipitation from the polymer solution (precipitation or reprecipitation solvent) may be a poor solvent of the polymer, and may be appropriately selected and used from hydrocarbons, halogenated hydrocarbons, nitro compounds, ethers, ketones, esters, carbonates, alcohols, carboxylic acids, water, and a mixed solvent including these solvents, depending on the type of polymer.

The amount of the precipitation or reprecipitation solvent used may be appropriately selected considering efficiency and yield, however, is 100 to 10,000 parts by mass, preferably 200 to 2,000 parts by mass, and is more preferably 300 to 1,000 parts by mass with regard to 100 parts by mass of the polymer solution, in general.

The precipitation or re-precipitation temperature may be appropriately selected considering efficiency and operability, however, is normally 0° C. to 50° C., and preferably around room temperature (for example, approximately, 20° C. to 35° C.). Precipitation or re-precipitation operation may be carried out by well-known methods of batch-type or continuous-type using a common mixing vessel such as a stirred tank.

Typically, the precipitated or reprecipitated polymer is provided for use after subjected to common solid-liquid separation such as filtration and centrifugation, and then dried. Filtration is carried out using a filtration material with solvent resistance, preferably under reduced pressure. Drying is carried out at a temperature of approximately 30° C. to 100° C., preferably of about approximately 30° C. to 50° C. under normal pressure or reduced pressure (preferably under reduced pressure).

In addition, after the resin is precipitated and separated once, the resin is re-dissolved in a solvent, and the resin may be contacted with a sparingly soluble or insoluble solvent. In other words, after the radical polymerization reaction above is complete, a method may be used in which the polymer is brought into contact with a sparingly soluble or insoluble solvent, and the resin is precipitated (step a), the resin is separated from the solution (step b), then, the resin is re-dissolved in a solvent and the resin solution A is prepared (step c), after that, the resin solid is precipitated by contacting the resin solution A with the sparingly soluble or insoluble solvent in 10 times or less volume amount of the resin solution A (preferably 5 times or less volume amount) (step d), and the resin precipitated is separated (step e).

In addition, in order to suppress aggregation of the resin after the composition is prepared, a step, in which the resin synthesized is dissolved in a solvent becoming a solution, and the solution is heated at approximately 30° C. to 90° C. for approximately 30 minutes to 4 hours, may be added as disclosed in, for example, JP2009-037108A.

The weight-average molecular weight of the resin (P) used in the composition of the present invention, as a polystyrene conversion value by GPC method, is preferably 1,000 to 200,000, more preferably 2,000 to 100,000, even more preferably 3,000 to 70,000, and particularly preferably 5,000 to 50,000. By keeping the weight average molecular weight as 1,000 to 200,000, deterioration of heat resistance and dry etching resistance may be prevented and deterioration of film formability due to developability deterioration or high viscosity may be prevented.

Also, by strictly controlling the weight-average molecular weight, solubility of the resin (P) for an organic-based developer can be controlled, therefore, pattern collapse and an occurrence of bridge defects after development can be suppressed, and residual film ratio can be also improved. The weight average molecular weight is particularly preferably 10,000 or more and most preferably 14,000 or more from the viewpoint of improving residual film ratio and suppressing pattern collapse and an occurrence of bridge defects after development. The upper limit of the weight average molecular weight is preferably 50,000 or less, more preferably 40,000 or less, and even more preferably 30,000 or less.

Degree of dispersion (molecular weight distribution, Mw/Mn) is typically in the range of 1.0 to 3.0. The range is preferably 1.0 to 2.6, more preferably 1.1 to 2.5, even more preferably 1.2 to 2.4, particularly preferably 1.3 to 2.2, and more particularly preferably 1.4 to 2.0. If the molecular weight distribution meets the above range, resolution and the resist shape are excellent, side wall of the resist pattern is also smooth, and roughness property is excellent.

In the present specification, the weight average molecular weight (Mw) and the number average molecular weight (Mn) of the resin (P), may be measured using, for example, HLC-8120 (manufactured by Tosoh Co., Ltd.), and, for a column, TSK gel Multipore HXL-M (manufactured by Tosoh Co., Ltd., 7.8 mmID×30.0 cm), and as an eluent, THF (tetrahydrofuran) are used.

In the actinic-ray-sensitive or radiation-sensitive resin composition of the present invention, the content of the resin (P) in the total composition is preferably 30 to 99% by mass, and more preferably 60 to 95% by mass in total solids.

In addition, in the present invention, the resin (P) may be used either alone or as a combination of two or more.

In addition, the actinic-ray-sensitive or radiation-sensitive resin composition of the present invention may include, together with the resin (P), an acid decomposable resin (a resin of which solubility is decreased for a developer including an organic solvent by polarity being increased due to an action of acid) other than the resin (P). The acid decomposable resin other than the resin (P) is an acid decomposable resin constituted from the repeating units as the same repeating units the resin (P) may include, and the preferable ranges of the repeating and the content in the resin are the same as those described for the resin (P).

If the acid decomposable resin other than the resin (P) is included, the content of the acid decomposable resin in the composition according to the present invention may be such that the content sum of the resin (P) and the acid decomposable resin other than the resin (P) is in the above range. The mass ratio of the resin (P) and the acid decomposable resin other than the resin (P) may be appropriately adjusted to be in the ranges which satisfactorily shows the effects of the present invention, however, [resin (P)/acid decomposable resin other than resin (P)] is preferably in the range of 99.9/0.1 to 10/90, and more preferably in the range of 99.9/0.1 to 60/40.

It is preferable that the actinic-ray-sensitive or radiation-sensitive resin composition of the present invention may only contain the resin (P) as the acid decomposable resin from the viewpoint of suppressing pattern collapse and an occurrence of bridge defects after development and improving residual film ratio.

Specific examples of the resin (P) used in the present invention are shown below, however, the present invention is not limited to these.

[Chem. 39]

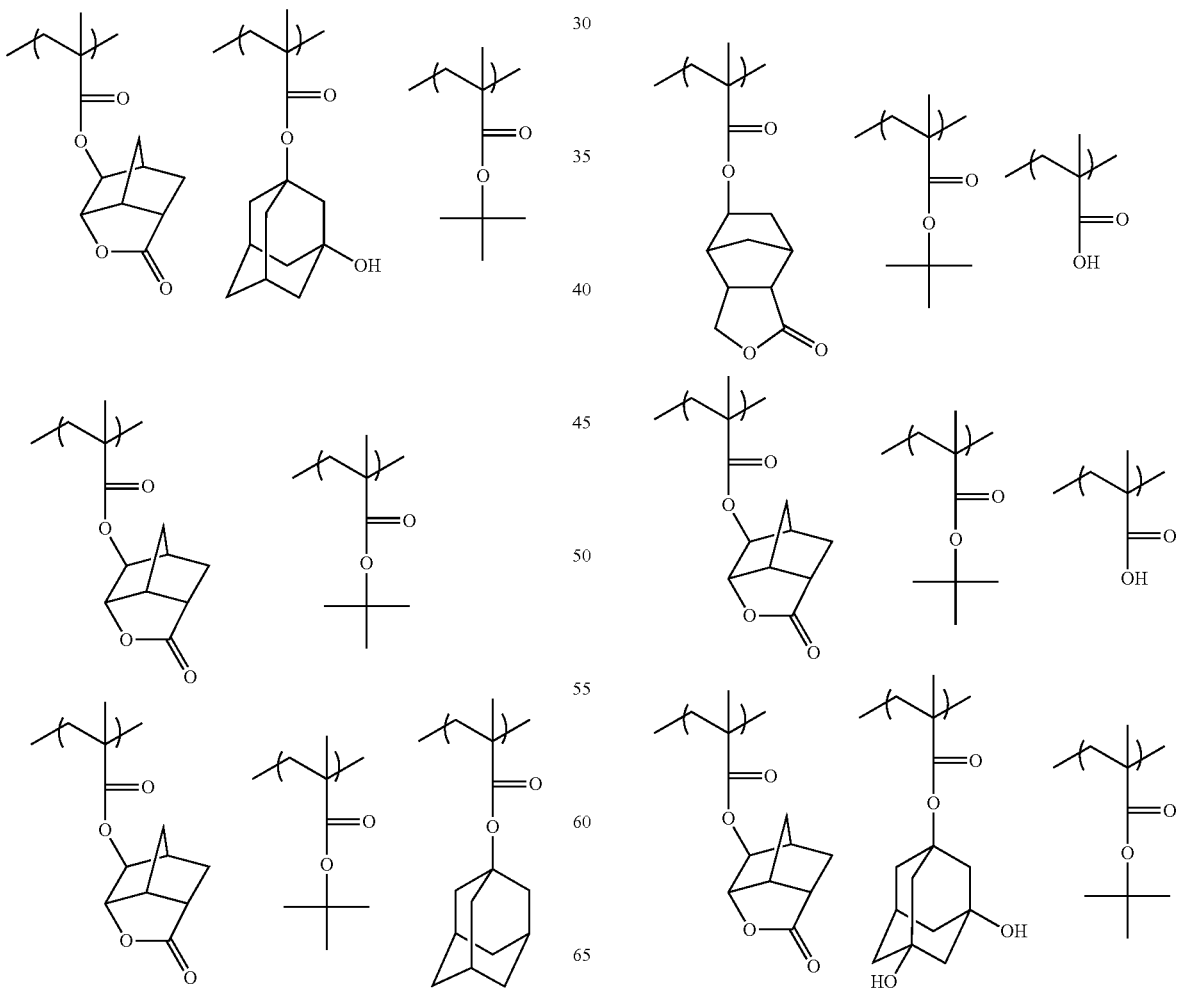

75
-continued
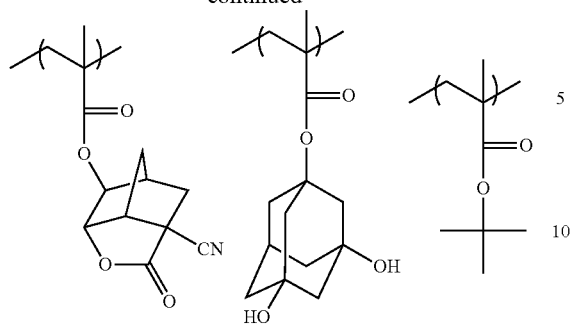
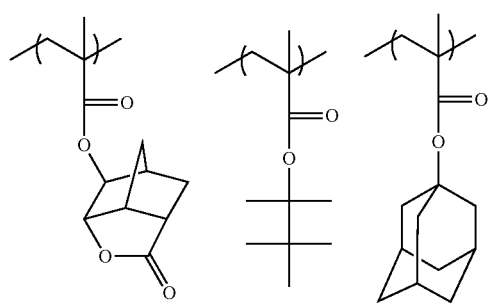
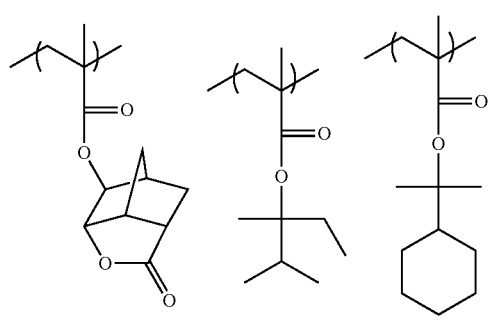
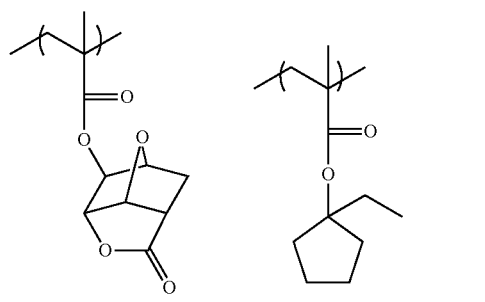
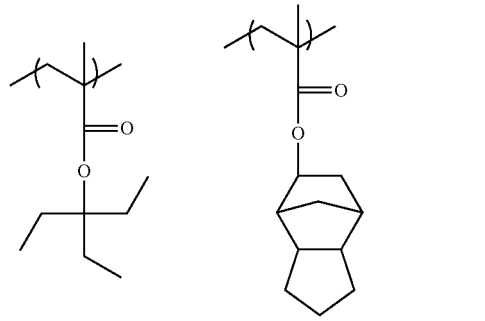
76
-continued
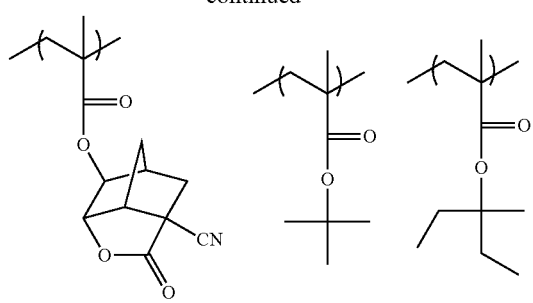
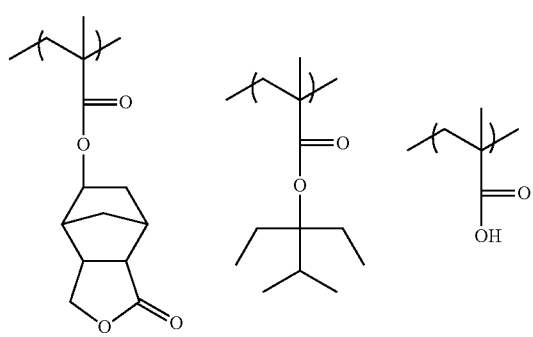
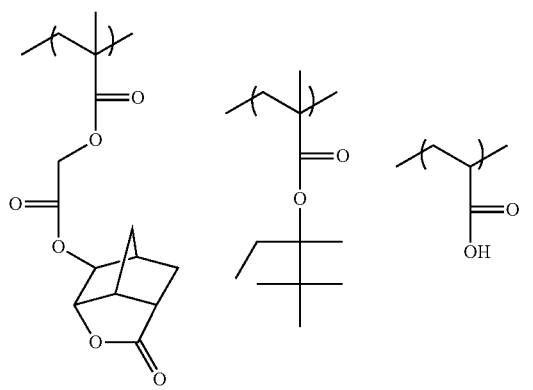
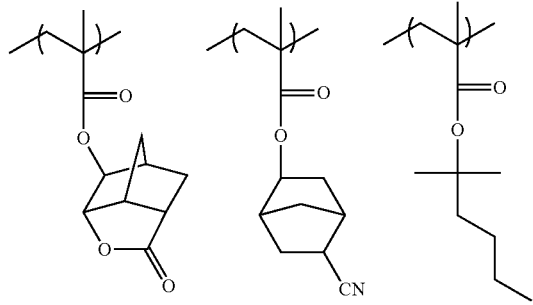
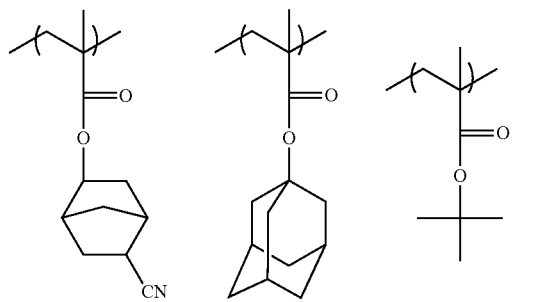

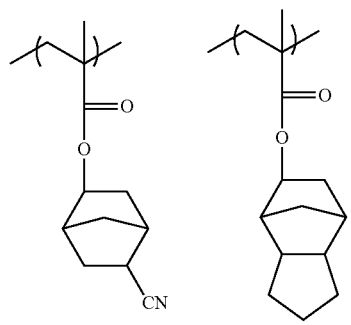
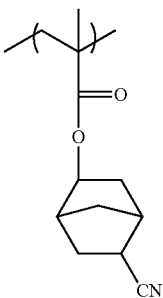
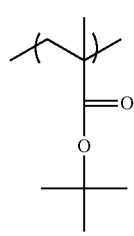
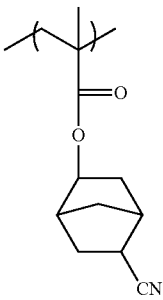
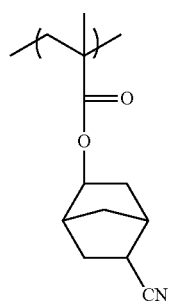
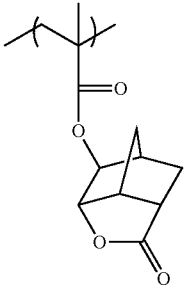
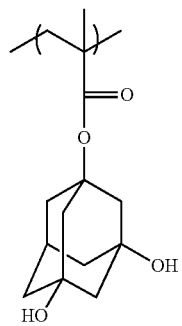
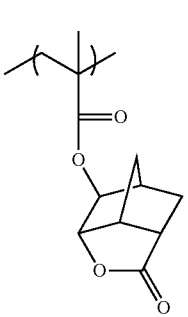
[Chem. 40]
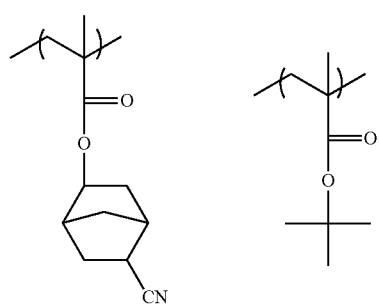
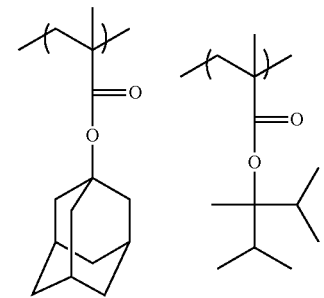

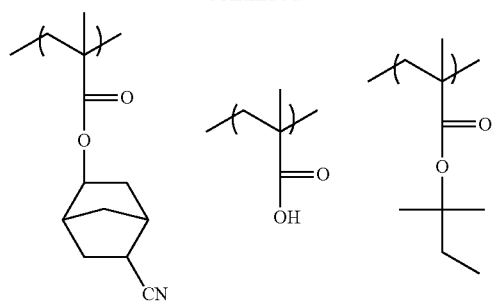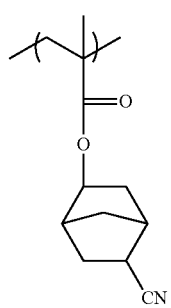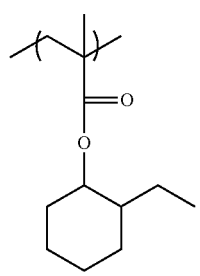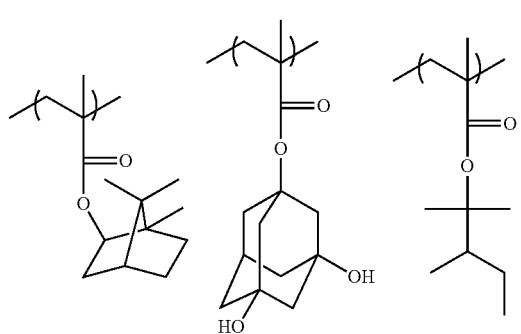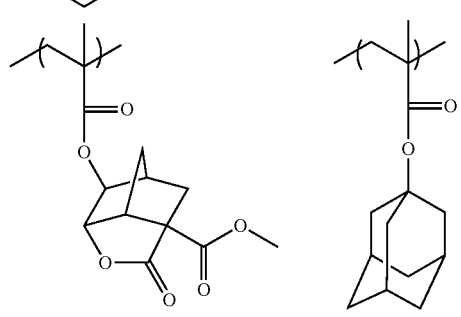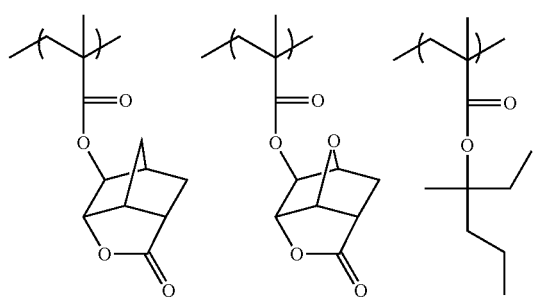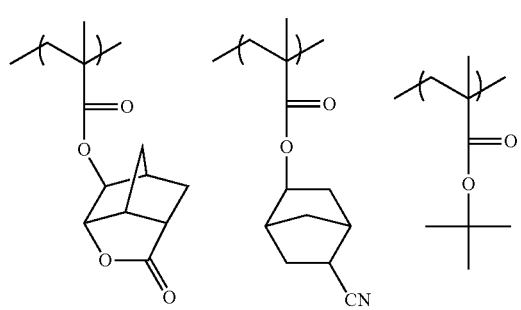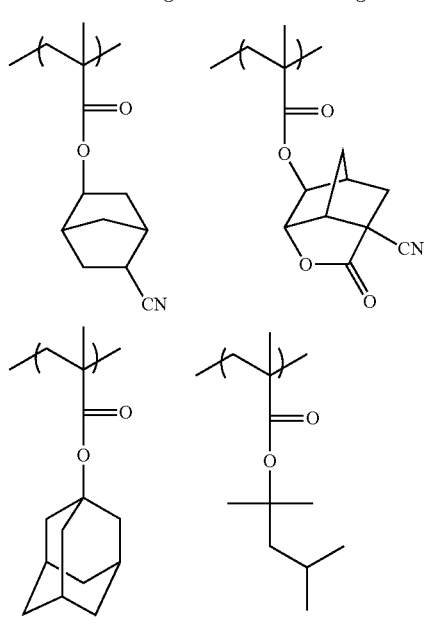

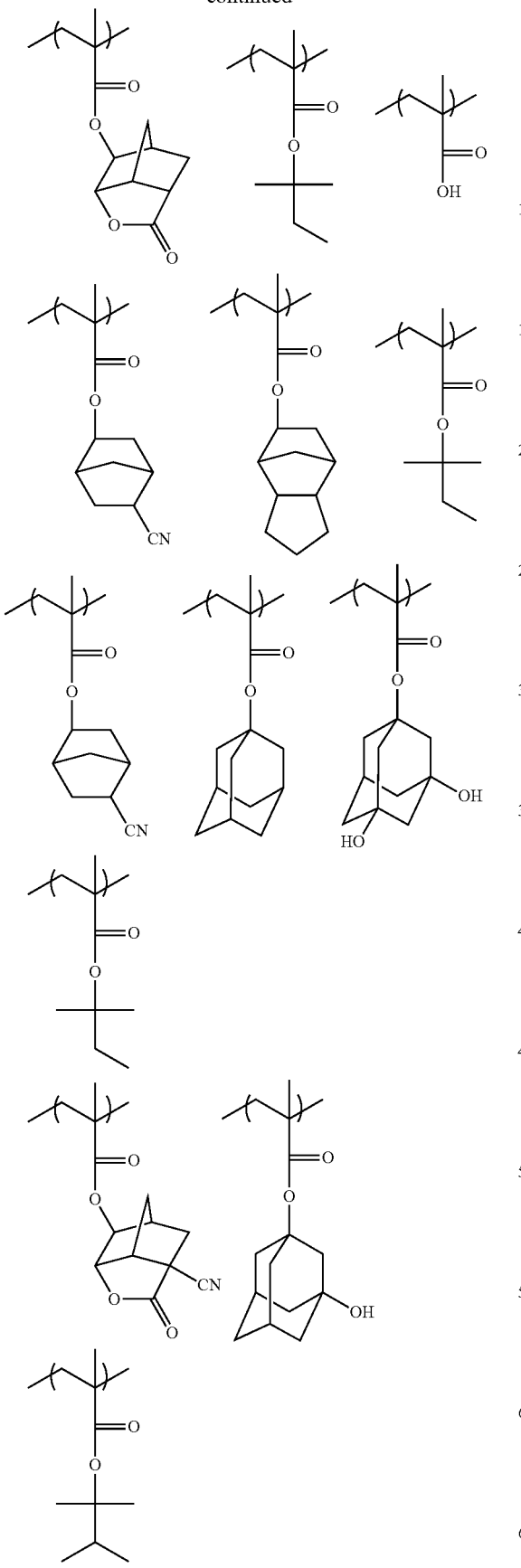
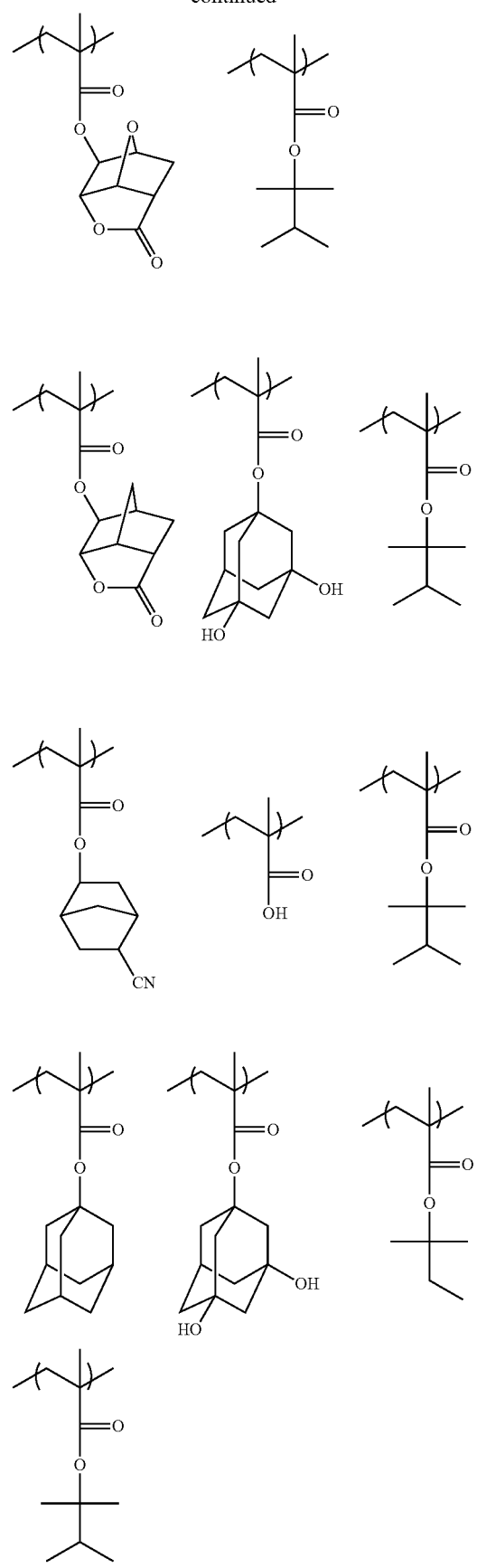

-continued
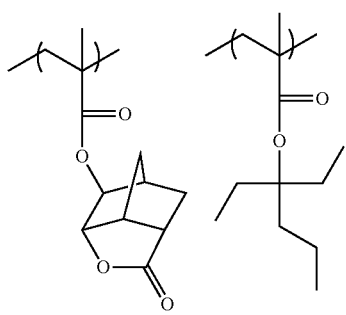 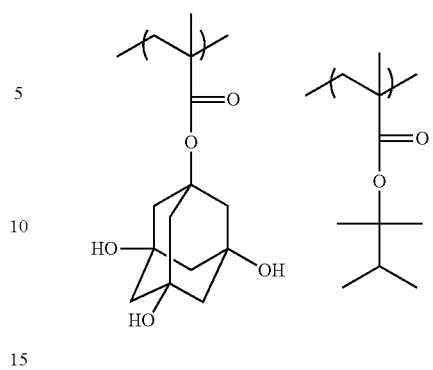
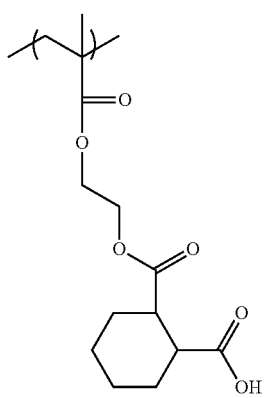 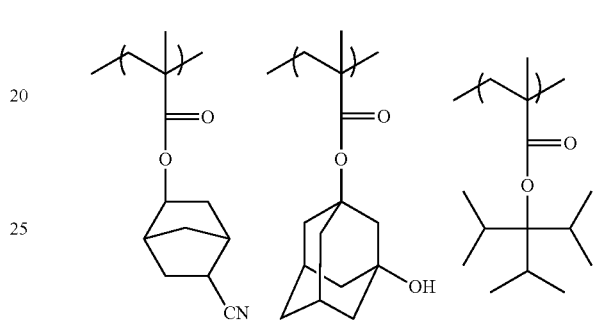
[Chem. 41]
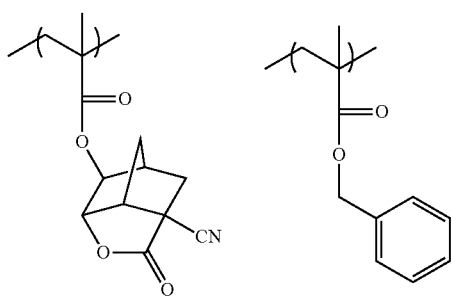 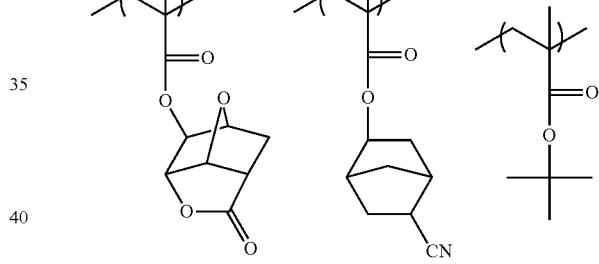
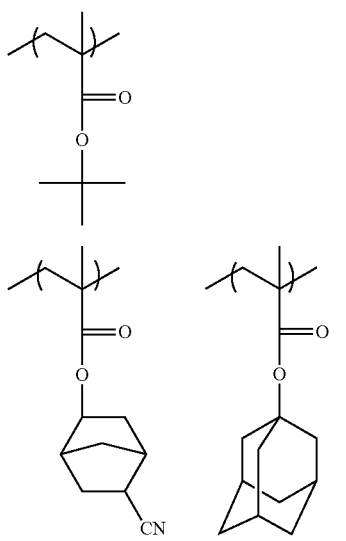 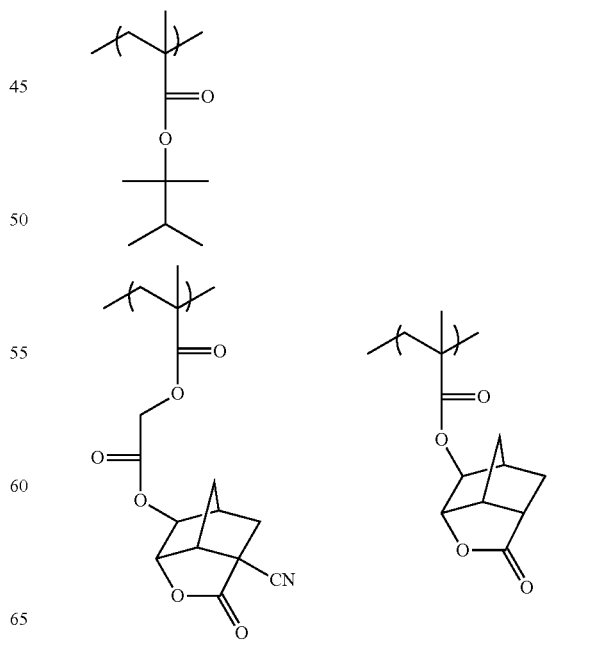

-continued

[Chem. 42]

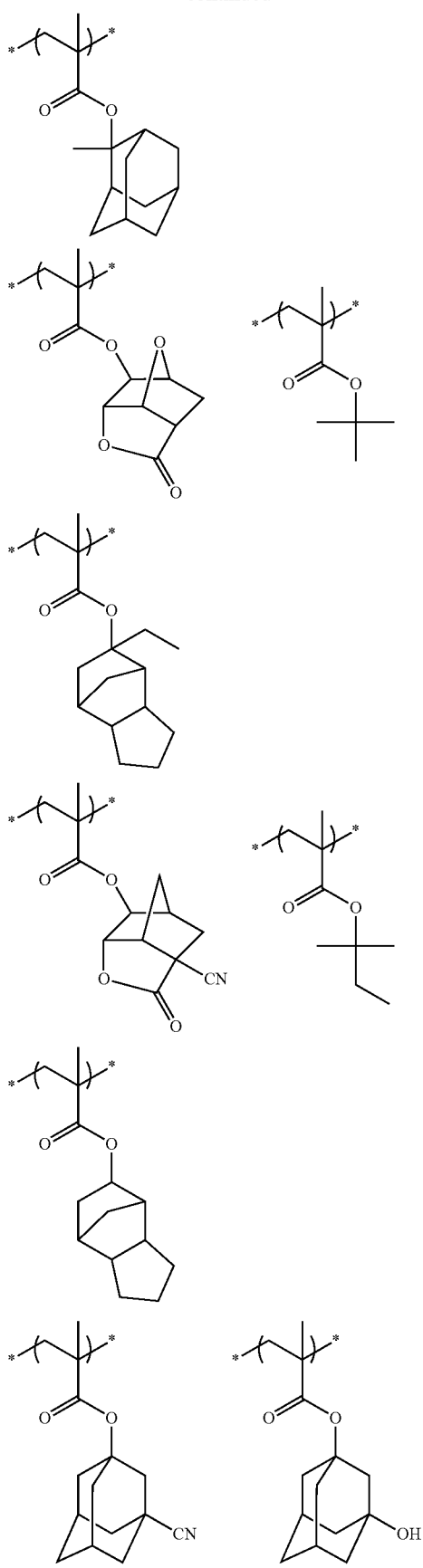
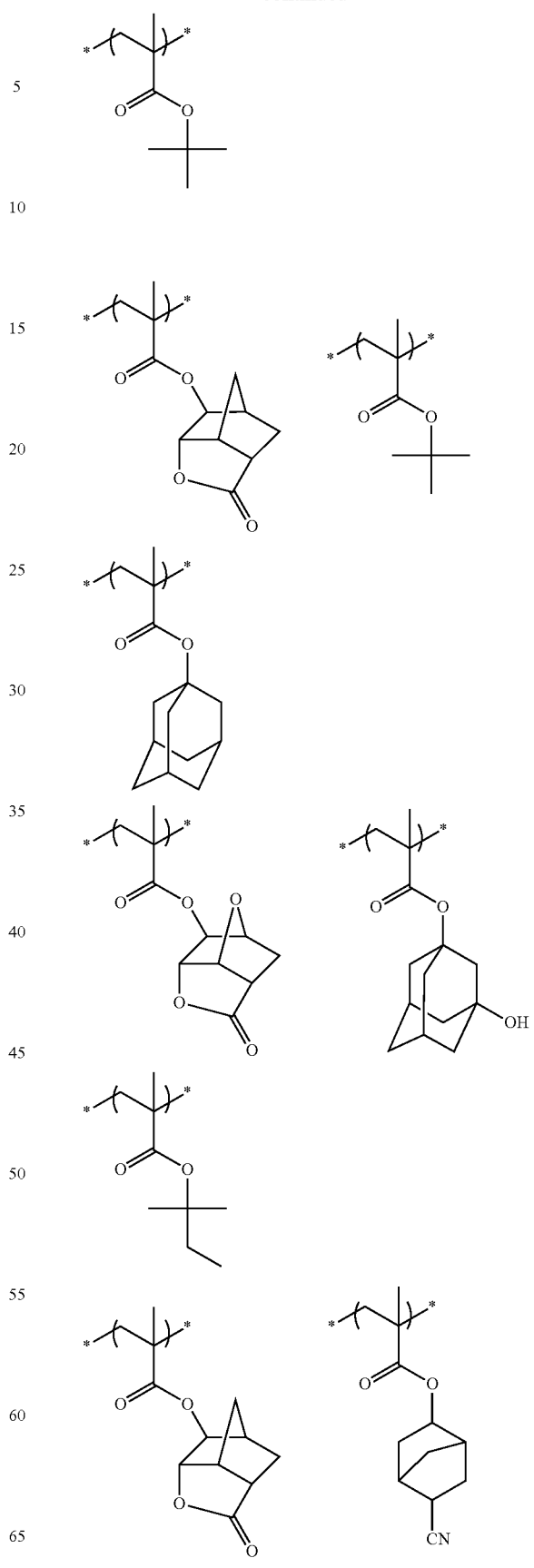

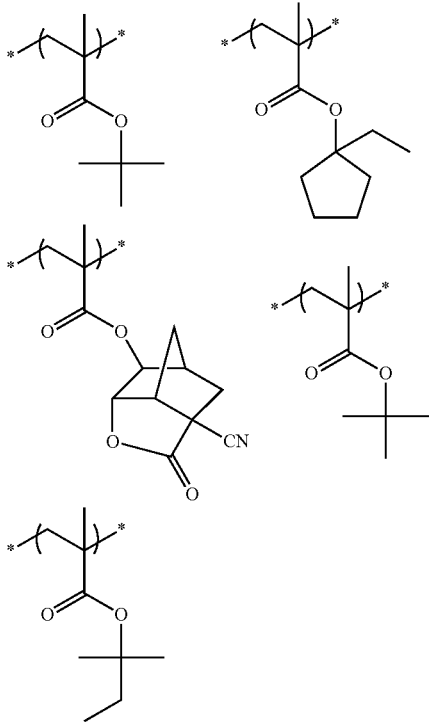

[2] Compound (B) Represented by Any of General Formula (B-1) to (B-3)

The composition in the present invention contains a compound (B) represented by any of following General Formula (B-1) to (B-3).

The compound (B) represented by any of following General Formula (B-1) to (B-3) is a compound generating organic acid by actinic rays or radiation irradiation (hereinafter, also referred to as the "acid generator").

First, the compound (B) represented by following General Formula (B-1) will be described.

[Chem. 43]

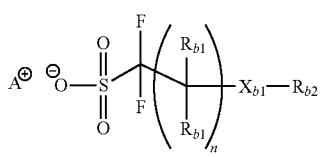

(B-1)

In General Formula (B-1), $A^+$ represents a sulfonium cation or an iodonium cation.

$R_{b1}$s, each independently, represent a hydrogen atom, a fluorine atom, or a trifluoromethyl group ($CF_3$).

n represents an integer of 1 to 4.

n is preferably an integer of 1 to 3 and more preferably 1 or 2.

$X_{b1}$ represents a single bond, an ether bond, an ester bond (—OCO— or —COO—) or a sulfonate bond (—OSO$_2$— or —SO$_3$—).

$X_{b1}$ is preferably an ester bond (—OCO— or —COO—) or a sulfonate bond (—OSO$_2$— or —SO$_3$—).

$R_{b2}$ represents a substituent having 6 or more carbon atoms.

As the substituent having 6 or more carbon atoms for $R_{b2}$, a bulky group is preferable, and an alkyl group, an alicyclic group, an aryl group, a heterocyclic group having 6 or more carbon atoms, and the like, may be included.

The alkyl group having 6 or more carbon atoms for $R_{b2}$ may be straight chain or branched, is preferably a straight chain or branched alkyl group having 6 to 20 carbons, and may include, for example, a straight chain or branched hexyl group, a straight chain or branched heptyl group, a straight chain or branched octyl group, or the like. A branched alkyl group is preferable from the viewpoint of bulkiness.

The alicyclic group having 6 or more carbon atoms for $R_{b2}$ may be monocyclic or polycyclic. As the monocyclic alicyclic group, for example, a monocyclic cycloalkyl group such as a cyclohexyl group and a cyclooctyl group may be included. As the polycyclic alicyclic group, for example, a polycyclic cycloalkyl group such as a norbornyl group, a tricyclodecanyl group, a tetracyclodecanyl group, a tetracyclododecanyl group and an adamantyl group may be included. Among these, an alicyclic group having a bulky structure of 7 or more carbon atoms such as a norbornyl group, a tricyclodecanyl group, a tetracyclodecanyl group, a tetracyclododecanyl group and an adamantyl group is preferable from the viewpoint of suppressing diffusivity in a film in PEB step (heating after exposure) and improving MEEF (Mask Error Enhancement Factor).

The aryl group having 6 or more carbon atoms for $R_{b2}$ may be monocyclic or polycyclic. As this aryl group, for example, a phenyl group, a naphthyl group, a phenanthryl group, and an anthryl group may be included. Among these, a naphthyl group of which light absorbance at 193 nm is relatively low is preferable.

The heterocyclic group having 6 or more carbon atoms for $R_{b2}$ may be monocyclic or polycyclic, however, a polycyclic heterocyclic group can suppress diffusion of acid more. In addition, the heterocyclic group may or may not have aromaticity. As the heterocyclic group which has aromaticity, for example, a benzofuran ring, a benzothiophene ring, a dibenzofuran ring, and a dibenzothiophene ring may be included. As the heterocyclic group which does not have aromaticity, for example, a tetrahydropyran ring, a lactone ring and a decahydro isoquinoline ring may be included. As the heterocyclic ring in the heterocyclic group, a benzofuran ring or a decahydro isoquinoline ring is particularly preferable. In addition, as examples of the lactone ring, the lactone structure exemplified in the resin (P) described above may be included.

The substituent having 6 or more carbon atoms for $R_{b2}$ may have further substituents. The further substituents may include, for example, an alkyl group (may be either straight chain or branched, and preferably 1 to 12 carbon atoms), a cycloalkyl group (may be either monocyclic, polycyclic or a spiro ring, and preferably 3 to 20 carbon atoms), an aryl group (preferably 6 to 14 carbon atoms), a hydroxy group, an alkoxy group, an ester group, an amide group, an urethane group, an ureido group, a thioether group, a sulfonamide group, and a sulfonate group. In addition, carbon constituting the alicyclic group, the aryl group or the heterocyclic group (carbon contributing to the ring formation) may also be carbonyl carbon.

Examples of the anion structure in the compound (B) represented by General Formula (B-1) are shown below, however, the present invention is not limited to these.

[Chem. 44]

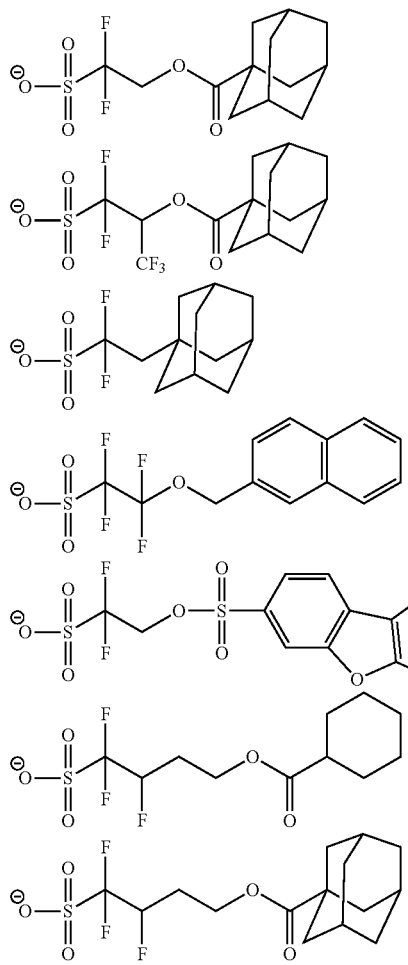

Next, the compound (B) represented by following General Formula (B-2) will be described.

[Chem. 45]

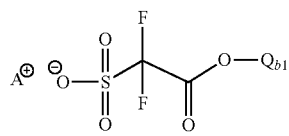

(B-2)

In General Formula (B-2), $A^+$ represents a sulfonium cation or an iodonium cation.

$Q_{b1}$ represents a group having a lactone structure, a group having a sultone structure, or a group having a cyclic carbonate structure.

As the lactone and sultone structure for $Q_{b1}$, for example, the same lactone structure and the same sultones structure in the repeating unit having a lactone structure and a sultone structure described in the resin (P) section may be included. Specifically, a lactone structure represented by any of General Formulae (LC1-1) to (LC1-17) and a sultone structure represented by any of General Formulae (SL1-1) to (SL1-3) may be included.

The lactone structure and the sultone structure may be bonded directly to the oxygen atom of the ester group in General Formula (B-2), however, the lactone structure and the sultone structure may also be bonded to the oxygen atom of the ester group through an alkylene group (for example, a methylene group or an ethylene group). In that case, the group having a lactone structure and a sultone structure may be an alkyl group having the lactone structure and the sultone structure as a substituent.

The cyclic carbonate structure for $Q_{b1}$ is preferably a cyclic carbonate structure having 5- to 7-membered ring, and may include 1,3-dioxolan-2-one, 1,3-dioxane-2-one, or the like.

The cyclic carbonate structure may be bonded directly to the oxygen atom of the ester group in General Formula (B-2), however, the cyclic carbonate structure may also be bonded to the oxygen atom of the ester group through an alkylene group (for example, a methylene group or an ethylene group). In that case, the group having a cyclic carbonate structure may be an alkyl group having the cyclic carbonate structure as a substituent.

Examples of the anion structure in the compound (B) represented by General Formula (B-2) are shown below, however, the present invention is not limited to these.

[Chem. 46]

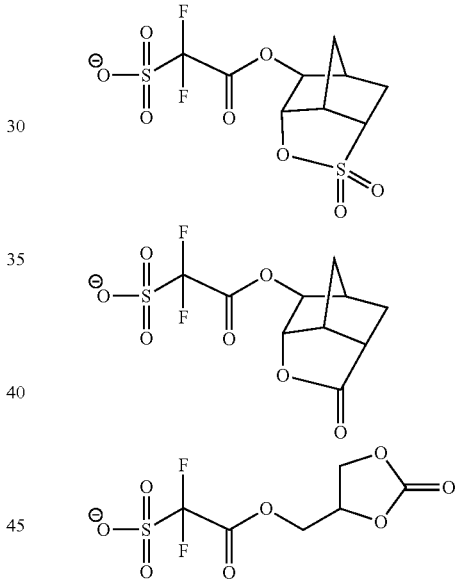

Next, the compound (B) represented by following General Formula (B-3) will be described.

[Chem. 47]

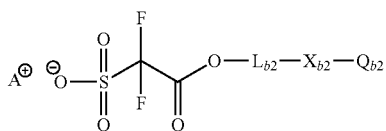

(B-3)

In General Formula (B-3), $A^+$ represents a sulfonium cation or an iodonium cation.

$L_{b2}$ represents an alkylene group having 1 to 6 carbon atoms, may include a methylene group, an ethylene group, a propylene group, a butylene group or the like, and, therefore, is preferably an alkylene group having 1 to 4 carbon atoms.

$X_{b2}$ represents an ether bond or an ester bond (—OCO— or —COO—).

$Q_{b2}$ represents an alicyclic group or a group having an aromatic ring.

The alicyclic group for $Q_{b2}$ may be monocyclic or polycyclic. As the monocyclic alicyclic group, for example, a monocyclic cycloalkyl group such as a cyclopentyl group, a cyclohexyl group and a cyclooctyl group may be included. As the polycyclic alicyclic group, for example, a polycyclic cycloalkyl group such as a norbornyl group, a tricyclodecanyl group, a tetracyclodecanyl group, a tetracyclododecanyl group and an adamantyl group may be included. Among these, an alicyclic group having a bulky structure of 7 or more carbon atoms such as a norbornyl group, a tricyclodecanyl group, a tetracyclodecanyl group, a tetracyclododecanyl group and an adamantyl group is preferable.

The aromatic ring in the group having an aromatic ring for $Q_{b2}$ is preferably an aromatic ring having 6 to 20 carbon atoms, and may include a benzene ring, a naphthalene ring, a phenanthrene ring, an anthracene ring or the like, and is more preferably a benzene ring or a naphthane ring. The aromatic ring may be substituted with at least one fluorine atom, and the aromatic ring substituted with at least one fluorine atom may include a perfluorophenyl group or the like.

The aromatic ring may be bonded directly to $X_{b2}$, however, the aromatic ring may also be bonded to $X_{b2}$ through an alkylene group (for example, a methylene group or an ethylene group). In that case, the group having an aromatic ring may be an alkyl group having the aromatic ring as a substituent.

Examples of the anion structure in the compound (B) represented by General Formula (B-3) are shown below, however, the present invention is not limited to these.

[Chem. 48]

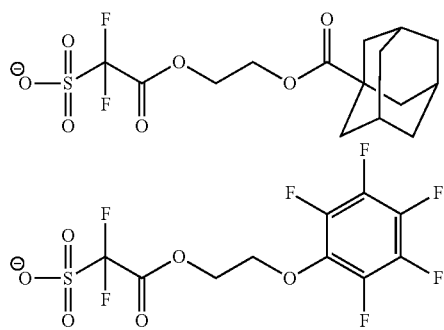

In General Formulae (B-1) to (B-3), the sulfonium cation for $A^+$ is preferably a cation structure represented by following General Formula (ZI), and the iodonium cation for $A^+$ is preferably a cation structure represented by following General Formula (ZII).

[Chem. 49]

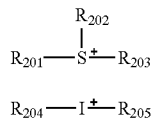

In General Formulae (ZI) and (ZII), $R_{201}$, $R_{202}$, and $R_{203}$, each independently, represent an organic group.

The number of carbons of the organic group as $R_{201}$, $R_{202}$ and $R_{203}$ is generally 1 to 30, and preferably 1 to 20.

In addition, two of $R_{201}$ to $R_{203}$ may be bonded and form a ring structure, and may include an oxygen atom, a sulfur atom, an ester bond, an amide bond or a carbonyl group in the ring. As the group formed by two of $R_{201}$ to $R_{203}$ being bonded, an alkylene group (for example, a butylene group or a pentylene group) may be included.

$R_{204}$ and $R_{205}$, each independently, represent an aryl group, an alkyl group, or a cycloalkyl group.

The aryl group of $R_{204}$ and $R_{205}$ is preferably a phenyl group or a naphthyl group, and more preferably a phenyl group. The aryl group of $R_{204}$ and $R_{205}$ may also be an aryl group having a heterocyclic structure having an oxygen atom, a nitrogen atom, a sulfur atom or the like. As the skeleton of the aryl group having a heterocyclic structure, for example, pyrrole, furan, thiophene, indole, benzofuran, benzothiophene, or the like, may be included.

The alkyl group and the cycloalkyl group in $R_{204}$ and $R_{205}$ may preferably include a straight-chain or branched alkyl group having 1 to 10 carbon atoms (for example, a methyl group, an ethyl group, a propyl group, a butyl group or a pentyl group), a cycloalkyl group having 3 to 10 carbon atoms (a cyclopentyl group, a cyclohexyl group, a norbonyl group).

The aryl group, the alkyl group, and the cycloalkyl group of $R_{204}$ and $R_{205}$ may have a substituent. As the substituent the aryl group, the alkyl group, and the cycloalkyl group of $R_{204}$ and $R_{205}$ may have, for example, an alkyl group (for example, 1 to 15 carbon atoms), a cycloalkyl group (for example, 3 to 15 carbon atoms), an aryl group (for example, 6 to 15 carbon atoms), an alkoxy group (for example, 1 to 15 carbon atoms), a halogen atom, a hydroxyl group, a phenylthio group, or the like, may be included.

As the organic group represented by $R_{201}$, $R_{202}$, and $R_{203}$, for example, corresponding groups in compounds (ZI-1), (ZI-2), (ZI-3) and (ZI-4) described later may be included.

The more preferable cation structure represented by General Formula (ZI) may include cation structures (ZI-1), (ZI-2), (ZI-3) and (ZI-4) described below.

The cation structure (ZI-1) is an aryl sulfonium cation structure in which at least one of $R_{201}$ to $R_{203}$ of general formula (ZI) is an aryl group.

In the aryl sulfonium cation structure, all of $R_{201}$ to $R_{203}$ may be an aryl group, or a part of $R_{201}$ to $R_{203}$ may be an aryl group and the rest is an alkyl group or a cycloalkyl group.

The aryl sulfonium cation structure may include, for example, a triarylsulfonium cation structure, a diaryl alkyl sulfonium cation structure, an aryl dialkyl sulfonium cation structure, a diaryl cycloalkyl sulfonium cation structure or an aryl di-cycloalkyl sulfonium cation structure.

As the aryl group of the aryl sulfonium cation structure, a phenyl group or a naphthyl group is preferable, and a phenyl group is more preferable. The aryl group may be an aryl group containing a heterocyclic structure having an oxygen atom, a nitrogen atom, a sulfur atom or the like. The heterocyclic structure may include a pyrrole residue, a furan residue, a thiophene residue, an indole residue, a benzofuran residue, a benzothiophene residue, or the like. When the aryl sulfonium cation structure has two or more aryl groups, the two or more aryl groups may be the same as or different from each other.

The alkyl group or the cycloalkyl group the aryl sulfonium cation structure has when necessary is preferably a straight chain or branched alkyl group having 1 to 15 carbon atoms and a cycloalkyl group having 3 to 15 carbon atoms, and may include, for example, a methyl group, an ethyl group, a propyl group, an n-butyl group, a sec-butyl group, a t-butyl group, a cyclopropyl group, a cyclobutyl group, a cyclohexyl group, an adamantyl group, or the like.

The aryl group, the alkyl group, and the cycloalkyl group of $R_{201}$ to $R_{203}$ may have an alkyl group (for example, 1 to 15 carbon atoms), a cycloalkyl group (for example, 3 to 15 carbon atoms), an aryl group (for example, 6 to 14 carbon atoms), an alkoxy group (for example, 1 to 15 carbon atoms), a halogen atom, a hydroxyl group, a phenylthio group, or a arylsulfonyl group as a substituent. The substituent is preferably a straight chain or branched alkyl group having 1 to 12 carbon atoms, a cycloalkyl group having 3 to 12 carbon atoms, or a straight chain, branched, or cyclic alkoxy group having 1 to 12 carbon atoms, and more preferably an alkyl group having 1 to 4 carbon atoms or an alkoxy group having 1 to 4 carbon atoms. The substituent may substitute any one of three $R_{201}$ to $R_{203}$, or may substitute all three. In addition, when $R_{201}$ to $R_{203}$ is the aryl group, the substituent preferably substitutes p-position of the aryl group.

Next, a cation structure (ZI-2) will be described.

The cation structure (ZI-2) is a cation structure in which $R_{201}$ to $R_{203}$ in Formula (ZI), each independently represent an organic group which does not have an aromatic ring. Here, the aromatic ring also includes an aromatic ring containing a hetero atom.

In the organic group which does not contain an aromatic ring as $R_{201}$ to $R_{203}$, the number of carbon atoms is generally 1 to 30 and the number of carbon atoms is preferably 1 to 20.

$R_{201}$ to $R_{203}$ is, each independently, preferably an alkyl group, a cycloalkyl group, an allyl group or a vinyl group, more preferably a straight chain or branched 2-oxo alkyl group, a 2-oxo cycloalkyl group, an alkoxycarbonyl methyl group, and particularly preferably a straight chain or branched 2-oxo alkyl group.

As the alkyl group and the cycloalkyl group of $R_{201}$ to $R_{203}$, a straight chain or branched alkyl group having 1 to 10 carbon atoms (for example, a methyl group, an ethyl group, a propyl group, a butyl group or a pentyl group), a cycloalkyl group having 3 to 10 carbon atoms (a cyclopentyl group, a cyclohexyl group or a norbonyl group) may be preferably included. As the more preferable alkyl group, a 2-oxo alkyl group or an alkoxycarbonyl methyl group may be included. As the more preferable cycloalkyl group, a 2-oxo cycloalkyl group may be included.

The 2-oxo alkyl group may be either straight chain or branched and preferably include a group having >C=O at 2-position of the above alkyl group.

The 2-oxo cycloalkyl group may preferably include a group having >C=O at 2-position of the above cycloalkyl group.

The alkoxy group in the alkoxycarbonyl methyl group may preferably include an alkoxy group having 1 to 5 carbon atoms (a methoxy group, an ethoxy group, a propoxy group, a butoxy group or a pentoxy group).

$R_{201}$ to $R_{203}$ may be further substituted with a halogen atom, an alkoxy group (for example, 1 to 5 carbon atoms), a hydroxyl group, a cyano group or a nitro group.

The cation structure (ZI-3) is a structure represented by General Formula (ZI-3) below, and is a compound having a phenacylsulfonium salt structure.

[Chem. 50]

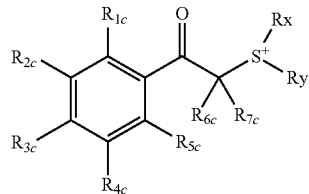

(ZI-3)

In General Formula (ZI-3), $R_{1c}$ to $R_{5c}$, each independently represent a hydrogen atom, an alkyl group, a cycloalkyl group, an aryl group, an alkoxy group, an aryloxy group, an alkoxycarbonyl group, an alkylcarbonyloxy group, a cycloalkylcarbonyloxy group, a halogen atom, a hydroxyl group, a nitro group, an alkylthio group or an arylthio group.

$R_{6c}$ and $R_{7c}$, each independently, represent a hydrogen atom, an alkyl group, a cycloalkyl group, a halogen atom, a cyano group or an aryl group.

$R_x$ and $R_y$, each independently, represent an alkyl group, a cycloalkyl group, and a 2-oxoalkyl group, a 2-oxocycloalkyl group, an alkoxycarbonyl alkyl group, an allyl group or a vinyl group.

Two or more of $R_{1c}$ to $R_{5c}$, $R_{5c}$ and $R_{6c}$, $R_{6c}$ and $R_{7c}$, $R_{5c}$ and $R_x$, and $R_x$ and $R_y$, may be bonded to each other and form a ring structure, and this ring structure may include an oxygen atom, a sulfur atom, a ketone group, an ester bond or an amide bond.

The ring structure may include an aromatic or non-aromatic hydrocarbon ring, an aromatic or non-aromatic heterocyclic ring, or a polycyclic condensed ring polycyclic ring formed by two or more of these rings being combined. As the ring structure, 3- to 10-membered ring may be included, 4- to 8-membered ring is preferable, and 5- or 6-membered ring is more preferable.

The group formed by two or more of $R_1$, to $R_{5c}$, $R_{6c}$ and $R_{7c}$, and $R_x$ and $R_y$ being bonded may include a butylene group, pentylene group or the like.

The group formed by $R_{5c}$ and $R_{6c}$, and $R_{5c}$ and $R_x$ being bonded may preferably include a single bond or an alkylene group, and as an alkylene group, a methylene group, an ethylene group or the like may be included.

The alkyl group as $R_{1c}$ to $R_{7c}$ may be either straight chain or branched, and may include, for example, an alkyl group having 1 to 20 carbon atoms, preferably a straight chain or branched alkyl group having 1 to 12 carbon atoms (for example, a methyl group, an ethyl group, a straight chain or branched propyl group, a straight chain or branched butyl group, or a straight chain or branched pentyl group), and the cycloalkyl group may include a cycloalkyl group having 3 to 10 carbon atoms (for example, a cyclopentyl group or a cyclohexyl group).

The aryl group as $R_{1c}$ to $R_{5c}$ preferably has 5 to 15 carbon atoms, and may include, for example, a phenyl group or a naphthyl group.

The alkoxy group as $R_{1c}$ to $R_{5c}$ may be any of straight chain, branched and cyclic, and may include, for example, an alkoxy group having 1 to 10 carbon atoms, preferably, a straight chain and branched alkoxy group having 1 to 5 carbon atoms (for example, a methoxy group, an ethoxy group, a straight chain or branched propoxy group, a straight chain or branched butoxy group, or a straight chain or branched pentoxy group), a cyclic alkoxy group having 3 to 10 carbon atoms (for example, a cyclopentyloxy group or a cyclohexyloxy group).

Specific examples of the alkoxy group in the alkoxycarbonyl group as $R_{1c}$ to $R_{5c}$ is the same as specific examples of the alkoxy group as $R_{1c}$ to $R_{5c}$ described above.

Specific examples of the alkyl group in the alkylcarbonyloxy group and the alkylthio group as $R_{1c}$ to $R_{5c}$ are the same as specific examples of the alkyl group as $R_{1c}$ to $R_{5c}$ described above.

Specific examples of the cycloalkyl group in the cycloalkyl carbonyloxy group as $R_{1c}$ to $R_{5c}$ are the same as specific examples of the cycloalkyl group of $R_{1c}$ to $R_{5c}$ described above.

Specific examples of the aryl group in the aryloxy group and the arylthio group as $R_{1c}$ to $R_{5c}$ are the same as specific examples of the aryl group $R_{1c}$ to $R_{5c}$ described above.

Preferably, any of $R_{1c}$ to $R_{5c}$ is a straight chain or branched alkyl group, a cycloalkyl group, or a straight chain, branched or cyclic alkoxy group, and more preferably, the sum of the number of carbon atoms in $R_{1c}$ to $R_{5c}$ is 2 to 15. As a result, solvent solubility is further improved and the generation of particles is suppressed when stored.

As the ring structure which may be formed by two or more of $R_{1c}$ to $R_{5c}$ being bonded to each other, 5-membered or 6-membered ring may be preferably included, and a 6-membered ring (for example, a phenyl ring) may be particularly preferably included.

The ring structure which may be formed by $R_{5c}$ and $R_{6c}$ being bonded to each other may include a 4-membered ring or more (particularly preferably 5- to 6-membered ring) formed together with a carbonyl carbon atom and a carbon atom in General Formula (I) by $R_{5c}$ and $R_{6c}$, being bonded to each other and constituting a single bond or an alkylene group (a methylene group, an ethylene group, or the like).

The aryl group as $R_{6c}$ and $R_{7c}$ preferably has 5 to 15 carbon atoms, and may include, for example, a phenyl group or a naphthyl group.

As an aspect of $R_{6c}$ and $R_{7c}$, it is preferable that both of them be an alkyl group. In particular, it is preferable that each of $R_{6c}$ and $R_{7c}$ be a straight chain or branched alkyl group having 1 to 4 carbon atoms, and particularly, it is preferable that both be a methyl group.

In addition, when $R_{6c}$ and $R_{7c}$ are bonded to each other and form a ring, the group formed by $R_{6c}$ and $R_{7c}$ being bonded and is preferably an alkylene group having 2 to 10 carbon atoms, and may include, for example, an ethylene group, a propylene group, a butylene group, a pentylene group, a hexylene group, or the like. In addition, the ring formed by $R_{6c}$ and $R_{7c}$ being bonded may have a hetero atom such as an oxygen atom in the ring.

The alkyl group and the cycloalkyl group as $R_x$ and $R_y$ may include the same alkyl group and the cycloalkyl group as $R_{1c}$ to $R_{7c}$.

The 2-oxoalkyl group and the 2-oxocycloalkyl group as $R_x$ and $R_y$ may include the group having >C=O at 2-position of the alkyl group and the cycloalkyl group as $R_{1c}$ to $R_{7c}$.

The alkoxy group in the alkoxycarbonyl alkyl group as $R_x$ and $R_y$ may include the same alkoxy group in $R_{1c}$ to $R_{5c}$, and the alkyl groups may include, for example, an alkyl group having 1 to 12 carbon atoms, and preferably include a straight chain alkyl group having 1 to 5 carbon atoms (for example, a methyl group or an ethyl group).

The allyl group as $R_x$ and $R_y$ is not particularly limited, however, an unsubstituted allyl group, or an allyl group substituted with a monocyclic or polycyclic cycloalkyl group (preferably a cycloalkyl group having 3 to 10 carbon atoms) is preferable.

The vinyl group as $R_x$ and $R_y$ is not particularly limited however, an unsubstituted vinyl group, or a vinyl group substituted with a monocyclic or polycyclic cycloalkyl group (preferably a cycloalkyl group having 3 to 10 carbon atoms) is preferable.

The ring structure which may be formed by $R_{5c}$ and $R_x$ being bonded to each other may include a 5-membered ring or more (particularly preferably 5-membered ring) formed together with a sulfur atom and a carbonyl carbon atom in General Formula (I) by $R_{5c}$ and $R_x$ being bonded to each other and constituting a single bond or an alkylene group (a methylene group, an ethylene group, or the like).

The ring structure which may be formed by $R_x$ and $R_y$ being bonded to each other may include a 5-membered or 6-membered ring, particularly preferably 5-membered ring (that is, a tetrahydrothiophene ring) formed by divalent $R_x$ and $R_y$ (for example, a methylene group, an ethylene group, a propylene group or the like) together with a sulfur atom in General Formula (XI-3).

$R_x$ and $R_y$ are preferably an alkyl group having 4 or more carbon atoms or a cycloalkyl group, and are an alkyl group having more preferably 6 or more, even more preferably 8 or more carbon atoms, or a cycloalkyl group.

$R_{1c}$ to $R_{7c}$, $R_x$, and $R_y$ may have further substituents and the substituent such as this may include a halogen atom (for example, a fluorine atom), a hydroxyl group, a carboxyl group, a cyano group, a nitro group, an alkyl group, a cycloalkyl group, an aryl group, an alkoxy group, an aryloxy group, an acyl group, an arylcarbonyl group, an alkoxyalkyl group, an aryloxy alkyl group, an alkoxycarbonyl group, an aryloxycarbonyl group, an alkoxycarbonyloxy group, an aryloxy carbonyloxy group, or the like.

$R_{1c}$, $R_{2c}$, $R_{4c}$, and $R_{5c}$ in General Formula (ZI-3), each independently, preferably represent a hydrogen atom, and $R_{3c}$ represents a group other than a hydrogen atom, that is, an alkyl group, a cycloalkyl group, an aryl group, an alkoxy group, an aryloxy group, an alkoxycarbonyl group, an alkylcarbonyloxy group, a cycloalkylcarbonyloxy group, a halogen atom, a hydroxyl group, a nitro group, an alkylthio group or an arylthio group.

As the cation structure (ZI-2) or (ZI-3) in the present invention, specific examples below may be included.

[Chem. 51]

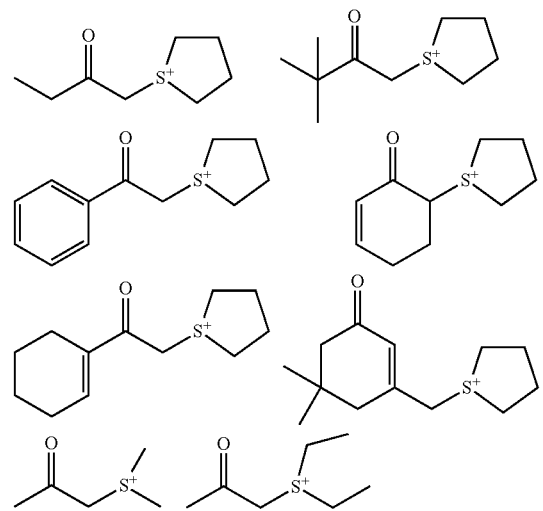

99
-continued
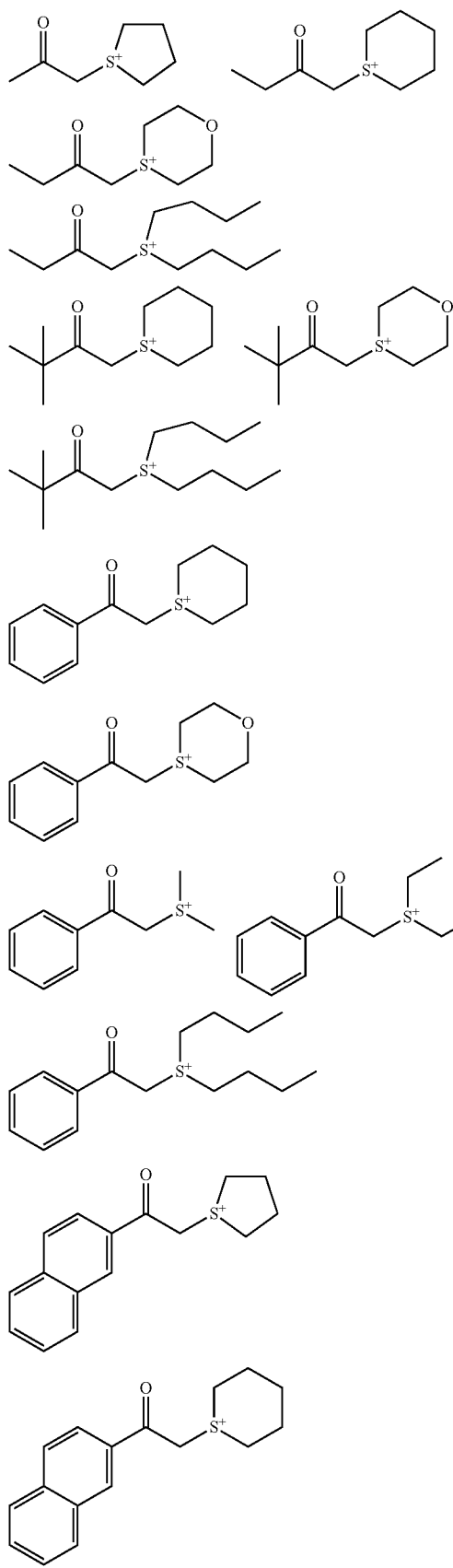
100
-continued
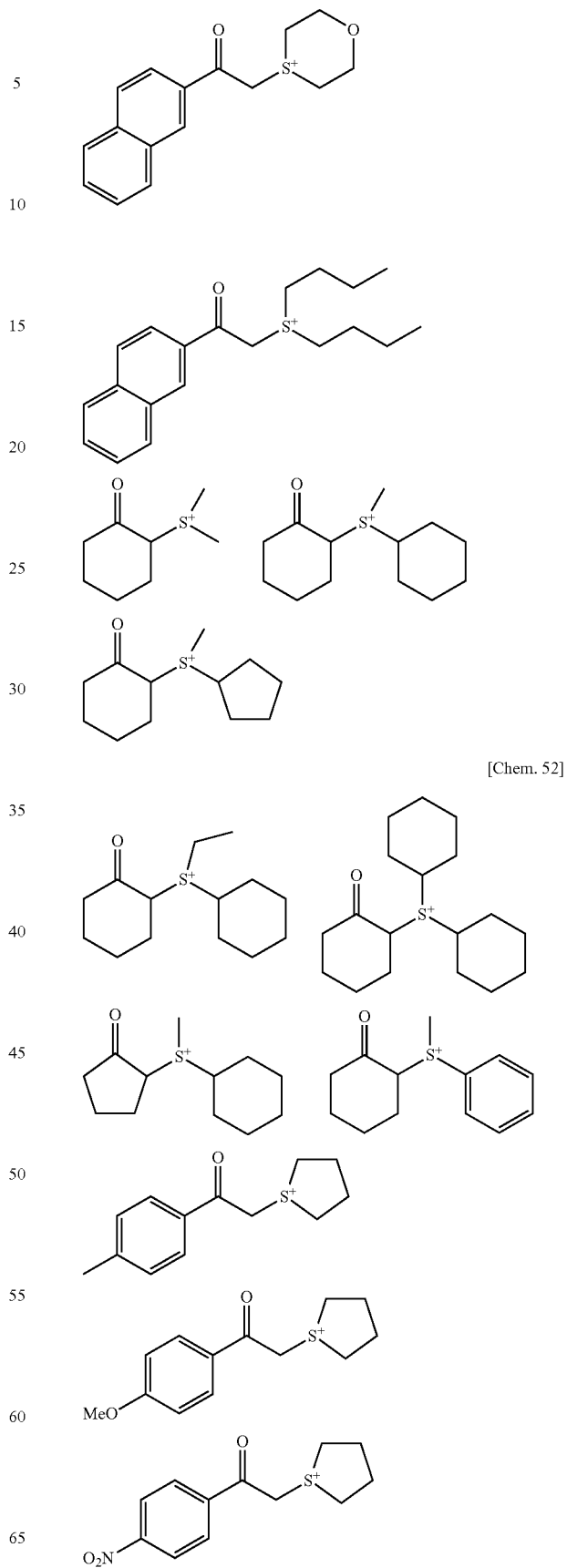
[Chem. 52]

101
-continued
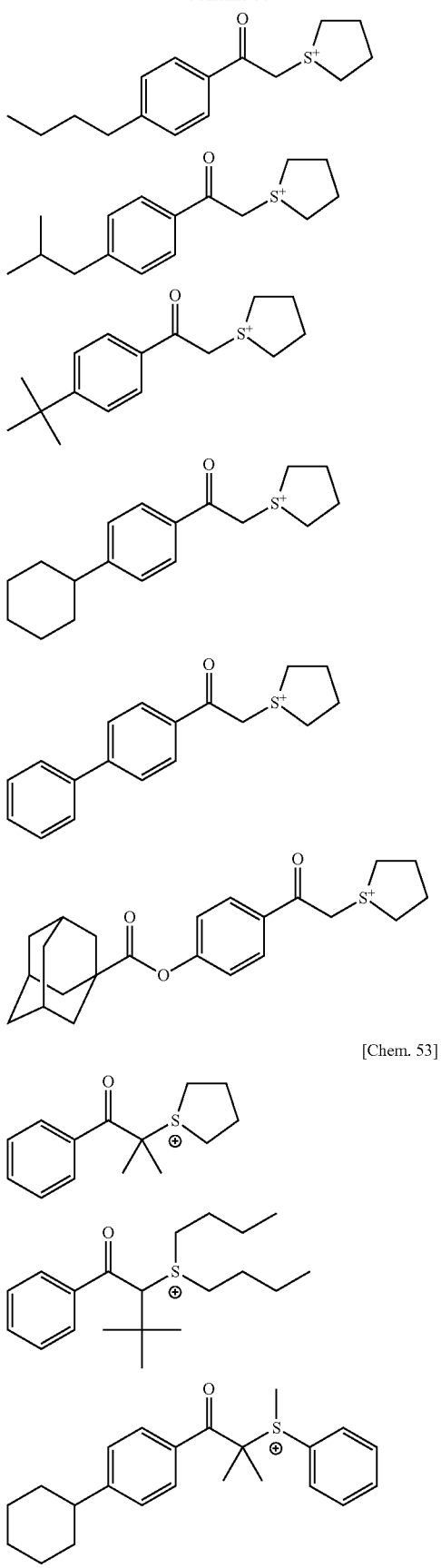
[Chem. 53]
102
-continued
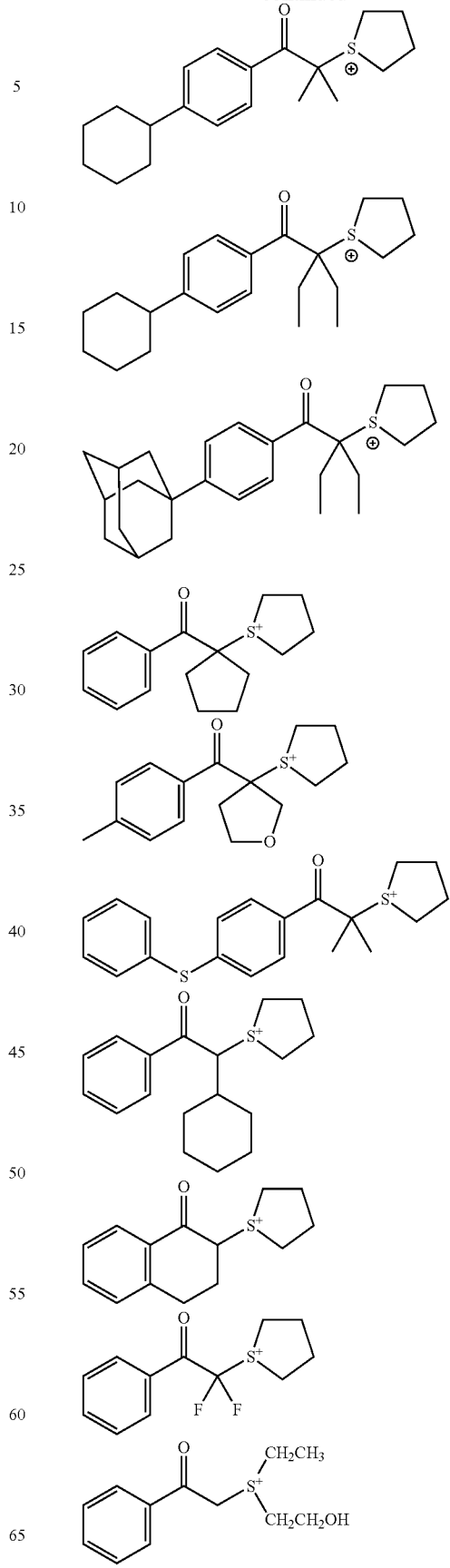
[Chem. 54]

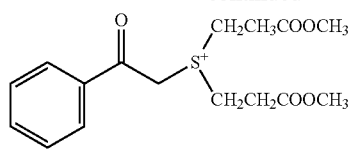
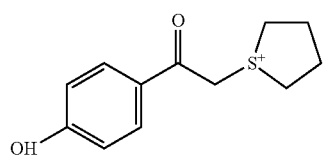
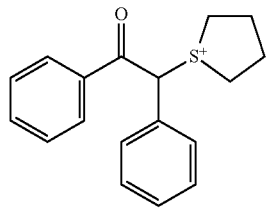
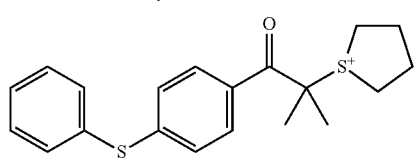
[Chem. 55]
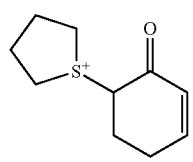 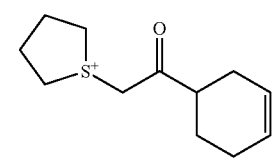
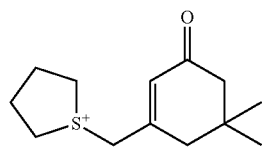
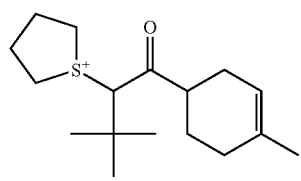
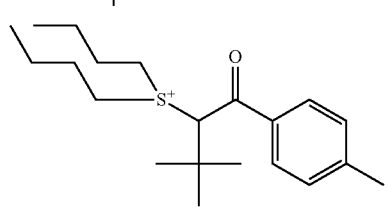
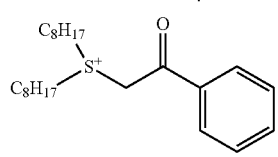
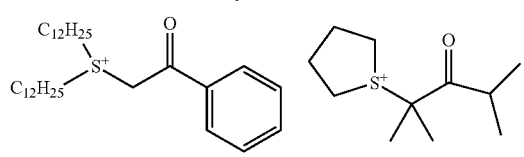
[Chem. 56]
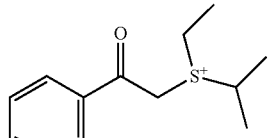
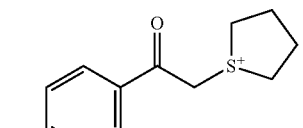
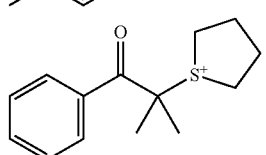
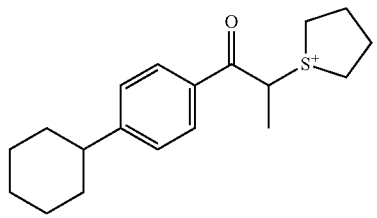
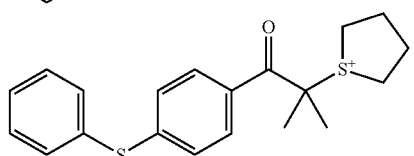
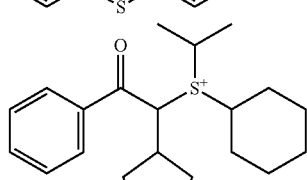
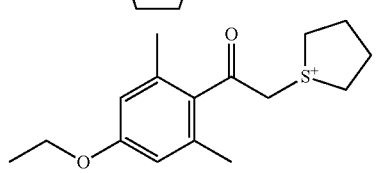
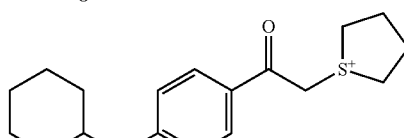
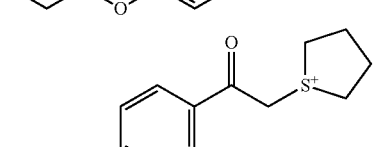
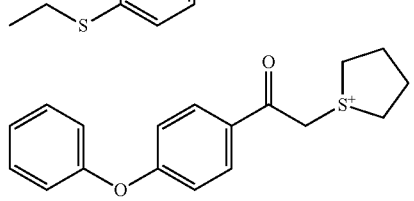

-continued

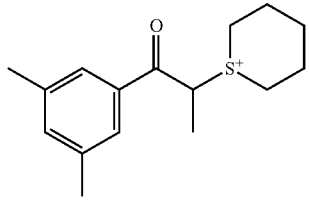

Next, a cation structure (ZI-4) will be described.
The cation structure (ZI-4) is represented by following General Formula (ZI-4).

[Chem. 57]

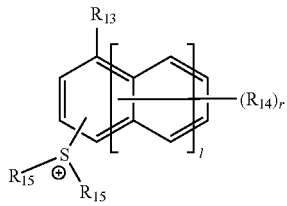

(ZI-4)

In General Formula (ZI-4), $R_{13}$ represents a hydrogen atom, a fluorine atom, a hydroxyl group, an alkyl group, a cycloalkyl group, an alkoxy group, an alkoxycarbonyl group, or a group having a cycloalkyl group. These groups may have a substituent.

$R_{14}$, if present in plural numbers, each independently represent a hydroxyl group, an alkyl group, a cycloalkyl group, an alkoxy group, an alkoxycarbonyl group, an alkylcarbonyl group, an alkylsulfonyl group, a cycloalkylsulfonyl group, or a group having a cycloalkyl group. These groups may have a substituent.

$R_{15}$s, each independently, represent an alkyl group, a cycloalkyl group or a naphthyl group. Two $R_{15}$s may be bonded to each other and form a ring. These groups may have a substituent.

l represents an integer of 0 to 2.
r represents an integer of 0 to 8.
In general formula (ZI-4), the alkyl group of $R_{13}$, $R_{14}$, and $R_{15}$ has a straight chain shape or a branched shape, preferably has 1 to 10 carbon atoms, and is preferably a methyl group, an ethyl group, an n-butyl group, a t-butyl group, or the like.

The cycloalkyl group of $R_{13}$, $R_{14}$, and $R_{15}$ may include a monocyclic or polycyclic cycloalkyl group (preferably a cycloalkyl group having 3 to 20 carbon atoms), and is preferably cyclopropyl, cyclopentyl, cyclohexyl, cycloheptyl or cyclooctyl.

The alkoxy group of $R_{13}$ and $R_{14}$ has a straight chain shape or a branched shape, preferably has 1 to 10 carbon atoms, and is preferably a methoxy group, an ethoxy group, an n-propoxy group, an n-butoxy group, or the like.

The alkoxycarbonyl group of $R_{13}$ and $R_{14}$ has a straight chain shape or a branched shape, preferably has 2 to 11 carbon atoms, and is preferably a methoxycarbonyl group, an ethoxycarbonyl group, an n-butoxycarbonyl group, or the like.

As the group having a cycloalkyl group of $R_{13}$, and $R_{14}$, may include a monocyclic or polycyclic cycloalkyl group (preferably a cycloalkyl group having 3 to 20 carbon atoms), and may include, for example, a monocyclic or polycyclic cycloalkyloxy group, or an alkoxy group having a monocyclic or polycyclic cycloalkyl group. These groups may have further substituents.

As the monocyclic or polycyclic cycloalkyloxy group of $R_{13}$, and $R_{14}$, the number of total carbon atoms is preferably 7 or more, the number of total carbon atoms is more preferably greater than or equal to 7 and less than or equal to 15, and, furthermore, having a monocyclic cycloalkyl group is preferable. The monocyclic cycloalkyloxy group having 7 or more total carbon atoms is a monocyclic cycloalkyloxy group in which a cycloalkyloxy group such as a cyclopropyloxy group, a cyclobutyloxy group, a cyclopentyloxy group, a cyclohexyloxy group, a cycloheptyloxy group, a cyclooctyloxy group, a cyclododecanyloxy groups has an arbitrary substituent such as an alkyl group such as a methyl group, an ethyl group, a propyl group, a butyl group, a pentyl group, a hexyl group, a heptyl group, an octyl group, a dodecyl group, a 2-ethylhexyl group, an isopropyl group, a sec-butyl group, a t-butyl group or an iso-amyl group, a hydroxyl group, a halogen atom (a fluorine atom, a chlorine atom, a bromine atom, an iodine atom), a nitro group, a cyano group, an amide group, a sulfonamide group, an alkoxy group such as a methoxy group, an ethoxy group, a hydroxyethoxy group, a propoxy group, a hydroxypropoxy group or a butoxy group, an alkoxycarbonyl group such as a methoxycarbonyl group or an ethoxycarbonyl group, an acyl group such as a formyl group, an acetyl group or a benzoyl group, an acyloxy group such as an acetoxy group or a butyryloxy group, a carboxyl group, or the like, and represents a monocyclic cycloalkyloxy group in which the number of total carbon atoms combined with an arbitrary substituent on the cycloalkyl group is 7 or more.

In addition, the polycyclic cycloalkyloxy group having a 7 or more total carbon atoms may include a norbonyloxy group, a tricyclodecanyloxy group, a tetracyclodecanyloxy group, an adamantyloxy group, or the like.

As the alkoxy group having a monocyclic or polycyclic cycloalkyl group of $R_{13}$, and $R_{14}$, the number of total carbon atoms is preferably 7 or more, the number of total carbon atoms is more preferably greater than or equal to 7 and less than or equal to 15, and, furthermore, an alkoxy group having a monocyclic cycloalkyl group is preferable. The alkoxy group having a monocyclic cycloalkyl group having 7 or more total carbon atoms is an alkoxy group such as a methoxy group, an ethoxy group, a propoxy group, a butoxy group, a pentyloxy group, a hexyloxy group, a heptoxy group, an octyloxy group, a dodecyloxy group, a 2-ethylhexyloxy group, an isopropoxy group, a sec-butoxy group, a t-butoxy group or an iso-amyloxy group substituted with the monocyclic cycloalkyl group described above, and represents a group in which the number of total carbon atoms including the substituent is 7 or more. For example, a cyclohexylmethoxy group, a cyclopentylethoxy group, a cyclohexylethoxy group or the like may be included, and a cyclohexylmethoxy group is preferable.

In addition, the alkoxy group having a polycyclic cycloalkyl group having a 7 or more total carbon atoms may include a norbornylmethoxy group, a norbornylethoxy group, a tricyclodecanylmethoxy group, a tricyclodecanylethoxy group, a tetracyclodecanylmethoxy group, a tetracyclodecanylethoxy group, an adamantylmethoxy group, an adamantylethoxy group or the like, and is preferably a norbornylmethoxy group, a norbornylethoxy group, or the like.

As the alkyl group of the alkylcarbonyl group of $R_{14}$, the same specific examples as $R_{13}$ to $R_{15}$ described above may be included.

The alkylsulfonyl group and the cycloalkylsulfonyl group of $R_{14}$ have a straight chain shape, a branched shape or a cyclic shape, and preferably has 1 to 10 carbon atoms, and is preferably, for example, a methanesulfonyl group, a ethanesulfonyl group, an n-propanesulfonyl group, an n-butanesulfonyl group, a cyclopentane sulfonyl group, a cyclohexanesulfonyl group, or the like.

The substituent each of the above groups may have includes a halogen atom (for example, a fluorine atom), a hydroxyl group, a carboxyl group, a cyano group, a nitro group, an alkoxy group, an alkoxyalkyl group, an alkoxycarbonyl group, an alkoxycarbonyloxy group, or the like.

The alkoxy group includes, for example, a straight chain, branched, or cyclic alkoxy group having 1 to 20 carbon atoms such as a methoxy group, an ethoxy group, an n-propoxy group, an i-propoxy group, an n-butoxy group, a 2-methylpropoxy group, a 1-methylpropoxy group, a t-butoxy group, a cyclopentyloxy group a cyclohexyloxy group, or the like.

The alkoxyalkyl group includes, for example, a straight chain, branched, or cyclic alkoxyalkyl group having 2 to 21 carbon atoms such as a methoxymethyl group, an ethoxymethyl group, a 1-methoxyethyl group, a 2-methoxyethyl group, a 1-ethoxyethyl group or a 2-ethoxyethyl group, or the like.

The alkoxycarbonyl group includes, for example, a straight chain, branched, or cyclic alkoxycarbonyl group having 2 to 21 carbon atoms such as a methoxycarbonyl group, an ethoxycarbonyl group, an n-propoxycarbonyl group, an 1-propoxycarbonyl group, an n-butoxycarbonyl group, a 2-methylpropoxycarbonyl group, a 1-methylpropoxycarbonyl group, a t-butoxycarbonyl group, a cyclopentyloxycarbonyl group or a cyclohexyloxycarbonyl group, or the like.

The alkoxycarbonyloxy group includes, for example, a straight chain, branched, or cyclic alkoxycarbonyloxy group having 2 to 21 carbon atoms such as a methoxycarbonyloxy group, an ethoxycarbonyloxy group, an n-propoxycarbonyloxy group, an i-propoxycarbonyloxy group, an n-butoxycarbonyloxy group, a t-butoxycarbonyloxy group, cyclopentyloxycarbonyloxy group or a cyclohexyloxycarbonyloxy, or the like.

The ring structure which may be formed by two $R_{15}$s being bonded to each other may include a 5-membered or 6-membered ring, particularly preferably 5-membered ring (that is, a tetrahydrothiophene ring) formed by two $R_{15}$s together with a sulfur atom in General Formula (ZI-4), and may be ring condensed with an aryl group or cycloalkyl group. This divalent $R_{15}$ may have a substituent, and may include, for example, a hydroxyl group, a carboxyl group, a cyano group, a nitro group, an alkyl group, a cycloalkyl group, an alkoxy group, an alkoxyalkyl group, an alkoxycarbonyl group, an alkoxycarbonyloxy group, or the like. The substituent for the ring structure may be present in plural numbers and these may be bonded to each other and form a ring (an aromatic or non-aromatic hydrocarbon ring, an aromatic or non-aromatic heterocyclic ring, or a polycyclic condensed ring formed by combining two or more of these rings).

$R_{15}$ in General Formula (ZI-4) is preferably a methyl group, an ethyl group, a naphthyl group, a divalent group in which two $R_{15}$s are bonded to each other and form a tetrahydrothiophene ring structure together with a sulfur atom, or the like.

The substituent $R_{13}$ and $R_{14}$ may have is preferably a hydroxyl group, an alkoxy group an alkoxycarbonyl group, or a halogen atom (particularly, a fluorine atom).

As l, 0 or 1 is preferable, and 1 is more preferable.

As r, 0 to 2 is preferable.

As the cation structure (ZI-4) in the present invention, specific examples below may be included.

[Chem. 58]

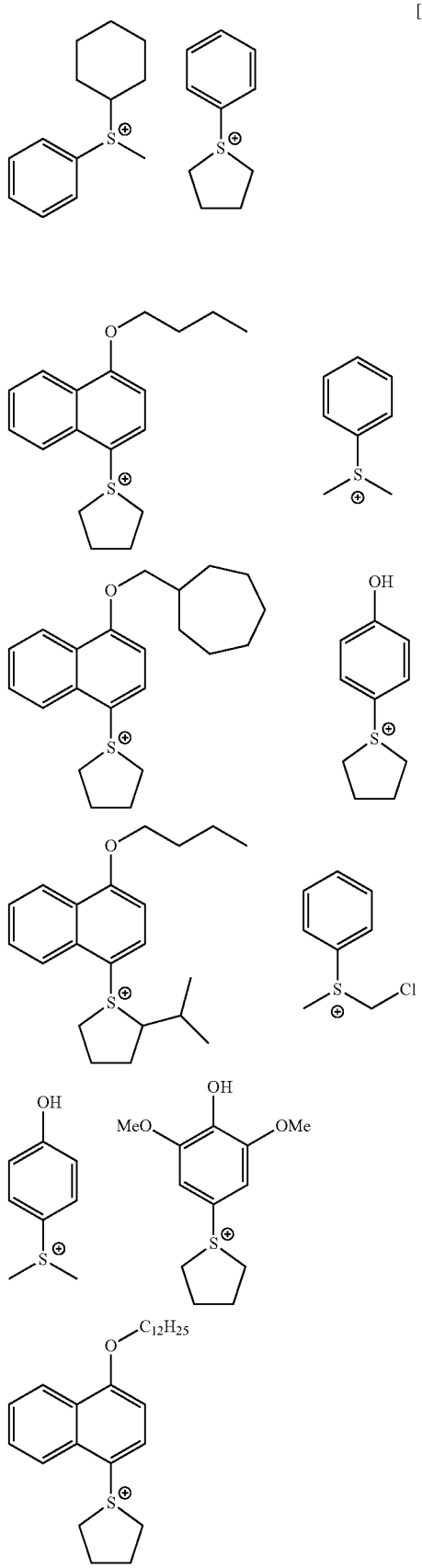

109
-continued
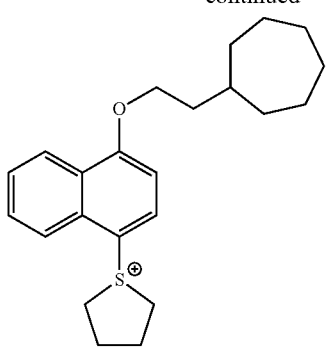
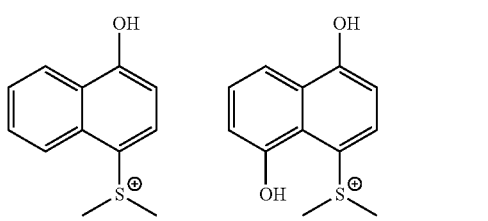
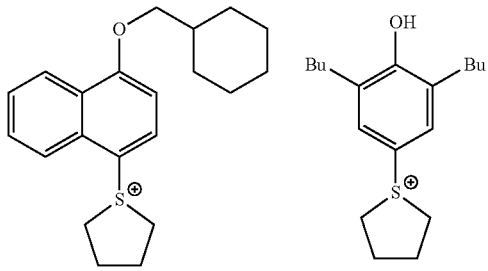
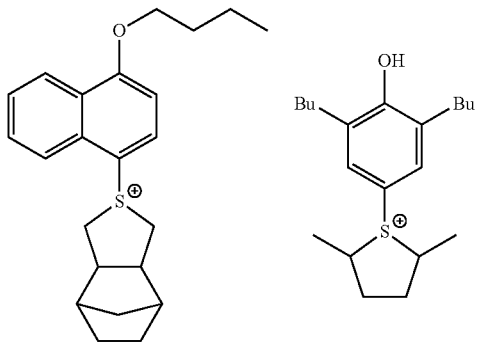
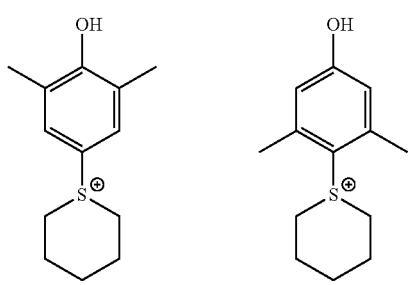
110
-continued
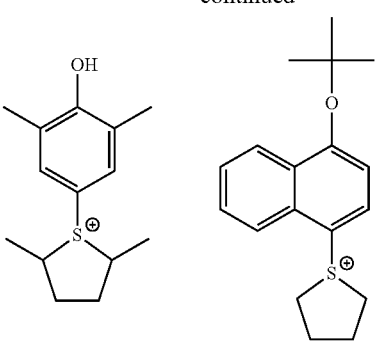
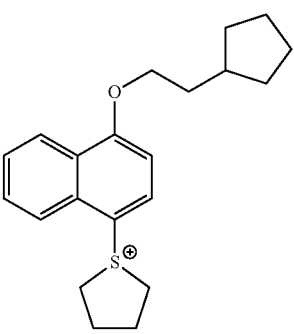
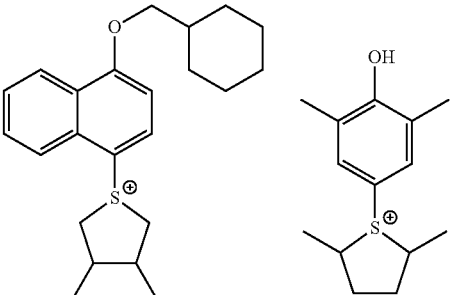
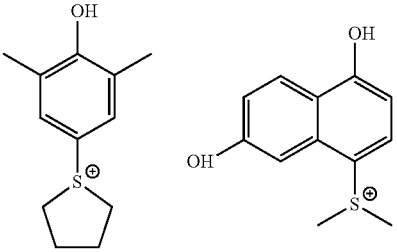
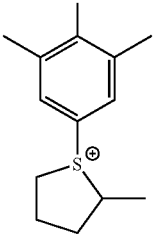

111
-continued
112
-continued
[Chem. 59]
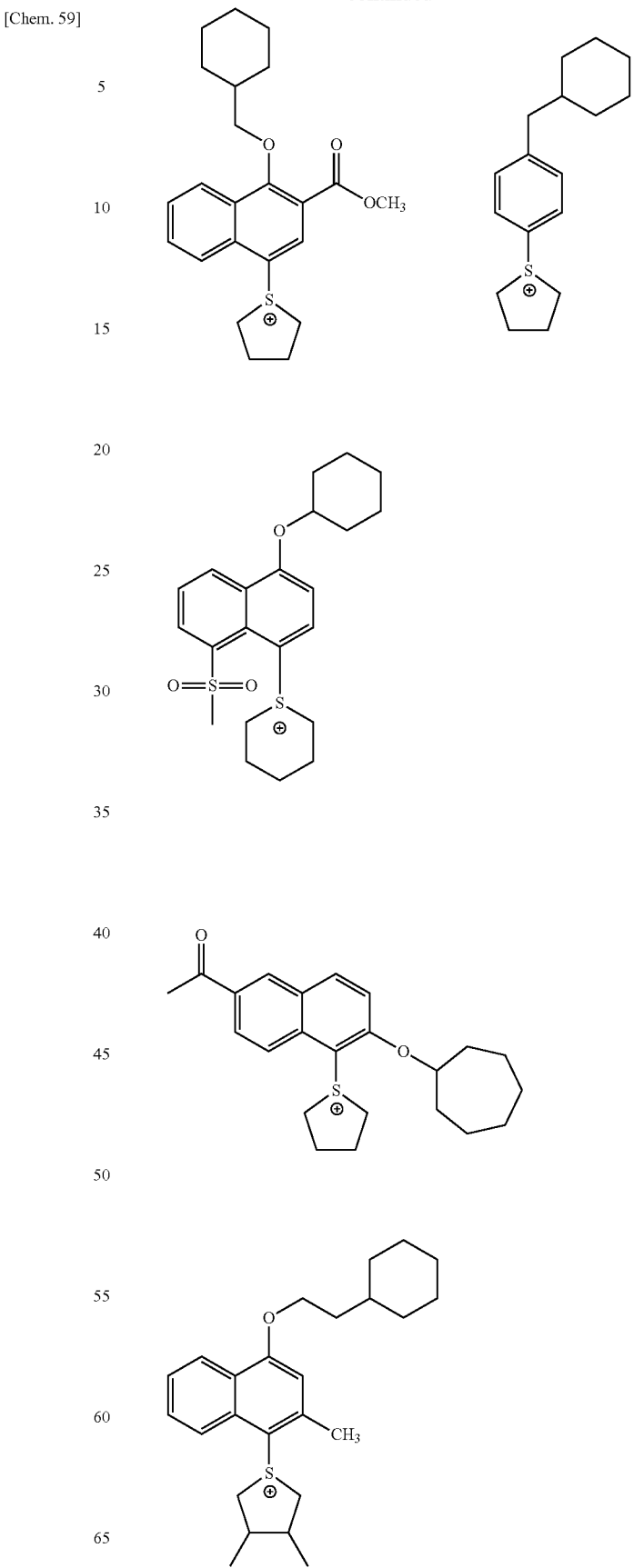

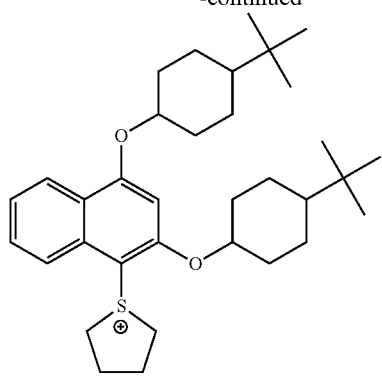
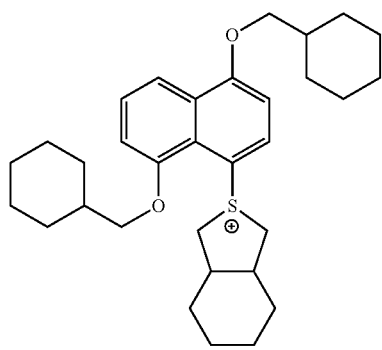
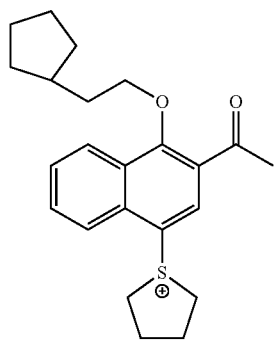
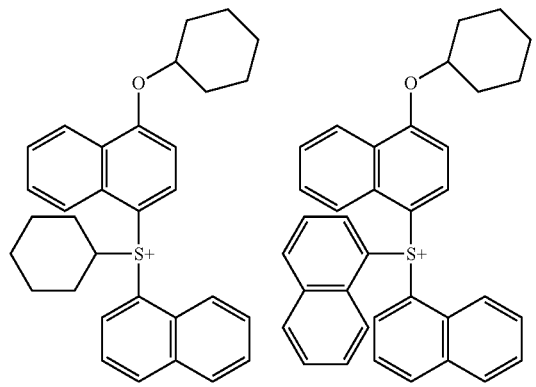
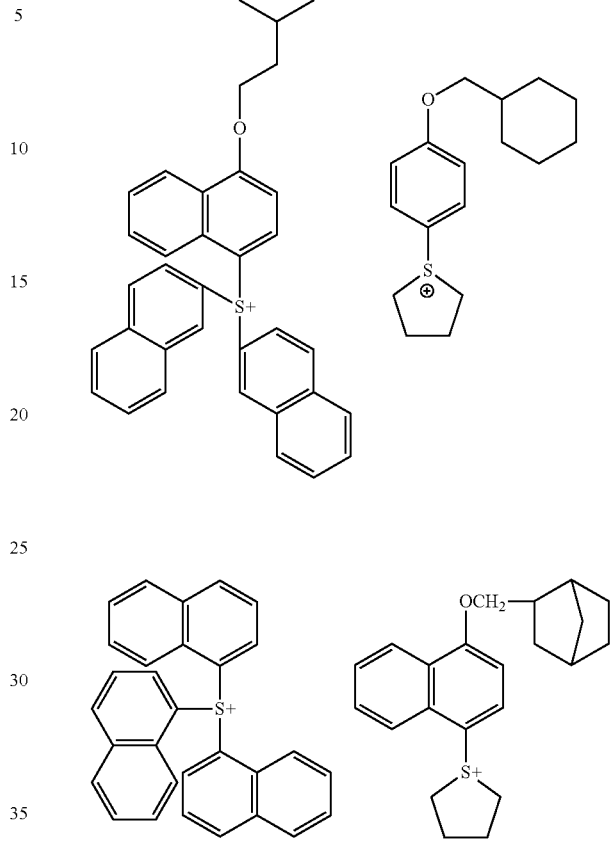
Particularly preferable examples among the compound (B) are shown below, however, the present invention is not limited to these.
[Chem. 60]
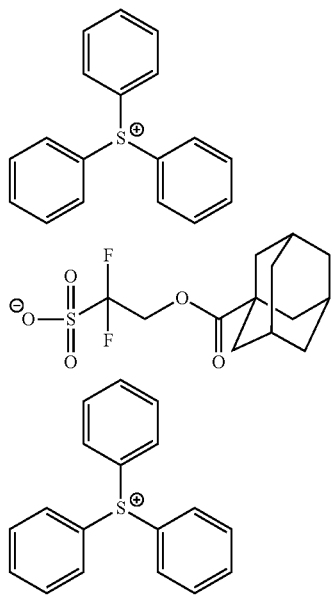

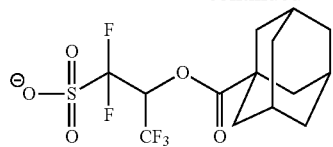
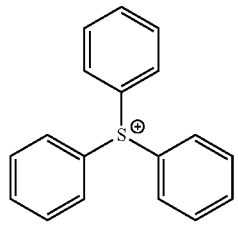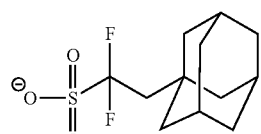
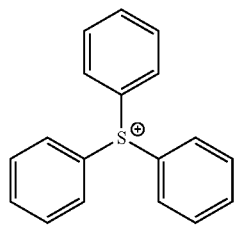
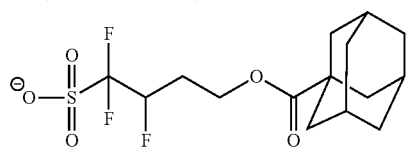
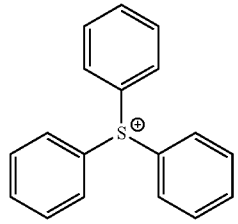
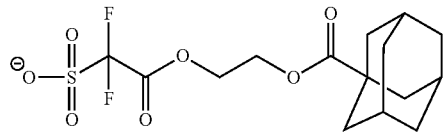
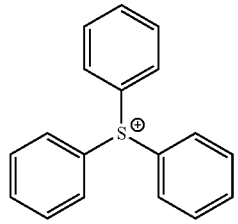
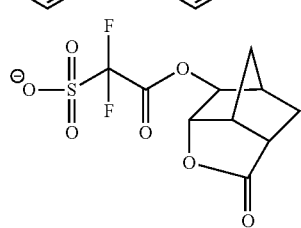
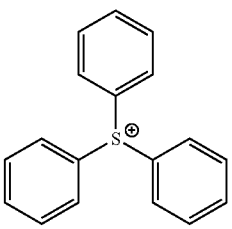
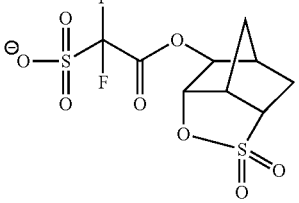
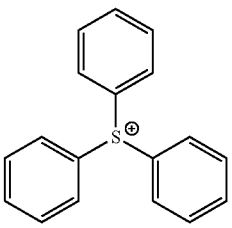
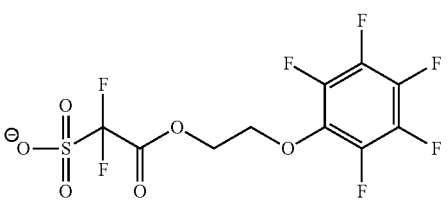
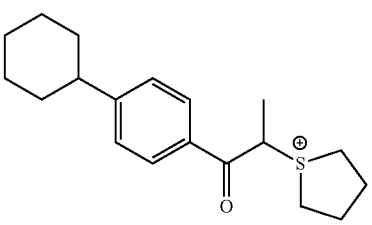
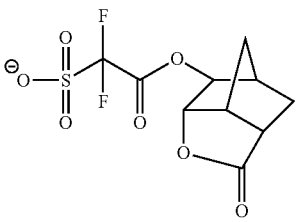
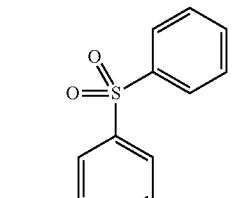
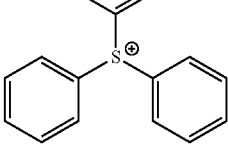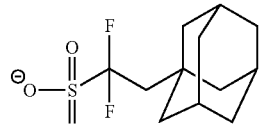

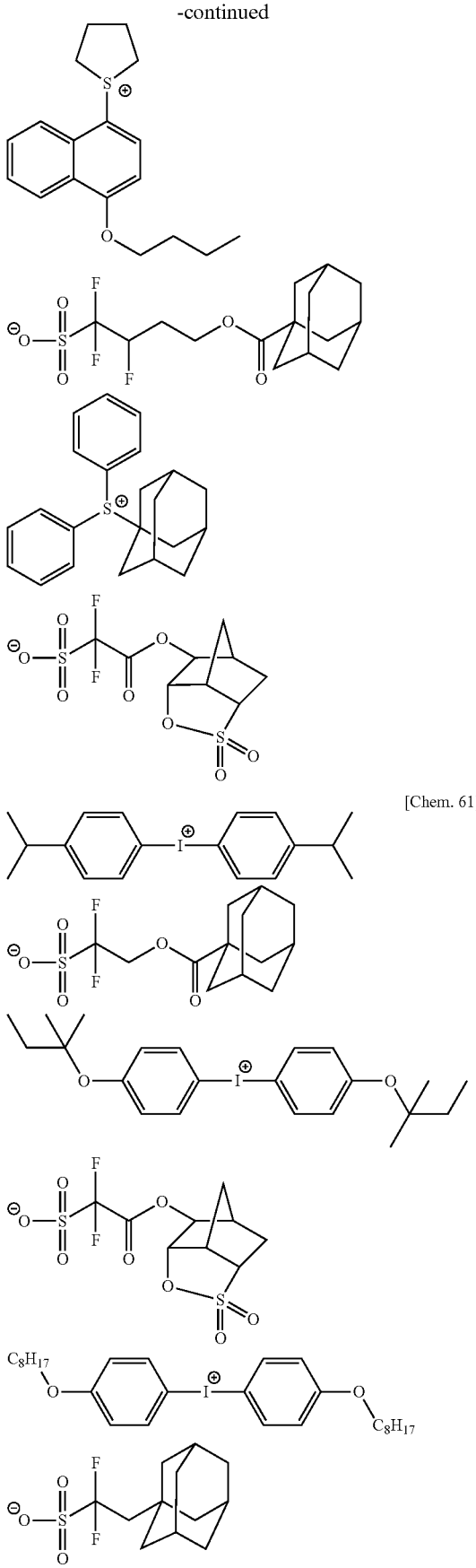

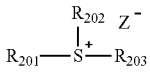

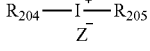

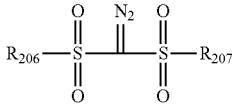

The compound (B) may be synthesized by well-known methods, and, for example, can be synthesized in accordance with the method disclosed in [0200] to [0210] of JP2010-100595A, [0051] to [0058] of WO2011/093280A, [0382] to [0385] of WO2008/153110A, and JP2007-161707A.

The compound (B) may be used either alone or as a combination of two or more.

The content of the compound (B) in the composition is preferably 0.1 to 30% by mass, more preferably 0.5 to 25% by mass, even more preferably 3 to 20% by mass, and particularly preferably 3 to 15% by mass with regard to total solids of the actinic-ray-sensitive or radiation-sensitive resin composition.

In addition, the compound (B) may be used combining with an acid generator other than the compound (B) (hereinafter, also referred to as a compound (B')).

As the compound (B'), a photoinitiator of photo cationic polymerization, a photoinitiator of photo radical polymerization, a photo color extinguishing agent of dyes, a photo discoloring agent, or well-known compounds and a mixture thereof generating organic acid by irradiation of actinic ray or radiation used for micro resist and the like, may be appropriately selected and used.

For example, a diazonium salt, a phosphonium salt, a sulfonium salt, a iodonium salt, imide sulfonate, oxime sulfonate, diazo disulfone, disulfone, o-nitrobenzyl sulfonate may be included.

The compound (B') is not particularly limited, however, may preferably include a compound represented by following General Formulae (ZI'), (ZII'), and (ZIII').

[Chem. 62]

$$R_{201}\!-\!\overset{\underset{\displaystyle R_{202}}{|}}{\underset{\displaystyle R_{203}}{S^{+}}}\quad Z^{-} \quad (ZI')$$

$$R_{204}\!-\!\overset{+}{I}\!-\!R_{205} \quad (ZII')$$
$$Z^{-}$$

$$R_{206}\!-\!\overset{\underset{\displaystyle O}{\|}}{\underset{\displaystyle O}{S}}\!-\!\overset{N_2}{\underset{\displaystyle \|}{C}}\!-\!\overset{\underset{\displaystyle O}{\|}}{\underset{\displaystyle O}{S}}\!-\!R_{207} \quad (ZIII')$$

In General Formula (ZI'), $R_{201}$, $R_{202}$, and $R_{203}$, each independently, represent an organic group.

Specific examples and preferable examples of the organic group as $R_{201}$, $R_{202}$, and $R_{203}$ are the same as those of the organic group described above as $R_{201}$, $R_{202}$, and $R_{203}$ for $A^+$ in General Formulae (B-1) to (B-3). The same applies to the fact that two of $R_{201}$ to $R_{203}$ may be bonded and form a ring structure, and may include an oxygen atom, a sulfur atom, an ester bond, an amide bond or a carbonyl group in the ring.

In addition, the organic group may also be a compound having a plurality of structures represented by general formula (ZI'). For example, a compound having a structure in which at least one of $R_{201}$ to $R_{203}$ of the compound represented by general formula (ZI') is bonded to at least one of $R_{201}$ to $R_{203}$ of another compound represented by general formula (ZI') through a single bond or a linking group may be included.

$Z^-$ represents a non-nucleophilic anion which is different from the anion in the compound represented by General Formulae (B-1) to (B-3) (an anion of which capacity to initiate a nucleophilic reactions is extremely low).

The non-nucleophilic anion as $Z^-$, for example, a sulfonate anion (an aliphatic sulfonate anion, an aromatic sulfonate anion, a camphorsulfonate anion, or the like), a carboxylate anion (an aliphatic carboxylate anion, an aromatic carboxylate anion, and an aralkyl carboxylate anion), a sulfonylimide anion, a bis(alkylsulfonyl)imide anion, a tris(alkylsulfonyl)methide anion or the like may be included.

The aliphatic site in the aliphatic sultanate anion and the aliphatic carboxylate anion may be an alkyl group or a cycloalkyl group, may preferably include a straight chain or branched alkyl group having 1 to 30 carbon atoms and a cycloalkyl group having 3 to 30 carbon atoms.

The aromatic group in the aromatic sulfonate anion and the aromatic carboxylate anion may preferably include an aryl group having 6 to 14 carbon atoms, and may include, for example, a phenyl group, a tolyl group, a naphthyl group, or the like.

The alkyl group, the cycloalkyl group, and the aryl group described above may have a substituent. Specific examples of these may include, for example, a nitro group, a halogen atom such as a fluorine atom, a carboxyl group, a hydroxyl group, an amino group, a cyano group, an alkoxy group (preferably 1 to 15 carbon atoms), a cycloalkyl group (preferably 3 to 15 carbon atoms), an aryl group (preferably 6 to 14 carbon atoms), an alkoxycarbonyl group (preferably 2 to 7 carbon atoms), an acyl group (preferably 2 to 12 carbon atoms), an alkoxycarbonyloxy group (preferably 2 to 7 carbon atoms), an alkylthio group (preferably 1 to 15 carbon atoms), an alkylsulfonyl group (preferably 1 to 15 carbon atoms), an alkyliminosulfonyl group (preferably 2 to 15 carbon atoms), an aryloxysulfonyl group (preferably 6 to 20 carbon atoms), an alkyl aryloxysulfonyl group (preferably 7 to 20 carbon atoms), a cycloalkyl aryloxysulfonyl group (preferably 10 to 20 carbon numbers), an alkyloxy alkyloxy group (preferably 5 to 20 carbon atoms), a cycloalkyl alkyloxy alkyloxy group (preferably 8 to 20 carbon atoms), or the like. Regarding the aryl group and the ring structure each group has, an alkyl group (preferably 1 to 15 carbon atoms) may be further included as a substituent.

The aralkyl group in the aralkyl carboxylate anion may preferably include an aralkyl group having 7 to 12 carbon atoms, and may include, for example, a benzyl group, a phenethyl group, a naphthylmethyl group, a naphthylethyl group, a naphthylbutyl group, or the like.

As the sulfonylimide anion, for example, a saccharin anion may be included.

The alkyl group in the bis(alkylsulfonyl)imide anion and the tris(alkylsulfonyl)methide anion is preferably an alkyl group having 1 to 5 carbon atoms.

The two alkyl groups in the bis(alkylsulfonyl)imide anion may be bonded to each other forming an alkylene group (preferably 2 to 4 carbon atoms), and may form a ring with the imide group and two sulfonyl groups.

The substituent the alkylene group formed by two alkyl groups in the bis(alkylsulfonyl)imide anion being bonded to each other may have, may include a halogen atom, or an alkyl group, an alkoxy group, an alkylthio group, an alkyloxysulfonyl group, an aryloxysulfonyl group, a cycloalkyl aryloxysulfonyl group substituted with a halogen atom, or the like, and a fluorine atom or an alkyl group substituted with a fluorine atom is preferable.

Examples of the other $Z^-$ may include fluorinated phosphate (for example, $PF_6^-$), fluorinated borate (for example, $BF_4^-$), fluorinated antimonate (for example, $SbF_6^-$), or the like.

$Z^-$ is preferably an aliphatic sulfonate anion in which at least α-position of the sulfonic acid is substituted with a fluorine atom, an aromatic sulfonate anion substituted with a fluorine atom or a group having a fluorine atom, a bis(alkylsulfonyl)imide anion of which alkyl group is substituted with a fluorine atom or a tris(alkylsulfonyl)methide anion of which alkyl group is substituted with a fluorine atom. The non-nucleophilic anion is more preferably a perfluoro aliphatic sulfonate anion (having 4 to 8 carbon atoms) or a benzene sulfonate anion having a fluorine atom, and is even more preferably a nonafluorobutane sulfonate anion, a perfluorooctane sulfonate anion, a pentafluorobenzene sulfonate anion or 3,5-bis(trifluoromethyl)benzene sulfonate anion.

From the viewpoint of acid strength, pKa of the acid generated is preferably −1 or less for sensitivity improvement.

The more preferable (Z1') component may include a compound having cation structures (Z1-1), (Z1-2), (Z1-3) or (Z1-4) as the compound (B) (However, anion structures are different from those of a compound represented by any of General Formulae (B-1) to (B-3)).

Next, General Formulae (ZII') and (ZIII') will be described.

The General Formulae (ZII') and (ZIII'), $R_{204}$ to $R_{207}$, each independently represent an aryl group, an alkyl group, or a cycloalkyl group.

The aryl group, the alkyl group, and the cycloalkyl group of $R_{204}$ to $R_{207}$ are the same aryl group, alkyl group, and cycloalkyl group of $R_{201}$ to $R_{203}$ for $A^+$ in General Formulae (B-1) to (B-3) described above.

The aryl group, the alkyl group, and the cycloalkyl group of $R_{204}$ to $R_{207}$ may have a substituent. This substituent may also include the same substituent the aryl group, the alkyl group, and the cycloalkyl group $R_{201}$ to $R_{203}$ for $A^+$ in General Formulae (B-1) to (B-3) described above may have.

$Z^-$ represents a non-nucleophilic anion, and may include the same non-nucleophilic anion as $Z^-$ in General Formula (ZI').

The acid generator (B') which may be combined with the acid generator of the present invention may also further include a compound represented by following General Formulae (ZIV'), (ZV'), and (ZVI').

[Chem. 63]

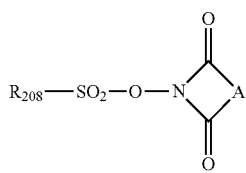

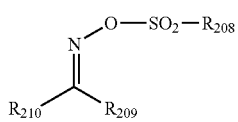
(ZVI′)

In General Formulae (ZIV′) to (ZVI′), Ar$_3$ and Ar$_4$, each independently, represent an aryl group.

R$_{208}$, R$_{209}$, and R$_{210}$, each independently, represent an alkyl group, a cycloalkyl group or an aryl group.

A represents an alkylene group, an alkenylene group or an arylene group.

Specific examples of the aryl group of Ar$_3$, Ar$_4$, R$_{208}$, R$_{209}$, and R$_{210}$ may include the same specific examples of the aryl group of R$_{201}$, R$_{202}$, and R$_{203}$ in General Formula (ZI′-1).

Specific examples of the alkyl group and the cycloalkyl group of R$_{208}$, R$_{209}$, and R$_{210}$ may include the same specific examples of the alkyl group and the cycloalkyl group of R$_{201}$, R$_{202}$, and R$_{203}$ for A$^+$ in General Formulae (B-1) to (B-3) described above.

The alkylene group of A may include an alkylene group having 1 to 12 carbon atoms (for example, a methylene group, an ethylene group, a propylene group, an isopropylene group, a butylene group, an isobutylene group, or the like), the alkenylene group of A may include an alkenylene group having 2 to 12 carbon atoms (for example, an ethenylene group, a propenylene group, a butenylene group, or the like), and the arylene group of A may include an arylene group having 6 to 10 carbon atoms (for example, a phenylene group, a tolylene group, a naphthylene group, or the like), respectively.

Among the acid generators which may be combined with the acid generator of the present invention, particularly preferable examples are shown below.

[Chem. 64]

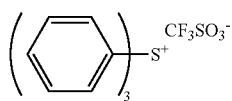
(z1)

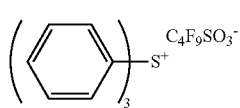
(z2)

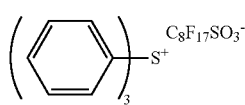
(z3)

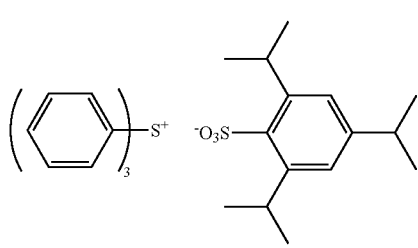
(z4)

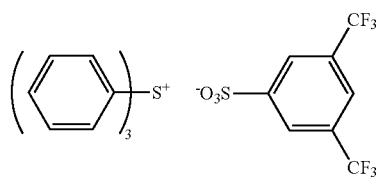
(z5)

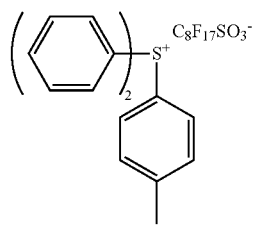
(z6)

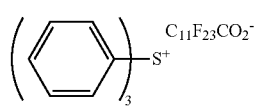
(z7)

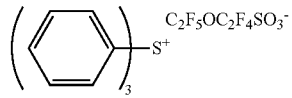
(z8)

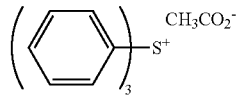
(z9)

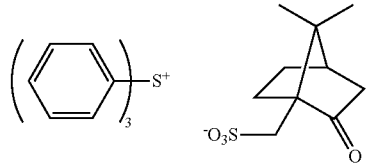
(z10)

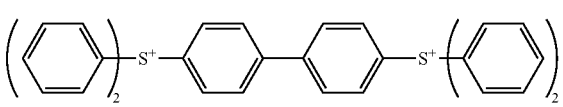
(z11)

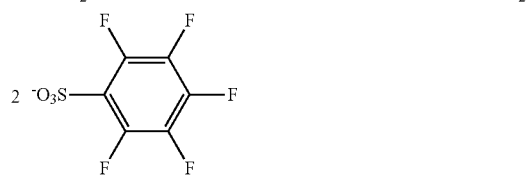
(z12)

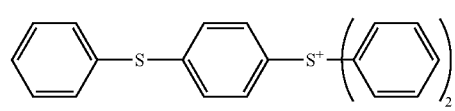
(z13)

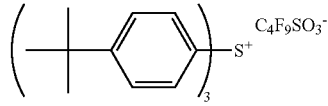

-continued
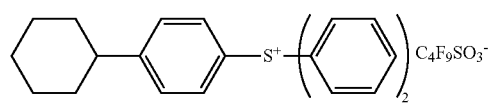 (z14)
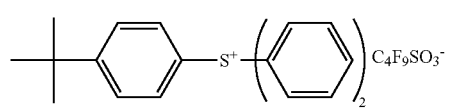 (z15)
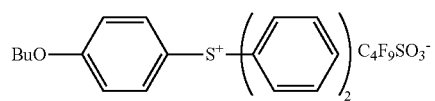 (z16)
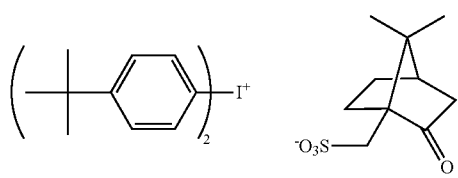 (z17)
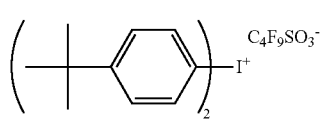 (z18)
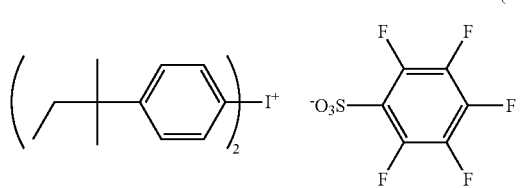 (z19)
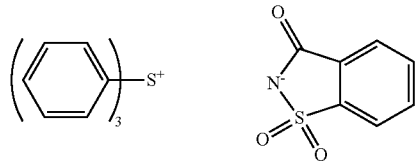 (z20)
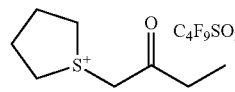 (z21)
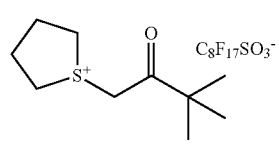 (z22)
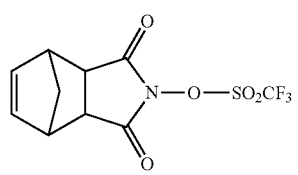 (z23)
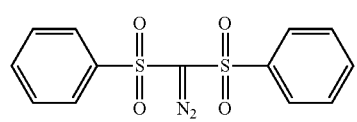 (z24)
-continued
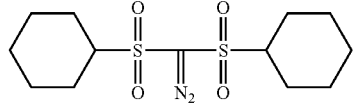 (z25)
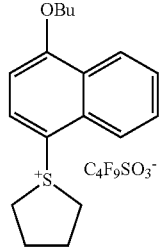 (z26)
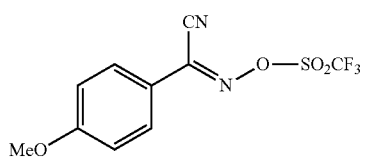 (z27)
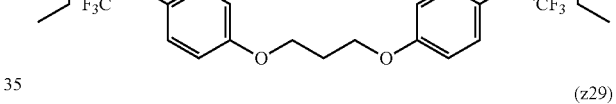 (z28)
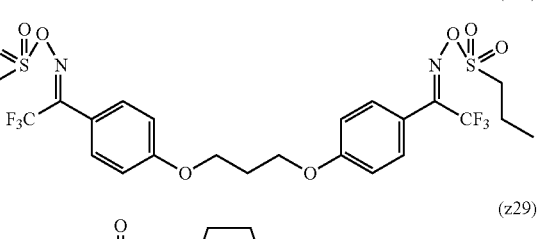 (z29)
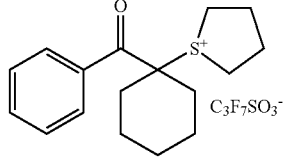 (z30)
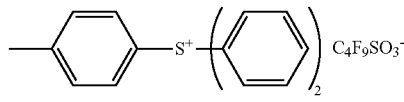 (z31)
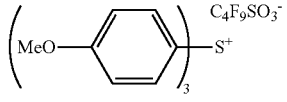 (z32)
(z33)
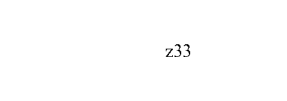

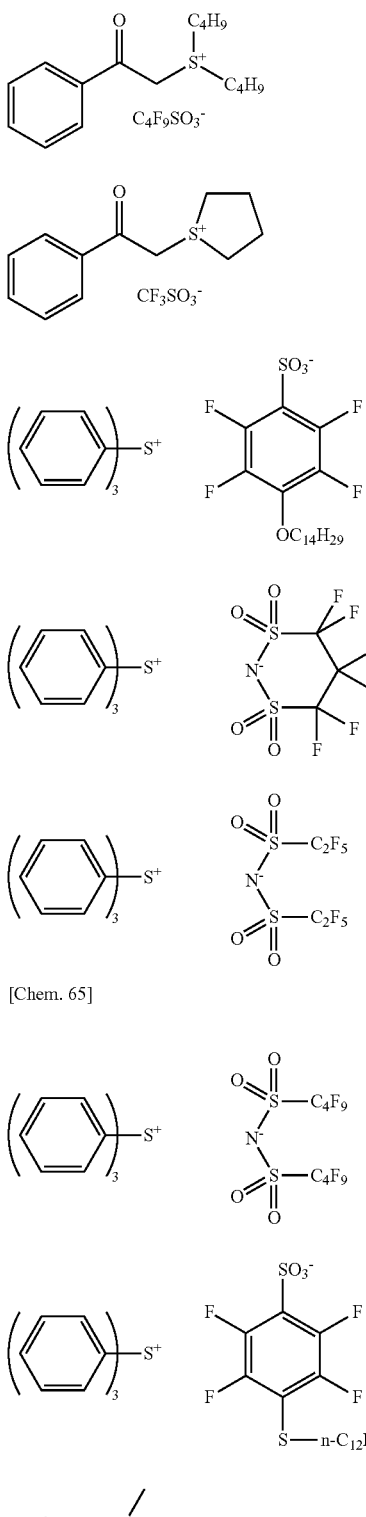
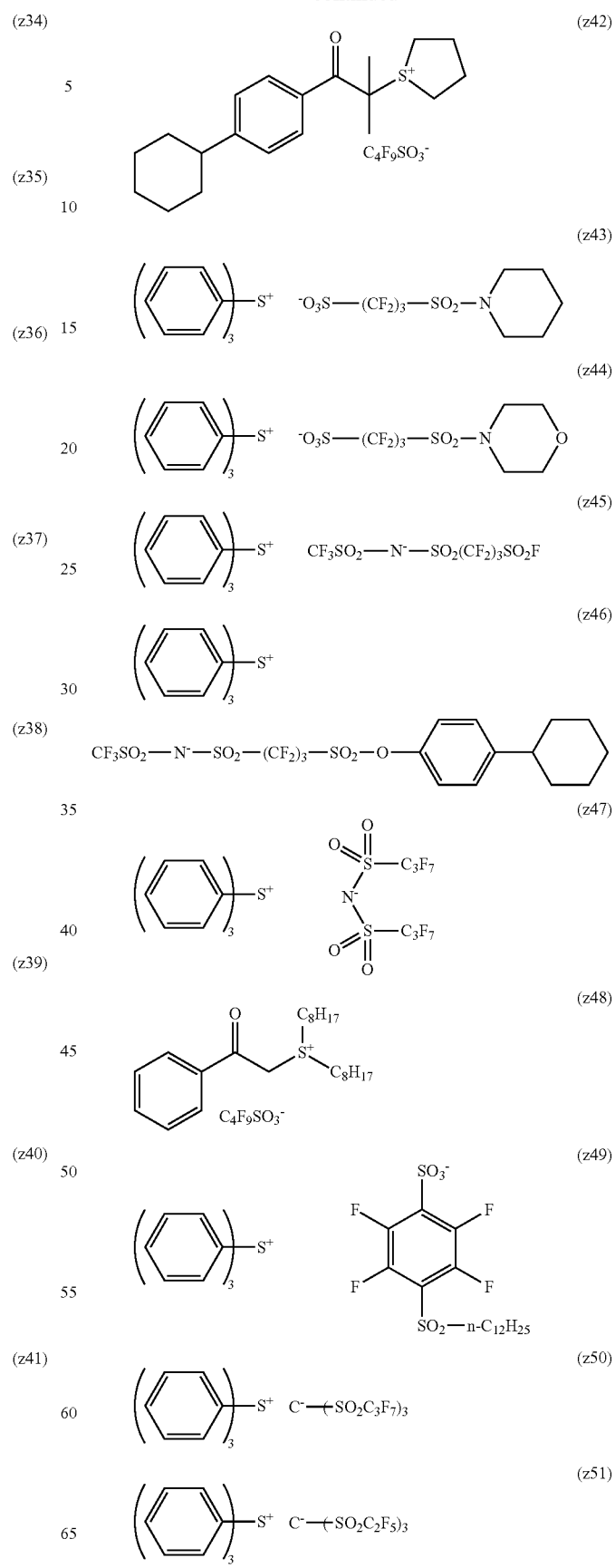

-continued

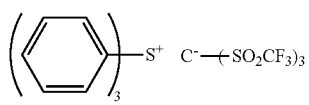 (z52)

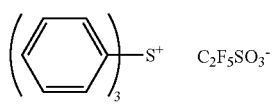 (z53)

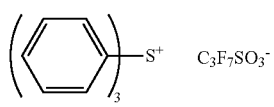 (z54)

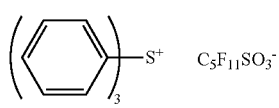 (z55)

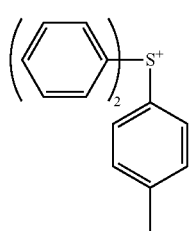 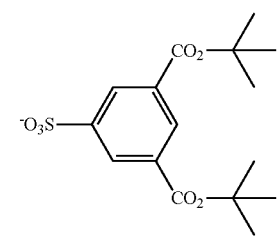 (z56)

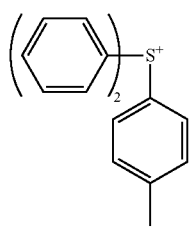 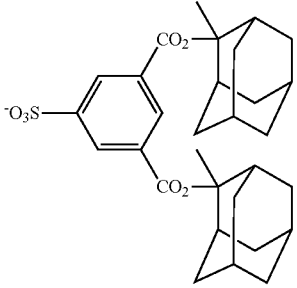 (z57)

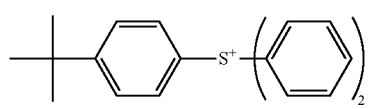 (z58)

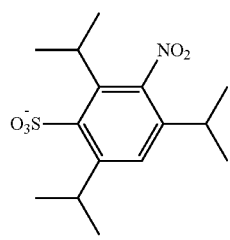 (z59)

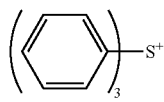

-continued

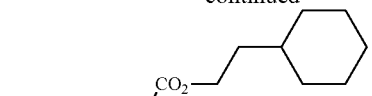 (z60)

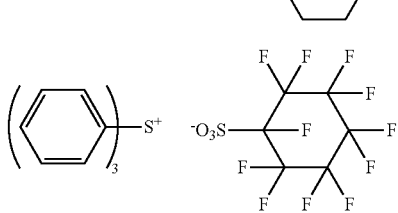 (z61)

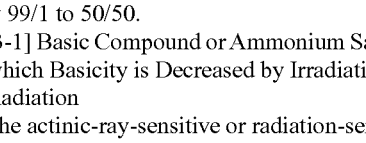 (z62)

The amount of the acid generator used when the compound (B) and the compound (B') are used in combination is preferably 99/1 to 20/80 as mass ratio (compound (B)/compound (B')), more preferably 99/1 to 40/60, and even more preferably 99/1 to 50/50.

[3-1] Basic Compound or Ammonium Salt Compound (C) of which Basicity is Decreased by Irradiation of Actinic Ray or Radiation The actinic-ray-sensitive or radiation-sensitive resin composition of the present invention preferably contains a basic compound or an ammonium salt compound (hereinafter, also referred to as a "compound (C)") of which basicity is decreased by irradiation of actinic ray or radiation.

The compound (C) is preferably a compound (C-1) having a basic functional group or an ammonium group, and a group generating an acidic functional group by irradiation of actinic ray or radiation. That is, the compound (C) is preferably a basic compound having a basic functional group and a group generating an acidic functional group by irradiation of actinic ray or radiation, or an ammonium salt compound having an ammonium group and a group generating an acidic functional group by irradiation of actinic ray or radiation.

Specifically, a compound in which an anion, in which a proton is detached from the basic functional group or the ammonium group, and the acidic functional group of the compound having an acidic functional group, and an onium cation form a salt, or the like, may be included.

Here, as the basic functional group, for example, an atomic group containing a structure such as a crown ether, a primary to tertiary amine, a nitrogen-containing heterocyclic ring (pyridine, imidazole, pyrazine, or the like) may be included. In addition, as the preferable structure of the ammonium group, for example, an atomic group containing a structure such as primary to tertiary ammonium, pyridinium, imidazolinium, pyrazinium or the like, may be included. In addition, as the basic functional group, a functional group having a nitrogen atom is preferable, a structure having a primary to tertiary amino group or a nitrogen-containing heterocyclic structure is more preferable. In these structures, all the atoms adjacent to the nitrogen atom included in the structure are preferably a carbon atom or a hydrogen atom from the viewpoint of improving basicity. In addition, from the viewpoint of improving basicity, it is preferable that an electron-withdrawing functional group (a carbonyl group, a sulfonyl group, a cyano group, a halogen atom, or the like) be not directly bonded to the nitrogen atom.

As the acidic functional group, a carboxylate group, a sulfonate group, a group having —X—NH—X— (X=CO or $SO_2$) structure, or the like, may be included.

As the onium cation, a sulfonium cation, an iodonium cation, or the like, may be included. More specifically, those described as the cation part of General Formulae (ZI) and (ZII) of the (B) acid generator, or the like, may be included.

More specifically, as the compound (C) or (C-1) generated by decomposition by irradiation of actinic ray or radiation, and of basicity is decreased, a compound represented by following General Formula (PA-I), (PA-II), or (PA-III), and a compound represented by following General Formula (PA-II) or (PA-III) is particularly preferable from the point of viewpoint of highly balancing excellent effects regarding LWR, uniformity of the local pattern dimension, and DOF.

First, a compound represented by General Formula (PA-I) will be described.

$$Q\text{-}A_1\text{-}(X)_n\text{—}B\text{—}R \qquad (PA\text{-}I)$$

In General Formula (PA-I), $A_1$ represents a single bond or a divalent linking group.

Q represents —$SO_3H$, or —$CO_2H$. Q is equivalent to an acidic functional group generated by irradiation of actinic ray or radiation.

X represents —$SO_2$—, or —CO—.

n represents 0 or 1.

B represents a single bond, an oxygen atom, or —N(Rx)-.

Rx represents a hydrogen atom or a monovalent organic group.

R represents a monovalent organic group having a basic functional group or a monovalent organic group having an ammonium group.

The divalent linking group in $A_1$ is preferably a divalent linking group having 2 to 12 carbon atoms, and may include, for example, an alkylene group, a phenylene group or the like. An alkylene group having at least one fluorine atom is more preferable, and the number of carbon atoms is preferably 2 to 6 and the number of carbon atoms is more preferably 2 to 4. A linking group such as an oxygen atom or a sulfur atom may be included in the alkylene chain. Particularly, the alkylene group is preferably an alkylene group in which 30 to 100% of the number of hydrogen atoms is substituted with a fluorine atom, and it is more preferable that the carbon atom bonded to a Q site have a fluorine atom. Furthermore, a perfluoroalkylene group is preferable, and a perfluoroalkylethylene group, a perfluoroalkylpropylene group or a perfluoroalkylbutylene group, is more preferable.

The monovalent organic group in Rx preferably has 4 to 30 carbon atoms, and may include, for example, an alkyl group, a cycloalkyl group, an aryl group, an aralkyl group, an alkenyl group, or the like.

The alkyl group in Rx may have a substituent, is preferably a straight chain or branched alkyl group having 1 to 20 carbon atoms, and may have an oxygen atom, a sulfur atom, a nitrogen atom in the alkyl chain.

As the alkyl group having a substituent group, a group in which a straight chain or branched alkyl group is substituted with a cycloalkyl group (for example, an adamantylmethyl group, an adamantylethyl group, a cyclohexylethyl group, a camphor-residue, or the like) may be included.

The cycloalkyl group in Rx may have a substituent, is preferably a cycloalkyl group having 3 to 20 carbon atoms, and may have an oxygen atom in the ring.

The aryl group in Rx may have a substituent, and is preferably an aryl group having 6 to 14 carbon atoms.

The aralkyl group in Rx may have a substituent, and is preferably an aralkyl group having 7 to 20 carbon atoms.

The alkenyl group in Rx may have a substituent, and may include, for example, a group having a double bond at any position of the alkyl group included as Rx.

The preferable partial structure of the basic functional group may include, for example, crown ether, primary to tertiary amine, a nitrogen-containing heterocyclic ring (pyridine, imidazole, pyrazine, or the like).

The preferable partial structure of the ammonium group may include, for example, primary to tertiary ammonium, pyridinium, imidazolinium, pyrazinium or the like.

In addition, as the basic functional group, a functional group having a nitrogen atom is preferable, a structure having a primary to tertiary amino group or a nitrogen-containing heterocyclic structure is more preferable. In these structures, all the atoms adjacent to the nitrogen atom included in the structure are preferably a carbon atom or a hydrogen atom from the viewpoint of improving basicity. In addition, from the viewpoint of improving basicity, it is preferable that an electron-withdrawing functional group (a carbonyl group, a sulfonyl group, a cyano group, a halogen atom, or the like) be not directly bonded to the nitrogen atom.

The monovalent organic group in the monovalent organic group including such a structure (R group) preferably has 4 to 30 carbon atoms, and may include, for example, an alkyl group, a cycloalkyl group, an aryl group, an aralkyl group, an alkenyl group or the like, and each group may have a substituent.

The alkyl group, the cycloalkyl group, the aryl group, the aralkyl group and the alkenyl group in the alkyl group, the cycloalkyl group, the aryl group, the aralkyl group and the alkenyl group including the basic functional group or the ammonium group in R are the same alkyl group, cycloalkyl group, aryl group, aralkyl group, and alkenyl group included as Rx, respectively.

As the substituent each group described above may have, for example, a halogen atom, a hydroxyl group, a nitro group, a cyano group, a carboxyl group, a carbonyl group, a cycloalkyl group (preferably 3 to 10 carbon atoms), an aryl group (preferably 6 to 14 carbon atoms), an alkoxy group (preferably 1 to 10 carbon atoms), an acyl group (preferably 2 to 20 carbon atoms), an acyloxy group (preferably 2 to 10 carbon atoms), an alkoxycarbonyl group (preferably 2 to 20 carbon atoms), an aminoacyl group (preferably, 2 to 20 carbon atoms), or the like, may be included. For a cyclic structure in the aryl group, the cycloalkyl group or the like, the substituent may further include an alkyl group (preferably 1 to 20 carbon atoms). For the aminoacyl group, the substituent may further include one or two alkyl groups (preferably 1 to 20 carbon atoms).

When B is —N(Rx)-, it is preferable that R and Rx may be bonded to each other and form a ring. By forming the ring structure, stability is improved and storage stability of the composition using this is improved. The number of carbon atoms forming a ring is preferably 4 to 20, the ring may be a monocyclic type or a polycyclic type, and may contain an oxygen atom, a sulfur atom, or a nitrogen atom in the ring.

The monocyclic structure may include a 4- to 8-membered ring containing a nitrogen atom. As the polycyclic structure, a structure formed by combining two, three or more monocyclic structures. The monocyclic structure and the polycyclic structure may have a substituent, and is preferably, for example, a halogen atom, a hydroxyl group, a cyano group, a carboxyl group, a carbonyl group, a cycloalkyl group (preferably 3 to 10 carbon atoms), an aryl group (preferably 6 to 14 carbon atoms), an alkoxy group (preferably 1 to 10 carbon atoms), an acyl group (preferably 2 to 15 carbon atoms), an acyloxy group (preferably 2 to 15 carbon atoms), an alkoxycarbonyl group (preferably 2 to 15 carbon atoms), an aminoacyl group (preferably 2 to 20 carbon atoms), or the like. For a cyclic structure in the aryl group, the cycloalkyl group or the like, the substituent may further include an alkyl group (preferably 1 to 15 carbon atoms). For the aminoacyl group, the substituent may further include one or two alkyl groups (preferably 1 to 15 carbon atoms).

Among the compounds represented by General Formula (PA-I), compounds of which Q site is sulfonic acid can be synthesized using a general sulfonamide reaction. For example, a method in which a sulfonamide bond is formed by selectively reacting one of the sulfonyl halide parts of a bis-sulfonyl halide compound with an amine compound, and then, the other sulfonyl halide part is hydrolyzed, or a method in which a cyclic sulfonic acid anhydride is reacted with an amine compound and is ring-opened, may be used.

Next, a compound represented by General Formula (PA-II) will be described.

$Q_1\text{-}X_1\text{—}NH\text{—}X_2Q_2$ (PA-II)

In General Formula (PA-II), $Q_1$ and $Q_2$, each independently, represent a monovalent organic group. However, any one of $Q_1$ and $Q_2$ has a basic functional group. $Q_1$ and $Q_2$ are bonded to each other forming a ring, and the ring formed may have a basic functional group.

$X_1$ and $X_2$, each independently, represent —CO— or —$SO_2$—.

In addition, —NH— is equivalent to an acidic functional group generated by irradiation of actinic ray or radiation.

In General Formula (PA-II), the monovalent organic group as $Q_1$ and $Q_2$ preferably has 1 to 40 carbon atoms, and may include, for example, an alkyl group, a cycloalkyl group, an aryl group, an aralkyl group, an alkenyl group, or the like.

The alkyl group in $Q_1$ and $Q_2$ may have a substituent, is preferably a straight chain or branched alkyl group having 1 to 30 carbon atoms, and may have an oxygen atom, a sulfur atom, a nitrogen atom in the alkyl chain.

The cycloalkyl group in $Q_1$ and $Q_2$ may have a substituent, is preferably a cycloalkyl group having 3 to 20 carbon atoms, and may have an oxygen atom or a nitrogen atom in the ring.

The aryl group in $Q_1$ and $Q_2$ may have a substituent, and is preferably an aryl group having 6 to 14 carbon atoms.

The aralkyl group in $Q_1$ and $Q_2$ may have a substituent, and is preferably an aralkyl group having 7 to 20 carbon atoms.

The alkenyl group in $Q_1$ and $Q_2$ may have a substituent, and may include, for example, a group having a double bond at any position of the above alkyl group.

As the substituent each group described above may have, for example, a halogen atom, a hydroxyl group, a nitro group, a cyano group, a carboxyl group, a carbonyl group, a cycloalkyl group (preferably 3 to 10 carbon atoms), an aryl group (preferably 6 to 14 carbon atoms), an alkoxy group (preferably 1 to 10 carbon atoms), an acyl group (preferably 2 to 20 carbon atoms), an acyloxy group (preferably 2 to 10 carbon atoms), an alkoxycarbonyl group (preferably 2 to 20 carbon atoms), an aminoacyl group (preferably, 2 to 10 carbon atoms), or the like, may be included. For a cyclic structure in the aryl group, the cycloalkyl group or the like, the substituent may further include an alkyl group (preferably 1 to 10 carbon atoms). For the aminoacyl group, the substituent may further include an alkyl groups (preferably 1 to 10 carbon atoms). The alkyl group having a substituent may include, for example, a perfluoroalkyl group such as a perfluoromethyl group, a perfluoroethyl group, a perfluoropropyl group or a perfluorobutyl group.

As a preferable partial structure of the basic functional group at least one of $Q_1$ and $Q_2$ may have, the same partial structure described as the basic functional group R of General Formula (PA-I) has may be included.

As the structure in which $Q_1$ and $Q_2$ are bonded to each other forming a ring and the ring formed may have a basic functional group, for example, a structure in which the organic group of $Q_1$ and $Q_2$ is further bonded to an alkylene group, an oxy group, an imino group or the like, may be included.

In General Formula (PA-II), at least one of $X_1$ and $X_2$ is preferably —$SO_2$—.

Next, a compound represented by General Formula (PA-III) will be described.

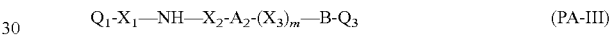

$Q_1\text{-}X_1\text{—}NH\text{—}X_2\text{-}A_2\text{-}(X_3)_m\text{—}B\text{-}Q_3$ (PA-III)

In General Formula (PA-III), $Q_1$ and $Q_3$, each independently, represent a monovalent organic group. However, any one of $Q_1$ and $Q_3$ has a basic functional group. $Q_1$ and $Q_3$ are bonded to each other forming a ring, and the ring formed may have a basic functional group.

$X_1$, $X_2$ and $X_3$, each independently, represent —CO— or —$SO_2$—.

$A_2$ represents a divalent linking group.

B represents a single bond, an oxygen atom or —N(Qx)-.

Qx represents a hydrogen atom or a monovalent organic group.

When B is —N(Qx)-, $Q_3$ and Qx may be bonded to each other and form a ring.

m represents 0 or 1.

In addition, —NH— is equivalent to an acidic functional group generated by irradiation of actinic ray or radiation.

$Q_1$ is synonymous with $Q_1$ in General Formula (PA-II).

The organic group of $Q_3$ may include the same organic group of $Q_1$ and $Q_2$ in General Formula (PA-II).

As the structure in which $Q_1$ and $Q_3$ are bonded to each other forming a ring and the ring formed may have a basic functional group, for example, a structure in which the organic group of $Q_1$ and $Q_3$ is further bonded to an alkylene group, an oxy group, an imino group or the like, may be included.

The divalent linking group in $A_2$ is preferably a divalent linking group (1 to 8 carbon atoms) having a fluorine atom, and may include, for example, an alkylene group (1 to 8 carbon atoms) having a fluorine atom, a phenylene group having a fluorine atom or the like. An alkylene group having a fluorine atom is more preferable, and the number of carbon atoms is preferably 2 to 6 and the number of carbon atoms is more preferably 2 to 4. A linking group such as an oxygen atom or a sulfur atom may be included in the alkylene chain. The alkylene group is preferably an alkylene group in which 30 to 100% of the number of hydrogen atoms are substituted with a fluorine atom, more preferably a perfluoroalkylene group, is preferable, and particularly preferably a perfluoroalkylene group having 2 to 4 carbon atoms.

The monovalent organic group in Qx is preferably an organic group having 4 to 30 carbon atoms, and may include, for example, an alkyl group, a cycloalkyl group, an aryl group, an aralkyl group, an alkenyl group, or the like. The alkyl group, the cycloalkyl group, the aryl group, the aralkyl group and the alkenyl group are the same as Rx in the above Formula (PA-1).

In General Formula (PA-III), $X_1$, $X_2$, and $X_3$ are preferably —$SO_2$—.

The compound (C) is preferably a sulfonium salt compound of the compound represented by General Formula (PA-I), (PA-II) or (PA-III), or an iodonium salt compound of the compound represented by General Formula (PA-I), (PA-II) or (PA-III), and more preferably a compound represented by following General Formula (PA1) or (PA2).

[Chem. 66]

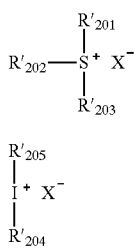

(PA1)

(PA2)

In General Formula (PA1), $R'_{201}$, $R'_{202}$ and $R'_{203}$, each independently, represent an organic group, and specifically, is the same $R_{201}$, $R_{202}$ and $R_{203}$ of Formula ZI in the above (B) component.

$X^-$ represents a sulfonate anion or a carboxylate anion in which a hydrogen atom of the —$SO_3H$ site or the —COOH site of the compound represented by General Formula (PA-I) is detached, or an anion in which a hydrogen atom of the —NH— site of the compound represented by General Formula (PA-II) or (PA-III) is detached.

In General Formula (PA2), $R'_{204}$ and $R'_{205}$, each independently, represent an aryl group, an alkyl group or a cycloalkyl group, and specifically, is the same $R_{204}$ and $R_{205}$ of Formula ZII in the above (B) component.

$X^-$ represents a sulfonate anion or a carboxylate anion in which a hydrogen atom of the —$SO_3H$ site or the —COOH site of the compound represented by General Formula (PA-I) is detached, or an anion in which a hydrogen atom of the —NH— site of the compound represented by General Formula (PA-II) or (PA-III) is detached.

The compound (C) is decomposed by irradiation of actinic ray or radiation, and produces, for example, a compound represented by General Formula (PA-I) (PA-II) or (PA-III).

The compound represented by General Formula (PA-I) is a compound of which basicity is reduced, disappeared, or changed from basicity to acidity compared to the compound (C), by having a sulfonate group or a carboxylate group with a basic functional group or an ammonium group.

The compound represented by General Formula (PA-II) or (PA-III) is a compound of which basicity is reduced, disappeared, or changed from basicity to acidity compared to the compound (C), by having an organic sulfonylimino group or an organic carbonylimino group with a basic functional group.

In the present invention, basicity being reduced by irradiation of actinic ray or radiation means that an acceptor property of the compound (C) for protons (acid generated by irradiation of actinic ray or radiation) is reduced by irradiation with radiation or actinic rays. And the acceptor property being reduced means that, when an equilibrium reaction in which a non-covalent bond complex, a proton adduct, is produced from the compound having a basic functional group and a proton, or an equilibrium reaction in which a counter-cation of the compound having an ammonium group is exchanged with a proton, an equilibrium constant in chemical equilibrium thereof is reduced.

It is postulated that, by containing the compound (C) of which basicity is reduced by active light or radiation irradiation in the resist film, the acceptor property of the compound (C) is sufficiently expressed in the unexposed area, an unintended reaction between acid diffused from the exposed area and the like, and the resin (P) may be suppressed, and the acceptor property of the compound (C) is reduced in the exposed area as well, therefore, the intended reaction between acid and the resin (P) occurs more reliably, and also with the contribution of such an action mechanism, line width roughness (LWR), uniformity of the local pattern dimension, depth of focus (DOF), and the pattern with an excellent pattern shape are obtained.

In addition, basicity can be confirmed by a pH measurement, and the calculated value can be determined by commercially available software.

Hereinafter, specific examples the compound (C) which produces a compound represented by General Formula (PA-I) by irradiation of actinic ray or radiation are shown below, however, the present invention is not limited to these.

[Chem. 67]

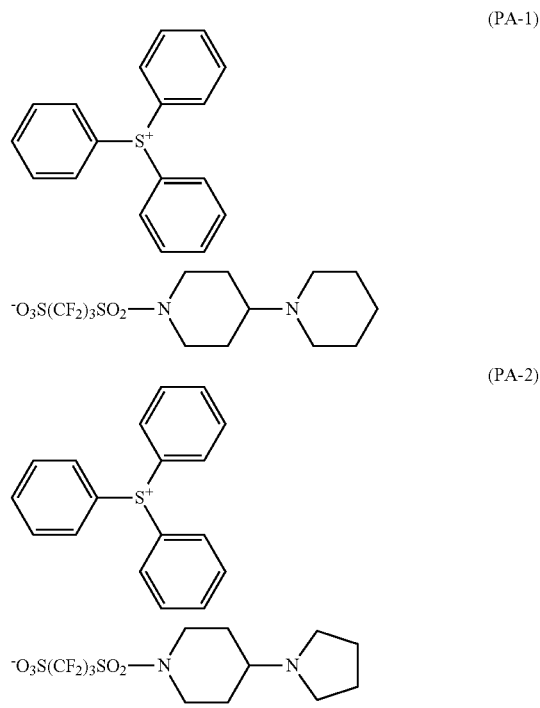

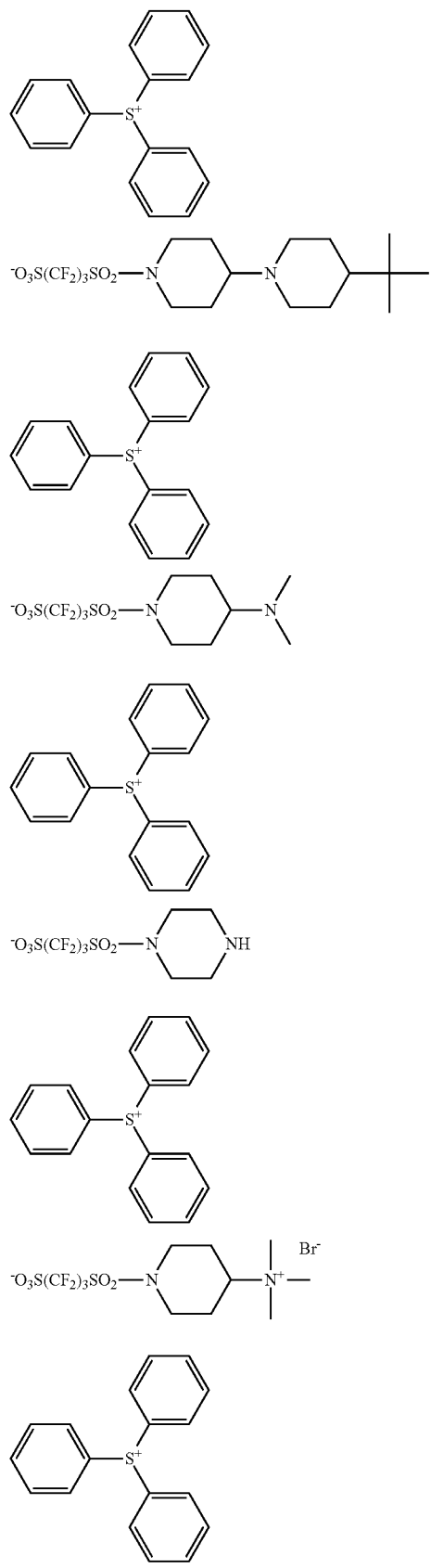

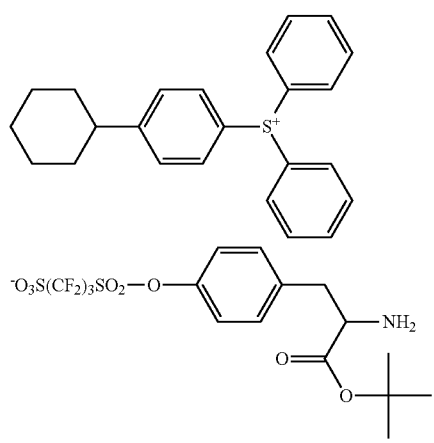 (PA-12)
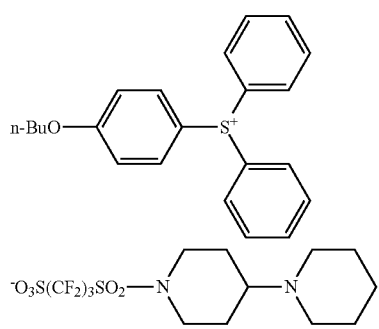 (PA-13)
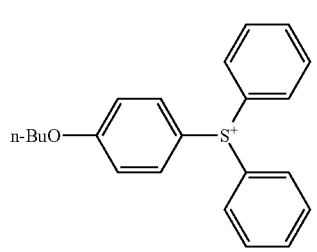 (PA-14)
(PA-15)
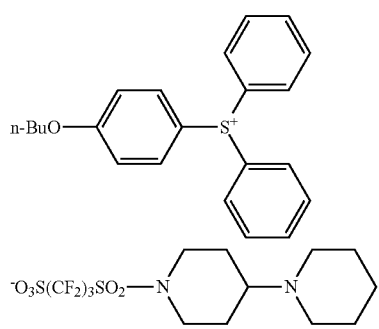
(PA-16)
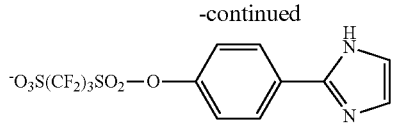
[Chem. 68]
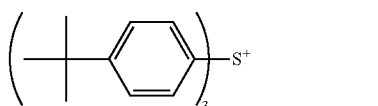 (PA-17)
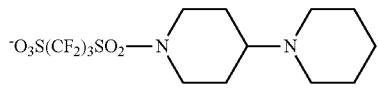 (PA-18)
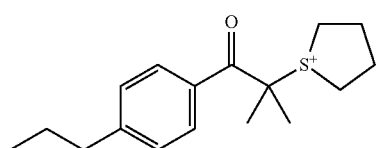 (PA-19)
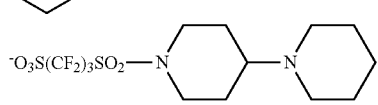 (PA-20)
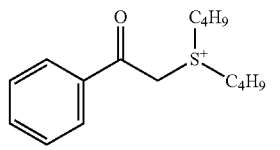
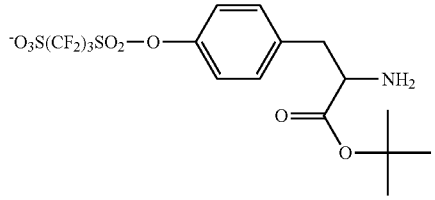 (PA-21)
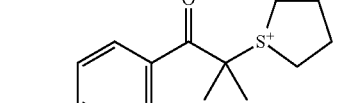
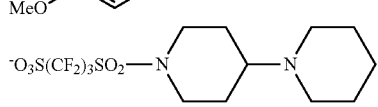 (PA-22)
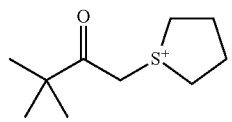
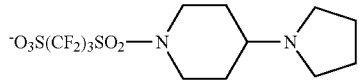
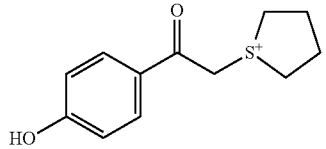

-continued
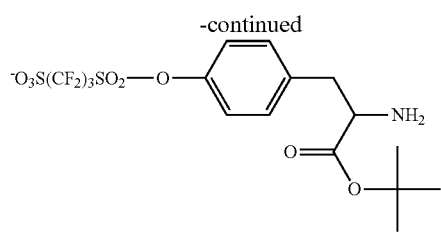
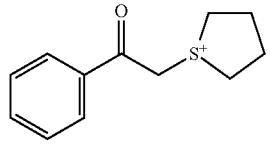
(PA-23)
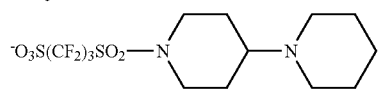
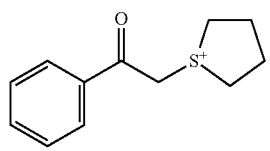
(PA-24)
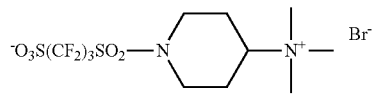
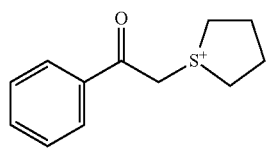
(PA-25)
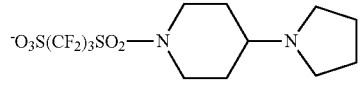
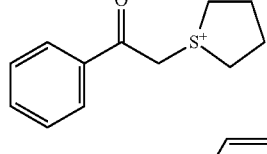
(PA-26)
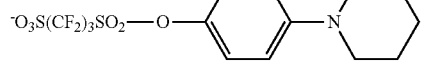
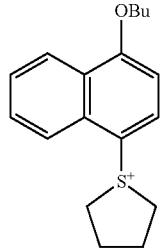
(PA-27)
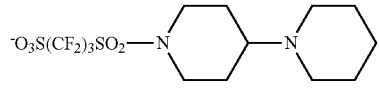
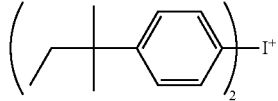
(PA-28)
-continued
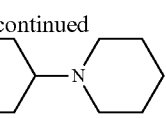
(PA-29)
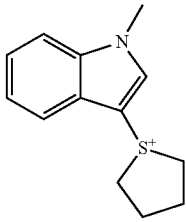
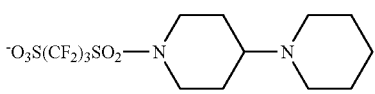
(PA-30)
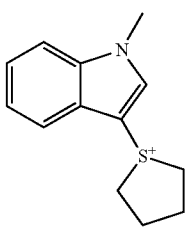
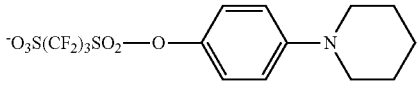
(PA-31)
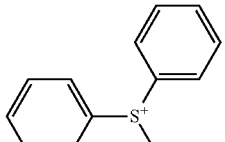
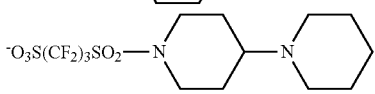
(PA-32)
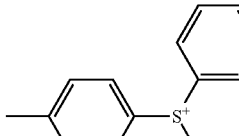
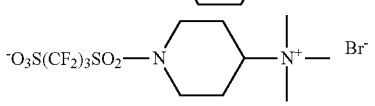

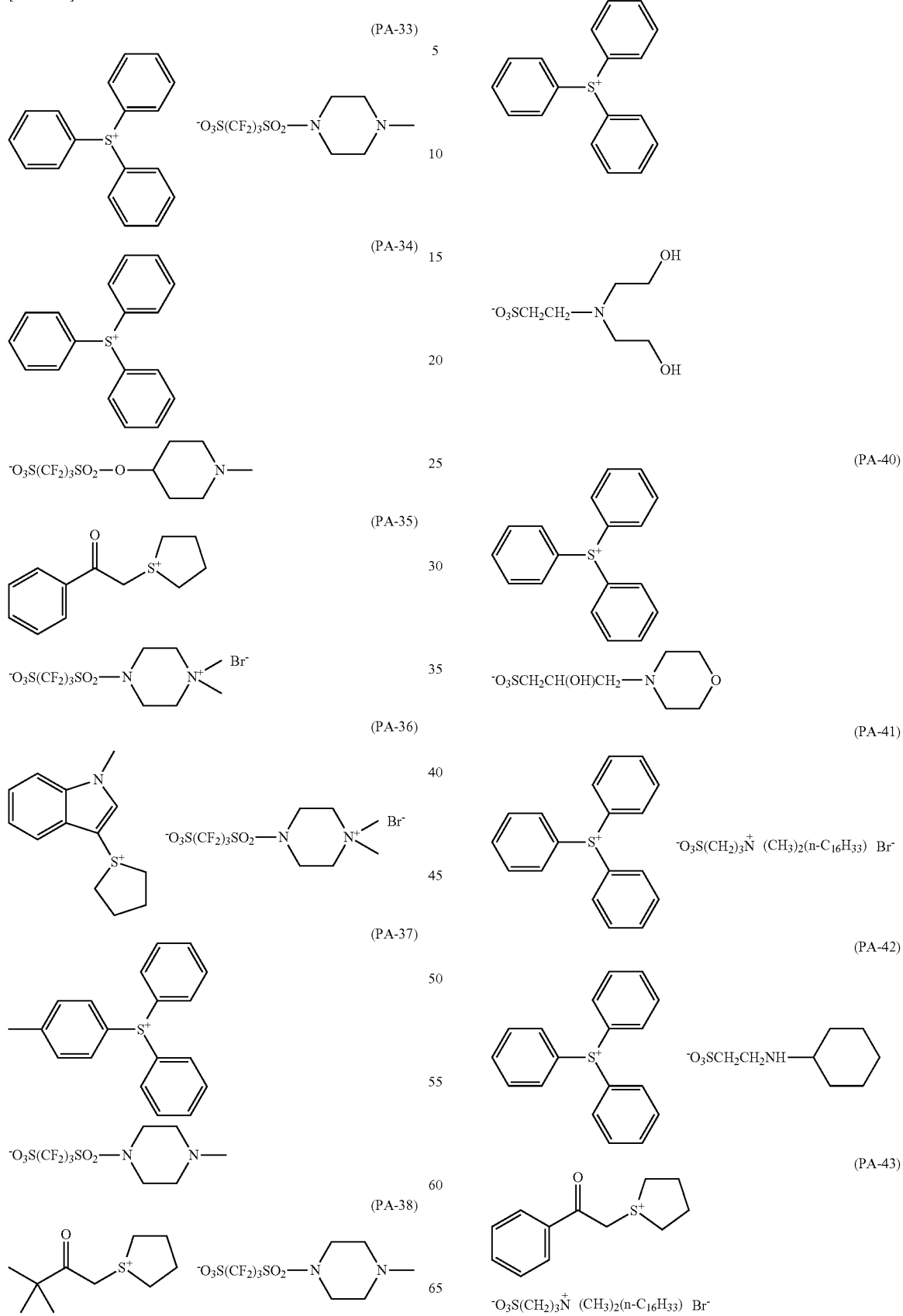

-continued
(PA-44)
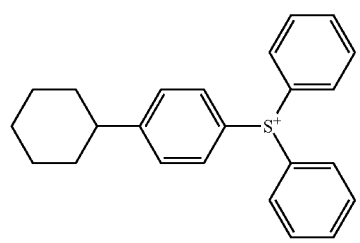
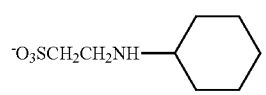
(PA-45)
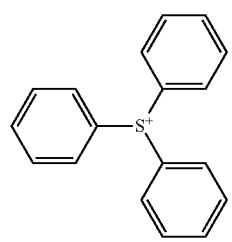
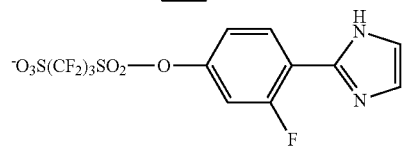
(PA-46)
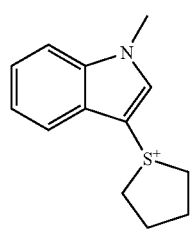 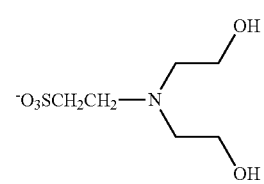
(PA-47)
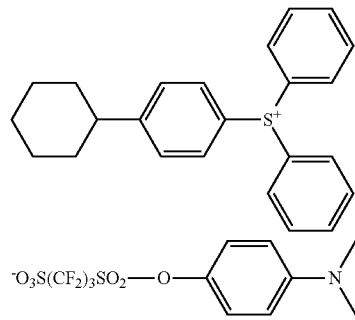
(PA-48)
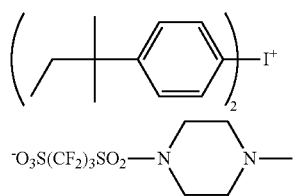
-continued
[Chem. 70]
(PA-49)
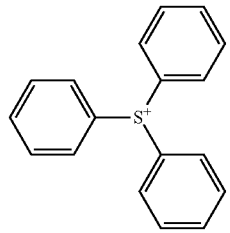
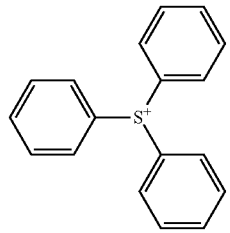
(PA-50)
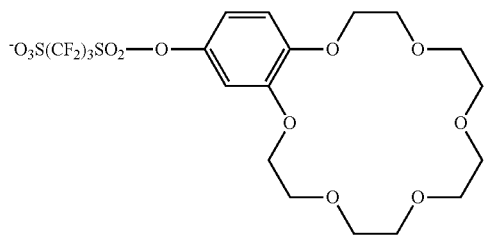
(PA-51)
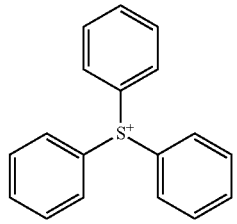 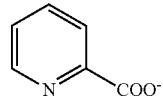
(PA-52)
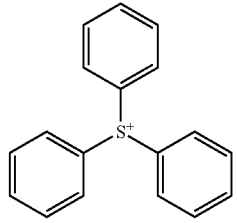 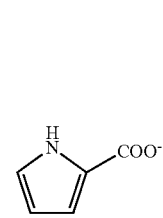
(PA-53)
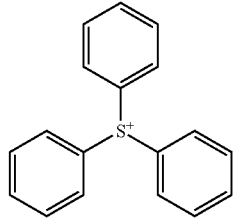 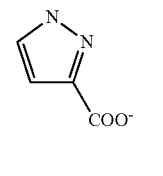
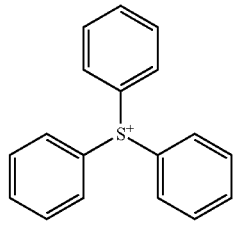 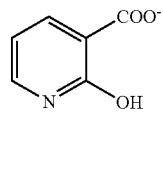

-continued (PA-54)
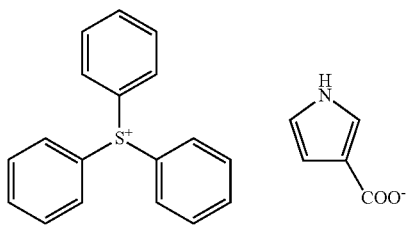

(PA-55)
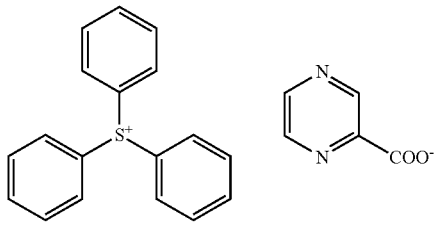

(PA-56)
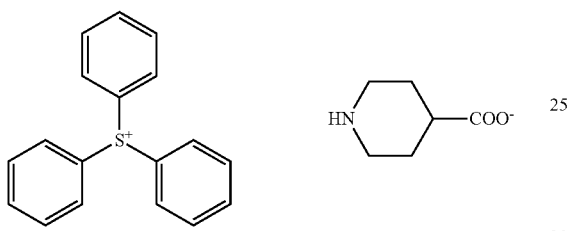

(PA-57)
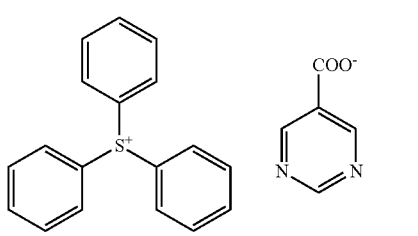

(PA-58)
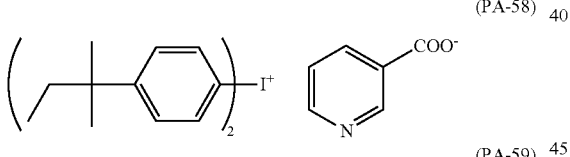

(PA-59)
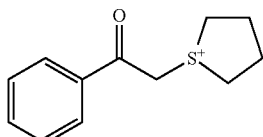

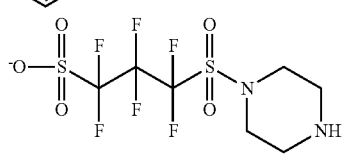

(PA-60)
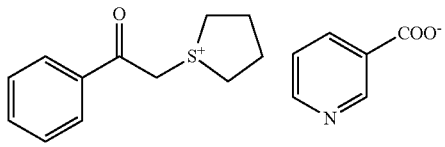

These compounds can be readily synthesized using a salt-exchange method disclosed in JP1999-501909A (JP-H11-501909A) or JP2003-246786A from a compound represented by General Formula (PA-I), or a lithium, a sodium and a potassium salt thereof, and a hydroxide, a bromide, or a chloride of sulfonium or iodonium. In addition, it can be synthesized in accordance with the synthesis methods disclosed in JP1995-333851A (JP-H07-333851A).

Hereinafter, specific examples the compound (C) which produces a compound represented by General Formula (PA-II) or (PA-III) by irradiation of actinic ray or radiation are shown below, however, the present invention is not limited to these.

[Chem. 71]

(PA-61)
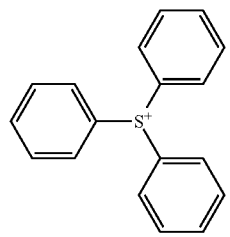
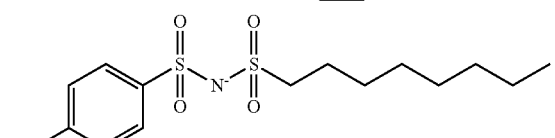

(PA-62)
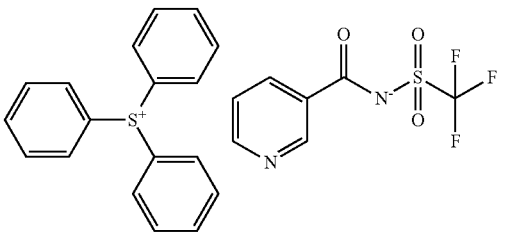

(PA-63)
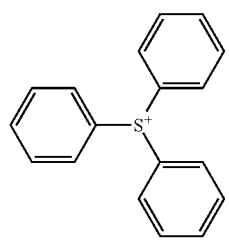
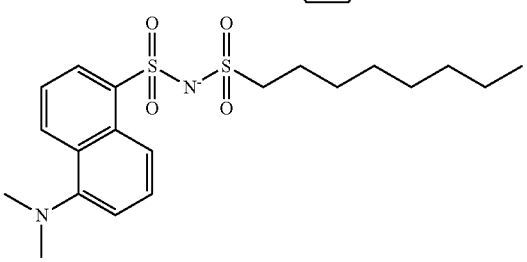

(PA-64)
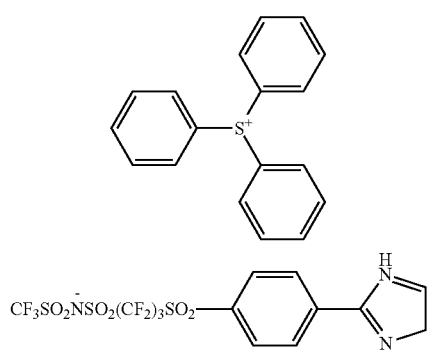
(PA-68)
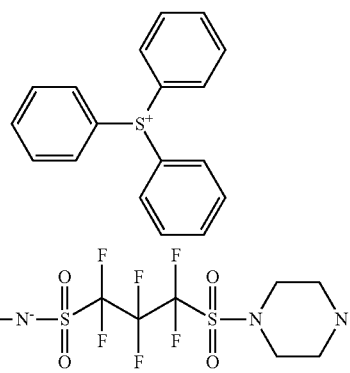
(PA-65)
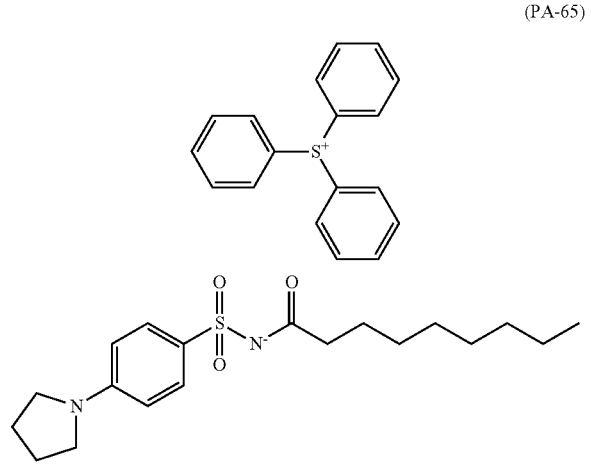
(PA-69)
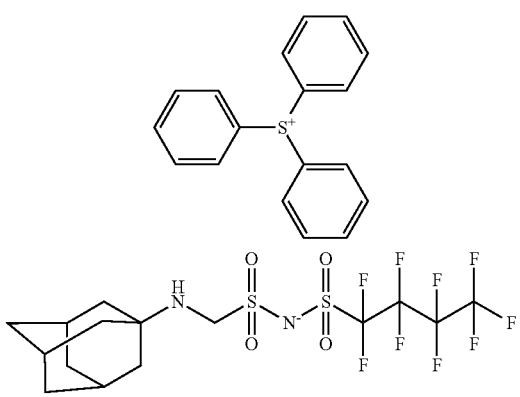
(PA-66)
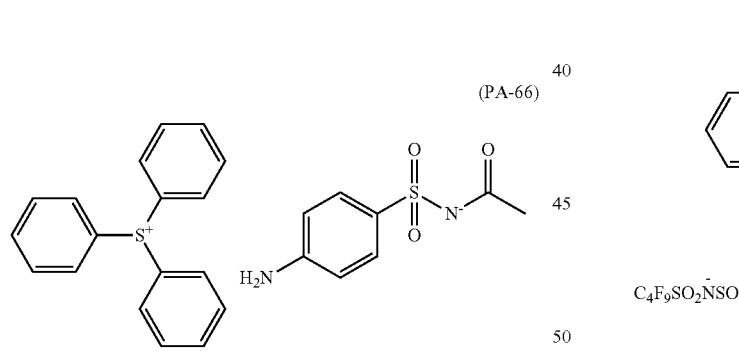
(PA-70)
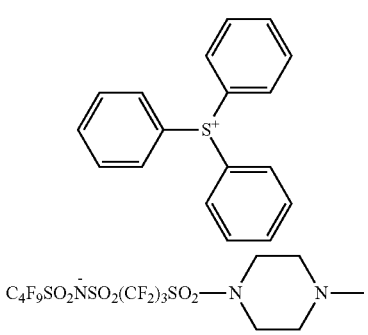
(PA-67)
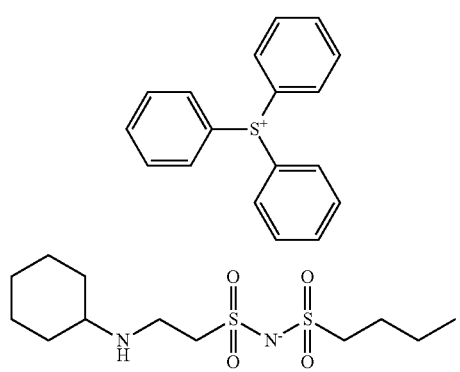
(PA-71)
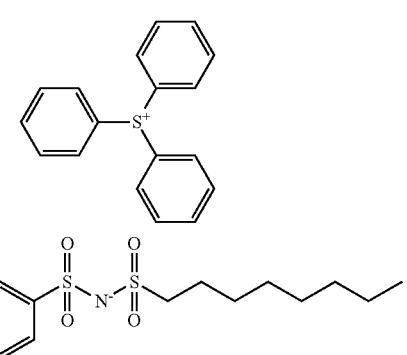

(PA-72)
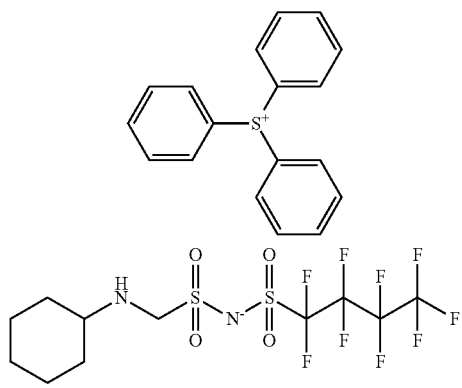
(PA-76)
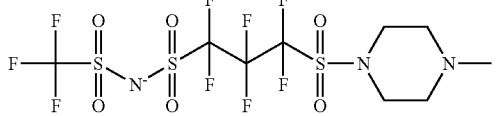
(PA-73)
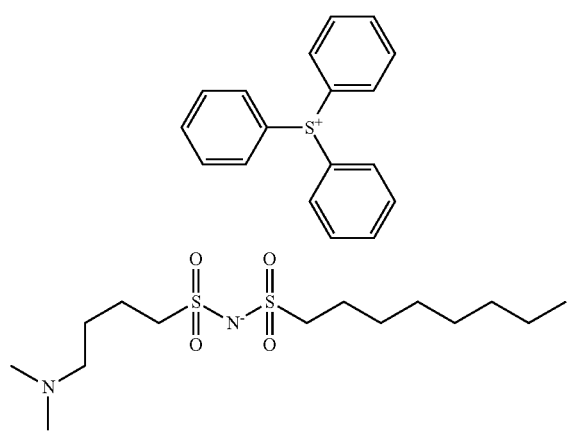
[Chem. 72]
(PA-77)
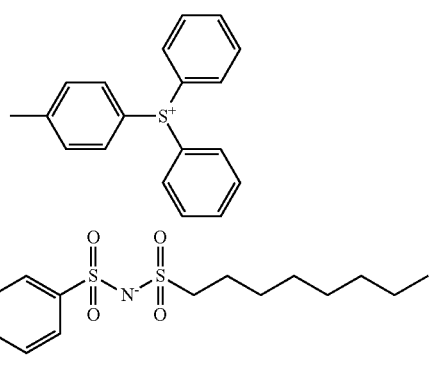
(PA-74)
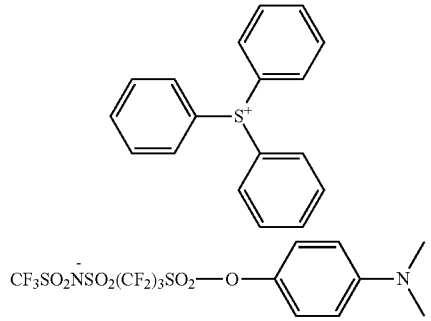
(PA-78)
CF$_3$SO$_2$NSO$_2$(CF$_2$)$_3$SO$_2$O—
(PA-75)
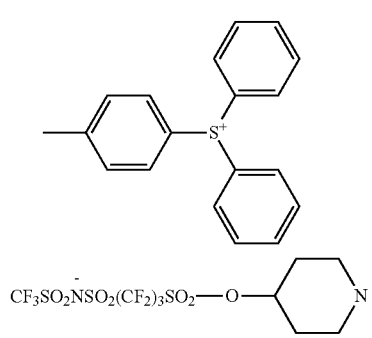
(PA-79)
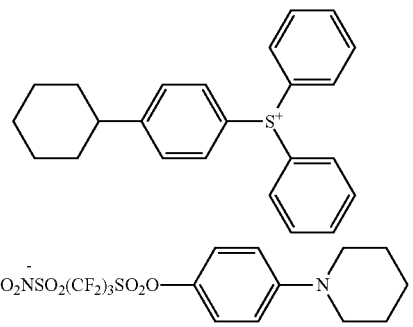

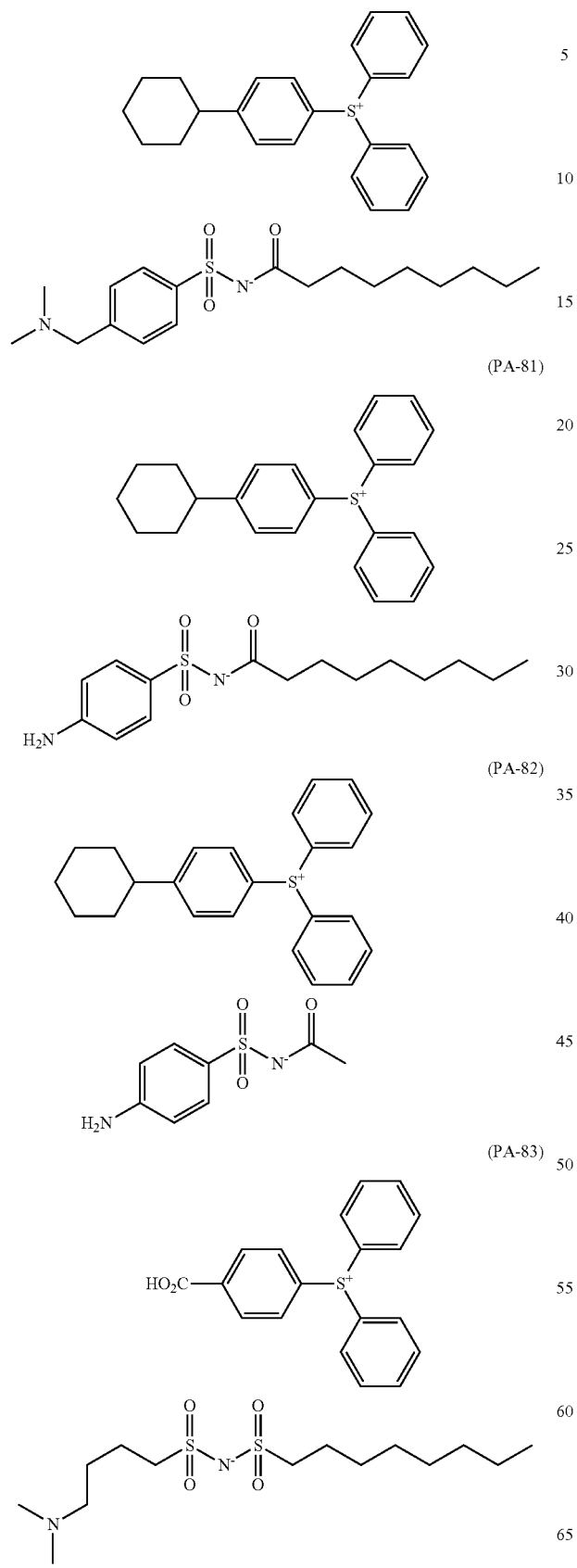

-continued
(PA-88)
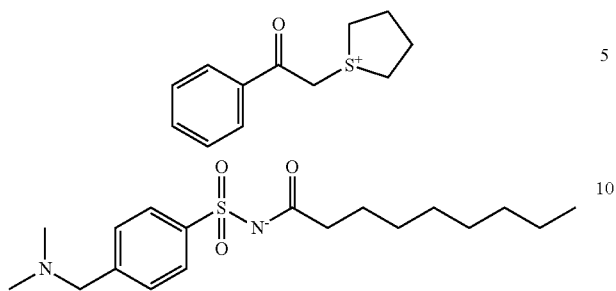
(PA-89)
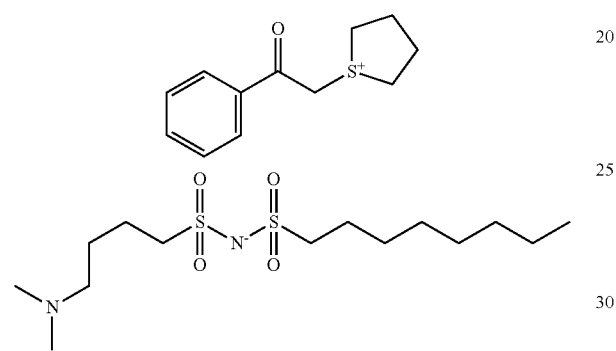
(PA-90)
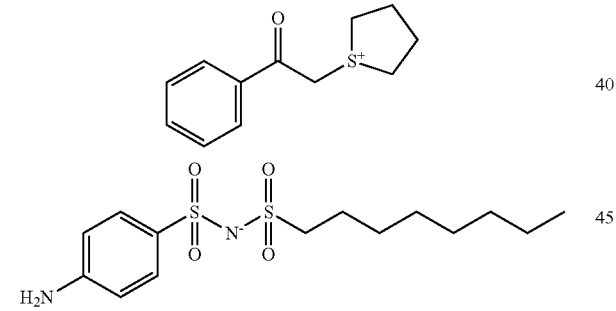
(PA-91)
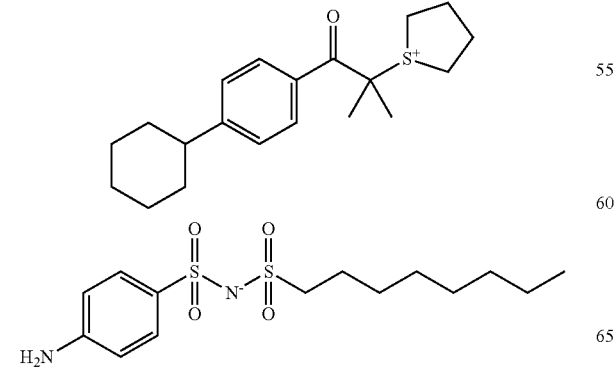
-continued
(PA-92)
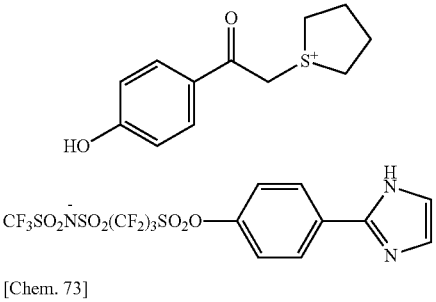
[Chem. 73]
(PA-93)
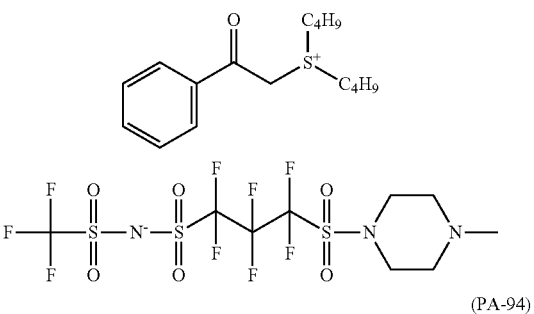
(PA-94)
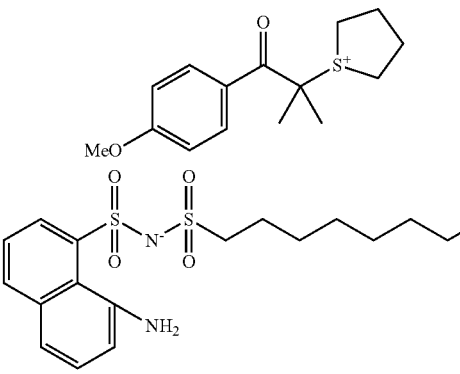
(PA-95)
(PA-96)

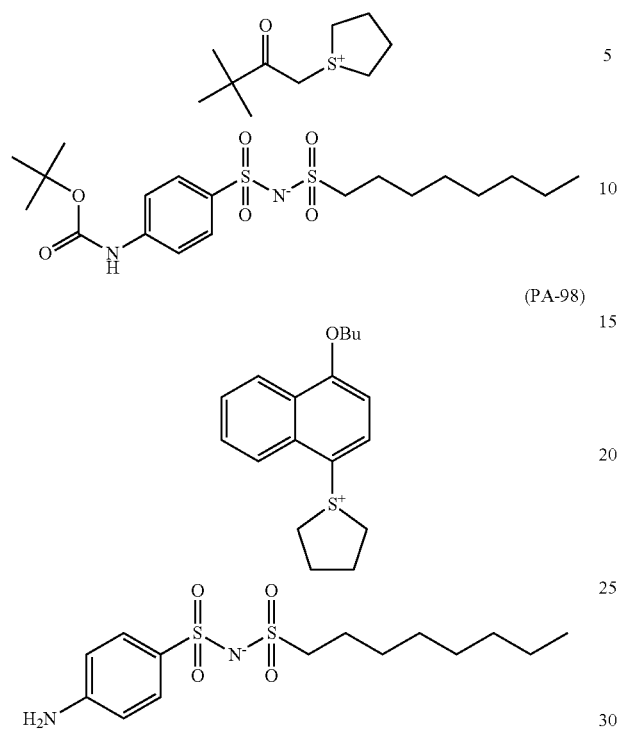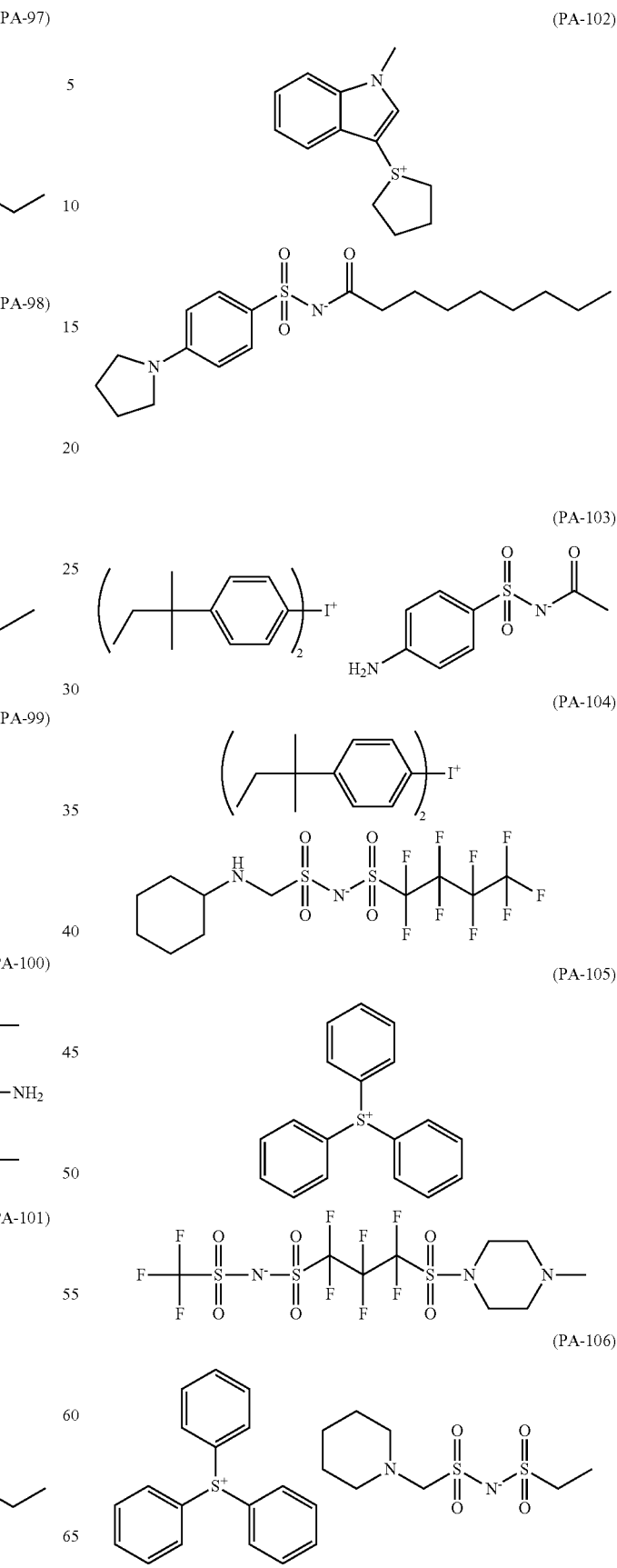

(PA-107)
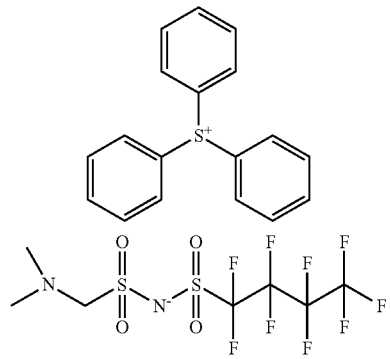
[Chem. 74]
(PA-108)
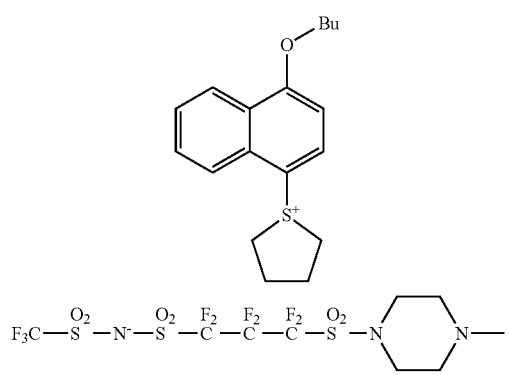
(PA-109)
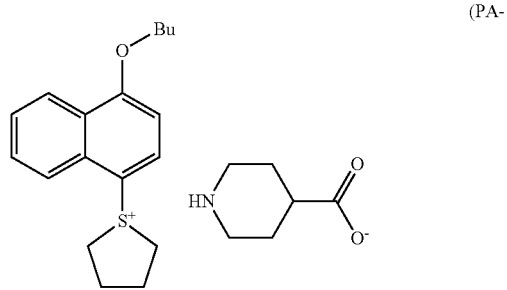
(PA-110)
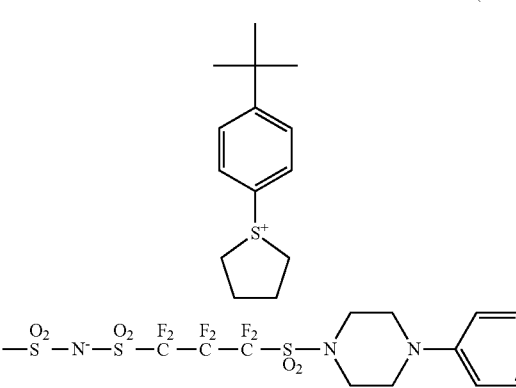
(PA-111)
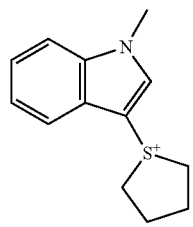
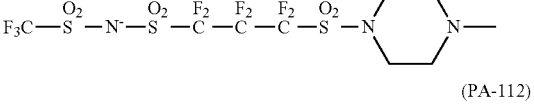
(PA-112)
(PA-113)
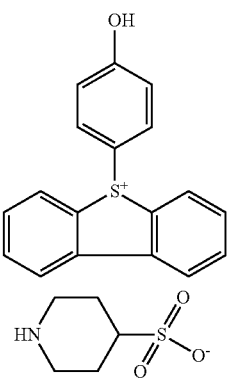
(PA-114)
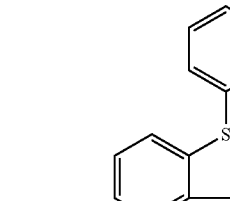
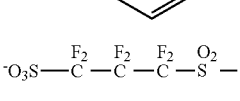
(PA-115)
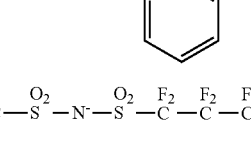

(PA-116)
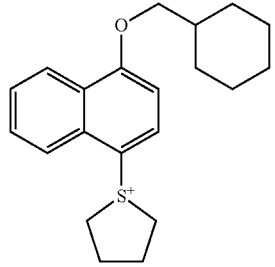
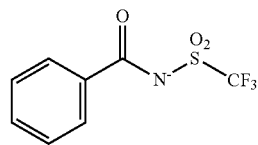
(PA-117)
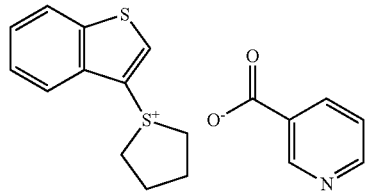
(PA-118)
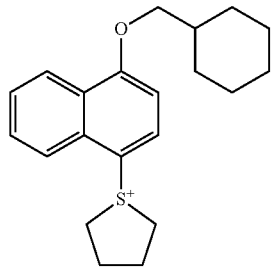
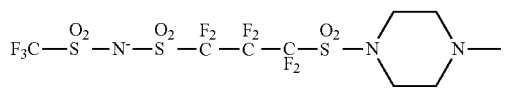
(PA-119)
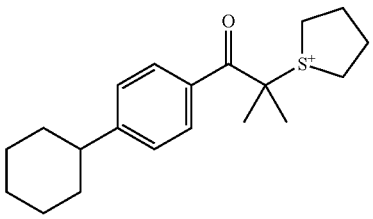
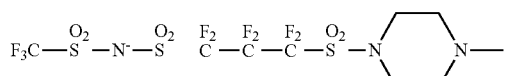
(PA-120)
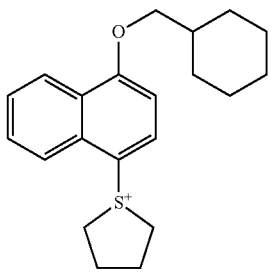
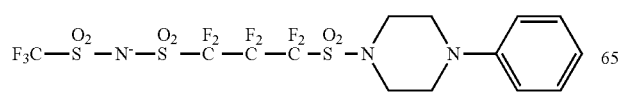
(PA-121)
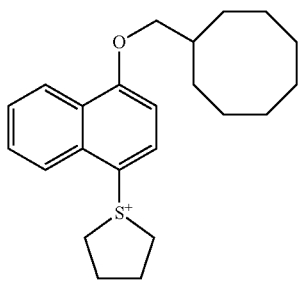
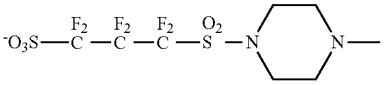
(PA-122)
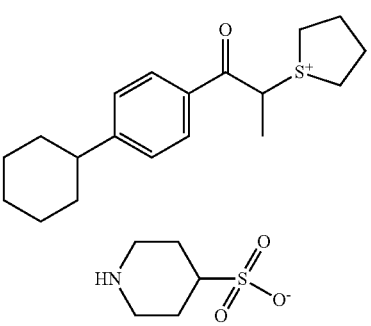
[Chem. 75]
(PA-123)
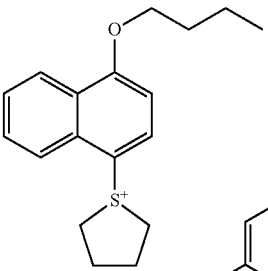
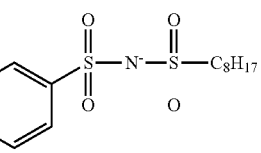
(PA-124)
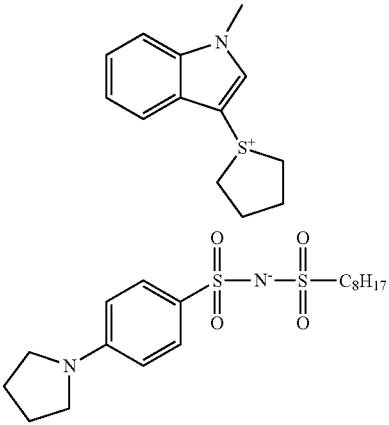

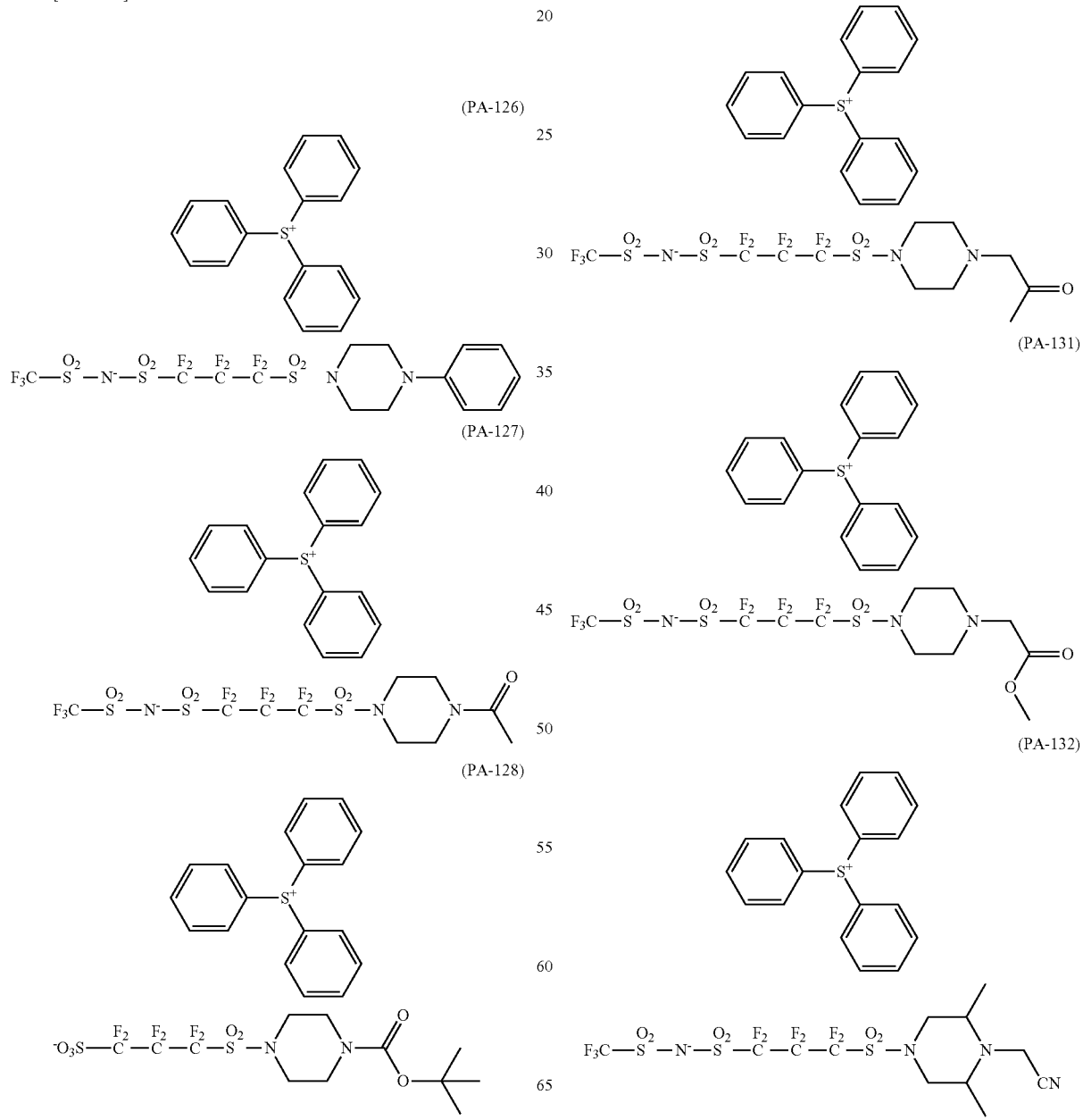

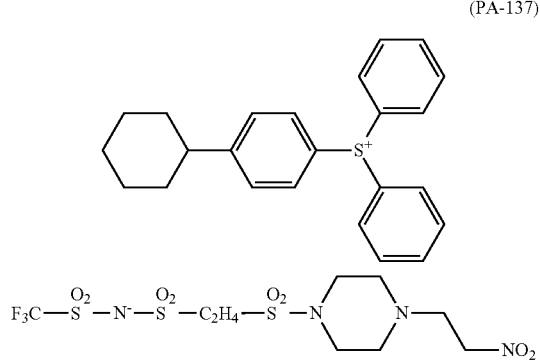
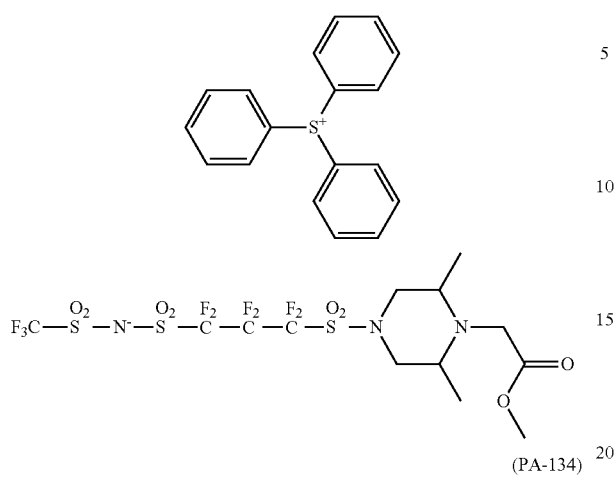
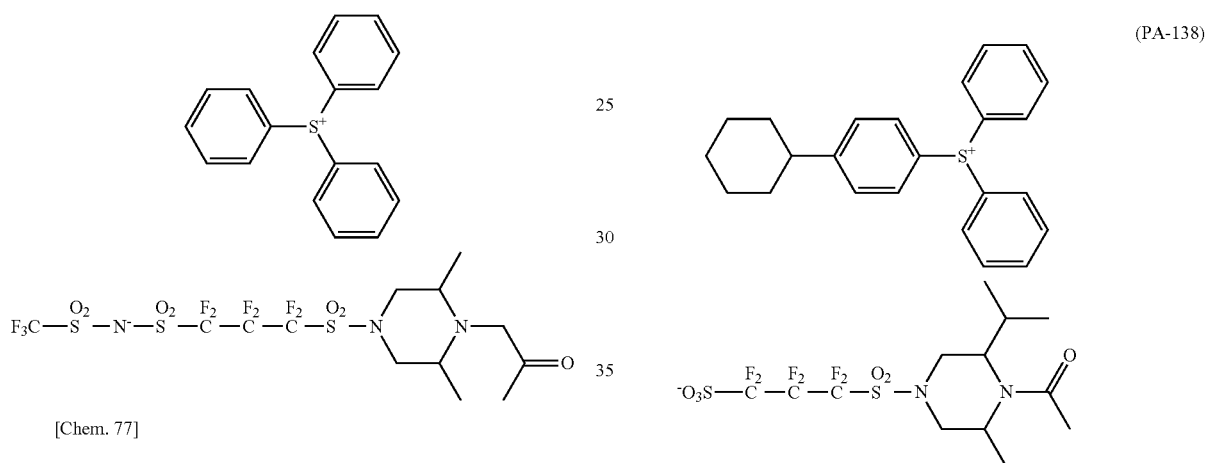
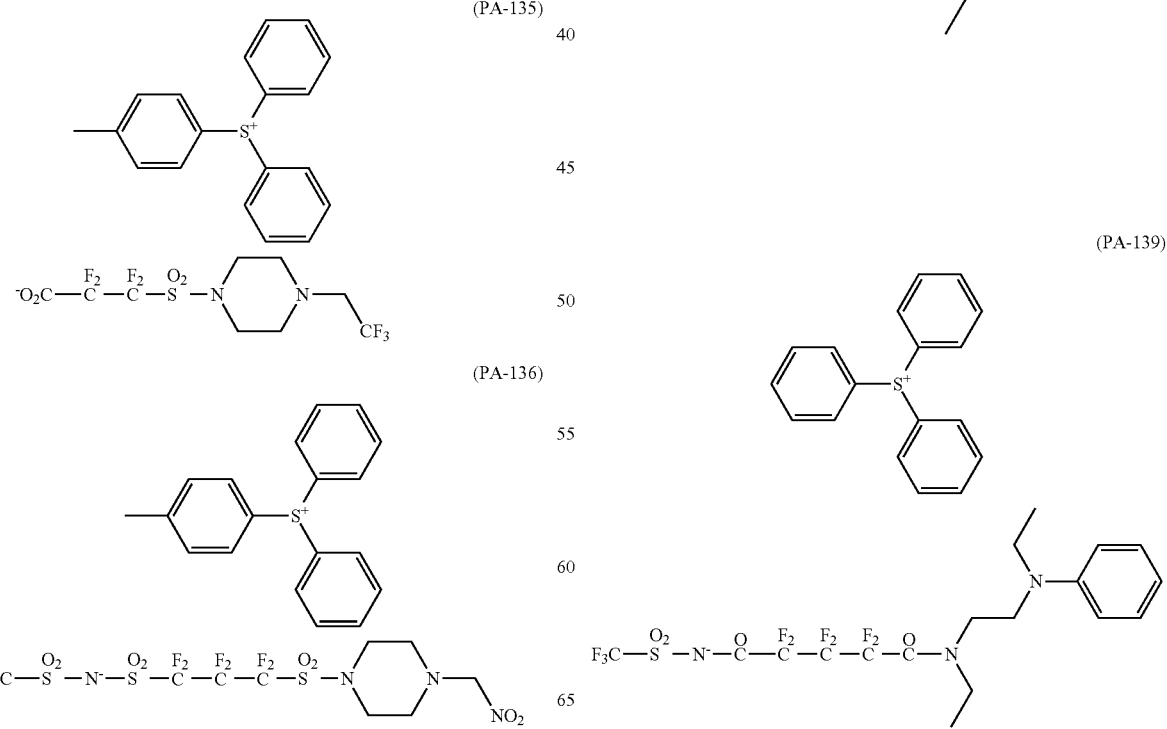

These compounds may be readily synthesized by using a general sulfonic acid esterification reaction or a sulfonamide reaction. For example, a method in which a sulfonamide bond or a sulfonate bond is formed by selectively reacting one of the sulfonyl halide parts of a bissulfonyl halide compound with amine, alcohol or the like including a partial structure represented by General Formula (PA-II) or (PA-III), and then, the other sulfonyl halide part is hydrolyzed, or a method in which a cyclic sulfonic acid anhydride is ring-opened by amine or alcohol including a partial structure represented by General Formula (PA-II), may be used. The amine or alcohol including a partial structure represented by General Formula (PA-II) or (PA-III) may be synthesized by reacting amine or alcohol with an anhydride such as (R'O$_2$C)$_2$O or (R'SO$_2$)$_2$O, or an acid chloride compound such as R'O$_2$CCl or R' SO$_2$Cl (R' is a methyl group, an n-octyl group, a trifluoromethyl group, or the like) under a basic condition. In particular, these compounds can be synthesized in accordance with the synthesis examples disclosed in JP2006-330098A.

A molecular weight of the compound (C) is preferably 500 to 1,000.

The actinic-ray-sensitive or radiation-sensitive resin composition of the present invention may or may not contain the compound (C), however, when the composition contains the compound (C), the content of the compound (C) is preferably 0.1 to 20 mol % and more preferably 0.1 to 10 mol % with regard to total solids of the actinic-ray-sensitive or radiation-sensitive resin composition.

[3-2] Basic Compound (C')

The actinic-ray-sensitive or radiation-sensitive resin composition in the present invention may contain a basic compound (C') in order to reduce performance changes over time from exposure to heating.

The basic compound may preferably include a compound having a structure represented by following Formulae (A) to (E).

[Chem. 79]

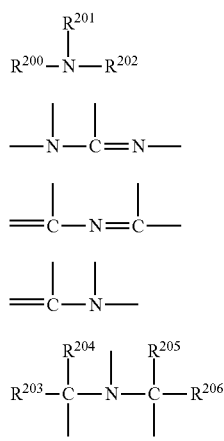

In General formulae (A) and (E), $R^{200}$, $R^{201}$ and $R^{202}$ may be the same as or different from each other, represent a hydrogen atom, an alkyl group (preferably 1 to 20 carbon atoms), a cycloalkyl group (preferably 3 to 20 carbon atoms) or an aryl group (preferably 6 to 20 carbon atoms), and $R^{201}$ and $R^{202}$ may be bonded to each other and form a ring. $R^{203}$, $R^{204}$, $R^{205}$ and $R^{206}$ may be the same as or different from each other, and represent an alkyl group having 1 to 20 carbon atoms.

For the above alkyl group, an alkyl group having a substituent is preferably an aminoalkyl group having 1 to 20 carbon atoms, a hydroxyalkyl group having 1 to 20 carbon atoms or a cyanoalkyl group having 1 to 20 carbon atoms.

The alkyl group in General Formulae (A) and (E) is preferably an unsubstituted alkyl group.

As the preferable compound, guanidine, aminopyrrolidine, pyrazole, pyrazoline, piperazine, amino morpholine, aminoalkyl morpholine, piperidine or the like may be included, and as the more preferable compound, a compound having an imidazole structure, a diazabicyclo structure, an onium hydroxide structure, an onium carboxylate structure, a trialkylamine structure, an aniline structure, or a pyridine structure, an alkylamine derivative having a hydroxyl group and/or an ether bond, an aniline derivative having a hydroxyl group and/or an ether bond, or the like, may be included.

The compound having an imidazole structure may include imidazole, 2,4,5-triphenyl imidazole, benzimidazole, or the like. The compound having a diazabicyclo structure may include 1,4-diazabicyclo[2,2,2]octane, 1,5-diazabicyclo[4,3,0]nona-5-ene-1,8-diazabicyclo[5,4,0]undeca-7-ene, or the like. The compound having a onium hydroxide structure may include triarylsulfonium hydroxide, phenacylsulfonium hydroxide, sulfonium hydroxide having an 2-oxo alkyl group, specifically, triphenylsulfonium hydroxide, tris(t-butylphenyl)sulfonium hydroxide, bis(t-butylphenyl)iodonium hydroxide, phenacylthiophenium hydroxide, 2-oxopropylthiophenium hydroxide, or the like. The compound having an onium carboxylate structure is a compound having an onium hydroxide structure of which anion part is carboxylated, and may include, for example, acetate, adamantane-1-carboxylate, perfluoroalkyl carboxylate, or the like. The compounds having a trialkylamine structure may include tri(n-butyl) amine, tri(n-octyl)amine, or the like. The compound having an aniline structure may include 2,6-diisopropyl aniline, N,N-dimethyl aniline, N,N-dibutyl aniline, N,N-dihexyl aniline, or the like. The alkylamine derivative having a hydroxyl group and/or an ether bond may include ethanolamine, diethanolamine, triethanolamine, and tris(methoxyethoxyethyl)amine, or the like. The aniline derivative having a hydroxyl group and/or an ether bond may include N,N-bis(hydroxyethyl)aniline, or the like.

The preferable basic compound may further include an amine compound having a phenoxy group, an ammonium salt compound having, a phenoxy group, an amine compound having a sulfonate group, and an ammonium salt compound having a sulfonate group.

In the amine compound having a phenoxy group, the ammonium salt compound having, a phenoxy group, the amine compound having a sulfonate group, and the ammonium salt compound having a sulfonate group, at least one alkyl group is bonded to the nitrogen atom. In addition, it is preferable that an oxygen atom be included and an oxyalkylene group be formed in the alkyl chain. The number of oxyalkylene groups is one or more in the molecule, preferably 3 to 9, and more preferably 4 to 6. As the oxyalkylene group, a structure of —CH$_2$CH$_2$O—, —CH(CH$_3$)CH$_2$O—, or —CH$_2$CH$_2$CH$_2$O— is preferable.

Specific examples of the amine compound having a phenoxy group, the ammonium salt compound having, a phenoxy group, the amine compound having a sulfonate group, and the ammonium salt compound having a sulfonate group include the compounds (C1-1) to (C3-3) exemplified in [0066] of US2007/0224539A, however, are not limited to these.

In addition, as one of the basic compound, a nitrogen-containing organic compound having a group detached by the action of acid may be used. Examples of this compound may include a compound represented by following General Formula (F). The compound represented by following General Formula (F) expresses the effective basicity in the system by the group detached by the action of acid being detached.

[Chem. 80]

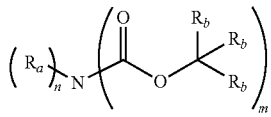

(F)

In General Formula (F), $R_a$s, each independently, represent a hydrogen atom, an alkyl group, a cycloalkyl group, an aryl group, or an aralkyl group. In addition, when n=2, the two $R_a$s may be the same as or different from each other, two of $R_a$ may be bonded to each other and form a divalent heterocyclic hydrocarbon group (preferably 20 or less carbon atoms) or a derivative thereof.

$R_b$s, each independently, represent a hydrogen atom, an alkyl group, a cycloalkyl group, an aryl group or an aralkyl group.

However, in $C(R_b)(R_b)(R_b)$, when one or more of $R_b$ is a hydrogen atom, at least one of the rest $R_b$ is a cyclopropyl group or an 1-alkoxyalkyl group.

At least two of $R_b$s may be bonded to each other and form an alicyclic hydrocarbon group, an aromatic hydrocarbon group, a heterocyclic hydrocarbon group, or a derivative thereof.

n represents an integer of 0 to 2, m represents an integer of 1 to 3, respectively, and n+m=3.

In General Formula (F), the alkyl group, the cycloalkyl group, the aryl group and the aralkyl group representing $R_a$ and $R_b$ may be substituted with a functional group such as a hydroxyl group, a cyano group, an amino group, a pyrrolidino group, a piperidino group, a morpholino group or an oxo group, an alkoxy group, or a halogen atom.

The alkyl group, the cycloalkyl group, the aryl group, and the aralkyl group of the above R (these alkyl group, cycloalkyl group, aryl group and aralkyl group may be substituted with the functional group described above, an alkoxy group, or a halogen atom) may include, for example, a group derived from a straight chain or branched alkane such as methane, ethane, propane, butane, pentane, hexane, heptane, octane, nonane, decane, undecane or dodecane, a group in which the group derived from alkane is substituted with one type or more, or one or more cycloalkyl groups such as, for example, a cyclobutyl group, cyclopentyl group or cyclohexyl group, a group derived from cycloalkane such as cyclobutane, cyclopentane, cyclohexane, cycloheptane, cyclooctane, norbornane, adamantane or noradamantan, a group in which the group derived from cycloalkane is substituted with one type or more, or one or more straight chain or branched alkyl groups such as, for example, a methyl group, an ethyl group, an n-propyl group, an i-propyl group, an n-butyl group, a 2-methylpropyl group, a 1-methylpropyl group or a t-butyl group, a group derived from an aromatic compound such as benzene, naphthalene, or anthracene, a group in which the group derived from an aromatic compound is substituted with one type or more, or one or more straight chain or branched alkyl groups such as, for example, a methyl group, an ethyl group, an n-propyl group, an i-propyl group, an n-butyl group, a 2-methylpropyl group, a 1-methylpropyl group or a t-butyl group, a group derived from a heterocyclic compound such as pyrrolidine, piperidine, morpholine, tetrahydrofuran, tetrahydropyran, indole, indoline, quinoline, perhydroquinoline, indazole or benzimidazole, a group in which the group derived from a heterocyclic compound is substituted with one type or more, or one or more straight chain or branched alkyl groups or groups derived from an aromatic compound, a group in which the group derived from straight chain or branched alkane the group derived from cycloalkane is substituted with one type or more, or one or more groups derived from an aromatic compound such as a phenyl group, a naphthyl group, or an anthracenyl group, or the like, or a group in which the substituents described above are substituted with a functional group such as a hydroxyl group, a cyano group, an amino group, a pyrrolidino group, a piperidino group, a morpholino group or an oxo group, or the like.

In addition, the divalent heterocyclic hydrocarbon group (preferably 1 to 20 carbon atoms) formed by the above $R_a$s being bonded to each other or a derivative thereof may include, for example, a group derived from a heterocyclic compound such as pyrrolidine, piperidine, morpholine, 1,4,5,6-tetrahydropyrimidine, 1,2,3,4-tetrahydroquinoline, 1,2,3,6-tetrahydropyridine, homopiperazine, 4-azabenzimidazole, benzotriazole, 5-azabenzotriazole, 1H-1,2,3-triazole, 1,4,7-triazacyclononane, tetrazole, 7-azaindole, indazole, benzimidazole, imidazo[1,2-a]pyridine, (1S,4S)-(+)-2,5-diazabicyclo[2.2.1]heptane, 1,5,7-triazabicyclo[4.4.0]DEC-5-ene, indole, indoline, 1,2,3,4-tetrahydroquinoxalin, perhydroquinoline, 1,5,9-triazacyclododecane or a group in which the group derived from a heterocyclic compound is substituted with one type or more, or one or more groups derived from straight chain or branched alkane, groups derived from cycloalkane, groups derived from an aromatic compound, groups derived from a heterocyclic compound, functional groups such as a hydroxyl group, a cyano group, an amino group, a pyrrolidino group, a piperidino group, a morpholino group or an oxo group, or the like.

Specific examples of the particularly preferable nitrogen-containing organic compounds having a group detached by an action of acid are shown below, however, the present invention is not limited to these.

[Chem. 81]

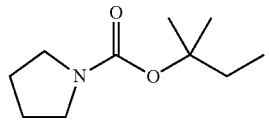

(D-1)

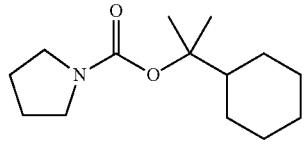

(D-2)

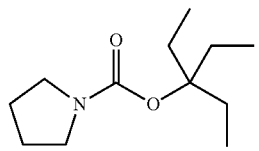

(D-3)

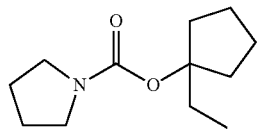

(D-4)

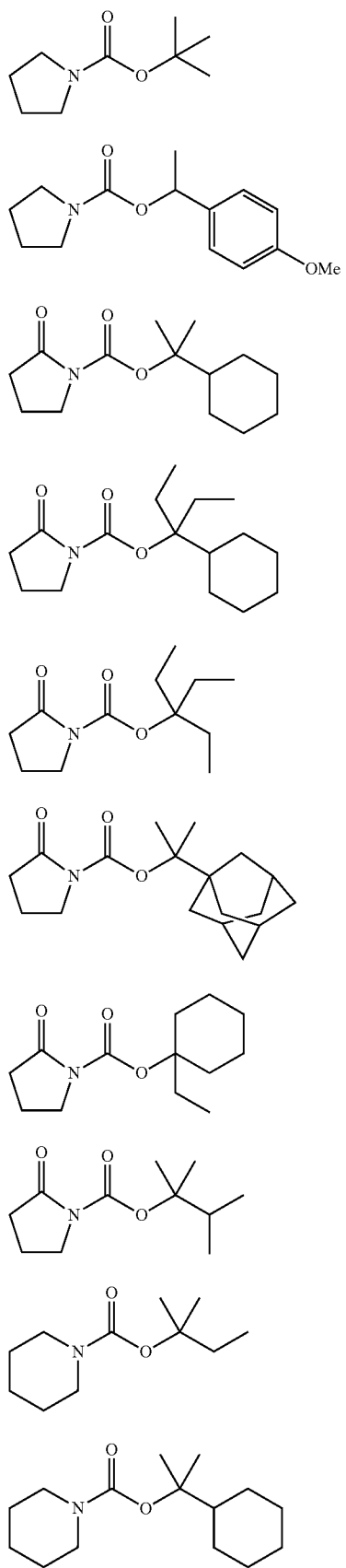
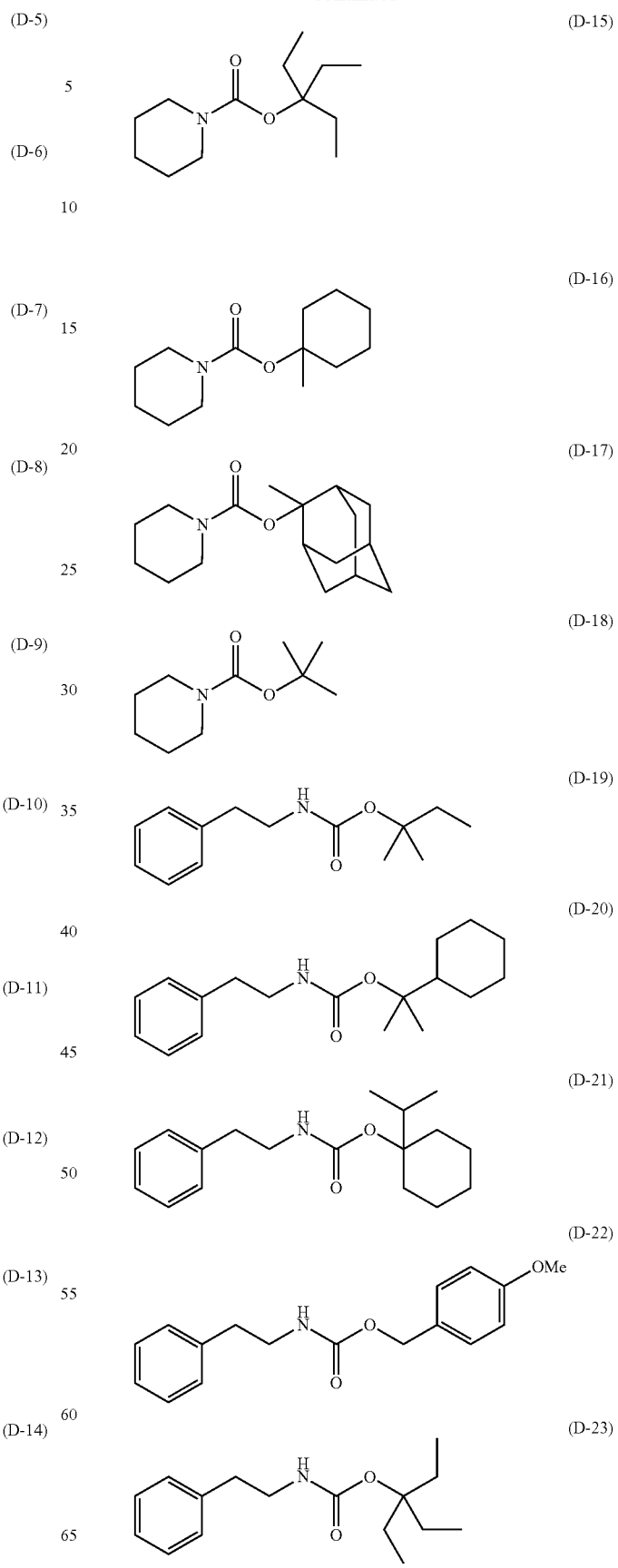

(D-24) 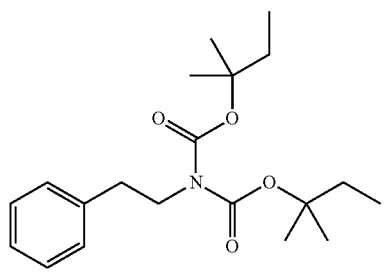
(D-29) 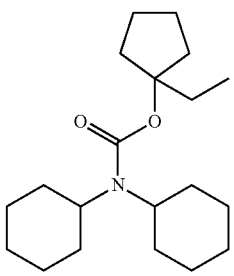
(D-25) 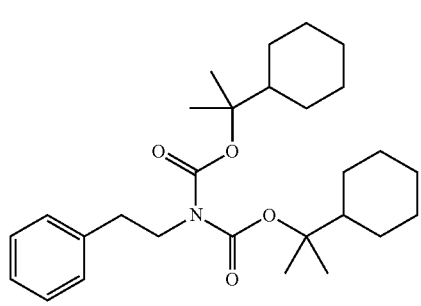
(D-30) 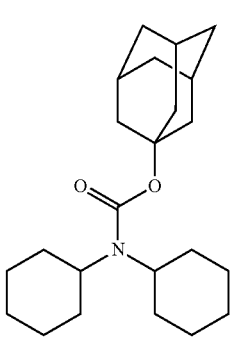
(D-26) 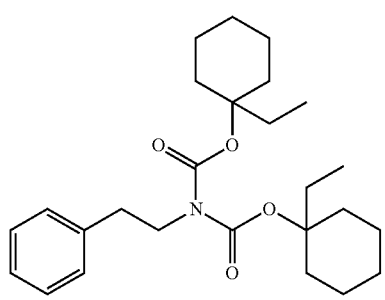
(D-31) 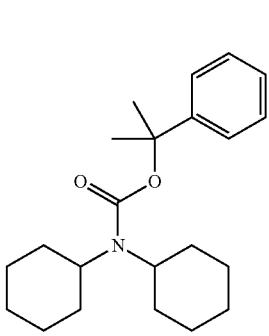
(D-27) 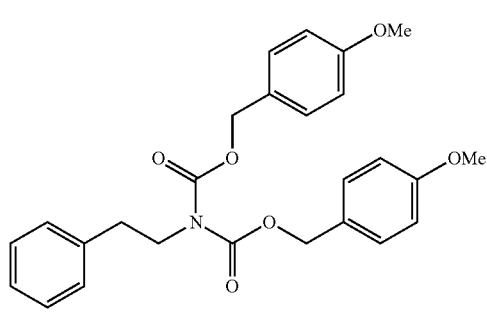
(D-32) 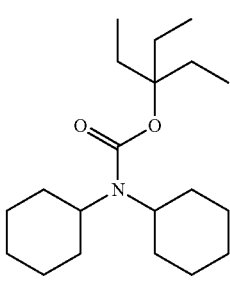
(D-28) 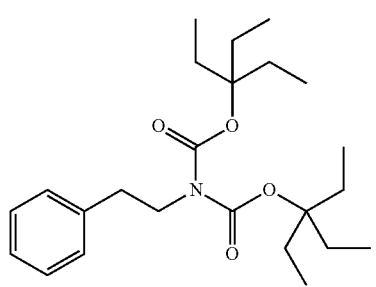
(D-33) 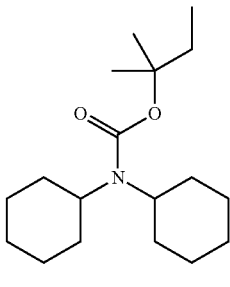

[Chem. 82]
(D-34)
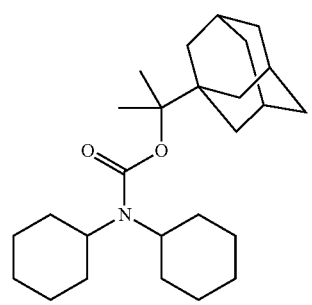
(D-35)
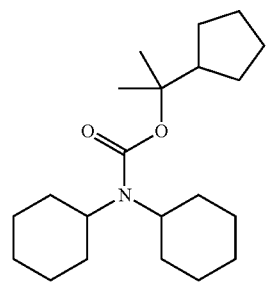
(D-36)
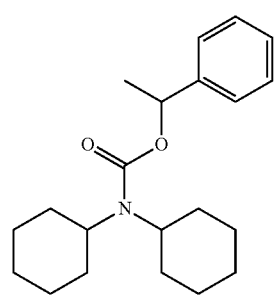
(D-37)
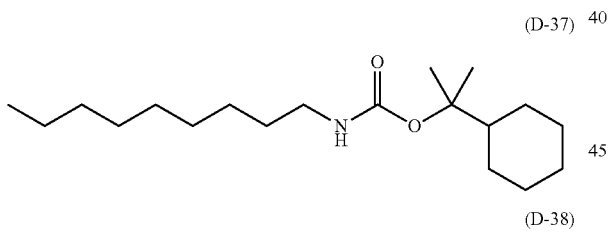
(D-38)
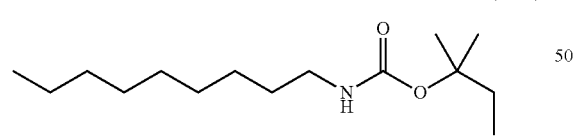
(D-39)
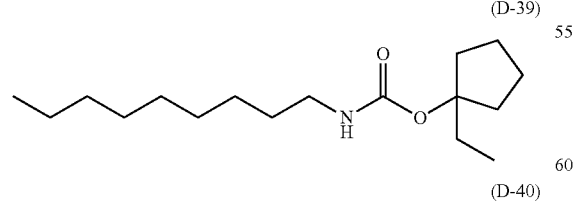
(D-40)
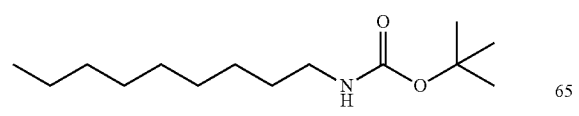
(D-41)
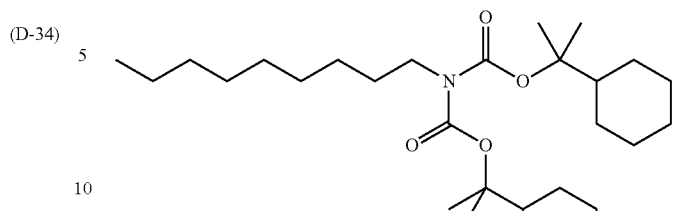
(D-42)
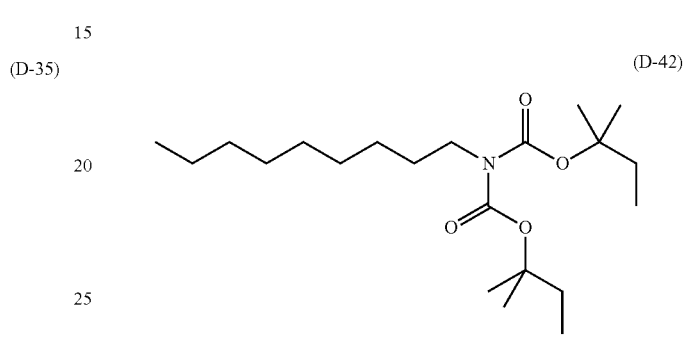
(D-43)
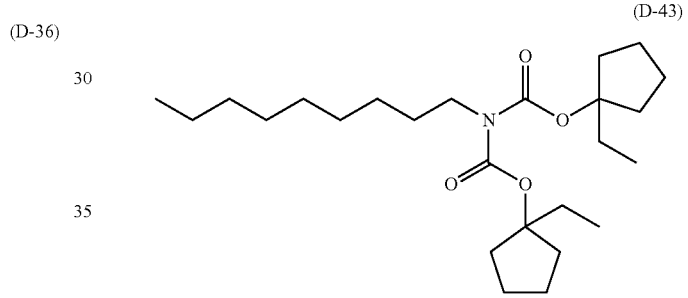
(D-44)
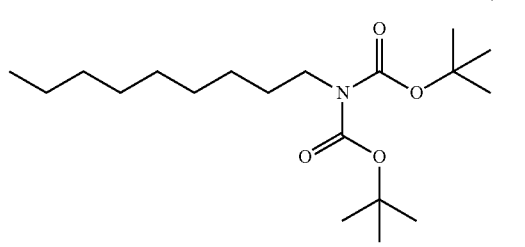
(D-45)
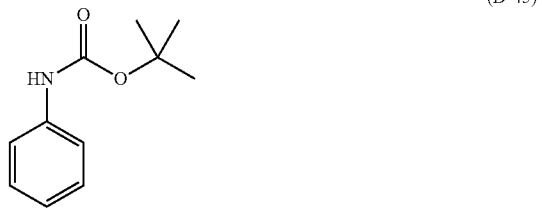
(D-46)
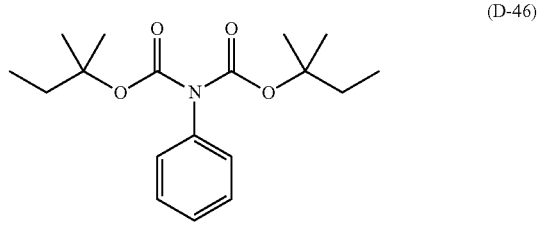

(D-47) 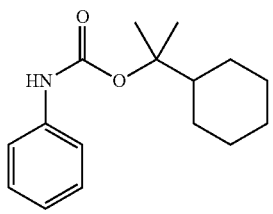

(D-48) 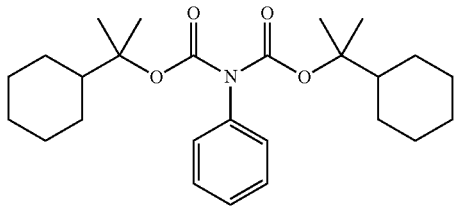

(D-49) 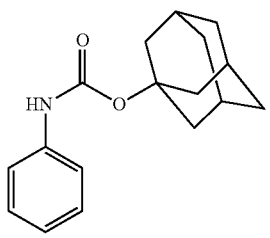

(D-50) 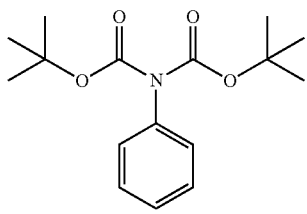

(D-51) 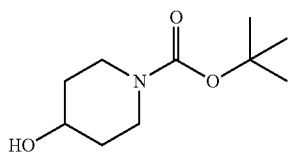

(D-52) 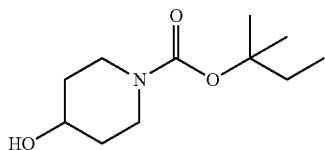

(D-53) 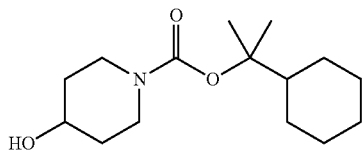

(D-54) 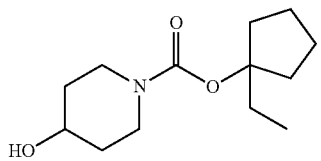

(D-55) 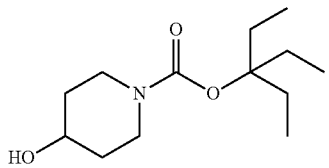

As the compounds represented by General Formula (F), commercially available compounds may be used, or the compounds may be synthesized from commercially available amines using method described in the Protective Groups in Organic Synthesis, fourth edition, and the like. As the most general method, for example, the compounds may be synthesized in accordance with the method disclosed in JP2009-199021A.

A molecular weight of the basic compound is preferably 250 to 2,000, and more preferably 400 to 1,000. The molecular weight of the basic compound is preferably is preferably 400 or more, more preferably 500 or more, and even more preferably 600 or more from the viewpoint of further reduction of LWR and uniformity of the local pattern dimension.

This basic compound may be used together with the above compound (C), and may be used either alone or as a combination of two or more.

The actinic-ray-sensitive or radiation-sensitive resin composition of the present invention may not contain the basic compound (C'), however, if the composition does, the amount of the basic compound (C') used is typically 0.001 to 10% by mass, and preferably 0.01 to 5% by mass with regard to solids of the actinic-ray-sensitive or radiation-sensitive resin composition.

The ratio of the acid generator and the basic compound used in the composition is preferably acid generator/basic compound (molar ratio)=2.5 to 300. In other words, the molar ratio is preferably 2.5 or more from the viewpoint of sensitivity and resolution, and is preferably 300 or less from the viewpoint of suppressing the reduction of the resolution by an enlargement of the resist pattern over time from the exposure to the heat treatment. The acid generator/basic compound (molar ratio) is more preferably 5.0 to 200, and even more preferably 7.0 to 150.

[4] Solvent (D)

A solvent which can be used to prepare the actinic-ray-sensitive or radiation-sensitive resin composition in the present invention may include an organic solvent such as, for example, alkylene glycol monoalkyl ether carboxylate, alkylene glycol monoalkyl ether, alkyl lactate, alkyl alkoxy propionate, cyclic lactone (preferably 4 to 10 carbon atoms), a monoketone compound which may also have a ring (preferably 4 to 10 carbon atoms), an alkylene carbonate, alkyl alkoxy acetate, or alkyl pyruvate.

Specific examples of these solvents may include those disclosed in [0441] to [0455] of US2008/0187860A.

In the present invention, a mixed solvent in which a solvent containing a hydroxyl group in the structure is mixed with a solvent not containing a hydroxyl group may be used as an organic solvent.

The solvent containing a hydroxyl group and the solvent not containing a hydroxyl group may be appropriately selected from the compounds exemplified above, however, as a solvent containing a hydroxyl group, alkylene glycol monoalkyl ether, alkyl lactate or the like is preferable, and propylene glycol monomethyl ether (PGME, alias 1-methoxy-2-propanol) or ethyl lactate is more preferable as a solvent containing a hydroxyl group. In addition, alkylene glycol mono alkyl ether acetate or alkyl alkoxy propionate, a monoketone compound which may also have a ring, cyclic lactone, alkyl acetate or the like is preferable as the solvent not containing a hydroxyl group, propylene glycol monomethyl ether acetate (PGMEA, alias 1-methoxy-2-acetoxypropane), ethyl ethoxy propionate, 2-heptanone, γ-butyrolactone, cyclohexanone or butyl acetate is particularly preferable, propylene glycol monomethyl ether acetate, ethyl ethoxy propionate, or 2-heptanone is the most preferable.

Mixing ratio of the solvent containing a hydroxyl group and a solvent containing no hydroxyl group (mass) is 1/99 to 99/1, preferably 10/90 to 90/10, more preferably is a 20/80 to 60/40. The mixed solvent containing 50% by mass or more of the solvent containing no hydroxyl group is particularly preferable in terms of coating uniformity.

The solvent may preferably contain propylene glycol monomethyl ether acetate, and is preferably a single solvent of propylene glycol monomethyl ether acetate or a mixed solvent of two or more containing propylene glycol monomethyl ether acetate.

[5] Hydrophobic Resin (E)

The actinic-ray-sensitive or radiation-sensitive resin composition in the present invention contains a hydrophobic resin (hereinafter, referred as a "hydrophobic resin (E)" or simply as a "resin (E)") which has at least one of an fluorine atom and a silicon atom, particularly when applied to liquid immersion exposure. As a result, the hydrophobic resin (E) can be localized on the surface layer portion, improves the static/dynamic contact angle of the resist film surface for water when a liquid immersion medium is water, therefore, may improve the immersion liquid traceability.

The hydrophobic resin (E) is preferably designed to be localized on the surface as described above, however, unlike surfactants, does not need to have a hydrophilic group within the molecule and does not necessarily contribute to uniformly mixing the polar/non-polar substances.

The hydrophobic resin (E) typically contains a fluorine atom and/or a silicon atom. The fluorine atom and/or the silicon atom in the hydrophobic resin (E) may be included in the main chain of the resin or included in the side chain.

If the hydrophobic resin (E) contains a fluorine atom, a resin having an alkyl group having a fluorine atom, a cycloalkyl group having a fluorine atom, or an aryl group having a fluorine atom is preferable as the partial structure having a fluorine atom.

The alkyl group having a fluorine atom (Preferably 1 to 10 carbon atoms and more preferably 1 to 4 carbon atoms) is a straight chain or branched alkyl group of which at least one hydrogen atom is substituted with a fluorine atom, and may have further substituents in addition to a fluorine atom.

The cycloalkyl group having a fluorine atom is a monocyclic or polycyclic cycloalkyl group of which at least one hydrogen atom is substituted with a fluorine atom, and may have further substituents in addition to a fluorine atom.

The aryl group having a fluorine atom is aryl group such as a phenyl group, a naphthyl group, or the like, of which at least one hydrogen atom is substituted with a fluorine atom, and may have further substituents in addition to a fluorine atom.

As the alkyl group having a fluorine atom, the cycloalkyl group having a fluorine atom, and the aryl group having a fluorine atom may include a group represented by following General Formulae (F2) to (F4), however, the present invention is not limited to these.

[Chem. 83]

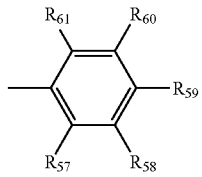

(F2)

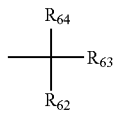

(F3)

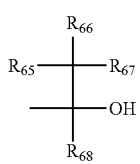

(F4)

In General Formulae (F2) to (F4), $R_{57}$ to $R_{68}$, each independently, represent a hydrogen atom, a fluorine atom, or an alkyl group (straight chain or branched). However, at least one of $R_{57}$ to $R_{61}$, at least one of $R_{62}$ to $R_{64}$ and at least one of $R_{65}$ to $R_{68}$, each independently, represent a fluorine atom or an alkyl group of which at least one hydrogen atom is substituted with a fluorine atom (preferably 1 to 4 carbon atoms).

$R_{57}$ to $R_{61}$ and $R_{65}$ to $R_{67}$ are preferably all fluorine atoms. $R_{62}$, $R_{63}$, and $R_{68}$ are preferably an alkyl group of which at least one hydrogen atom is substituted with a fluorine atom (preferably 1 to 4 carbon atoms), and more preferably a perfluoroalkyl group having 1 to 4 carbon atoms. $R_{62}$ and $R_{63}$ may be bonded to each other and form a ring.

Specific examples of the group represented by General Formula (F2) may include a p-fluorophenyl group, a pentafluorophenyl group, and a 3,5-di(trifluoromethyl)phenyl group, or the like.

Specific examples of the group represented by General Formula (F3) may include a trifluoromethyl group, a pentafluoropropyl group, a pentafluoroethyl group, a heptafluorobutyl group, a hexafluoroisopropyl group, a heptafluoroisopropyl group, a hexafluoro(2-methyl)isopropyl group, a nonafluorobutyl group, an octafluoroisobutyl group, a nonafluorohexyl group, a nonafuruoro-t-butyl group, a perfluoroalkyl isopentyl group, a perfluorooctyl group, a perfluoro (trimethyl)hexyl group, a 2,2,3,3-tetrafluorocyclobutyl group, a perfluorocyclohexyl group, or the like. A hexafluoroisopropyl group, a heptafluoroisopropyl group, a hexafluoro (2-methyl) isopropyl group, an octafluoroisobutyl group, a nonafuruoro-t-butyl group or a perfluoroisopentyl group is preferable, and a hexafluoroisopropyl group or a heptafluoroisopropyl group is more preferable.

Specific examples of the group represented by General Formula (F4) may include —C(CF$_3$)$_2$OH, —C(C$_2$F$_5$)$_2$OH, —C(CF$_3$)(CH$_3$)OH, —CH(CF$_3$)OH, or the like, and —C(CF$_3$)$_2$OH is preferable.

The partial structure including a fluorine atom may be bonded directly to the main chain, or may be bonded to the main chain through a group selected from the group consisting of an alkylene group, a phenylene group, an ether bond, a thioether bond, a carbonyl group, an ester bond, an amide bond, an urethane bond, and a ureiren bond, or a group combining two or more of these.

The very suitable repeating unit having a fluorine atom may include a unit shown below.

[Chem. 84]

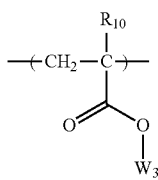
(C-Ia)

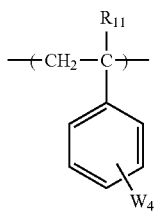
(C-Ib)

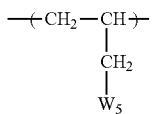
(C-Ic)

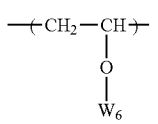
(C-Id)

In the formula, $R_{10}$ and $R_{11}$, each independently, represent a hydrogen atom, a fluorine atom or an alkyl group. The alkyl group is preferably a straight chain or branched alkyl group having 1 to 4 carbon atoms, may have a substituent, and the alkyl group having a substituent may particularly include a fluorinated alkyl group.

$W_3$ to $W_6$, each independently, represent an organic group containing at least one or more fluorine atom. Specifically, an atomic group of (F2) to (F4) may be included.

Furthermore, in addition to these, the hydrophobic resin (E) may have a unit represented below as a repeating unit having a fluorine atom.

[Chem. 85]

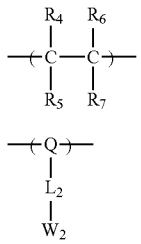

(C-II)

(C-III)

In the formula, $R_4$ to $R_7$, each independently, represent a hydrogen atom, a fluorine atom, or an alkyl group. The alkyl group is preferably a straight chain or branched alkyl group having 1 to 4 carbon atoms, may have a substituent, and the alkyl group having a substituent may particularly include a fluorinated alkyl group.

However, at least one of $R_4$ to $R_7$ represents a fluorine atom. $R_4$ and $R_5$ or $R_6$ and $R_7$ may form a ring.

$W_2$ represents an organic group containing at least one fluorine atom. Specifically, an atomic group of (F2) to (F4) may be included.

$L_2$ represents a single bond or a divalent linking group. As the divalent linking group, a substituted or unsubstituted arylene group, a substituted or unsubstituted alkylene group, a substituted or unsubstituted cycloalkylene group, —O—, —SO$_2$—, —CO—, —N(R)— (In the formula, R represents a hydrogen atom or an alkyl group), —NHSO$_2$— or a divalent linking group combining a plurality of these.

Q represents an alicyclic structure. The alicyclic structure may have a substituent, be a monocyclic type, or a polycyclic type, and may be a bridge type in case of a polycyclic type. The monocyclic type is preferably a cycloalkyl group having 3 to 8 carbon atoms, and may include, for example, a cyclopentyl group, a cyclohexyl group, a cyclobutyl group, a cyclooctyl group or the like. The polycyclic type may include a group having a bicycle structure, a tricycle structure, a tetracyclo structure, or the like, having 5 or more carbon atoms, is preferably a cycloalkyl group having 6 to 20 carbon atoms, and may include, for example, a adamantyl group, a norbornyl group, a dicyclopentyl group, a tricyclodecanyl group, a tetracyclododecyl group, or the like. In addition, part of carbon atoms in the cycloalkyl group may be substituted with a hetero atom such as an oxygen atom. The particularly preferable Q may include a norbornyl group, a tricyclodecanyl group, a tetracyclododecyl group, or the like.

Specific examples of the repeating unit having a fluorine atom are shown below, however, the present invention is not limited to these.

In the specific examples, $X_1$ represents a hydrogen atom, —CH$_3$, —F or —CF$_3$. $X_2$ represents —F or —CF$_3$.

[Chem. 86]

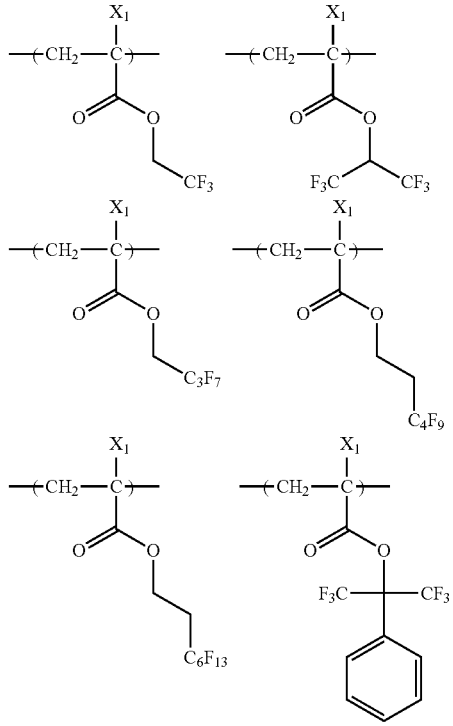

183
-continued
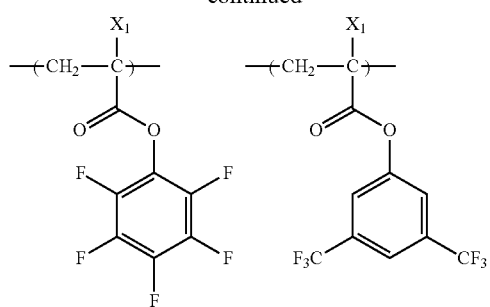
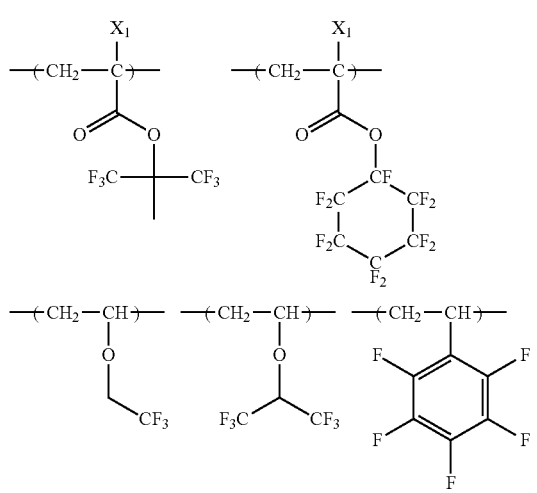
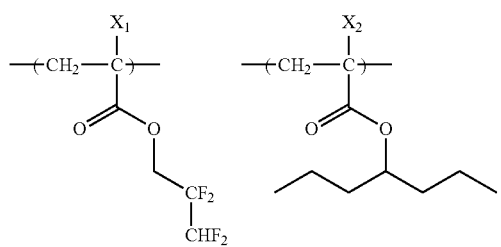
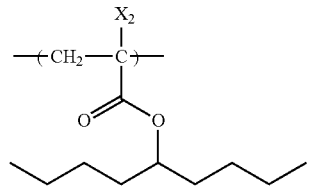
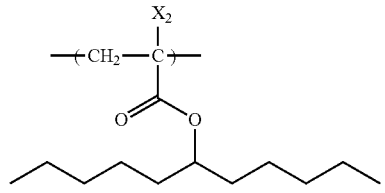
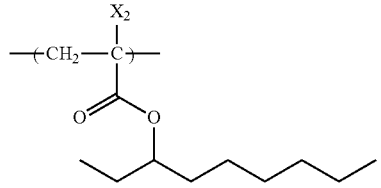
184
-continued
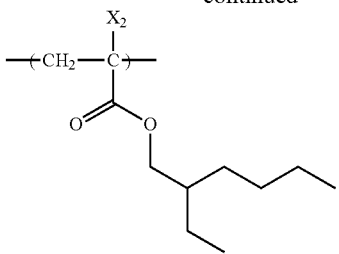
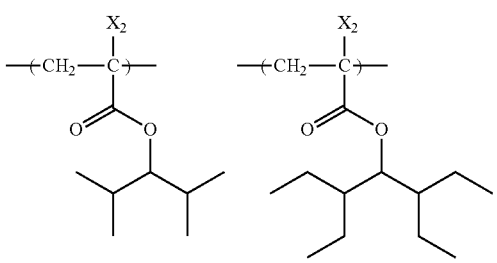
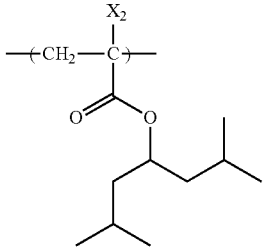
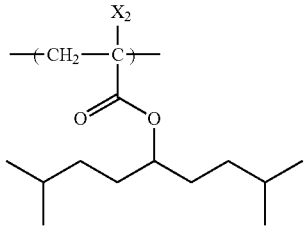
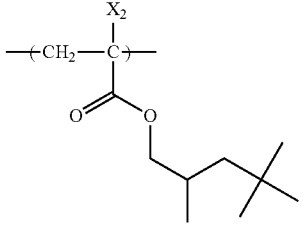
[Chem. 87]
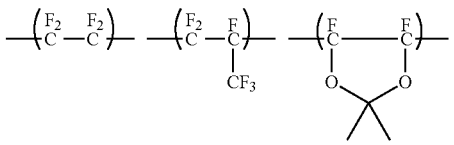
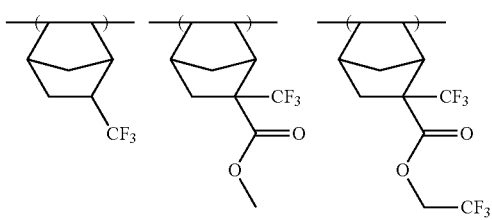

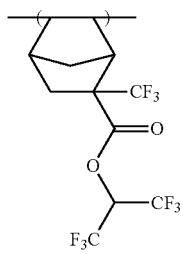

The hydrophobic resin (E) may also contain a silicon atom. As the partial structure having a silicon atom, a resin having an alkylsilyl structure (preferably a trialkylsilyl group) or a cyclic siloxane structure is preferable.

The alkylsilyl structure or the cyclic siloxane structure may include, specifically, a group represented by following General Formulae (CS-1) to (CS-3).

[Chem. 88]

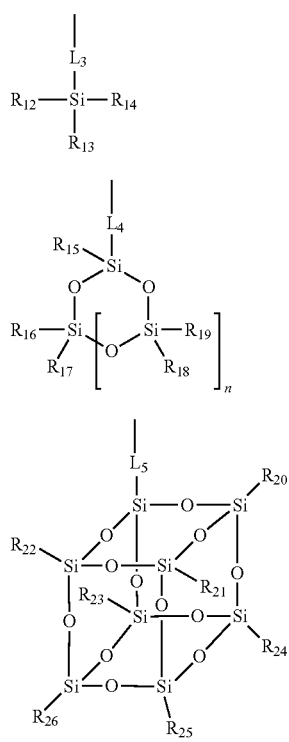

In General Formulae (CS-1) to (CS-3), $R_{12}$ to $R_{26}$, each independently, represent a straight chain or branched alkyl group (preferably 1 to 20 carbon atoms) or a cycloalkyl group (preferably 3 to 20 carbon atoms).

$L_3$ to $L_5$ represent a single bond or a divalent linking group. As the divalent linking group, a single group or a combination of two or more groups (preferably 12 or less total carbon atoms) selected from the group consisting of an alkylene group, a phenylene group, an ether bond, a thioether bond, a carbonyl group, an ester bond, an amide bond, an urethane bond and a urea bond, may be included.

n represents an integer of 1 to 5. n is preferably an integer of 2 to 4.

Specific examples of the repeating units having a group represented by General Formulae (CS-1) to (CS-3), however, the present invention is not limited to these. In addition, in the specific examples, $X_1$ represents a hydrogen atom, $-CH_3$, $-F$ or $-CF_3$.

[Chem. 89]

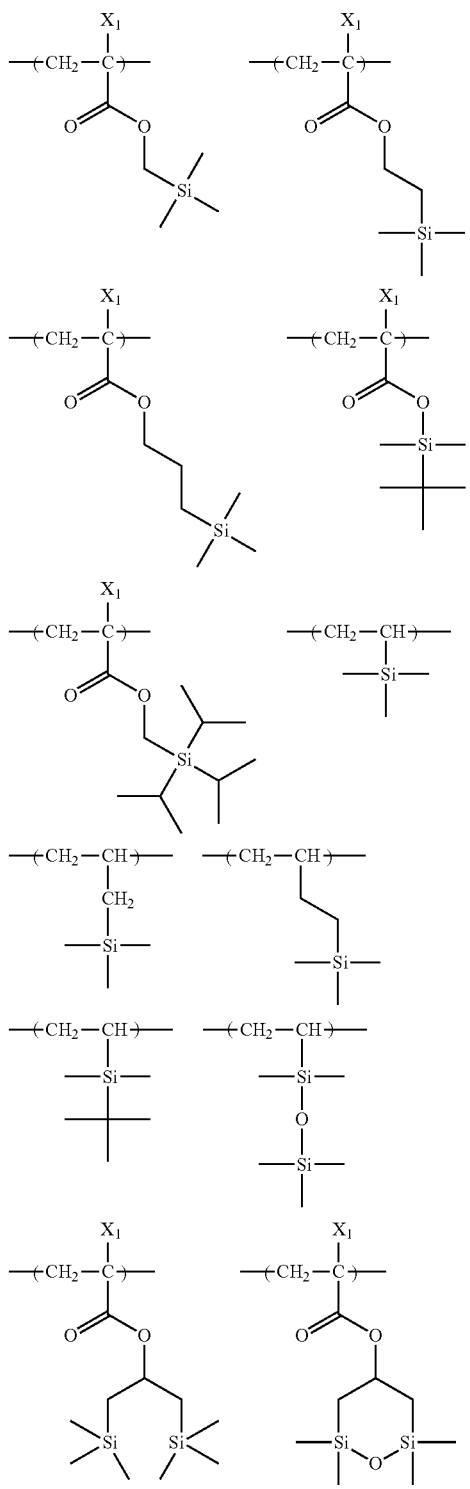

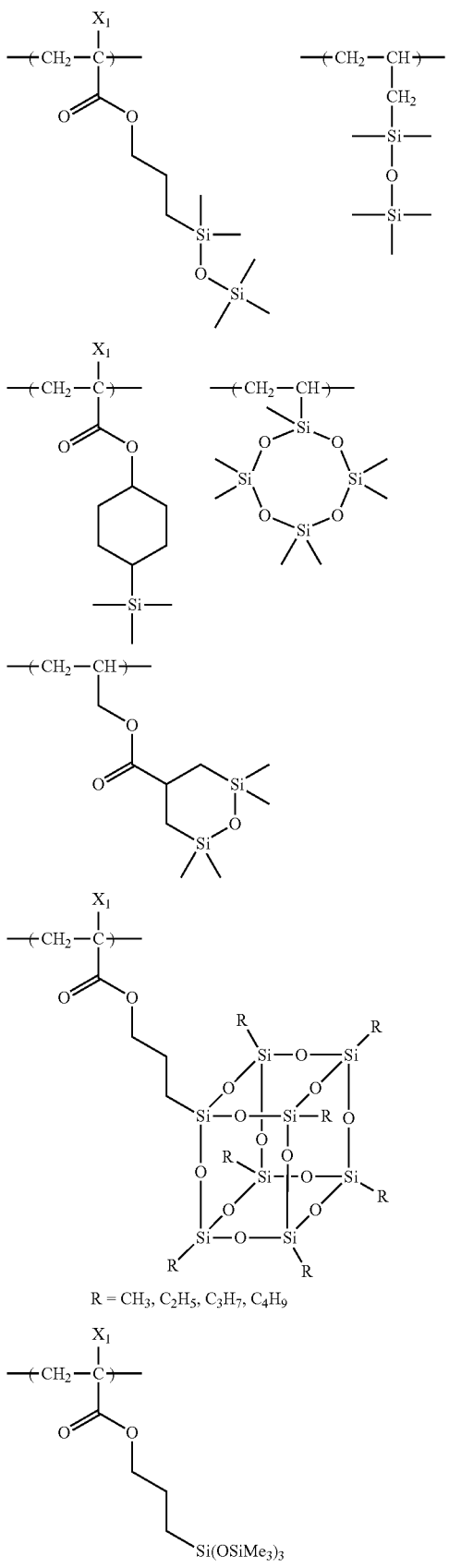

Furthermore, the hydrophobic resin (E) may have at least one group selected from the group consisting of following (x) to (z).

(x) an acid group (y) a group having a lactone structure, an acid anhydride group, or an acid imide group (z) a group decomposed by the action of acid As the acid group (x), a phenolic hydroxyl group, a carboxylate group, a fluorinated alcohol group, a sulfonate group, a sulfonamide group, a sulfonylimide group, an (alkylsulfonyl)(alkylcarbonyl)methylene group, an (alkylsulfonyl)(alkylcarbonyl) imide group, a bis(alkylcarbonyl)methylene group, a bis(alkylcarbonyl) imide group, a bis(alkylsulfonyl)methylene group, a bis(alkylsulfonyl) imide group, a tris(alkylcarbonyl)methylene group, a tris(alkylsulfonyl)methylene group or the like, may be included.

The preferable acid group may include a fluorinated alcohol group (preferably hexafluoroisopropanol), a sulfonimide group, a bis(alkylcarbonyl)methylene group.

As the repeating unit having an acid group (x), a repeating unit in which the acid group is bonded directly to the main chain of the resin such as a repeating unit by acrylic acid or methacrylic acid, a repeating unit in which the acid group is bonded to the main chain of the resin through a linking group, or the like, may be included, or introducing the repeating unit to the end of the polymer chain using a polymerization initiator or a chain transfer agent having an acid group when polymerized is also possible, and any of the cases is preferable. The repeating unit having an acid group (x) may have at least one of a fluorine atom and a silicon atom.

The content of the repeating unit having an acid group (x) is preferably 1 to 50 mol %, more preferably 3 to 35 mol %, and even more preferably 5 to 20 mol % with regard to all repeating units in the hydrophobic resin (E).

Specific examples of the repeating unit having an acid group (x) are shown below, however, the present invention is not limited to these. In the formula, Rx represents a hydrogen atom, $CH_3$, $CF_3$, or $CH_2OH$.

[Chem. 90]

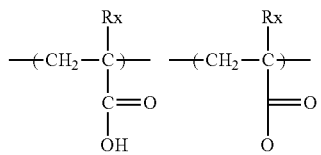

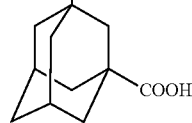

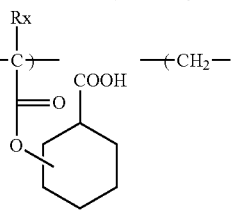
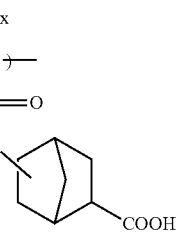

-continued
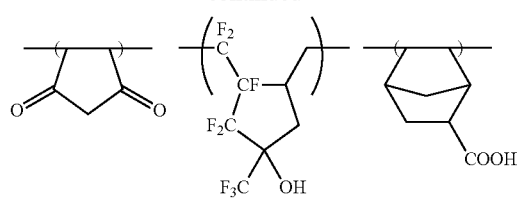
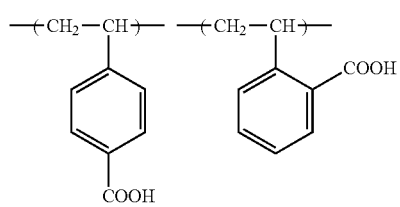
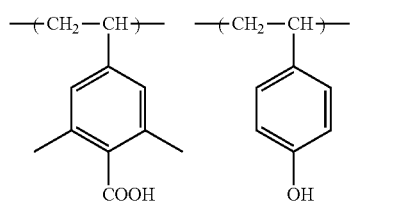
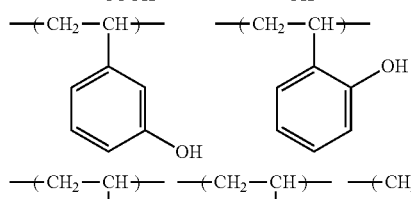
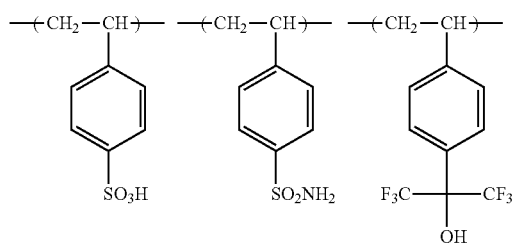
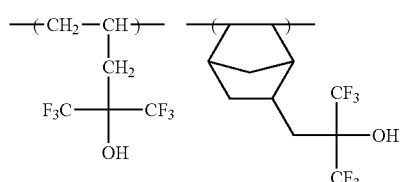
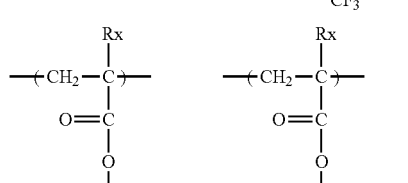
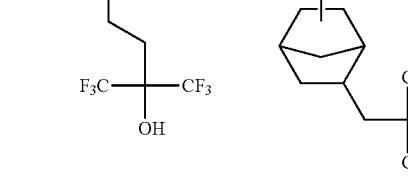
-continued
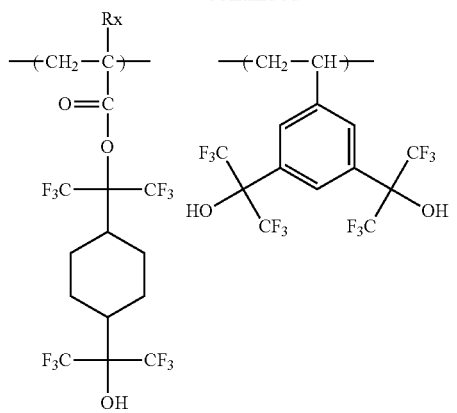
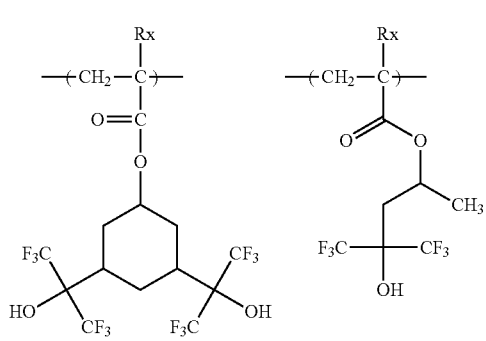
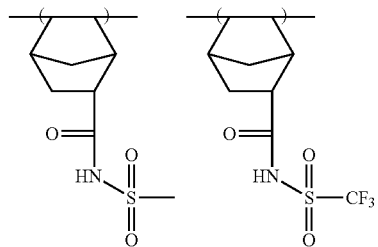
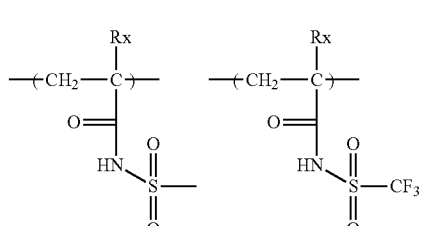
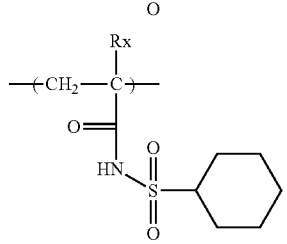

-continued

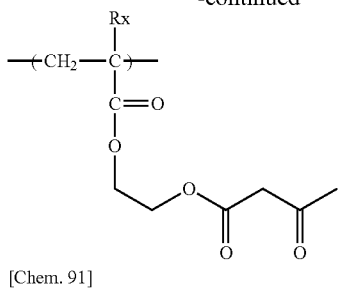

[Chem. 91]

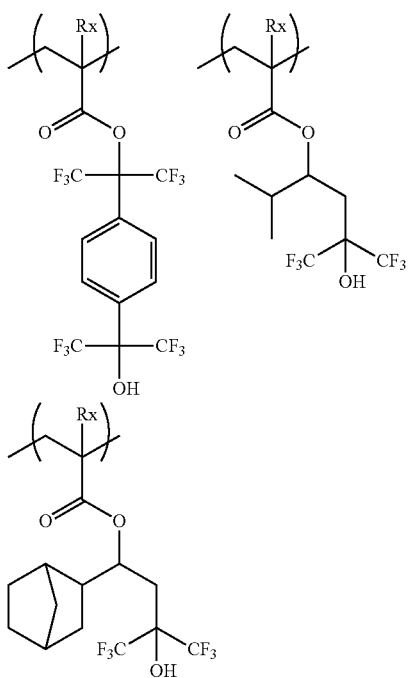

As the group having a lactone structure, the acid anhydride group, or the acid imide group (y), a group having a lactone structure is particularly preferable.

The repeating unit including these groups is, for example, a repeating unit in which this group is bonded directly to the main chain of the resin, such as a repeating unit by acrylate and methacrylate. This repeating unit may alternatively be a repeating unit in which this group is bonded to the main chain of the resin through a linking group. This repeating group may also be introduced at the end of the resin using a polymerization initiator or a chain transfer agent having this group when polymerized.

The repeating unit having a group having a lactone structure may include, for example, the same repeating unit having a lactone structure described above in the acid decomposable resin (P) section.

The content of the repeating unit having the group having a lactone structure, the acid anhydride group, or the acid imide group is preferably 1 to 100 mol %, more preferably 3 to 98 mol %, and even more preferably 5 to 95 mol % with regard to all repeating units in the hydrophobic resin.

The repeating unit having a group (z) decomposed by the action of acid in the hydrophobic resin (E) may include the same repeating unit having an acid decomposable group described in the resin (P) section. The repeating unit having a group (z) decomposed by the action of acid may have at least one of a fluorine atom and a silicon atom. The content of the repeating unit having a group (z) decomposed by the action of acid in the hydrophobic resin (E) is preferably 1 to 80 mol %, more preferably 10 to 80 mol %, even more preferably 20 to 60 mol % with regard to all repeating units in the resin (E).

The hydrophobic resin (E) may further have a repeating unit represented by following General Formula (III).

[Chem. 92]

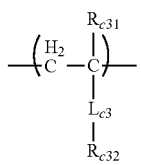
(III)

In General Formula (III), $R_{c31}$ represents a hydrogen atom, an alkyl group, (may be substituted with a fluorine atom or the like), a cyano group, or a $—CH_2—O—R_{ac2}$ group. In the formula, $R_{ac2}$ represents a hydrogen atom, an alkyl group or an acyl group. $R_{c31}$ is preferably a hydrogen atom, a methyl group, a hydroxymethyl group or a trifluoromethyl group, and particularly preferably a hydrogen atom or a methyl group.

$R_{c32}$ represents a group having an alkyl group, a cycloalkyl group, an alkenyl group, a cycloalkenyl group or an aryl group. These groups may be substituted with a group containing a fluorine atom or a silicon atom.

$L_{c3}$ represents a single bond or a divalent linking group.

In General Formula (III), the alkyl group of $R_{c32}$ is preferably a straight chain or branched alkyl group having 3 to 20 carbon atoms.

The cycloalkyl group is preferably a cycloalkyl group having 3 to 20 carbon atoms.

The alkenyl group is preferably an alkenyl group having 3 to 20 carbon atoms.

The cycloalkenyl group is preferably a cycloalkenyl group having 3 to 20 carbon atoms.

The aryl group is preferably an aryl group having 6 to 20 carbon atoms, more preferably a phenyl group or a naphthyl group, and these may have a substituent.

$R_{c32}$ is preferably an unsubstituted alkyl group or an alkyl group substituted with a fluorine atom.

The divalent linking group of $L_{c3}$ is preferably an alkylene group (preferably having 1 to 5 carbon atoms), an ether bond, a phenylene group, or an ester bond (a group represented by $—COO—$).

The content of the repeating unit represented by General Formula (III) is preferably 1 to 100 mol %, more preferably 10 to 90 mol %, and even more preferably 30 to 70 mol % with regard to all repeating units in the hydrophobic resin.

The hydrophobic resin (E) may preferably further have a repeating unit represented by following General Formula (CII-AB).

[Chem. 93]

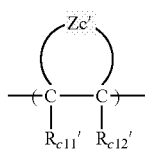
(CII-AB)

In Formula (CII-AB), $R_{c11}'$ and $R_{c12}'$, each independently, represent a hydrogen atom, a cyano group, a halogen atom or an alkyl group.

Zc' represents an atomic group to form an alicyclic structure, including two carbon atoms bonded (C—C).

The content of the repeating unit represented by General Formula (CII-AB) is preferably 1 to 100 mol %, more preferably 10 to 90 mol %, and even more preferably 30 to 70 mol % with regard to all repeating units in the hydrophobic resin.

Specific examples of the repeating unit represented by General Formulae (III) and (CII-AB) are shown below, however, the present invention is not limited to these. In the formula, Ra represents H, $CH_3$, $CH_2OH$, $CF_3$, or CN.

[Chem. 94]

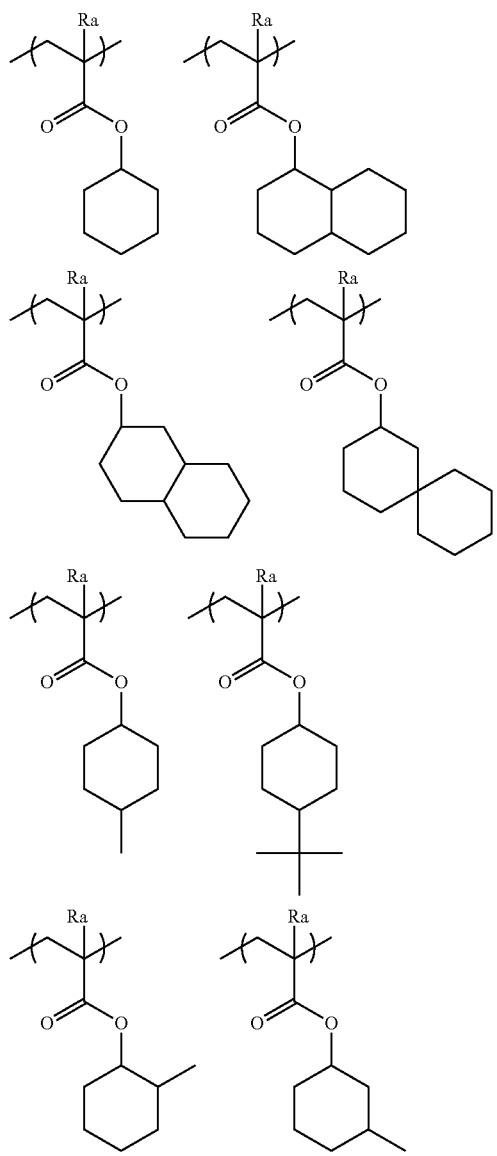

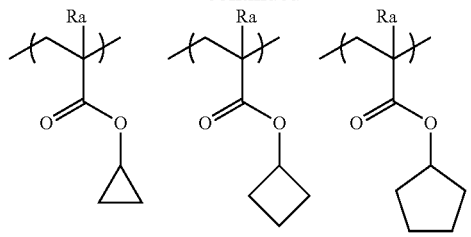

-continued

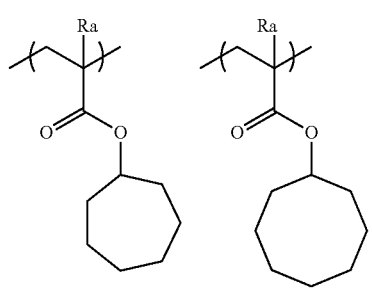

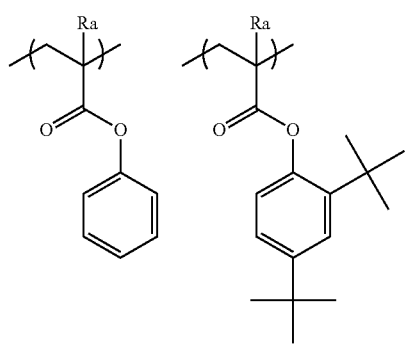

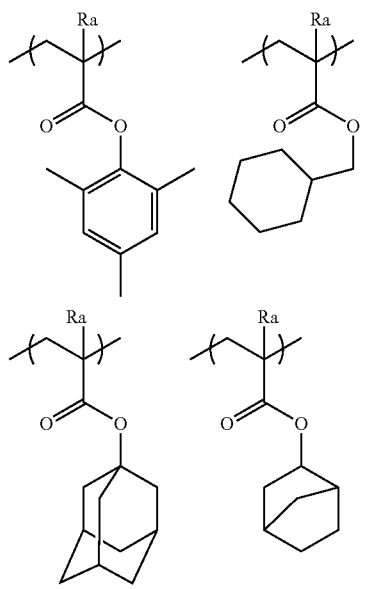

-continued

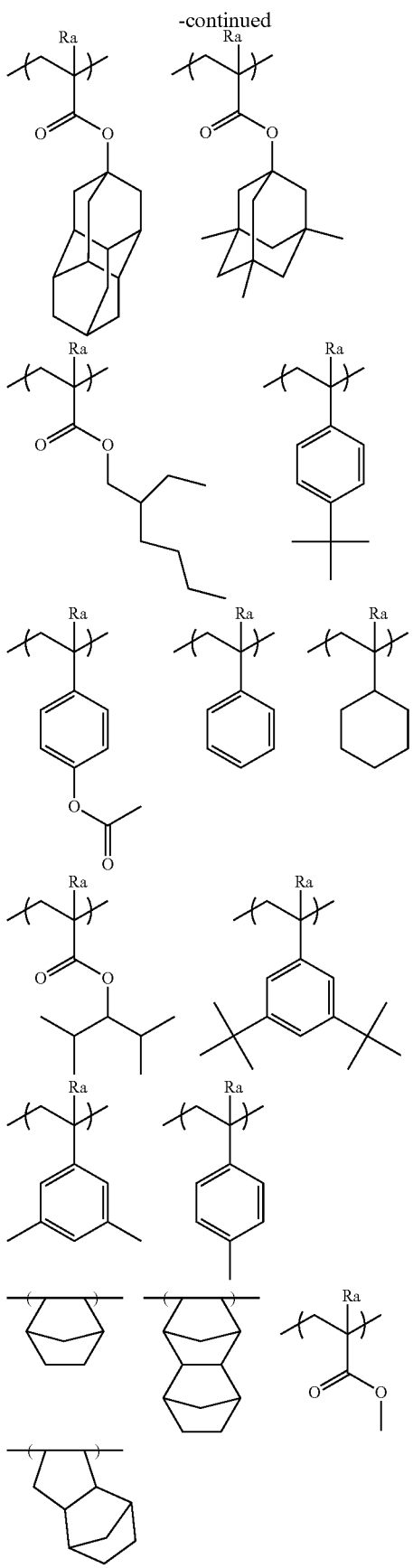

If the hydrophobic resin (E) has a fluorine atom, the content of the fluorine atom is preferably 5 to 80 mol % and more preferably 10 to 80 mol % with regard to a weight-average molecular weight of the hydrophobic resin (E). In addition, the repeating unit including a fluorine atom is preferably 10 to 100 mol % and more preferably 30 to 100 mol % with regard to all repeating units in the hydrophobic resin (E).

If the hydrophobic resin (E) has a silicon atom, the content of the silicon atom is preferably 2 to 50 mol % and more preferably 2 to 30 mol % with regard to a weight-average molecular weight of the hydrophobic resin (E). In addition, the repeating unit including a silicon atom is preferably 10 to 100 mol % and more preferably 20 to 100 mol % with regard to all repeating units in the hydrophobic resin (E).

The standard weight average molecular weight of the hydrophobic resin (E) using polystyrene conversion is preferably 1,000 to 100,000, more preferably 1,000 to 50,000, and even more preferably 2,000 to 15,000.

In addition, the hydrophobic resin (E) may be used either alone or as a combination of two or more.

The content of the hydrophobic resin (E) in the composition is preferably 0.01 to 10% by mass, more preferably 0.05 to 8% by mass, and even more preferably 0.1 to 5% by mass with regard to total solids in the composition of the present invention.

The hydrophobic resin (E), similar to the resin (P), naturally has fewer impurities such as metal, however, a residual monomer or an oligomer component is preferably 0.01 to 5% by mass, more preferably 0.01 to 3% by mass, and even more preferably 0.05% to 1% by mass. Thus, the actinic-ray-sensitive or radiation-sensitive resin composition with no changes over time such as impurities in liquid or sensitivity may be obtained. In addition, a molecular weight distribution (Mw/Mn, also referred to as degree of dispersion) is preferably in the range of 1 to 5, more preferably 1 to 3, and even more preferably is in the range of 1 to 2 from the viewpoint of resolution, a resist shape, a sidewall of the resist pattern, roughness, and the like.

A variety of commercially available products may be used as the hydrophobic resin (E), or the hydrophobic resin (E) may be synthesized in accordance with conventional methods (for example, radical polymerization). For example, as the general synthesis method, a bulk polymerization method in which polymerization is carried out by dissolving monomer species and an initiator in a solvent and heating the solution, a dropwise adding polymerization method in which a solution of monomer species and an initiator is added dropwise to a heating solvent over 1 to 10 hours, or the like may be included, and a dropwise adding polymerization method is preferable.

The reaction solvent, the polymerization initiator, the reaction condition (temperature, concentration, and the like), and purification method after the reaction, are similar to those described in the resin (P), however, the reaction concentration is preferably 30 to 50% by mass in the synthesis of the hydrophobic resin (E).

Specific examples of the hydrophobic resin (E) are shown below. In addition, the molar ratio of the repeating unit in each resin (corresponding to each repeating unit from left to right), the weight-average molecular weight, and the degree of dispersion are shown in the tables below.

[Chem. 95]
(HR-1) 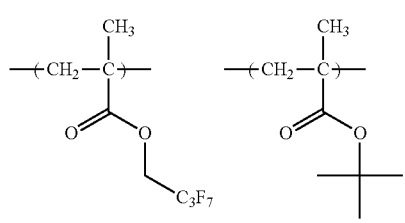
(HR-2) 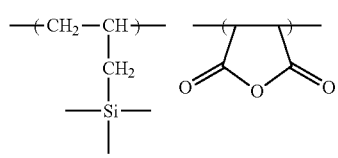
(HR-3) 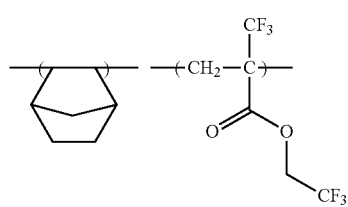
(HR-4) 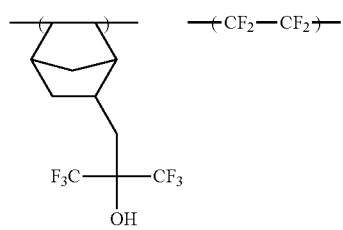
(HR-5) 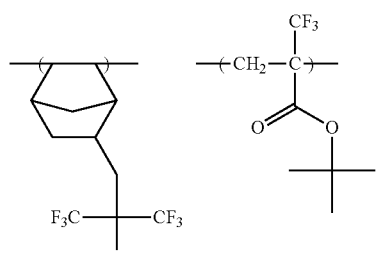
(HR-6) 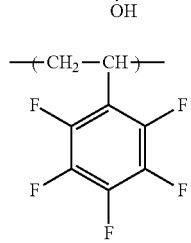
(HR-7) 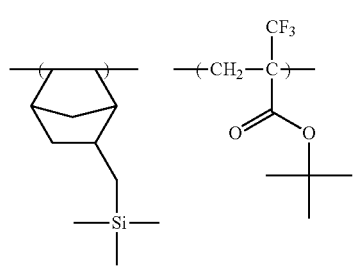
(HR-8) 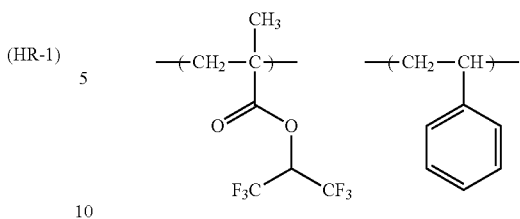
(HR-9) 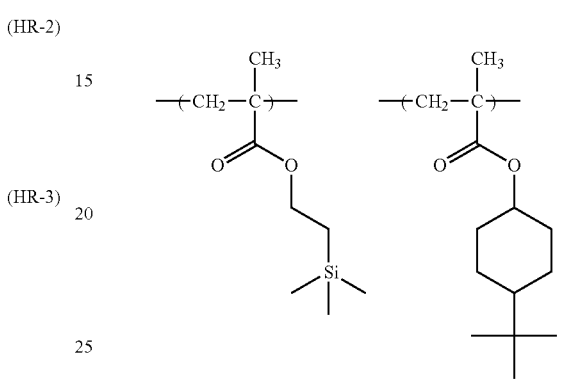
(HR-10) 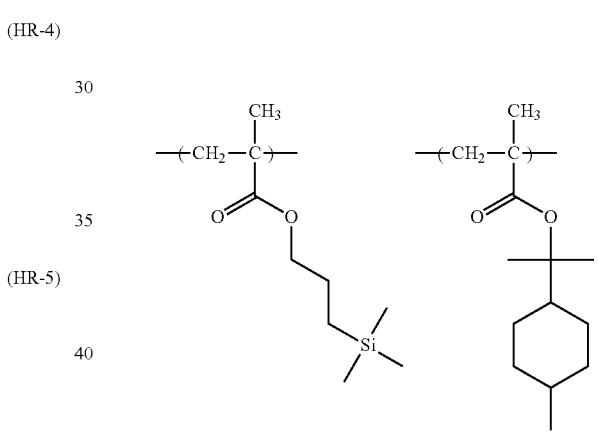
(HR-11) 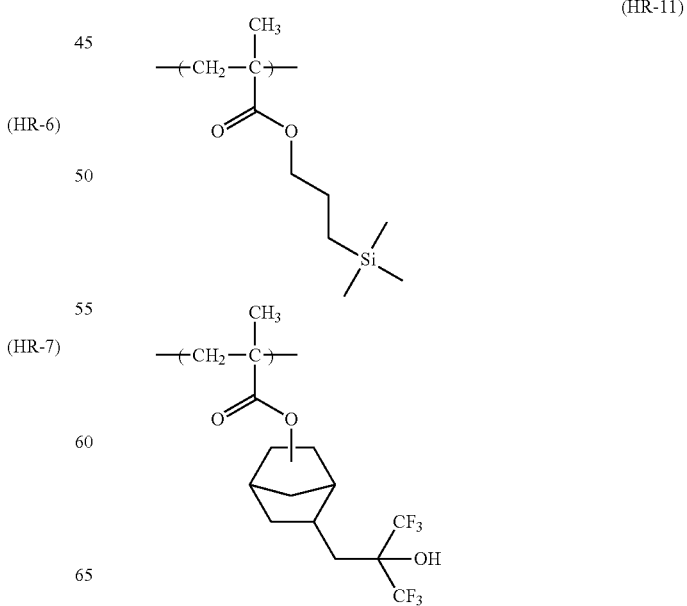
-continued (HR-12) 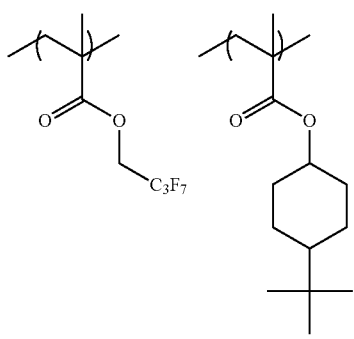
(HR-13) 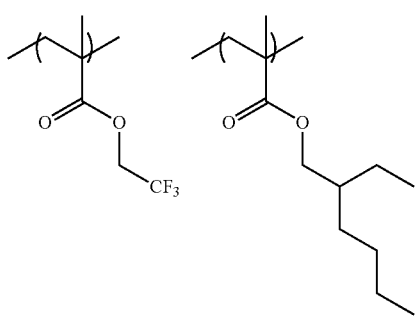
(HR-14) 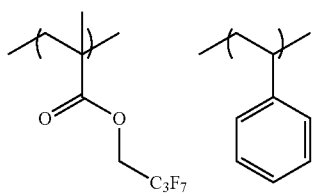
(HR-15) 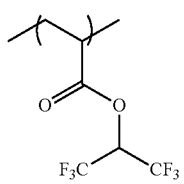
(HR-16) 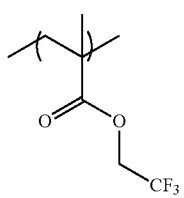
(HR-17) 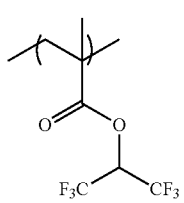
(HR-18) 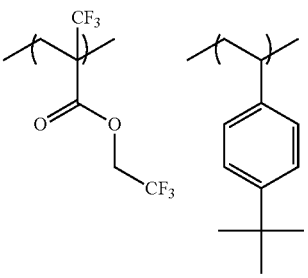
(HR-19) 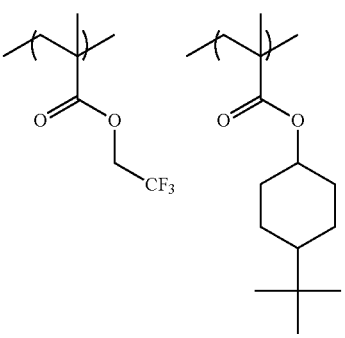
(HR-20) 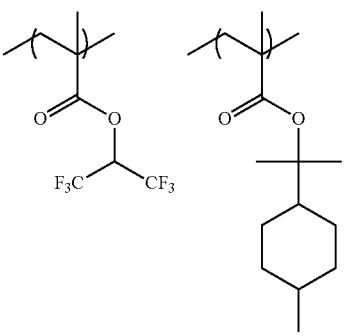
(HR-21) 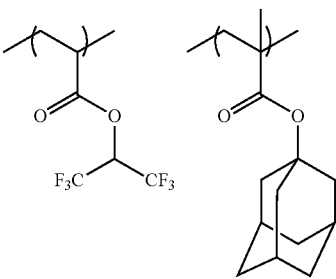
(HR-22) 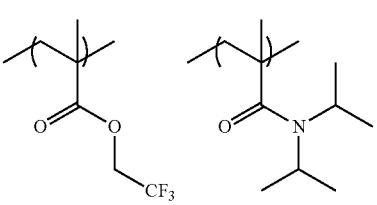

201
-continued
(HR-23)
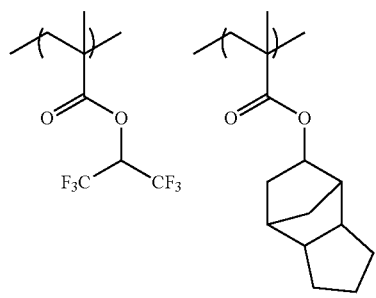
(HR-24)
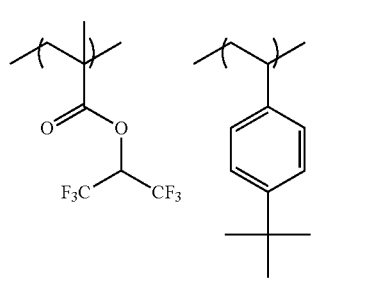
(HR-25)
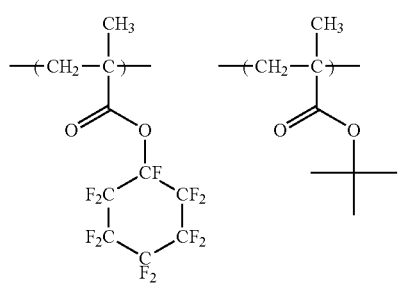
(HR-26)
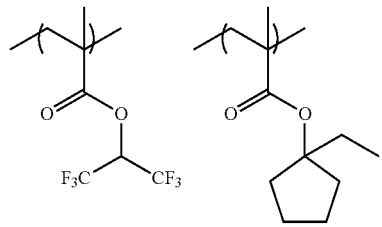
[Chem. 96]
(HR-27)
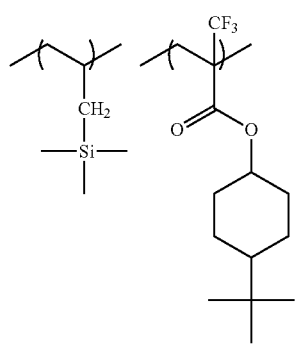
202
-continued
(HR-28)
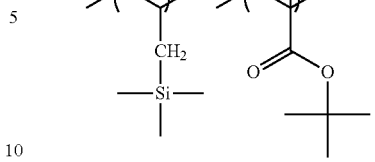
(HR-29)
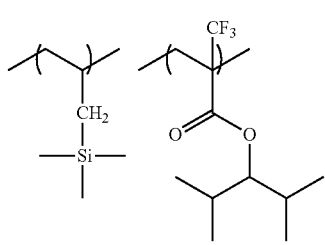
(HR-30)
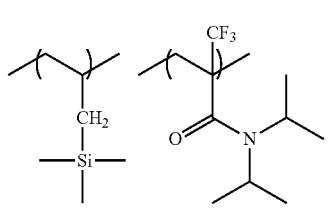
(HR-31)
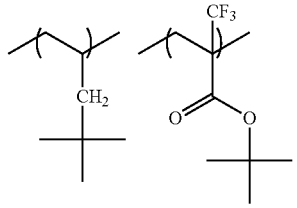
(HR-32)
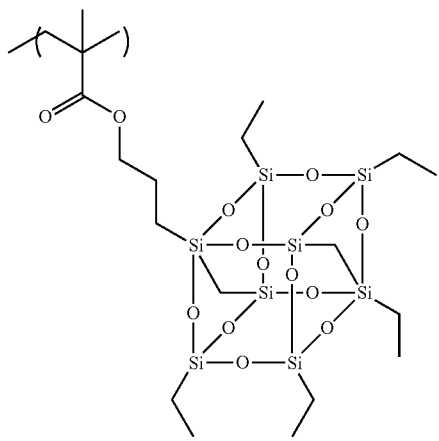

(HR-33)
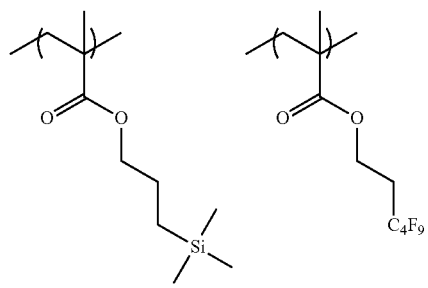
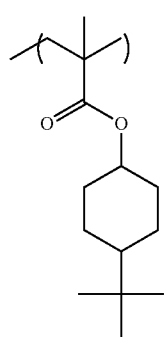
(HR-34)
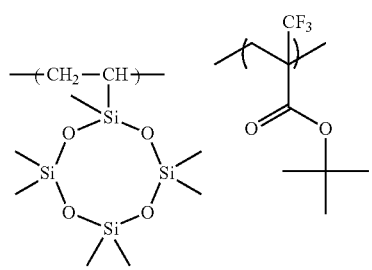
(HR-35)
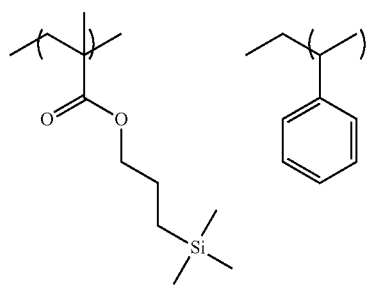
(HR-36)
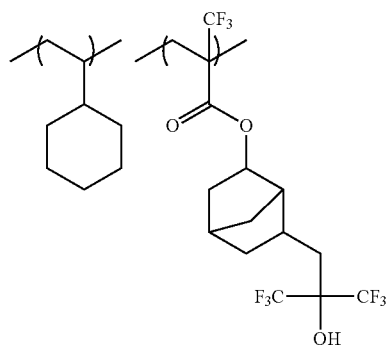
(HR-37)
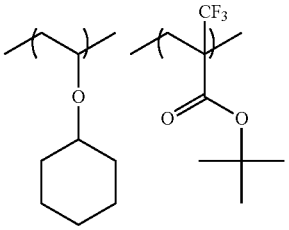
(HR-38)
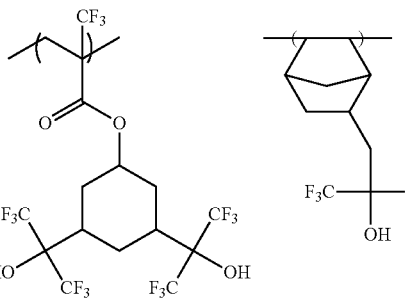
(HR-39)
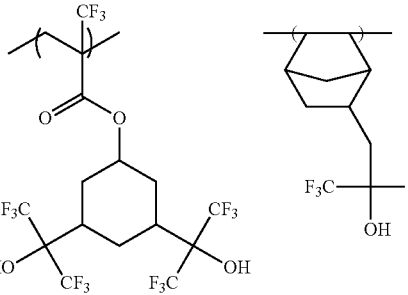
(HR-40)
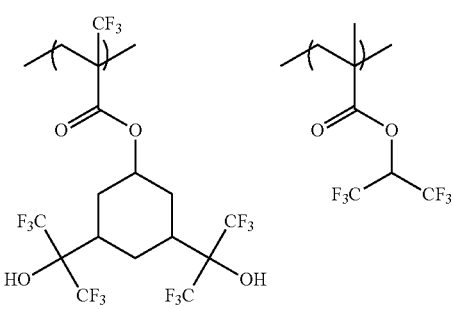
(HR-41)
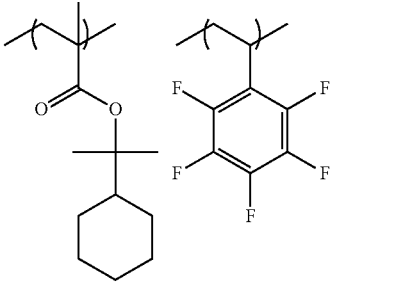
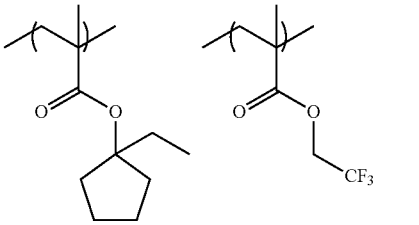
(HR-42)
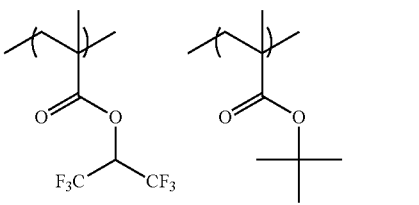

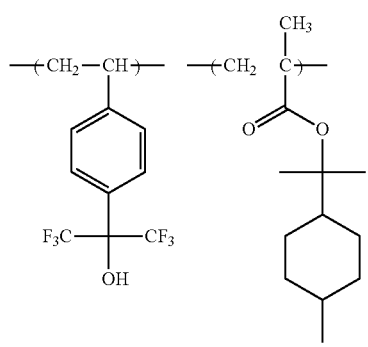
(HR-43)
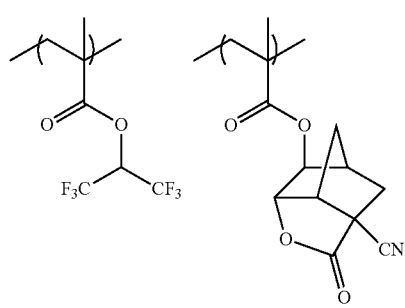
(HR-44)
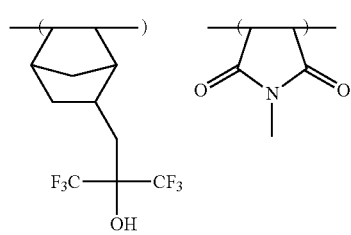
(HR-45)
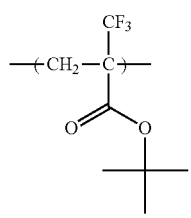
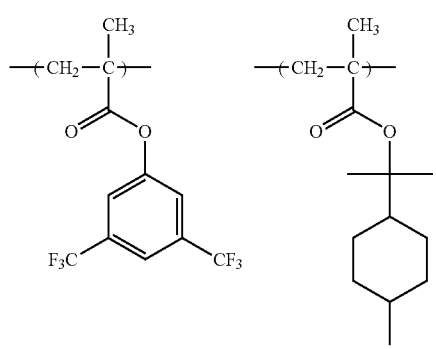
(HR-46)
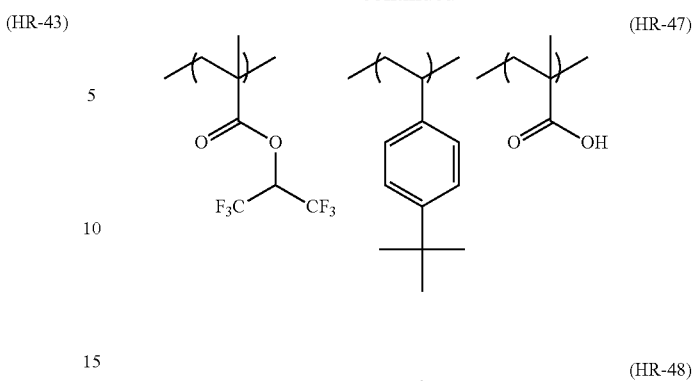
(HR-47)
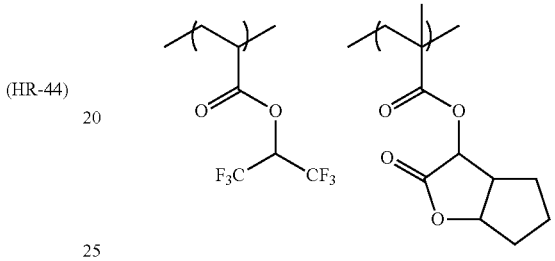
(HR-48)
[Chem. 97]
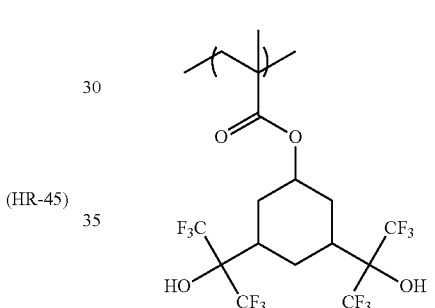
(HR-49)
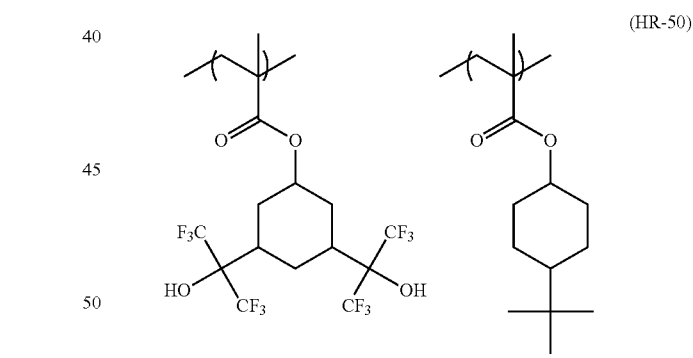
(HR-50)
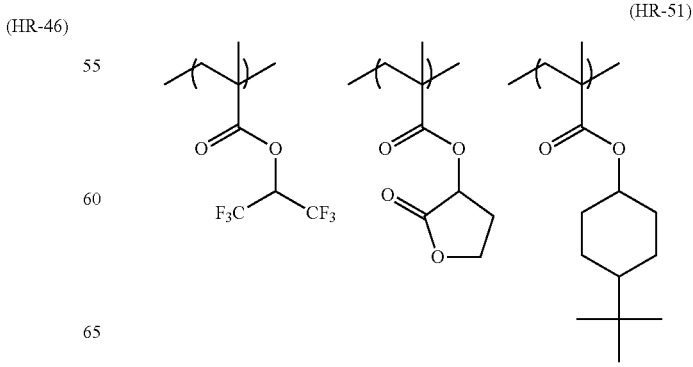
(HR-51)

(HR-52)
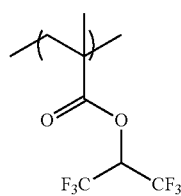 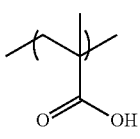
(HR-53)
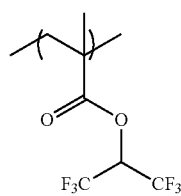 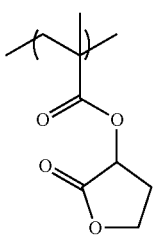 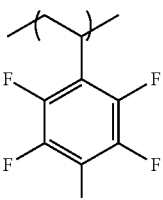
(HR-54)
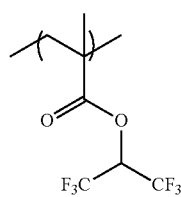 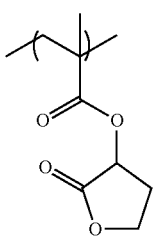
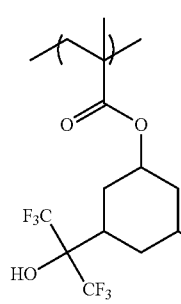
(HR-55)
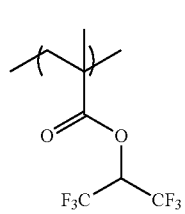 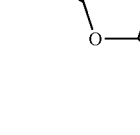
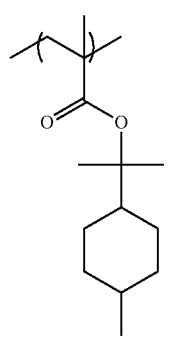
(HR-56)
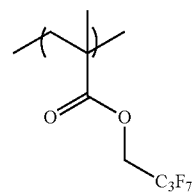
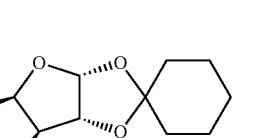
(HR-57)
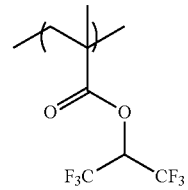 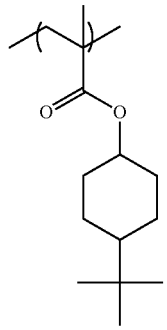
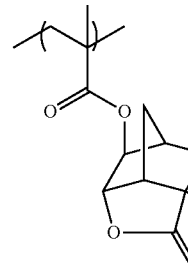
(HR-58)
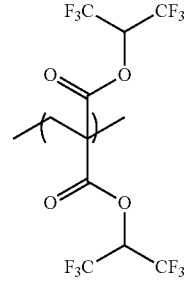 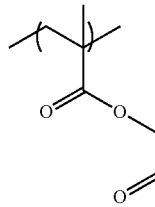
(HR-59)
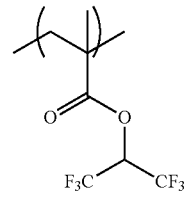 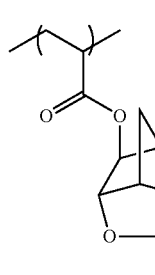

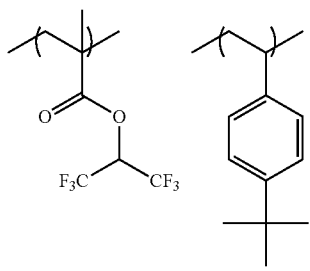
(HR-60)
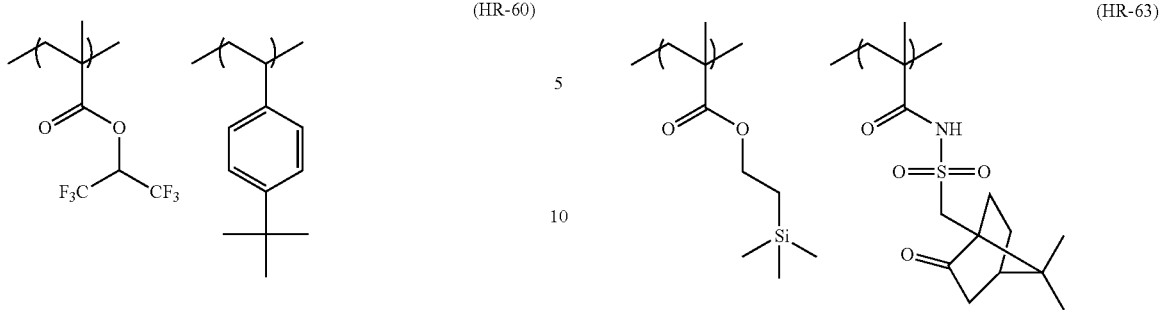
(HR-63)
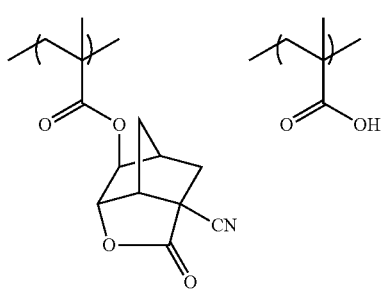
(HR-61)
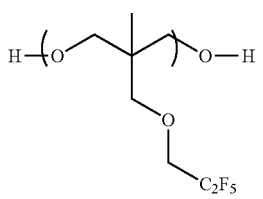
(HR-64)
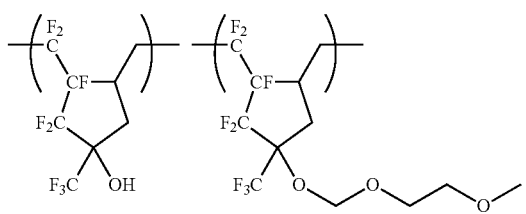
(HR-65)
[Chem. 98]
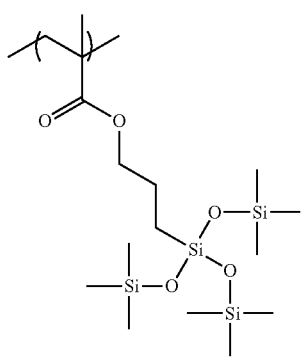
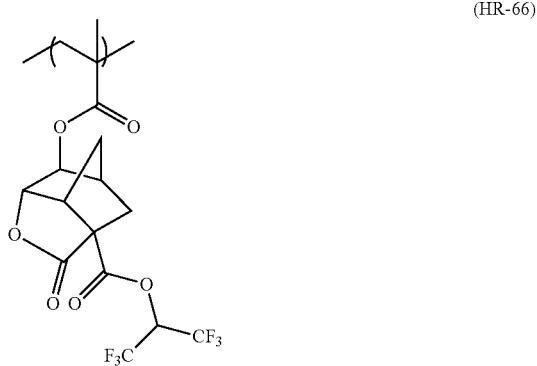
(HR-66)
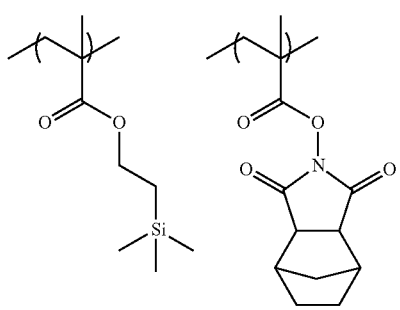
(HR-62)
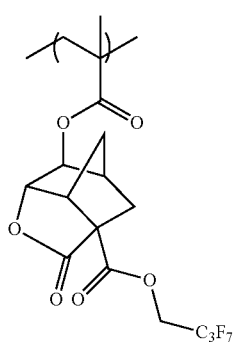
(HR-67)

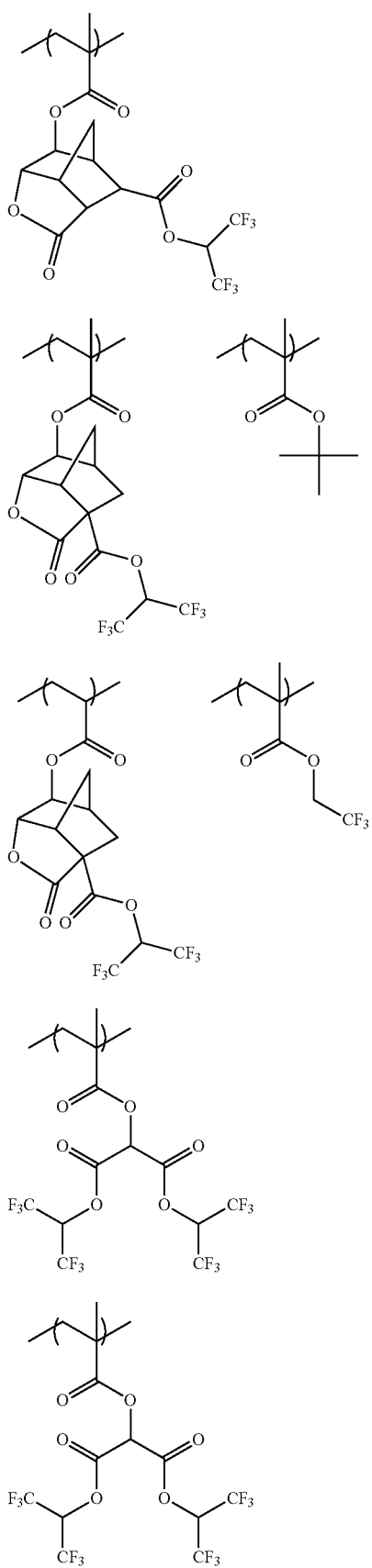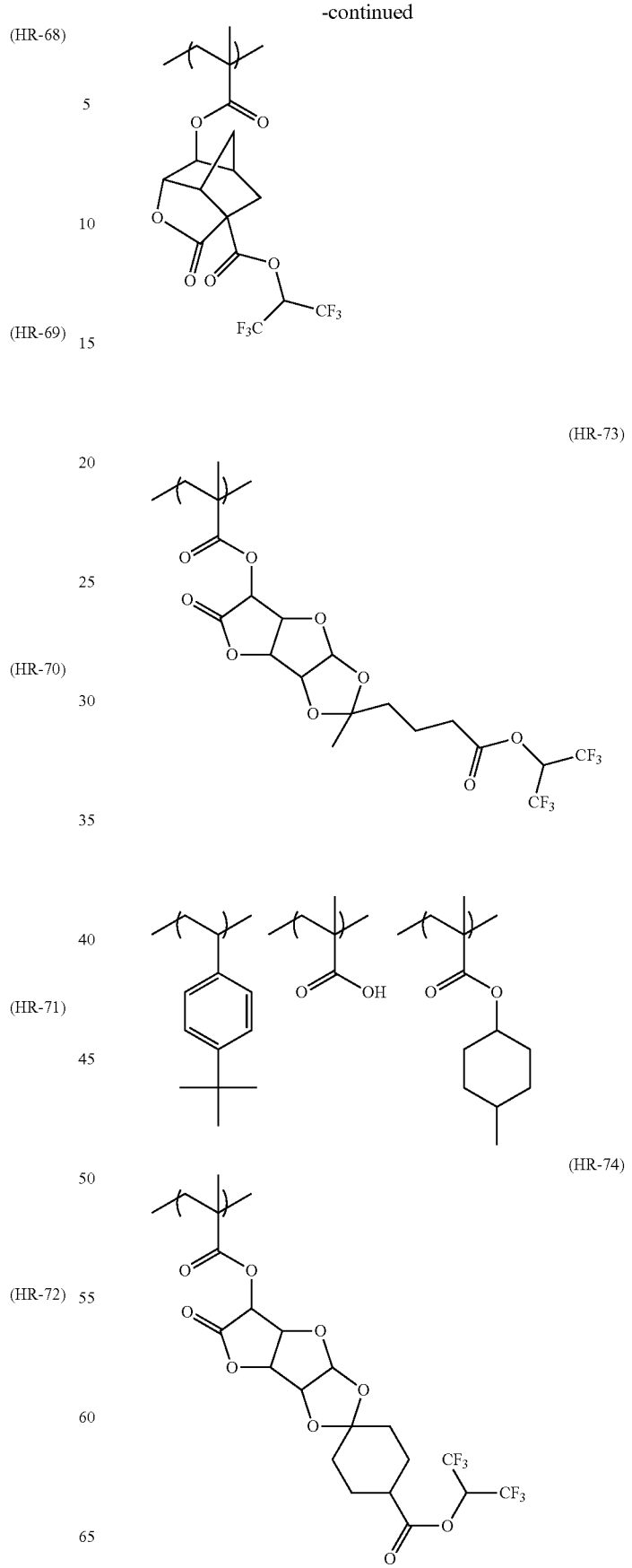

(HR-75)
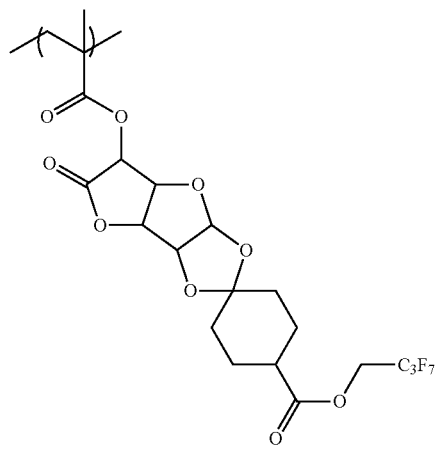
(HR-76)
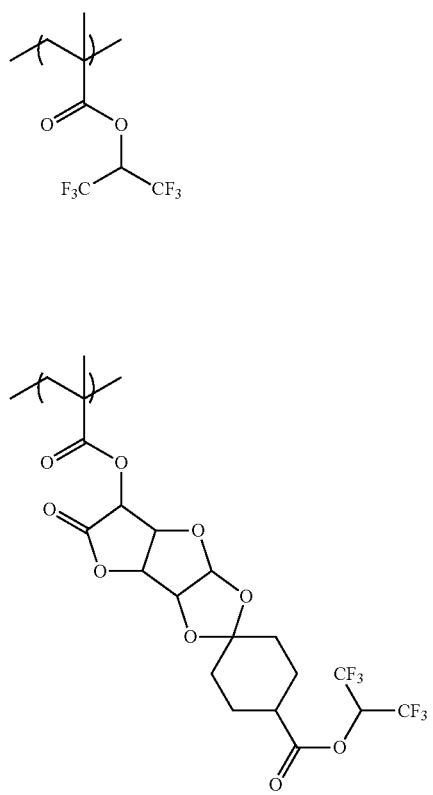
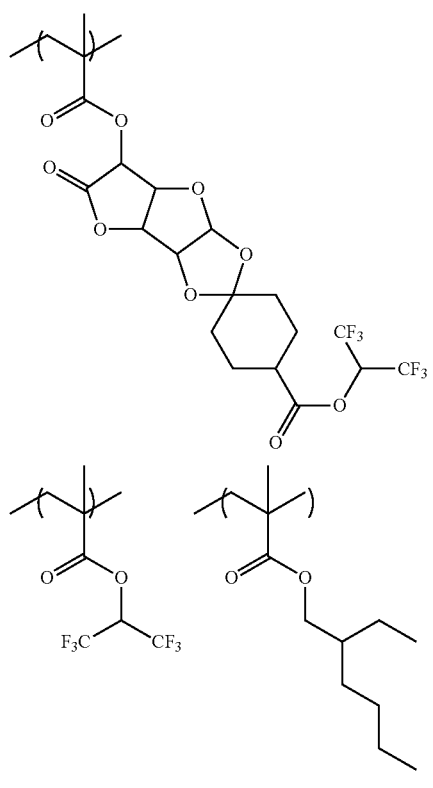
(HR-77)
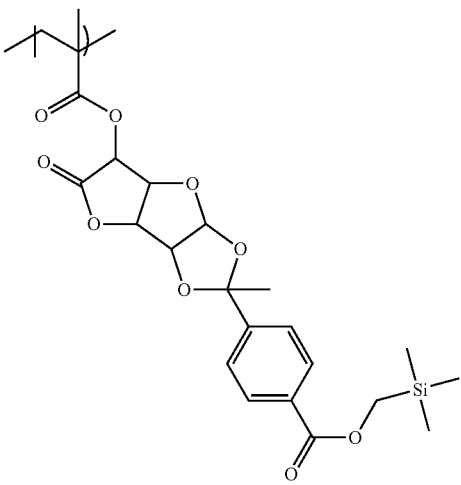
(HR-78)
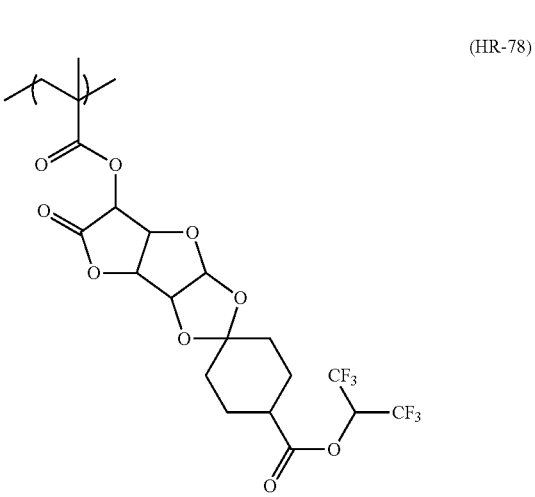
(HR-79)
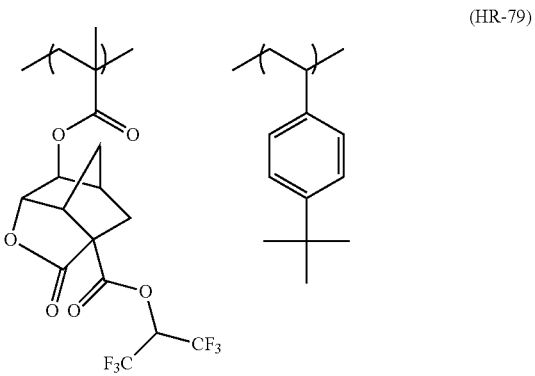

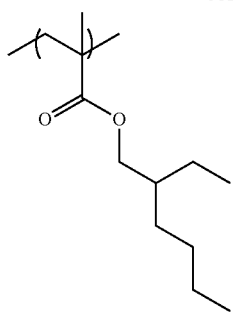
(HR-80)
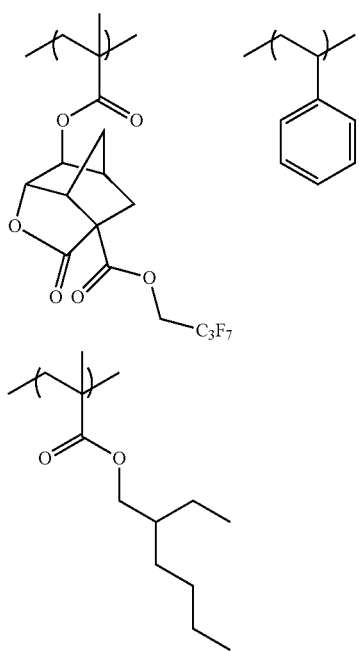
[Chem. 99]
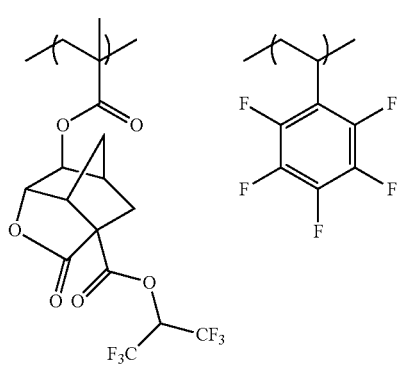
(HR-81)
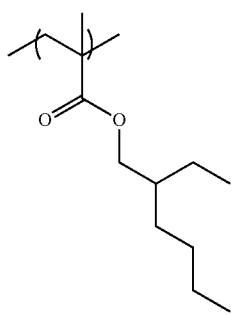
(HR-82)
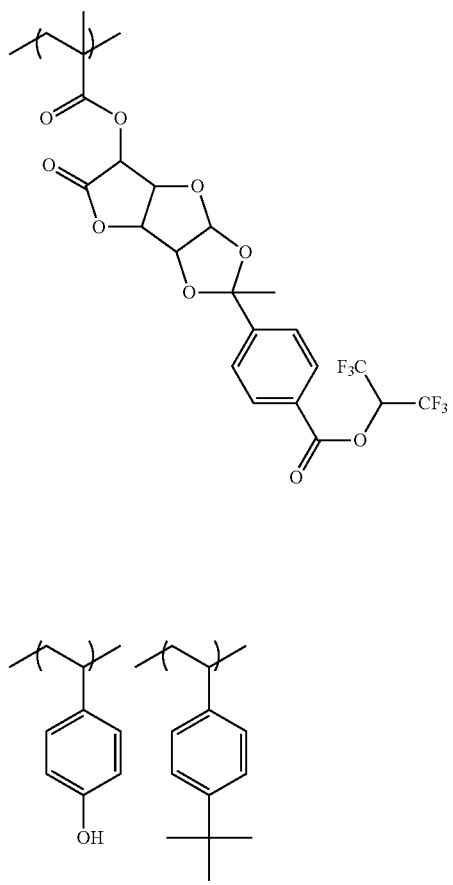
(HR-83)
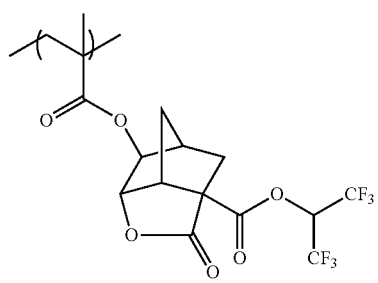
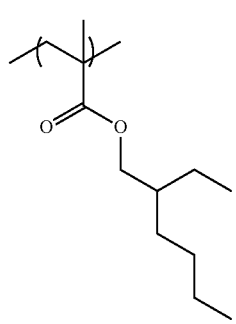

(HR-84)
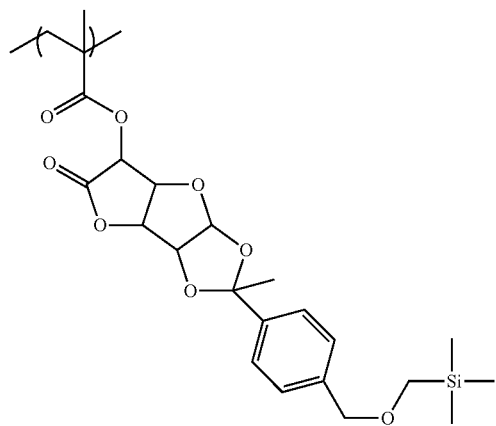
(HR-85)
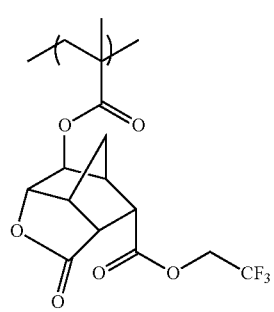
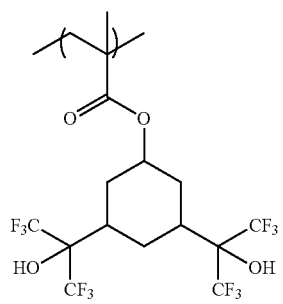
(HR-86)
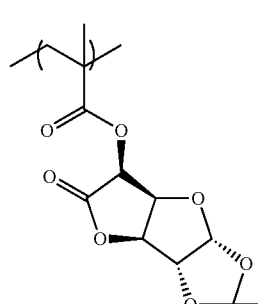
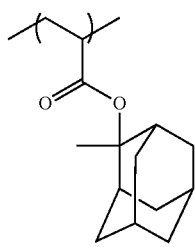
(HR-87)
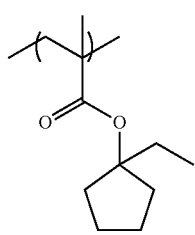
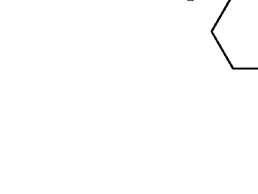
(HR-88)
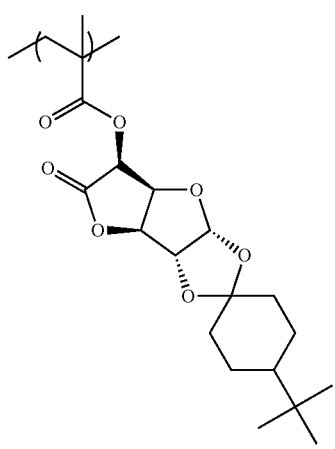

-continued

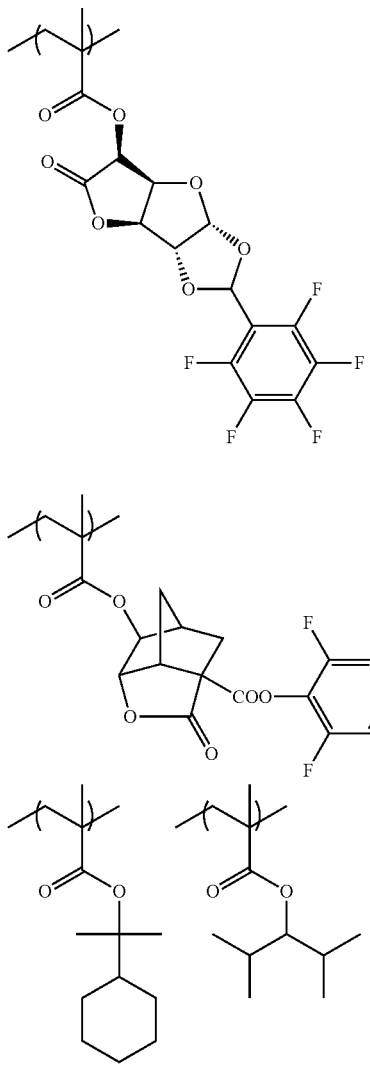

(HR-89)

(HR-90)

TABLE 1

| Resin | Composition | Mw | Mw/Mn |
|---|---|---|---|
| HR-1 | 50/50 | 4900 | 1.4 |
| HR-2 | 50/50 | 5100 | 1.6 |
| HR-3 | 50/50 | 4800 | 1.5 |
| HR-4 | 50/50 | 5300 | 1.6 |
| HR-5 | 50/50 | 4500 | 1.4 |
| HR-6 | 100 | 5500 | 1.6 |
| HR-7 | 50/50 | 5800 | 1.9 |
| HR-8 | 50/50 | 4200 | 1.3 |
| HR-9 | 50/50 | 5500 | 1.8 |
| HR-10 | 40/60 | 7500 | 1.6 |
| HR-11 | 70/30 | 6600 | 1.8 |
| HR-12 | 40/60 | 3900 | 1.3 |
| HR-13 | 50/50 | 9500 | 1.8 |
| HR-14 | 50/50 | 5300 | 1.6 |
| HR-15 | 100 | 6200 | 1.2 |
| HR-16 | 100 | 5600 | 1.6 |
| HR-17 | 100 | 4400 | 1.3 |
| HR-18 | 50/50 | 4300 | 1.3 |
| HR-19 | 50/50 | 6500 | 1.6 |
| HR-20 | 30/70 | 6500 | 1.5 |
| HR-21 | 50/50 | 6000 | 1.6 |
| HR-22 | 50/50 | 3000 | 1.2 |
| HR-23 | 50/50 | 5000 | 1.5 |

TABLE 1-continued

| Resin | Composition | Mw | Mw/Mn |
|---|---|---|---|
| HR-24 | 50/50 | 4500 | 1.4 |
| HR-25 | 30/70 | 5000 | 1.4 |
| HR-26 | 50/50 | 5500 | 1.6 |
| HR-27 | 50/50 | 3500 | 1.3 |
| HR-28 | 50/50 | 6200 | 1.4 |
| HR-29 | 50/50 | 6500 | 1.6 |
| HR-30 | 50/50 | 6500 | 1.6 |
| HR-31 | 50/50 | 4500 | 1.4 |
| HR-32 | 30/70 | 5000 | 1.6 |
| HR-33 | 30/30/40 | 6500 | 1.8 |
| HR-34 | 50/50 | 4000 | 1.3 |
| HR-35 | 50/50 | 6500 | 1.7 |
| HR-36 | 50/50 | 6000 | 1.5 |
| HR-37 | 50/50 | 5000 | 1.6 |
| HR-38 | 50/50 | 4000 | 1.4 |
| HR-39 | 20/80 | 6000 | 1.4 |
| HR-40 | 50/50 | 7000 | 1.4 |
| HR-41 | 50/50 | 6500 | 1.6 |
| HR-42 | 50/50 | 5200 | 1.6 |
| HR-43 | 50/50 | 6000 | 1.4 |
| HR-44 | 70/30 | 5500 | 1.6 |
| HR-45 | 50/20/30 | 4200 | 1.4 |
| HR-46 | 30/70 | 7500 | 1.6 |
| HR-47 | 40/58/2 | 4300 | 1.4 |
| HR-48 | 50/50 | 6800 | 1.6 |
| HR-49 | 100 | 6500 | 1.5 |
| HR-50 | 50/50 | 6600 | 1.6 |
| HR-51 | 30/20/50 | 6800 | 1.7 |
| HR-52 | 95/5 | 5900 | 1.6 |
| HR-53 | 40/30/30 | 4500 | 1.3 |
| HR-54 | 50/30/20 | 6500 | 1.8 |
| HR-55 | 30/40/30 | 7000 | 1.5 |
| HR-56 | 60/40 | 5500 | 1.7 |
| HR-57 | 40/40/20 | 4000 | 1.3 |
| HR-58 | 60/40 | 3800 | 1.4 |
| HR-59 | 80/20 | 7400 | 1.6 |
| HR-60 | 40/40/15/5 | 4800 | 1.5 |
| HR-61 | 60/40 | 5600 | 1.5 |
| HR-62 | 50/50 | 5900 | 2.1 |
| HR-63 | 80/20 | 7000 | 1.7 |
| HR-64 | 100 | 5500 | 1.8 |
| HR-65 | 50/50 | 9500 | 1.9 |

TABLE 2

| Resin | Composition | Mw | Mw/Mn |
|---|---|---|---|
| HR-66 | 100 | 6000 | 1.5 |
| HR-67 | 100 | 6000 | 1.4 |
| HR-68 | 100 | 9000 | 1.5 |
| HR-69 | 60/40 | 8000 | 1.3 |
| HR-70 | 80/20 | 5000 | 1.4 |
| HR-71 | 100 | 9500 | 1.5 |
| HR-72 | 40/60 | 8000 | 1.4 |
| HR-73 | 55/30/5/10 | 8000 | 1.3 |
| HR-74 | 100 | 13000 | 1.4 |
| HR-75 | 70/30 | 8000 | 1.3 |
| HR-76 | 50/40/10 | 9500 | 1.5 |
| HR-77 | 100 | 9000 | 1.6 |
| HR-78 | 80/20 | 3500 | 1.4 |
| HR-79 | 90/8/2 | 13000 | 1.5 |
| HR-80 | 85/10/5 | 5000 | 1.5 |
| HR-81 | 80/18/2 | 6000 | 1.5 |
| HR-82 | 50/20/30 | 5000 | 1.3 |
| HR-83 | 90/10 | 8000 | 1.4 |
| HR-84 | 100 | 9000 | 1.6 |
| HR-85 | 80/20 | 15000 | 1.6 |
| HR-86 | 70/30 | 4000 | 1.42 |
| HR-87 | 60/40 | 8000 | 1.32 |
| HR-88 | 100 | 3800 | 1.29 |
| HR-89 | 100 | 6300 | 1.35 |
| HR-90 | 50/40/10 | 8500 | 1.51 |

[6] Surfactant (F)

The actinic-ray-sensitive or radiation-sensitive resin composition in the present invention may or may not include a further surfactant, however, if the composition does, may preferably contain any one of fluorine- and/or silicon-based surfactants (fluorine-based surfactants, silicon-based surfactants, surfactants having both a fluorine atom and a silicon atom) or two or more types of surfactants.

By the actinic-ray-sensitive or radiation-sensitive resin composition in the present invention containing a surfactant, a resist pattern with satisfactory sensitivity and resolution, therefore, less adhesion and developing defects may be obtained when exposure light source of 250 nm or less, particularly 220 nm or less, is used.

The fluorine- and/or silicon-based surfactant may include surfactants disclosed in of US2008/0248425A, and may include, for example, F-Top EF301 and EF303 (manufactured by Shin Akita Kasei Co., Ltd.), Fluorad FC430, 431, and 4430 (manufactured by Sumitomo 3M Limited), Megafag F171, F173, F176, F189, F113, F110, F177, F120, and R08 (manufactured by DIC Corporation), Surflon S-382, SC101, 102, 103, 104, 105, 106, and KH-20 (manufactured by Asahi Glass Co., Ltd.), Troysol S-366 (manufactured by Troy Chemical Co., Ltd.), GF-300 and GF-150 (manufactured by To a Synthetic Chemical Co., Ltd.), Surflon S-393 (manufactured by Seimi Chemical Co., Ltd.), F-top EF121, EF122A, EF122B, RF122C, EF125M, EF135M, EF351, EF352, EF801, EF802, and EF601 (manufactured by Jemco, Inc.), PF636, PF656, PF6320, and PF6520 (manufactured by OMNOVA Solutions Inc.), FTX-204G, 208G 218G 230G 204D, 208D, 212D, 218D, and 222D (manufactured by Neos Co., Ltd.), or the like. In addition, a polysiloxane polymer KP-341 (manufactured by Shin-Etsu Chemical Co., Ltd.) may also be used as the silicon-based surfactant.

In addition, as the surfactant, a surfactant using a polymer having a fluoro aliphatic group derived from a fluoro aliphatic compound prepared by a telomerization method (also referred to as a telomer method) or an oligomerization (also known as a oligomer method) in addition to those well-known in the art shown above, may be used. The fluoro aliphatic compound may be synthesized by methods disclosed in JP 2002-90991A.

The surfactant corresponding to the above may include Megafac F178, F-470, F-473, F-475, F-476, F-472 (manufactured by DIC Corporation), a copolymer of acrylate (or methacrylate) having a $C_6F_{13}$ groups and (poly(oxyalkylene)) acrylate (or methacrylate), a copolymer of acrylate (or methacrylate) having a $C_3F_7$ groups, (poly(oxyethylene)) acrylate (or methacrylate), and (poly(oxypropylene)) acrylate (or methacrylate), or the like.

In addition, in the present invention, other surfactants, besides the fluorine-based and/or silicon-based surfactants, which is disclosed in [0280] of US2008/0248425A may be used.

These surfactants may be used either alone or as a combination of two or more.

If the actinic-ray-sensitive or radiation-sensitive resin composition contains the surfactant, the amount of the surfactant used is preferably 0.0001 to 2% by mass, and more preferably 0.0005 to 1% by mass with regard to total amount of the actinic-ray-sensitive or radiation-sensitive resin composition (excluding the solvent).

On the other hand, by keeping the addition amount of the surfactant to be 10 ppm or less with regard to total amount of the actinic-ray-sensitive or radiation-sensitive resin composition (excluding the solvent), surface localization of the hydrophobic resin is enhanced, thereby traceability of water may be improved when liquid immersion exposure is carried out since the surface of the resist film is made to be more hydrophobic.

[7] Other Additives (G)

The actinic-ray-sensitive or radiation-sensitive resin composition in the present invention may or may not contain a onium salt carboxylate. The onium salt carboxylate such as this may include those described in [0605] to [0606] of US2008/0187860A.

The onium salt carboxylate such as this can be synthesized by reacting sulfonium hydroxide, iodonium hydroxide, ammonium hydroxide and carboxylic acid with silver oxide in an appropriate solvent.

If the actinic-ray-sensitive or radiation-sensitive resin composition contains the onium salt carboxylate, the content is typically 0.1 to 20% by mass, preferably 0.5 to 10% by mass, and more preferably 1 to 7% by mass with regard to total solids of the composition.

The actinic-ray-sensitive or radiation-sensitive resin composition in the present invention may further contain, if necessary, a dye, a plasticizer, a light sensitizer, a light absorbent, an alkali-soluble resin, a dissolution inhibitor, a compound promoting solubility for a developer (for example, a phenol compound with a molecular weight of 1,000 or less, an alicyclic compound or aliphatic compound having a carboxyl group), and the like.

The phenol compound with a molecular weight of 1,000 or less may be readily synthesized by those skilled in the art with reference to the method disclosed in, for example, JP1992-122938A (JP-H04-122938A), JP1990-28531A (JP-H02-28531A), U.S. Pat. No. 4,916,210A EP219294B, and the like.

Specific examples of the alicyclic compound or aliphatic compound having a carboxyl group may include a carboxylic acid derivative having a steroid structure such as cholic acid, deoxycholic acid or lithocholic acid, an adamantane carboxylic acid derivative, adamantane dicarboxylic acid, cyclohexane carboxylic acid, cyclohexane dicarboxylic acid, or the like, however, are not limited to these.

The actinic-ray-sensitive or radiation-sensitive resin composition in the present invention is preferably used in a film thickness of 30 to 250 nm, and more preferably used in a film thickness of 30 to 200 nm from the viewpoint of improving resolution. This film thickness is possible by improving coating properties and film formability through setting the solid concentration in the composition being in an appropriate range to have a moderate viscosity.

The solid concentration of the actinic-ray-sensitive or radiation-sensitive resin composition in the present invention is typically 1.0 to 10% by mass, preferably 2.0 to 5.7% by mass, and more preferably 2.0 to 5.3% by mass. By having the solid concentration in this range, the resist solution may be uniformly applied on the substrate, and forming a resist pattern with excellent line width roughness is possible. The reason is not clear, however, it is believed that, by having the solid concentration at 10% by mass or less and preferably 5.7% by mass or less, aggregation of materials in the resist solution, particularly, the photoacid generator is suppressed and as a result, a uniform resist film may be formed.

The solid concentration is a weight percentage of the weight of other resist components except the solvent with regard to the total weight of the actinic-ray-sensitive or radiation-sensitive resin composition.

The actinic-ray-sensitive or radiation-sensitive resin composition in the present invention is used by the above component being dissolved in a predetermined organic solvent, preferably the mixed solvent described above, filtered by a filter, and then coated on a predetermined support (substrate). Pore size of the filter used in the filtration by a filter is preferably 0.1 µm or less, more preferably 0.05 µm or less, and more preferably 0.03 µm or less and made of polytetrafluoroethylene, polyethylene, or nylon. In the filtration by a filter, filtration may be carried out by cyclical filtration or by connecting a plurality of types of filters in series or in parallel, as disclosed in JP2002-62667A. In addition, the composition may also be filtered a plurality of times. Furthermore, degassing treatment, and the like, may be carried out for the composition before and after filtration.

[8] Pattern Forming Method

A pattern forming method of the present invention (a negative-type pattern forming method) includes, at least, (a) a step for forming a film (a resist film) by the actinic-ray-sensitive or radiation-sensitive resin composition of the present invention, (b) a step for exposing the film, and (c) a step for developing the film after the exposure using a developer.

Exposure in the step (b) may be liquid immersion exposure.

The pattern forming method of the present invention preferably has (d) a heating step after (b) the exposure step.

The pattern forming method of the present invention may further have (e) a step for developing using an alkaline developer.

The pattern forming method of the present invention may have (b) the exposure step for a plurality of times.

The pattern forming method of the present invention can have (e) the heating step for a plurality of times.

The resist film of the present invention is formed from the actinic-ray-sensitive or radiation-sensitive resin composition of the present invention described above, and more specifically, is preferably a film formed by coating the actinic-ray-sensitive or radiation-sensitive resin composition on a substrate In the pattern forming method of the present invention, the step for forming a film by the actinic-ray-sensitive or radiation-sensitive resin composition on a substrate, and the step for exposing the film and the development step may be performed by generally known methods.

It is preferable that a pre-heating step (PB: Prebake) be included after the film formation and prior to the exposure step.

It is also preferable that, a heating step (PEB: Post Exposure Bake) after the exposure be included after the exposure step and prior to the development step.

The heating temperature for both PB and PEB is preferably 70 to 130° C., and more preferably 80 to 120° C.

The heating time is preferably 30 to 300 seconds, more preferably 30 to 180 seconds, and even more preferably 30 to 90 seconds.

Heating can be carried out using means that are included in normal exposure and development machine, and may also be carried out using a hot plate or the like.

Sensitivity or pattern profile is improved by the reaction of the exposed area being accelerated due to bake.

The wavelength of the light source used in the exposure apparatus of the present invention is not particularly limited, however, may include infrared light, visible light, ultraviolet light, far ultraviolet light, extreme ultraviolet light, X-rays, an electron beam, or the like, is preferably far ultraviolet light with the wavelength of 250 nm or less, more preferably 220 nm or less and particularly preferably 1 to 200 nm, more specifically, is a KrF excimer laser (248 nm), an ArF excimer laser (193 nm), a $F_2$ excimer laser (157 nm), X-rays, EUV (13 nm), an electron beam or the like, preferably a KrF excimer laser, an ArF excimer laser, EUV or an electron beam, and more preferably an ArF excimer laser.

In addition, in the step for performing the exposure of the present invention, a liquid immersion exposure method may be applied.

The liquid immersion exposure method is a technology improving resolution, and is a technology of exposure in which high refractive index liquid (hereinafter also referred to as "immersion liquid") is filled between the projection lens and a sample.

As described earlier, this "effect of the liquid immersion", resolution and depth of focus when liquid immersed, may be represented by the following equation when $\lambda_0$ is a wavelength in air of the exposure light, n is a refractive index of the immersion liquid to air, θ is a convergence half-angle of the ray and is made to be $NA_0 = \sin\theta$. Here, $k_1$ and $k_2$ are coefficients related to the process.

$$(\text{resolution}) = K_1 \cdot (\lambda_0/n)/NA_0$$

$$(\text{depth of focus}) = \pm k_2 \cdot (\lambda_0/n)/NA_0^2$$

That is, effect of the liquid immersion is equivalent to the wavelength using the exposure wavelength of 1/n. In other words, for NA of the same projection optical system, the depth of focus may be made to be n times by the liquid immersion. This is valid for all pattern shapes, and furthermore, combining with super-resolution technologies such as a phase shift method or a modified illumination method currently considered is possible.

When the liquid immersion exposure is carried out, (1) after forming the film on the substrate and prior to the exposure step, and/or (2) after the step for exposing the film by the immersion liquid and prior to the step for heating the film, a step in which the surface of the film is cleaned with a water-based chemical solution may be performed.

As the immersion liquid, liquid with as small temperature coefficient of the refractive index as possible is preferable so that the liquid is transparent to the exposure wavelength and suppresses the distortion of the optical image projected on the film to a minimum level, however, especially when the exposure light source is an ArF excimer laser (wavelength: 193 nm), the use of water is preferable in terms of availability and ease of handling, in addition to the viewpoints described above.

When water is used, an additive (liquid) increasing the surfactant potency along with reducing the surface tension of water may be added in a small percentage. This additive is preferably an additive which does not dissolve the resist layer on a wafer and can ignore the effects on the optical coat at the lower surface of the lens element.

The additive such as this is preferably an aliphatic alcohol having approximately the same refractive index as water, and specifically, may include, methyl alcohol, ethyl alcohol, isopropyl alcohol, or the like. An advantage of adding the alcohol having approximately the same refractive index as water is that changes of the refractive index of the liquid as a whole may be extremely small even when the content concentration changes by the alcohol component in water being evaporated.

On the other hand, materials opaque to light of 193 nm or impurities whose refractive index is significantly different from water is incorporated causes a distortion of the optical image projected on the resist, distilled water is preferable as the water used. Pure water filtered through an ion exchange filter or the like may also be used.

Electrical resistance of the water used as the immersion liquid is preferably 18.3 MΩcm or more, TOC (Total Organic Carbon) is preferably 20 ppb or less, and it is preferable that a degassing treatment be carried out.

In addition, performance of lithography can be improved by increasing the refractive index of the immersion liquid. From this point of view, an addition of additives increasing the refractive index to water or using heavy water ($D_2O$) instead of water is possible.

When the film formed using the composition of the present invention is exposed through a liquid immersion medium, the hydrophobic resin (E) described above may be further added, if necessary. By adding the hydrophobic resin (E), a receding contact angle of the surface is improved. The receding contact angle of the film is preferably 60° to 90°, and more preferably 70° or more.

In the liquid immersion exposure step, the contact angle of the immersion liquid for the resist film in a dynamic state becomes critical since the immersion liquid need to move on the wafer following the movement of the exposure head scanning on the wafer at high speed and forming a exposure pattern, therefore, the resist is required to have an ability to follow the high-speed scan of the exposure head without the remaining droplets.

A film sparingly soluble in the immersion liquid (hereinafter, also referred to as "overcoat") may be provided between the film formed using the compositions of the present invention and the immersion liquid so that the film is not in direct contact with the immersion liquid. As a function required for the overcoat, coating suitability for the resist upper layer portion, transparency to radiation, particularly, radiation with a wavelength of 193 nm, and sparing solubility in the immersion liquid may be included. It is preferable that the overcoat be not mixed with the resist, and can be coated uniformly on the resist upper layer.

The overcoat is preferably a polymer which does not contain an aromatic group from the viewpoint of transparency in 193 nm.

Specifically, a hydrocarbon polymer, an acrylate polymer, polymethacrylate, polyacrylate, polyvinyl ether, a silicon-containing polymer, a fluorine-containing polymer and the like, may be included. The hydrophobic resin (E) described above is also very suitable as an overcoat. The residual monomer component of the polymer included in the overcoat is preferably smaller since an optical lens is contaminated when impurities are eluted to the immersion liquid from the overcoat.

When stripping the overcoat, a developer may be used or a separate stripping agent may be used. As the stripping agent, a solvent with small penetration to the film is preferable. Stripping by an alkaline developer is preferable in terms that the stripping step may be performed simultaneously with the developing treatment step of the film. The overcoat is preferably an acid from the viewpoint of stripping with the alkaline developer, however, from the viewpoint of a non-intermixing property with the film, the overcoat may be either neutral or alkaline.

The refractive index difference between the overcoat and the immersion liquid is preferably is none or small. In this case, improving the resolution is possible. When the exposure light source is an ArF excimer laser (wavelength: 193 nm), the use of water is preferable as the immersion liquid, therefore, the overcoat for ArF liquid immersion exposure preferably has refractive index closer to that of water (1.44). In addition, the overcoat is preferably a thin film from the viewpoint of transparency and refractive index.

The overcoat is preferably mixed neither with the film nor with the immersion liquid. From this point of view, when the immersion liquid is water, it is preferable that the solvent used for the overcoat be sparingly soluble in the solvent used in the composition of the present invention, and be a non-water soluble medium. In addition, when the immersion liquid is an organic solvent, the overcoat may be either water-soluble or non-water-soluble.

The substrate forming a film in the present invention is not particularly limited, and a substrate generally used in a semiconductor manufacturing process such as IC, a circuit board manufacturing process such as liquid crystal and thermal head, and also a lithography process of photofabrication in addition to these, such as an inorganic substrate such as silicon, SiN or $SiO_2$, or a coating-based inorganic substrate such as SOG, or the like, may be used. In addition, an organic anti-reflective film may be formed between the film and the substrate, if necessary.

If the pattern forming method of the present invention further include the step for developing using an alkaline developer, and, as the alkaline developer, for example, an alkaline aqueous solution such as inorganic alkalis such as sodium hydroxide, potassium hydroxide, sodium carbonate, sodium silicate, sodium metasilicate or ammonia water, primary amines such as ethylamine or n-propyl amine, secondary amines such as diethylamine or di-n-butylamine, tertiary amines such as triethylamine or methyldiethylamine, alcohol amines such as dimethylethanolamine or triethanolamine, quaternary ammonium salts such as tetramethylammonium hydroxide or tetraethylammonium hydroxide, cyclic amines such as pyrrole or piperidine, may be used.

In addition, an appropriate amount of alcohol or surfactant may be added to the alkaline aqueous solution described above and used.

An alkali concentration of the alkaline developer is typically 0.1 to 20% by mass.

The pH of the alkaline developer is typically 10.0 to 15.0.

In particular, an aqueous solution of 2.38% by mass tetramethylammonium hydroxide is preferable.

As the rinsing solution in the rinsing treatment carried out after the alkaline development, pure water may be used, and the rinsing solution may be used adding an appropriate amount of the surfactant.

In addition, a treatment for removing the developer or the rinsing solution deposited on the pattern may be carried out by supercritical fluid after the development or the rinsing treatment.

As the developer of the development step using a developer including an organic solvent (hereinafter, also referred to as organic-based developer) in the pattern forming method of the present invention, polar solvents and hydrocarbon-based solvents such as ketone-based solvents, ester-based solvents, alcohol-based solvents, amide-based solvents or ether-based solvents may be used.

Examples of the ketone-based solvents may include 1-octanone, 2-octanone, 1-nonanone, 2-nonanone, acetone, 2-heptanone (methyl amyl ketone), 4-heptanone, 1-hexanone, 2-hexanone, diisobutyl ketone, cyclohexanone, methyl cyclohexanone, phenyl acetone, methyl ethyl ketone, methyl isobutyl ketone, acetylacetone, acetonylacetone, ionone, diacetonyl alcohol, acetyl carbinol, acetophenone, methyl naphthyl ketone, isophorone, propylene carbonate, or the like.

Examples of the ester-based solvents may include methyl acetate, butyl acetate, ethyl acetate, isopropyl acetate, pentyl acetate, isopentyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxy propionate, 3-methoxy butyl acetate, 3-methyl-3-methoxy butyl acetate, methyl formate, ethyl formate, butyl formate, propyl formate, ethyl lactate, butyl lactate, propyl lactate, or the like.

Examples of the alcohol-based solvents may include alcohols such as methyl alcohol, ethyl alcohol, n-propyl alcohol, isopropyl alcohol, n-butyl alcohol, sec-butyl alcohol, tert-butyl alcohol, isobutyl alcohol, n-hexyl alcohol, n-heptyl alcohol, n-octyl alcohol or n-decanol, glycol-based solvents such as ethylene glycol, diethylene glycol or triethylene glycol, glycol ether-based solvents such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, methoxymethyl butanol, or the like.

Examples of the ether-based solvents may include dioxane, tetrahydrofuran, or the like, in addition to the above glycol ether-based solvents.

Examples of the amide-based solvents may include N-methyl-2-pyrrolidone, N,N-dimethylacetamide, N,N-dimethylformamide, hexamethylphosphoric triamide, 1,3-dimethyl-2-imidazolidinone, or the like.

Examples of the hydrocarbon-based solvents may include aromatic hydrocarbon-based solvents such as toluene or xylene, or aliphatic hydrocarbon-based solvents such as pentane, hexane, octane or decane.

The above solvents may be mixed plurally, or may be used being mixed with other types of solvents or water. However, in order to exert sufficient effects of the present invention, the water content of the developer as a whole is preferably less than 10% by mass, and practically, it is more preferable that water be not included.

That is, the amount of the organic solvent used with regard to the organic-based developer is preferably greater than or equal to 90% by mass and less than or equal to 100% by mass, and more preferably greater than or equal to 95% by mass and less than or equal to 100% by mass with regard to the total amount of the developer.

In particular, the organic-based developer is preferably a developer including at least one organic solvent selected from the group consisting of ketone-based solvents, ester-based solvents, alcohol-based solvents, amide-based solvents, and ether-based solvents.

Vapor pressure of the organic-based developer is preferably 5 kPa or less, more preferably 3 kPa or less, is particularly preferably 2 kPa or less, at 20° C. By making the vapor pressure of the organic-based developer be 5 kPa or less, evaporation of the developer on the substrate or in the development cup is suppressed, and temperature uniformity within the wafer surface is improved, and as a result, dimension uniformity within the wafer surface is improved.

Specific examples of the organic-based developer having vapor pressure of 5 kPa or less may include ketone-based solvents such as 1-octanone, 2-octanone, 1-nonanone, 2-nonanone, 2-heptanone (methyl amyl ketone), 4-heptanone, 2-hexanone, diisobutyl ketone, cyclohexanone, methyl cyclohexanone, phenyl acetone or methyl isobutyl ketone, ester-based solvents such as butyl acetate, pentyl acetate, isopentyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxy propionate, 3-methoxy butyl acetate, 3-methyl-3-methoxy butyl acetate, butyl formate, propyl formate, ethyl lactate, butyl lactate or propyl lactate, alcohol-based solvents such as n-propyl alcohol, isopropyl alcohol, n-butyl alcohol, sec-butyl alcohol, tert-butyl alcohol, isobutyl alcohol, n-hexyl alcohol, n-heptyl alcohol, n-octyl alcohol or n-decanol, glycol-based solvents such as ethylene glycol, diethylene glycol or triethylene glycol, glycol ether-based solvents such as ethylene glycol monomethyl ether, propylene glycol monomethyl ether, ethylene glycol monoethyl ether, propylene glycol monoethyl ether, diethylene glycol monomethyl ether, triethylene glycol monoethyl ether or methoxymethyl butanol, ether-based solvents such as tetrahydrofuran, amide-based solvents such as N-methyl-2-pyrrolidone, N,N-dimethylacetamide or N,N-dimethylformamide, aromatic hydrocarbon-based solvents such as toluene or xylene, or aliphatic hydrocarbon-based solvents such as octane or decane.

Specific examples of the organic-based developer having vapor pressure of 2 kPa or less which is a particularly preferable range may include ketone-based solvents such as 1-octanone, 2-octanone, 1-nonanone, 2-nonanone, 4-heptanone, 2-hexanone, diisobutyl ketone, cyclohexanone, methyl cyclohexanone or phenyl acetone, ester-based solvents such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxy propionate, 3-methoxy butyl acetate, 3-methyl-3-methoxy butyl acetate, ethyl lactate, butyl lactate or propyl lactate, alcohol-based solvents such as n-butyl alcohol, sec-butyl alcohol, tert-butyl alcohol, isobutyl alcohol, n-hexyl alcohol, n-heptyl alcohol, n-octyl alcohol or n-decanol, glycol-based solvents such as ethylene glycol, diethylene glycol or triethylene glycol, glycol ether-based solvents such as ethylene glycol monomethyl ether, propylene glycol monomethyl ether, ethylene glycol monoethyl ether, propylene glycol monoethyl ether, diethylene glycol monomethyl ether, triethylene glycol monoethyl ether or methoxymethyl butanol, amide-based solvents such as N-methyl-2-pyrrolidone, N,N-dimethyl acetamide or N,N-dimethylformamide, aromatic hydrocarbon-based solvents such as xylene, or aliphatic hydrocarbon-based solvents such as octane or decane.

An appropriate amount of surfactant may be added to the organic-based developer, if necessary.

The surfactant is not particularly limited, however, for example, an ionic or non-ionic fluorine-based and/or silicon-based surfactants or the like may be used. These fluorine-based and/or silicon-based surfactants may include surfactants, disclosed in, for example, JP1988-36663A (JP-S62-36663A), JP1987-226746A (JP-S61-226746A), JP1987-226745A (JP-S61-226745A), JP1988-170950A (JP-S62-170950A), JP1989-34540A (JP-S63-34540A), JP1995-230165A (JP-H07-230165A), JP1996-62834A (JP-H08-62834A), JP1997-54432A (JP-H09-54432A), JP1997-5988A (JP-H09-5988A), U.S. Pat. No. 5,405,720A U.S. Pat. No. 5,360,692A, U.S. Pat. No. 5,529,881A U.S. Pat. No. 5,296,330A, U.S. Pat. No. 5,436,098A U.S. Pat. No. 5,576,143A, U.S. Pat. No. 5,294,511A and U.S. Pat. No. 5,824,451A, and are preferably non-ionic surfactants. The non-ionic surfactant is not particularly limited, however, the use of fluorine-based surfactants or silicon-based surfactants is more preferable.

The amount of surfactant used is typically 0.001 to 5% by mass, preferably 0.005 to 2% by mass, and more preferably 0.01 to 0.5% by mass with regard to the total amount of the developer.

As the developing method, for example, a method in which a substrate is immersed in a tank filled with a developer for a certain period of time (dip method), a method in which a developer is heaped up to the surface of a substrate by surface tension and developed by resting for a certain period of time (a paddle method), a method in which a developer is sprayed on the surface of the substrate (a spray method), a method in which a developer is continuously discharged on a substrate rotated at a constant rate while scanning a developer discharging nozzle at a constant rate (a dynamic dispense method), or the like, may be applied.

If a variety of developing methods described above include a step in which a developer is discharged from a development nozzle of a development apparatus toward a resist film, discharge pressure of the developer discharged (flow rate per unit area of the developer discharged) is preferably 2 mL/sec/mm$^2$ or less, more preferably 1.5 mL/sec/mm$^2$ or less, and even more preferably 1 mL/sec/mm$^2$ or less. There is no particular lower limit of the flow rate, however, 0.2 mL/sec/mm$^2$ or more is preferable if throughput is considered.

By making the discharge pressure of the developing liquid discharged be in this range, defects of the pattern derived from the resist residue after development may be significantly reduced.

Details of this mechanism is not clear, however, it is believed that, by making the discharge pressure be in the above range, pressure on the resist film by the developer becomes smaller, therefore, the resist film and the resist pattern being scraped or broken carelessly is suppressed.

In addition, discharge pressure of the developer (mL/sec/mm$^2$) is a value at the developing nozzle exit in the development apparatus.

The method for adjusting the discharge pressure of the developer may include, for example, a method in which discharge pressure is adjusted by a pump and the like, or a method in which pressure is adjusted from the supply of pressurized tank and changed, and the like.

In addition, a step for stopping the development may be performed, while being substituted with other solvents, after the development step using the developer including an organic solvent.

It is preferable that a step for cleaning using a rinsing solution be performed after the development step using the developer including an organic solvent.

The rinsing solution used in the rinsing step after the development step using the developer including an organic solvent is not particularly limited as long as it does not dissolve the resist pattern, and a solution including general organic solvents may be used. As the rinsing solution, a rinsing solution containing at least one organic solvent selected from the group consisting of ketone-based solvents, ester-based solvents, alcohol-based solvents, amide-based solvents, and ether-based solvents is preferably used.

Specific examples of the hydrocarbon-based solvents, ketone-based solvents, the ester-based solvents, the alcohol-based solvents, the amide-based solvents, and the ether-based solvents may be the same as those described in the developer including an organic solvent.

The cleaning step is more preferably performed using the rinsing solution containing at least one organic solvent selected from the group consisting of ketone-based solvents, ester-based solvents, alcohol-based solvents, and amide-based solvents, the cleaning step is even more preferably performed using the rinsing solution containing alcohol-based solvents or ester-based solvents, the cleaning step is particularly preferably performed using the rinsing solution containing monohydric alcohol, and the cleaning step is the most preferably performed using the rinsing solution containing monohydric alcohol having 5 or more carbon atoms.

Here, the monohydric alcohol used in the rinsing step may include a straight chain, branched, or cyclic monohydric alcohol, and specifically, 1-butanol, 2-butanol, 3-methyl-1-butanol, tert-butyl alcohol, 1-pentanol, 2-pentanol, 1-hexanol, 4-methyl-2-pentanol, 1-heptanol, 1-octanol, 2-hexanol, cyclopentanol, 2-heptanol, 2-octanol, 3-hexanol, 3-heptanol, 3-octanol, 4-octanol or the like, may be used, and as the particularly preferable monohydric alcohol having 5 or more carbon atoms, 1-hexanol, 2-hexanol, 4-methyl-2-pentanol, 1-pentanol, 3-methyl-1-butanol or the like, may be used.

Each component described above may be mixed plurally, or may be used being mixed with organic solvents other than those described above.

Moisture content in the rinsing solution is preferably 10% by mass or less, more preferably 5% by mass or less, and particularly preferably 3% by mass or less. By making the moisture content be 10% by mass or less, satisfactory development characteristics may be obtained.

Vapor pressure of the rinsing solution used after the development step using the developer including an organic solvent is preferably greater than or equal to 0.05 kPa and less than or equal to 5 kPa, more preferably greater than or equal to 0.1 kPa and less than or equal to 5 kPa, the most preferably greater than or equal to 0.12 kPa and less than or equal to 3 kPa at 20° C. By making the vapor pressure of the rinsing solution be greater than or equal to 0.05 kPa and less than or equal to 5 kPa, temperature uniformity within the wafer surface is improved and swelling due to the penetration of the rinsing solution is suppressed, therefore, dimension uniformity within the wafer surface is improved.

An appropriate amount of surfactant may be added to the rinsing solution and used.

In the rinsing step, the wafer developed using the developer including an organic solvent is cleaned using the rinsing solution containing an organic solvent described above. The cleaning method is not particularly limited, however, a method in which a rinsing solution is continuously discharged on a substrate rotating at a constant rate (a spin coating method), a method in which a substrate is immersed in a tank filled with a rinsing solution for a certain period of time (a dip method), a method in which a rinsing solution is sprayed on a substrate surface (a spray method), or the like, may be applied, and among these, it is preferable that cleaning treatment be carried out using the spin coating method, the substrate be rotated at a rotational speed of 2,000 rpm to 4,000 rpm after cleaning, and the rinsing solution be removed from the surface of the substrate. It is also preferable that the heating step (Post Bake) be included after the rinsing step. The residual developer and the rinsing solution between and inside the patterns are removed by bake. The heating step after the rinsing step is typically performed at 40 to 160° C. and preferably at 70 to 95° C., and typically for 10 seconds to 3 minutes and preferably for 30 seconds to 90 seconds.

In addition, the present invention also relates to an electronic devices manufacturing method including the pattern forming method of the present invention described above, and an electronic device manufactured by this manufacturing method.

The electronic device of the present invention is suitably installed in electrical and electronic devices (home appliances, OA and media related apparatuses, optical apparatuses, communication apparatuses, and the like).

EXAMPLES

Hereinafter, the present invention will be described in detail by examples, however, the present invention is not limited by these.

Synthesis Example

Synthesis of Resin P-1

70 parts by mass of cyclohexanone was heated to 80° C. under a stream of nitrogen. A mixed solution of 20.0 parts by mass of a monomer represented by following Structure A, 15.6 parts by mass of a monomer represented by following Structure B, 130 parts by mass of cyclohexanone, and 2.86 parts by mass of dimethyl 2,2'-azobisisobutyrate [V-601, manufactured by Wako Pure Chemical Industries, Ltd.] was added dropwise thereto over 6 hours while stirring. After completion of the dropwise addition, the mixture was further stirred for 2 hours at 80° C. After cooling the reaction solution, the reaction solution was re-precipitated by a large quantity of hexane/ethyl acetate (mass ratio of 8:2), filtered, and the solid was vacuum-dried to obtain, 30.5 parts by mass of the resin (P-1) of the present invention.

[Chem. 100]

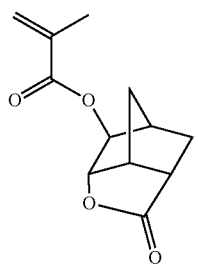

A

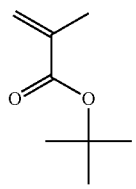

B

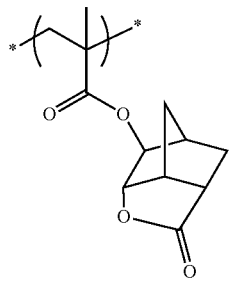

P-1


The weight-average molecular weight (Mw: polystyrene conversion) determined from GPC of the resin obtained (carrier: tetrahydrofuran (THF)) was 8,100, and the degree of dispersion (Mw/Mn) was 1.70. The composition ratio measured by $^{13}$C-NMR was 45/55.

<Acid Decomposable Resin>

The resins P-1' to P-1", P2 to P12 and RP-1 were synthesized in the same manner. The polymer structures synthesized are shown below.

[Chem. 101]

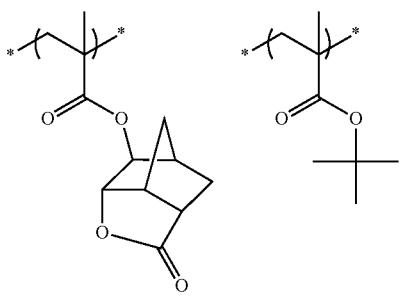

P-1
P-1'
P-1"

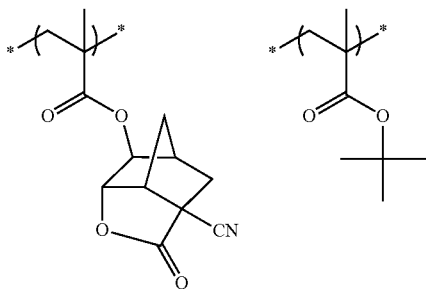

P-2

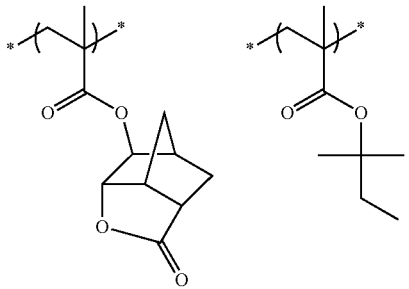

P-3

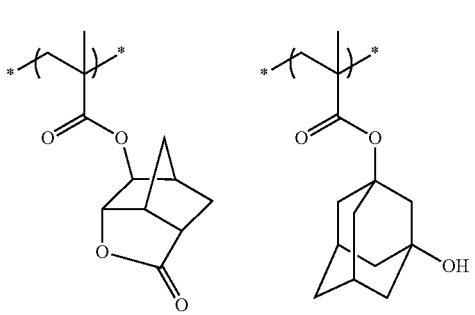

P-4

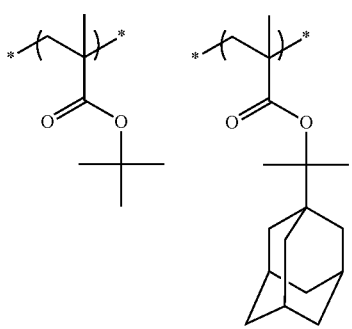
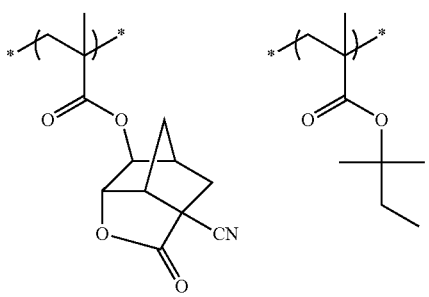
P-7
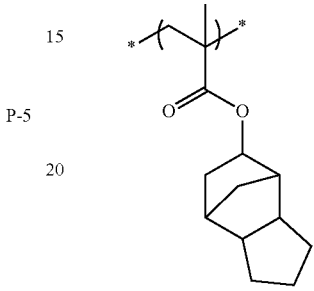
P-5
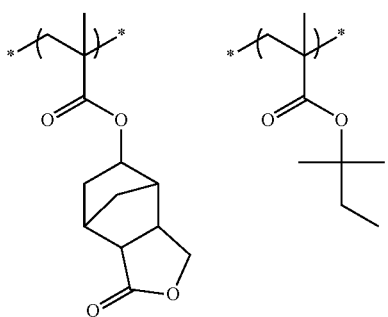
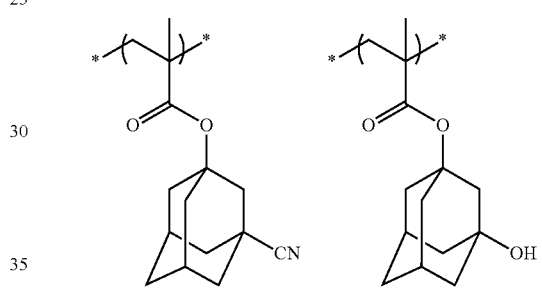
P-8
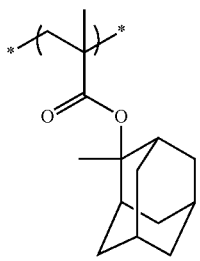
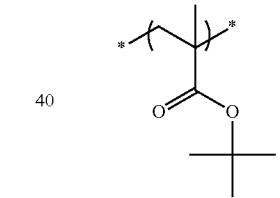
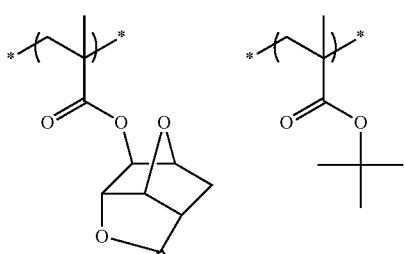
P-6
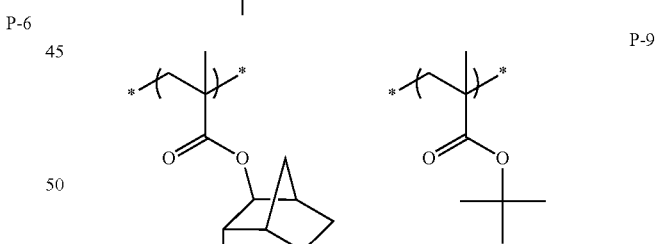
P-9
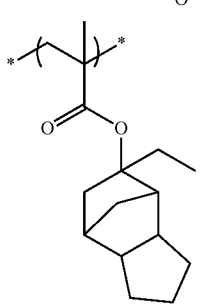
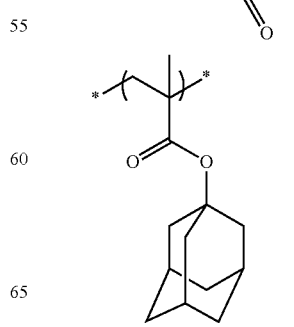

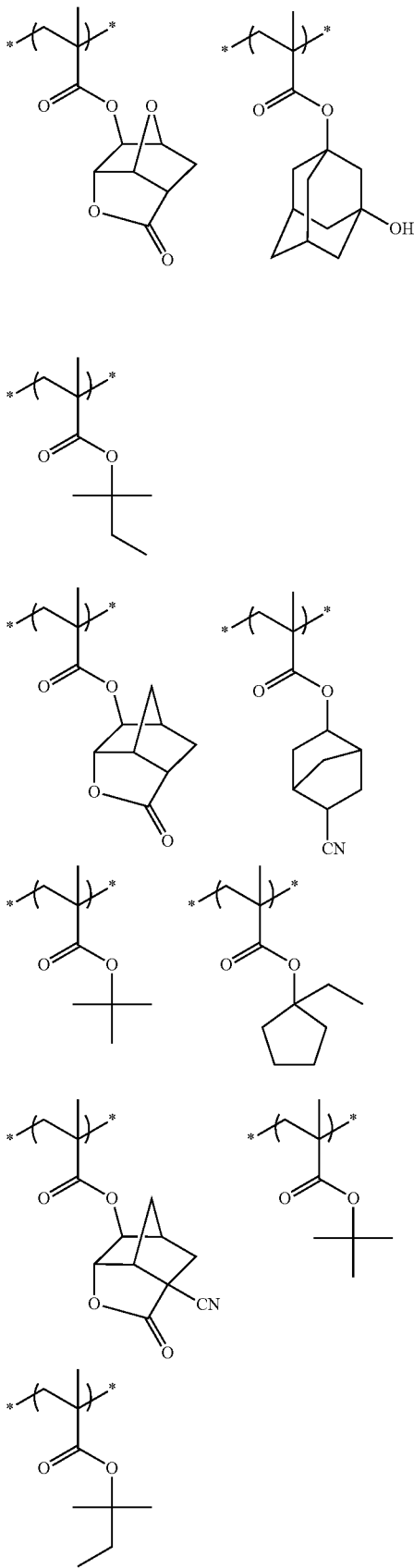

P-10

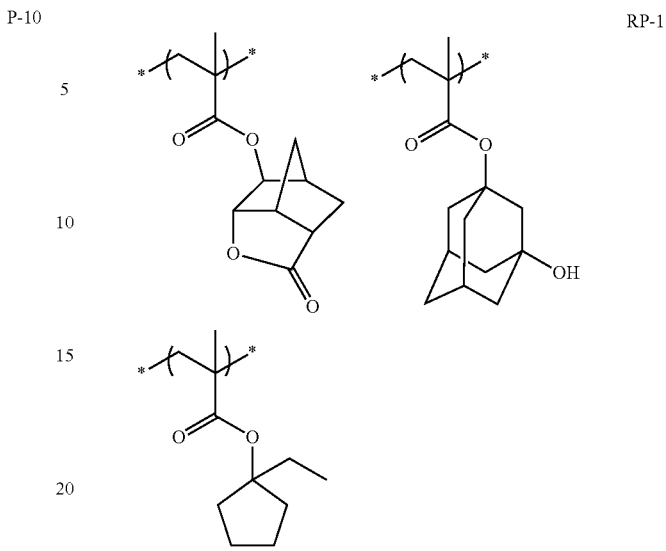

RP-1

In addition, the composition ratio of each repeating unit (molar ratio; corresponding in order from left to right), the weight-average molecular weight (Mw), and the degree of dispersion (Mw/Mn) are shown in the table below.

TABLE 3

| Resin | Mw | Mw/Mn | Composition | | | |
|---|---|---|---|---|---|---|
| P-1 | 8100 | 1.70 | 45 | 55 | | |
| P-1' | 15200 | 1.71 | 45 | 55 | | |
| P-1" | 8100 | 1.70 | 55 | 45 | | |
| P-2 | 13800 | 1.77 | 40 | 50 | 10 | |
| P-3 | 11500 | 1.65 | 40 | 55 | 5 | |
| P-4 | 8100 | 1.55 | 30 | 10 | 50 | 10 |
| P-5 | 7200 | 1.71 | 40 | 50 | 10 | |
| P-6 | 17500 | 1.56 | 45 | 45 | 10 | |
| P-7 | 11000 | 1.77 | 40 | 50 | 10 | |
| P-8 | 6500 | 1.49 | 30 | 15 | 55 | |
| P-9 | 12500 | 1.88 | 40 | 50 | 10 | |
| P-10 | 10500 | 1.65 | 40 | 10 | 50 | |
| P-11 | 8200 | 1.65 | 35 | 10 | 45 | 10 |
| P-12 | 19500 | 1.81 | 40 | 35 | 25 | |
| PR-1 | 10500 | 1.70 | 40 | 10 | 50 | |

<Acid Generator>

As the acid generator, the following compounds were used,

In addition, each acid generator was synthesized in accordance with synthesis methods disclosed in [0200] to [0210] of JP2010-100595A, [0051] to [0058] of WO2011/093280A, [0382] to [0385] of WO2008/153110A, and the like.

[Chem. 102]

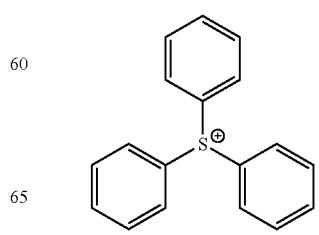

PAG-1

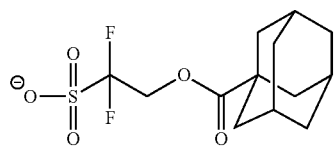
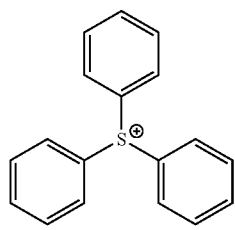
PAG-2
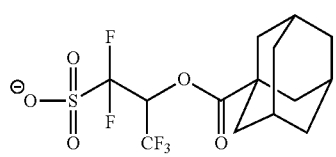
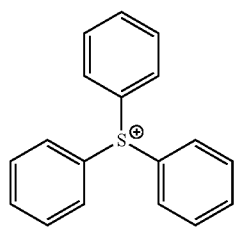
PAG-3
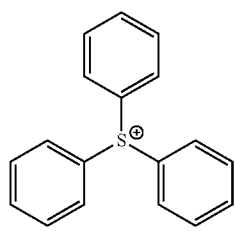
PAG-4
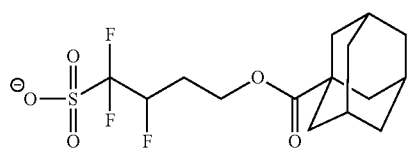
PAG-5
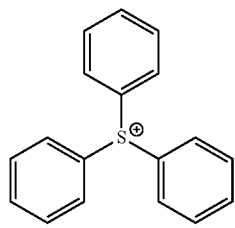
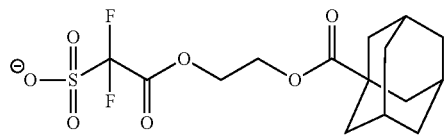
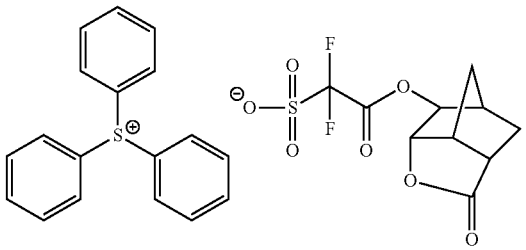
PAG-6
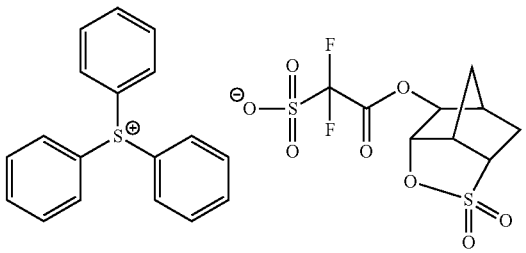
PAG-7
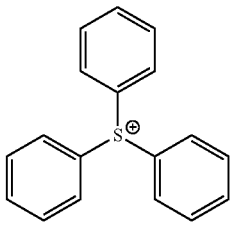
PAG-8
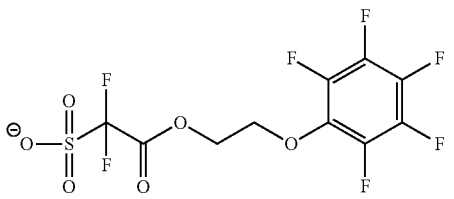
PAG-9
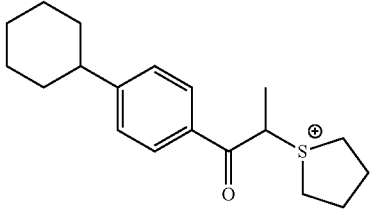
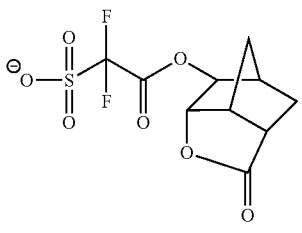

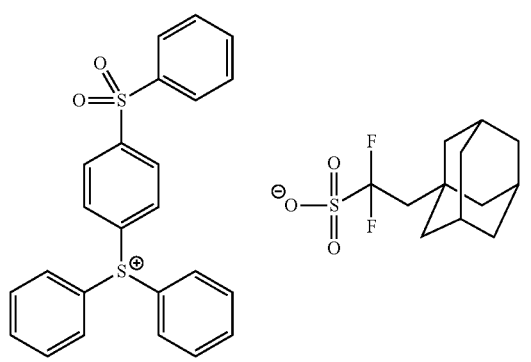
PAG-10
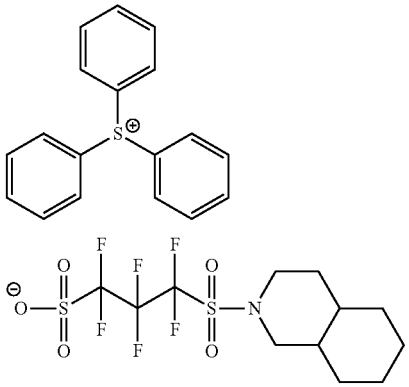
CB-2
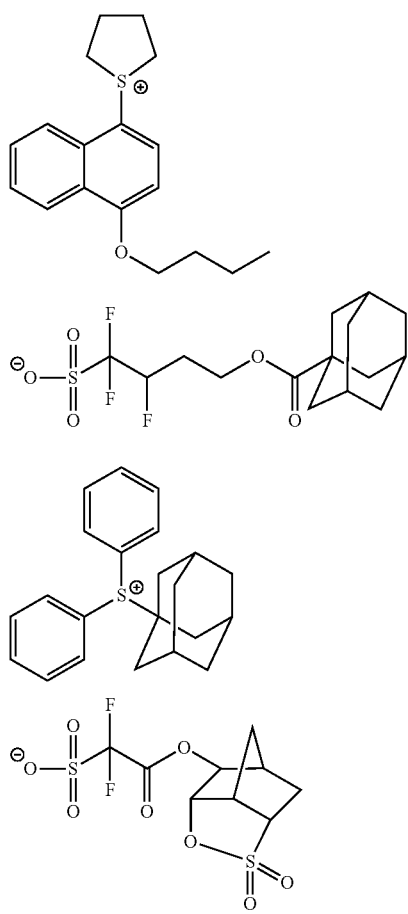
PAG-11
PAG-12
CB-1
<Basic compound (C) of which Basicity is Decreased by Irradiation of Actinic Ray and Radiation, and Basic Compound (C')>
As the basic compound (C) of which basicity is decreased by irradiation of actinic ray and radiation or the basic Compound (C'), the following compounds were used.
[Chem. 103]
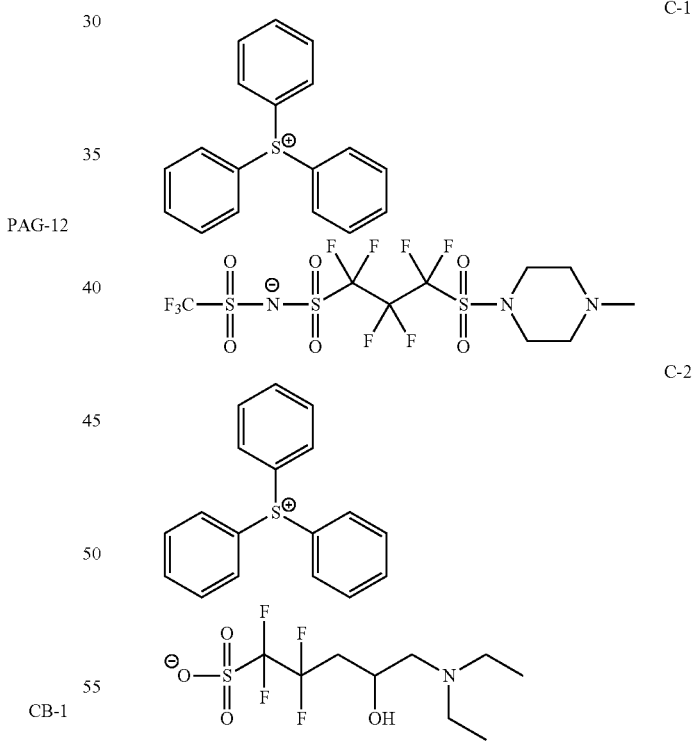
C-1
C-2
C-3
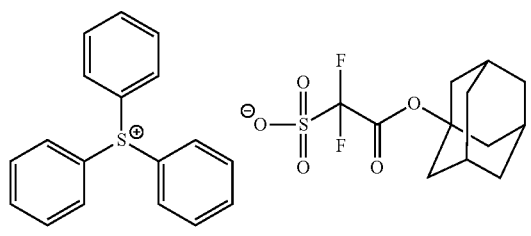

-continued

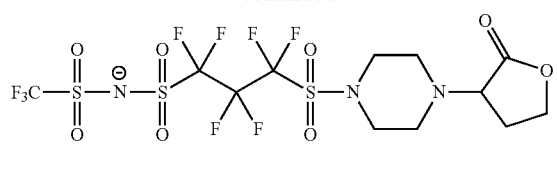

[Chem. 104]

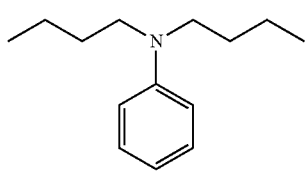
N-1

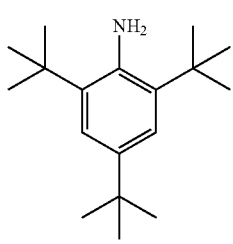
N-2

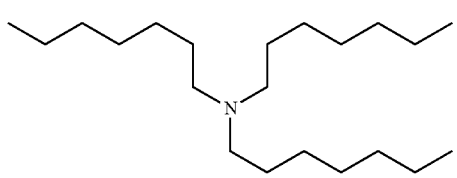
N-3

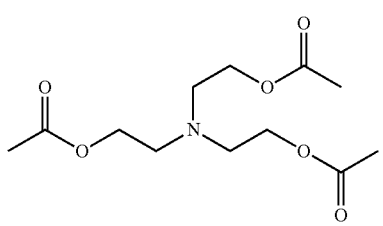
N-4

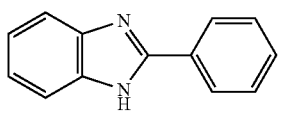
N-5

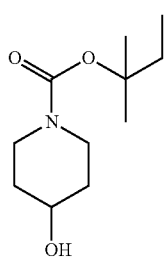
N-6

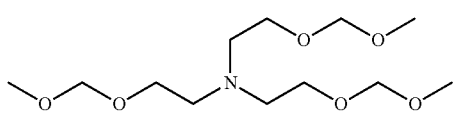
N-7

-continued

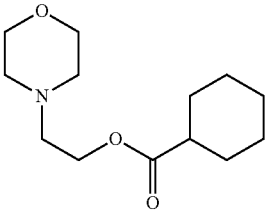
N-8

<Hydrophobic Resin>

As the hydrophobic resin, following hydrophobic resins 1 to 8 were used.

In addition the composition ratio of following hydrophobic resins 1 to 8 (molar ratio; corresponding in order from left to right), the weight-average molecular weight (Mw), and the degree of dispersion (Mw/Mn) are shown in following Table 4.

[Chem. 105]

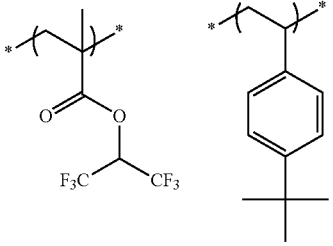
1

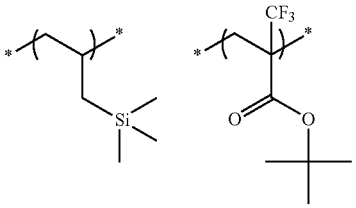
2

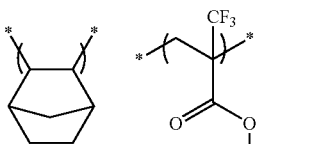
3

4

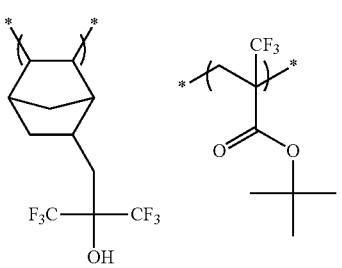

-continued

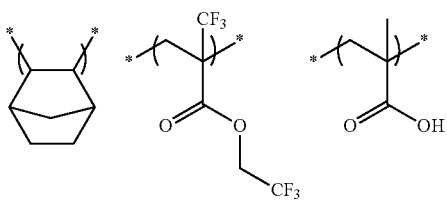

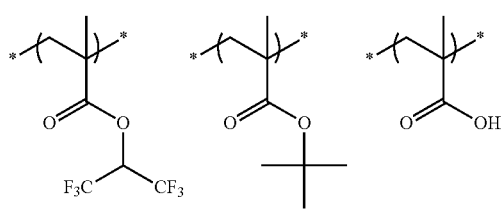

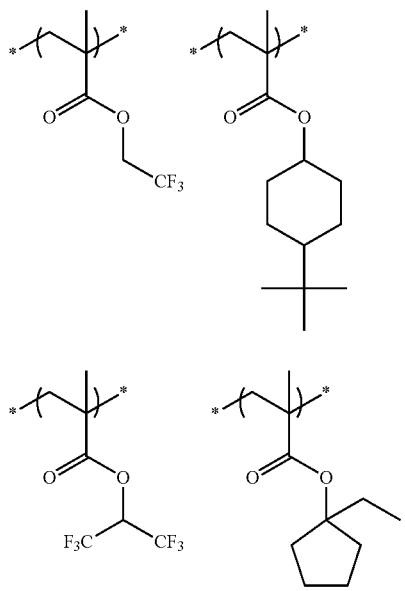

TABLE 4

| Hydrophobic Resin | Mw | Mw/Mn | Composition | | |
|---|---|---|---|---|---|
| 1 | 6500 | 1.53 | 20 | 80 | |
| 2 | 4500 | 1.52 | 50 | 50 | |
| 3 | 3600 | 1.44 | 25 | 75 | |
| 4 | 5100 | 1.40 | 40 | 60 | |
| 5 | 4100 | 1.35 | 40 | 55 | 5 |
| 6 | 7500 | 1.65 | 37 | 60 | 3 |
| 7 | 10000 | 1.75 | 30 | 70 | |
| 8 | 3500 | 1.21 | 45 | 55 | |

\<Additives\>

As the additives in the table below, the following compounds were used.

[Chem. 106]

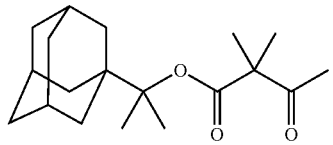

AD-1

\<Surfactant\>

The followings were prepared as the surfactant.

W-1: Megafac F176 (manufactured by DIC Corporation; fluorine-based)

W-2: Megafac R08 (manufactured by DIC Corporation; fluorine- and silicon-based)

W-3: polysiloxane polymer KP-341 (manufactured by Shin-Etsu Chemical Co., Ltd.; silicon-based)

W-4: Troysol S-366 (manufactured by Troy Chemical Co., Ltd.)

W-5: KH-20 (manufactured by Asahi Glass Co., Ltd.)

W-6: PolyFox PF-6320 (manufactured by OMNOVA Solutions Inc., fluorine-based)

\<Solvent\>

The followings were prepared as the solvent.

(Group a)

SL-1: propylene glycol monomethyl ether acetate (PGMEA)

SL-2: propylene glycol monomethyl ether propionate

SL-3: 2-heptanone (Group b)

SL-4: ethyl lactate

SL-5: propylene glycol monomethyl ether (PGME)

SL-6: cyclohexanone (Group c)

SL-7: γ-butyrolactone

SL-8: propylene carbonate

\<ArF Liquid Immersion Exposure\>

(Resist Preparation)

The actinic-ray-sensitive or radiation-sensitive resin composition (the resist composition) was prepared by dissolving 3.8% by mass of the components shown in following Table 5 as solids in the solvent shown in the same table, and then filtering each of these by a polyethylene filter having a pore size of 0.03 μm.

ARC29SR (manufactured by Nissan Chemical Industries, Ltd.) for organic anti-reflective film was coated on the silicon wafer, bake was carried out for 60 seconds at 205° C., and the anti-reflective film was formed with thickness of 86 nm. The resist composition in Example 1 was coated on top of the anti-reflective film, bake (PB: Prebake) was carried out for 60 seconds at 100° C., and the resist film with a film thickness of 100 nm was formed. Pattern exposure was carried out on the obtained wafer through a 6% half-tone mask of 1:1 line and space pattern with a line width of 50 nm using an ArF excimer laser liquid immersion scanner (manufactured by ASML; XT1700i, NA1.20, C-Quad, outer sigma 0.981, inner sigma 0.895, XY deflection). Ultra-pure water was used as the immersion liquid. After that, heating (PEB) was carried out for 60 seconds at 105°, then, paddle development was carried out for 30 seconds using the developer (butyl acetate), and the rinsing solution (4-methyl-2-pentanol) was supplied on the wafer for 24 seconds while rotating the wafer at a rotation speed of 1000 rpm, and then the chemical solution on the wafer was shaken off by rotating the wafer for 20 seconds at a rotation speed of 2000 rpm. As a result, 1:1 line and space resist pattern with a line width of 50 nm was obtained.

<Evaluation Method>
[Evaluation of Pattern Collapse]

The amount of exposure and focus that reproduce a mask pattern of line and space having a line width of 50 nm (line:space=1:1) were taken as an optimum exposure amount and an optimum focus, respectively. A limited minimum line width, which resolves without collapsing the pattern when the line width of the line pattern formed by the amount of exposure being reduced further from the optimum exposure amount was made to be thin, was defined.

A smaller value indicates that a finer pattern resolves without pattern collapse, therefore, pattern collapse is less likely to occur, and resolution is high.

[Bridge Defects]

Bridge defect performance was confirmed for the resist pattern of line and space of 50 nm (1:1) in optimum exposure amount and optimum focus using U-VISION.

A level in which bridge defects (a state in which each line pattern on the wafer is connected involuntarily) were not observed was made to be A, a level in which bridge defects were not observed, however, the pattern was slightly a T-top shape was made to be B, and a level in which bridge defects were observed was made to be C.

[Residual Film Ratio]

Film thickness of the exposed area was measured after development, and residual film ratio at the time of the organic solvent development was evaluated by calculating the ratio to the film thickness prior to exposure and after coating ((film thickness of the exposed area after development÷film thickness prior to exposure and after coating)×100(%)).

The evaluation results are shown in Table 5 below.

TABLE 5

| | Resin (P) | | Combining Resin | | Hydrophobic Resin | | Acid Generator 1 | | Acid Generator 2 | | Basic Compound 1 | | Basic Compound 2 | |
|---|---|---|---|---|---|---|---|---|---|---|---|---|---|---|
| | Compound Number | Parts by Mass | Compound Number | Parts by Mass | Compound Number | Parts by Mass | Compound Number | Parts by Mass | Compound Number | Parts by Mass | Compound Number | Parts by Mass | Compound Number | Parts by Mass |
| Example 1 | P-1 | 89.8 | | | 1 | 0.8 | PAG-1 | 5.0 | PAG-3 | 3.0 | N-6 | 0.80 | N-4 | 0.10 |
| Example 2 | P-1' | 89.8 | | | 1 | 0.8 | PAG-1 | 5.0 | PAG-3 | 3.0 | N-6 | 0.80 | N-4 | 0.10 |
| Example 3 | P-1" | 89.8 | | | 1 | 0.8 | PAG-1 | 5.0 | PAG-3 | 3.0 | N-6 | 0.80 | N-4 | 0.10 |
| Example 4 | P-2 | 88.2 | | | 2 | 0.6 | PAG-4 | 5.0 | PAG-12 | 5.0 | N-6 | 1.10 | N-1 | 0.10 |
| Example 5 | P-3 | 85.1 | | | 3 | 1.9 | PAG-8 | 2.0 | PAG-2 | 8.0 | N-5 | 0.90 | N-3 | 0.10 |
| Example 6 | P-4 | 62.8 | P-1 | 20.0 | 4 | 1.8 | PAG-3 | 6.0 | PAG-4 | 6.5 | N-5 | 0.90 | C-1 | 1.50 |
| Example 7 | P-5 | 84.8 | | | 5 | 1.7 | PAG-6 | 10.0 | PAG-1 | 2.0 | N-4 | 0.75 | C-2 | 0.80 |
| Example 8 | P-6 | 81.1 | | | 6 | 1.5 | PAG-11 | 12.0 | PAG-6 | 2.0 | N-5 | 1.20 | C-3 | 1.20 |
| Example 9 | P-7 | 53.8 | P-11 | 30.0 | 7 | 2.8 | PAG-1 | 8.0 | PAG-10 | 4.0 | N-2 | 1.30 | N-8 | 0.10 |
| Example 10 | P-8 | 86.0 | | | 8 | 2.2 | PAG-7 | 4.0 | PAG-2 | 3.5 | N-7 | 1.20 | N-1 | 0.10 |
| Example 11 | P-9 | 88.3 | | | 1 | 1.0 | PAG-5 | 6.0 | PAG-7 | 4.0 | N-7 | 0.50 | N-5 | 0.20 |
| Example 12 | P-10 | 87.0 | | | 4 | 2.5 | PAG-5 | 7.0 | PAG-9 | 2.0 | N-8 | 0.80 | N-6 | 0.20 |
| Example 13 | P-11 | 79.5 | RP-1 | 10.0 | 8 | 0.8 | PAG-8 | 6.5 | PAG-11 | 1.5 | N-8 | 0.50 | N-4 | 0.20 |
| Example 14 | P-12 | 86.3 | | | 6 | 0.8 | PAG-2 | 10.0 | CB-2 | 1.0 | N-2 | 0.80 | N-1 | 0.10 |
| Reference Example 1 | P-1 | 88.7 | | | 1 | 1.0 | CB-1 | 8.0 | | | N-3 | 1.30 | | |
| Comparative Example 1 | RP-1 | 89.5 | | | 4 | 2.0 | PAG-1 | 7.0 | | | N-6 | 1.00 | | |

| | Additive | | Surfactant | | Solvent | | | | | | Performance Evaluation Results | | |
|---|---|---|---|---|---|---|---|---|---|---|---|---|---|
| | Compound Number | Parts by Mass | Compound Number | Parts by Mass | Solvent 1 | Parts by Mass | Solvent 2 | Parts by Mass | Solvent 3 | Parts by Mass | Pattern Collapse (nm) | Bridge Defects | Residual Film Ratio (%) |
| Example 1 | | | W-1 | 0.50 | SL-1 | 1770 | SL-6 | 600 | SL-7 | 30 | 41.0 | A | 88 |
| Example 2 | | | W-1 | 0.50 | SL-1 | 1770 | SL-6 | 600 | SL-7 | 30 | 38.0 | A | 93 |
| Example 3 | | | W-1 | 0.50 | SL-1 | 1770 | SL-6 | 600 | SL-7 | 30 | 43.0 | A | 86 |
| Example 4 | | | | | SL-1 | 1730 | SL-5 | 600 | SL-7 | 70 | 40.0 | A | 91 |
| Example 5 | AD-1 | 1 | W-2 | 1.00 | SL-1 | 1800 | SL-6 | 600 | | | 41.0 | A | 90 |
| Example 6 | | | W-4 | 0.50 | SL-1 | 1900 | SL-4 | 400 | SL-7 | 100 | 40.0 | A | 88 |
| Example 7 | | | | | SL-1 | 1980 | SL-3 | 400 | SL-8 | 20 | 38.0 | A | 88 |
| Example 8 | | | W-6 | 1.00 | SL-6 | 1750 | SL-1 | 650 | | | 39.0 | A | 92 |
| Example 9 | | | | | SL-1 | 1900 | SL-4 | 500 | | | 42.0 | A | 90 |
| Example 10 | AD-1 | 2.0 | W-3 | 1.00 | SL-2 | 1938 | SL-6 | 442 | SL-8 | 20 | 41.0 | A | 88 |
| Example 11 | | | | | SL-1 | 1550 | SL-5 | 800 | SL-7 | 50 | 38.0 | A | 90 |
| Example 12 | | | W-3 | 0.50 | SL-1 | 1350 | SL-5 | 1000 | SL-7 | 50 | 41.0 | A | 90 |
| Example 13 | | | W-6 | 1.00 | SL-1 | 1400 | SL-6 | 1000 | | | 40.0 | A | 88 |
| Example 14 | | | W-6 | 1.00 | SL-1 | 1500 | SL-6 | 900 | | | 39.0 | A | 92 |
| Reference Example 1 | | | W-1 | 1.00 | SL-1 | 1800 | SL-6 | 600 | | | 45.0 | B | 84 |
| Comparative Example 1 | | | W-5 | 0.50 | SL-1 | 2400 | | | | | 49.0 | C | 76 |

As is apparent from the results shown in Table 5, in Reference Example 1, in which the acid decomposable resin contains a repeating unit represented by General Formula (I), however, the acid generator corresponds to none of General Formulae (B-1) to (B-3), the limited minimum line width which resolves without collapsing the pattern was slightly large, there was a T-top shape in the bridge defect evaluation, and the residual film ratio was also slightly small.

In addition, in Comparative Example 1, in which the acid generator represented by General Formula (B-1) was used, however, the acid decomposable resin does not contain a repeating unit represented by General Formula (I), the limited minimum line width which resolves without collapsing the pattern was large, bridge defects occurred, and the residual film ratio was also small.

On the other hand, in Examples 1 to 14, in which the resin (P) contains a repeating unit represented by General Formula (I) and the acid generator represented by General Formulae (B-1) to (B-3) were used, the limited minimum line width which resolves without collapsing the pattern was small, bridge defects did not occur, and the residual film ratio was also large.

In particular, in Examples 2, 4, 5, 8, 9, 11, 12, and 14, in which a weight-average molecular weight of the resin (P) is 10,000 or more, the residual film ratio turned out to be particularly large.

In addition, in Examples 1 to 10, even when the developer was changed from butyl acetate to methyl amyl ketone and 2-ethoxy ethyl propionate, respectively, pattern collapse and bridge defects were less likely to occur, and the residual film ratio was also large.

This application claims priority under 35 U.S.C. §119 of Japanese Patent application JP 2011-207018, filed on Sep. 22, 2011, the entire contents of which are hereby incorporated by reference.

What is claimed is:

1. An actinic-ray-sensitive or radiation-sensitive resin composition comprising:
a resin (P) having a repeating unit (a) represented by a following General Formula (I);
a compound (B) represented by any of following General Formulae (B-1) to (B-3); and
a solvent,
wherein the resin (P) is a resin containing 45 mol % or more of the repeating unit (a) with regard to all repeating units in the resin (P):

[Chem. 1]

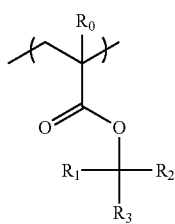

(I)

wherein, in General Formula (I), $R_0$ represents a hydrogen atom or a methyl group, $R_1$, $R_2$, and $R_3$ each independently represent a straight chain or branched alkyl group,

[Chem. 2]

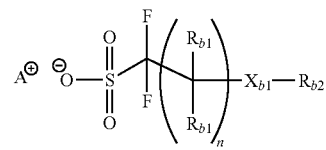

(B-1)

in General Formula (B-1), $A^+$ represents a sulfonium cation or an iodonium cation, $R_{b1}$s, each independently, represent a hydrogen atom, a fluorine atom, or a trifluoromethyl group, n represents an integer of 1 to 4, $X_{b1}$ represents a single bond, an ether bond, an ester bond (—OCO— or —COO—) or a sulfonate bond (—OSO$_2$— or —SO$_3$—), $R_{b2}$ represents a substituent having 6 or more carbon atoms,

[Chem. 3]

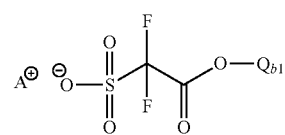

(B-2)

in General Formula (B-2), $A^+$ represents a sulfonium cation or an iodonium cation, $Q_{b1}$ represents a group having a lactone structure, a group having a sultone structure, or a group having a cyclic carbonate structure,

[Chem. 4]

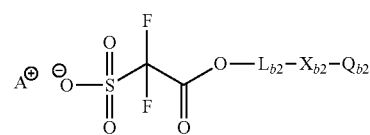

(B-3)

in General Formula (B-3), $A^+$ represents a sulfonium cation or an iodonium cation, $L_{b2}$ represents an alkylene group having 1 to 6 carbon atoms, $X_{b2}$ represents an ether bond or an ester bond (—OCO— or —COO—), and $Q_{b2}$ represents an alicyclic group or a group having an aromatic ring.

2. The actinic-ray-sensitive or radiation-sensitive resin composition according to claim 1,
wherein a weight-average molecular weight of the resin (P) is 10,000 or more.

3. The actinic-ray-sensitive or radiation-sensitive resin composition according to claim 1, further comprising:
a basic compound or an ammonium salt compound (C) of which basicity is decreased by irradiation of actinic ray or radiation.

4. The actinic-ray-sensitive or radiation-sensitive resin composition according to claim 1,
wherein the straight chain or branched alkyl group of $R_1$, $R_2$, and $R_3$ in General Formula (I) is an alkyl group having 1 to 4 carbon atoms.

5. The actinic-ray-sensitive or radiation-sensitive resin composition according to claim 1,
wherein the resin (P) is a resin having an alicyclic hydrocarbon structure.

6. The actinic-ray-sensitive or radiation-sensitive resin composition according to claim 1, further comprising:
a hydrophobic resin having at least one of a fluorine atom and a silicon atom.

7. A resist film which is formed by the actinic-ray-sensitive or radiation-sensitive resin composition according to claim 1.

8. A pattern forming method comprising:
(a) forming a film by the actinic-ray-sensitive or radiation-sensitive resin composition according to claim 1;
(b) exposing the film; and
(c) developing the film after the exposure using a developer including an organic solvent to form a negative-type pattern.

9. The pattern forming method according to claim 8, wherein the developer is a developer containing at least one organic solvent selected from the group consisting of ketone-based solvents, ester-based solvents, alcohol-based solvents, amide-based solvents and ether-based solvents.

10. The pattern forming method according to claim 8, further comprising:
cleaning using a rinsing solution containing an organic solvent.

11. An electronic device manufacturing method comprising:
the pattern forming method according to claim 8.

12. An electronic device which is manufactured by the electronic device manufacturing method according to claim 11.

13. The actinic-ray-sensitive or radiation-sensitive resin composition according to claim 1,
wherein the resin (P) contains 5 mol % or less of a repeating unit having an aromatic group, or does not contain the repeating unit having the aromatic group.

14. The actinic-ray-sensitive or radiation-sensitive resin composition according to claim 1,
wherein the resin (P) does not have an aromatic group.

15. The actinic-ray-sensitive or radiation-sensitive resin composition according to claim 1,
wherein the resin (P) contains a repeating unit represented by following General Formula (AI):

[Chem. 5]

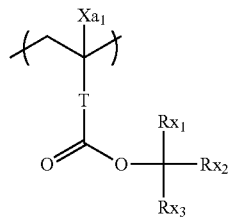

(AI)

wherein, in General Formula (AI), $Xa_1$ represents a hydrogen atom, a methyl group which may have a substituent, or a group expressed by $—CH_2—R_9$, $R_9$ represents a hydroxyl group or a monovalent organic group, T represents a single bond or a divalent linking group, $Rx_1$ to $Rx_3$, each independently, represent an alkyl group or a cycloalkyl group, two of $Rx_1$ to $Rx_3$ may be bonded and form a cycloalkyl group.

16. An actinic-ray-sensitive or radiation-sensitive resin composition comprising:
a resin (P) having a repeating unit (a) represented by a following General Formula (I);
a compound (B) represented by any of following General Formulae (B-2) to (B-3); and
a solvent,

[Chem. 6]

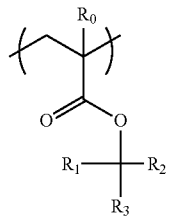

(I)

wherein, in General Formula (I), $R_0$ represents a hydrogen atom or a methyl group, $R_1$, $R_2$, and $R_3$ each independently represent a straight chain or branched alkyl group,

[Chem. 7]

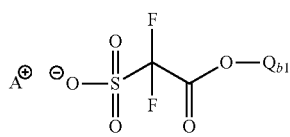

(B-2)

in General Formula (B-2), $A^+$ represents a sulfonium cation or an iodonium cation, $Q_{b1}$ represents a group having a lactone structure, a group having a sultone structure, or a group having a cyclic carbonate structure,

[Chem. 8]

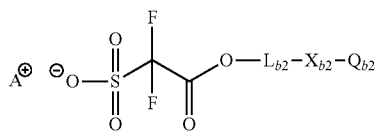

(B-3)

in General Formula (B-3), $A^+$ represents a sulfonium cation or an iodonium cation, $L_{b2}$ represents an alkylene group having 1 to 6 carbon atoms, $X_{b2}$ represents an ether bond or an ester bond (—OCO— or —COO—), and $Q_{b2}$ represents an alicyclic group or a group having an aromatic ring;
wherein the resin (P) is a resin containing 45 mol % or more of the repeating unit (a) with regard to all repeating units in the resin (P).

17. The actinic-ray-sensitive or radiation-sensitive resin composition according to claim 16,
wherein a weight-average molecular weight of the resin (P) is 10,000 or more.

18. The actinic-ray-sensitive or radiation-sensitive resin composition according to claim 16, further comprising:
a basic compound or an ammonium salt compound (C) of which basicity is decreased by irradiation of actinic ray or radiation.

19. The actinic-ray-sensitive or radiation-sensitive resin composition according to claim 16,
wherein the resin (P) is a resin having an alicyclic hydrocarbon structure.

20. The actinic-ray-sensitive or radiation-sensitive resin composition according to claim 16, further comprising:
a hydrophobic resin having at least one of a fluorine atom and a silicon atom.

21. The actinic-ray-sensitive or radiation-sensitive resin composition according to claim 16,
wherein the resin (P) contains 5 mol % or less of a repeating unit having an aromatic group, or does not contain the repeating unit having the aromatic group.

22. The actinic-ray-sensitive or radiation-sensitive resin composition according to claim 16,
wherein the resin (P) contains a repeating unit represented by following General Formula (AI):

[Chem. 9]

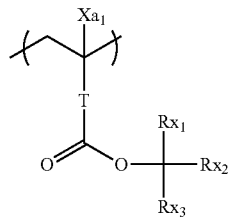

(AI)

wherein, in General Formula (AI), $Xa_1$ represents a hydrogen atom, a methyl group which may have a substituent, or a group expressed by $-CH_2-R_9$, $R_9$ represents a hydroxyl group or a monovalent organic group, T represents a single bond or a divalent linking group, $Rx_1$ to $Rx_3$, each independently, represent an alkyl group or a cycloalkyl group, two of $Rx_1$ to $Rx_3$ may be bonded and form a cycloalkyl group.

23. An actinic-ray-sensitive or radiation-sensitive resin composition comprising:
a resin (P) having a repeating unit (a) represented by a following General Formula (I);
a compound (B) represented by any of following General Formulae (B-1-1) to (B-1-6); and
a solvent,

[Chem. 10]

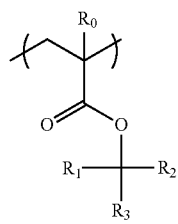

(I)

wherein, in General Formula (I), $R_0$ represents a hydrogen atom or a methyl group, $R_1$, $R_2$, and $R_3$ each independently represent a straight chain or branched alkyl group,

[Chem. 11]

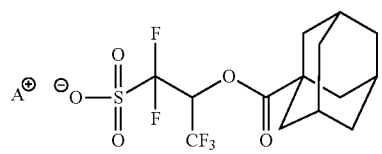

(B-1-1)

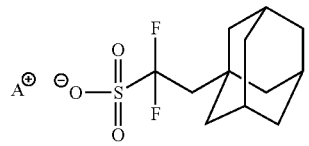

(B-1-2)

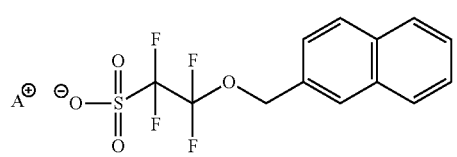

(B-1-3)

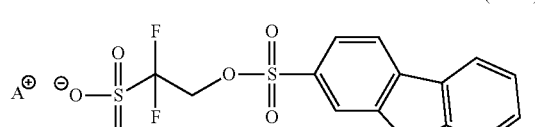

(B-1-4)

(B-1-5)

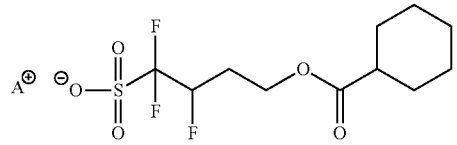

(B-1-6)

in General Formula (B-1-1) to (B-1-6), $A^+$ represents a sulfonium cation or an iodonium cation.

24. The actinic-ray-sensitive or radiation-sensitive resin composition according to claim 23,
wherein the resin (P) is a resin containing 45 mol % or more of the repeating unit (a) with regard to all repeating units in the resin (P).

25. The actinic-ray-sensitive or radiation-sensitive resin composition according to claim 23,
wherein a weight-average molecular weight of the resin (P) is 10,000 or more.

26. The actinic-ray-sensitive or radiation-sensitive resin composition according to claim 23, further comprising:
a basic compound or an ammonium salt compound (C) of which basicity is decreased by irradiation of actinic ray or radiation.

27. The actinic-ray-sensitive or radiation-sensitive resin composition according to claim 23,
wherein the resin (P) is a resin having an alicyclic hydrocarbon structure.

28. The actinic-ray-sensitive or radiation-sensitive resin composition according to claim 23, further comprising:
a hydrophobic resin having at least one of a fluorine atom and a silicon atom.

29. The actinic-ray-sensitive or radiation-sensitive resin composition according to claim 23,
wherein the resin (P) contains 5 mol % or less of a repeating unit having an aromatic group, or does not contain the repeating unit having the aromatic group.

30. The actinic-ray-sensitive or radiation-sensitive resin composition according to claim 23,
wherein the resin (P) contains a repeating unit represented by following General Formula (AI):

[Chem. 12]

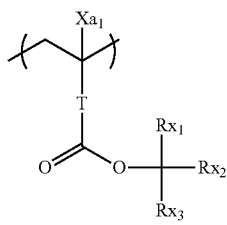

(AI)

wherein, in General Formula (AI), $Xa_1$ represents a hydrogen atom, a methyl group which may have a substituent, or a group expressed by $—CH_2—R_9$, $R_9$ represents a hydroxyl group or a monovalent organic group, T represents a single bond or a divalent linking group, $Rx_1$ to $Rx_3$, each independently, represent an alkyl group or a cycloalkyl group, two of $Rx_1$ to $Rx_3$ may be bonded and form a cycloalkyl group.

31. An actinic-ray-sensitive or radiation-sensitive resin composition comprising:
a resin (P) having a repeating unit (a) represented by a following General Formula (I);
a compound (B) represented by any of following General Formulae (B-1-7) to (B-1-8); and
a solvent,

[Chem. 13]

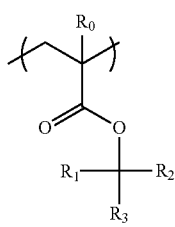

(I)

wherein, in General Formula (I), $R_0$ represents a hydrogen atom or a methyl group, $R_1$, $R_2$, and $R_3$ each independently represent a straight chain or branched alkyl group,

[Chem. 14]

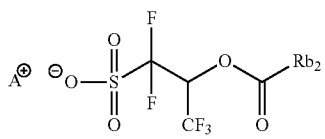

(B-1-7)

-continued

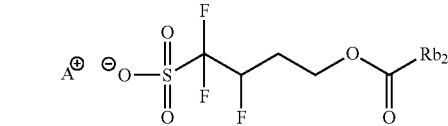

(B-1-8)

in General Formula (B-1-7) to (B-1-8), $A^+$ represents a sulfonium cation or an iodonium cation, $R_{b2}$ represents a substituent having 6 or more carbon atoms.

32. The actinic-ray-sensitive or radiation-sensitive resin composition according to claim 31,
wherein the resin (P) is a resin containing 45 mol % or more of the repeating unit (a) with regard to all repeating units in the resin (P).

33. The actinic-ray-sensitive or radiation-sensitive resin composition according to claim 31,
wherein a weight-average molecular weight of the resin (P) is 10,000 or more.

34. The actinic-ray-sensitive or radiation-sensitive resin composition according to claim 31, further comprising:
a basic compound or an ammonium salt compound (C) of which basicity is decreased by irradiation of actinic ray or radiation.

35. The actinic-ray-sensitive or radiation-sensitive resin composition according to claim 31,
wherein the resin (P) is a resin having an alicyclic hydrocarbon structure.

36. The actinic-ray-sensitive or radiation-sensitive resin composition according to claim 31, further comprising:
a hydrophobic resin having at least one of a fluorine atom and a silicon atom.

37. The actinic-ray-sensitive or radiation-sensitive resin composition according to claim 31,
wherein the resin (P) contains 5 mol % or less of a repeating unit having an aromatic group, or does not contain the repeating unit having the aromatic group.

38. The actinic-ray-sensitive or radiation-sensitive resin composition according to claim 31,
wherein the resin (P) contains a repeating unit represented by following General Formula (AI):

[Chem. 15]

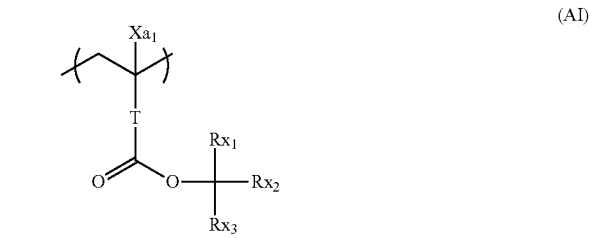

(AI)

wherein, in General Formula (AI), $Xa_1$ represents a hydrogen atom, a methyl group which may have a substituent, or a group expressed by $—CH_2—R_9$, $R_9$ represents a hydroxyl group or a monovalent organic group, T represents a single bond or a divalent linking group, $Rx_1$ to $Rx_3$, each independently, represent an alkyl group or a cycloalkyl group, two of $Rx_1$ to $Rx_3$ may be bonded and form a cycloalkyl group.

39. The actinic-ray-sensitive or radiation-sensitive resin composition according to claim 1, further comprising:

a compound represented by following General Formula (F):

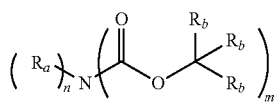

(F)

wherein, in General Formula (F), $R_a$s, each independently, represents a hydrogen atom, an alkyl group, a cycloalkyl group, an aryl group, or an aralkyl group, $R_b$s, each independently, represents a hydrogen atom, an alkyl group, a cycloalkyl group, an aryl group or an aralkyl group, however, in $C(R_b)(R_b)(R_b)$, when one or more of $R_b$ is a hydrogen atom, at least one of the rest $R_b$ is a cyclopropyl group or an 1-alkoxyalkyl group, n represents an integer of 0 to 2,
m represents an integer of 1 to 3, and
n+m=3.

40. The actinic-ray-sensitive or radiation-sensitive resin composition according to claim 16, further comprising:

a compound represented by following General Formula (F):

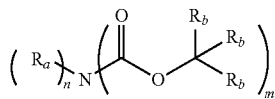

(F)

wherein, in General Formula (F), $R_a$s, each independently, represents a hydrogen atom, an alkyl group, a cycloalkyl group, an aryl group, or an aralkyl group, $R_b$s, each independently, represents a hydrogen atom, an alkyl group, a cycloalkyl group, an aryl group or an aralkyl group, however, in $C(R_b)(R_b)(R_b)$, when one or more of $R_b$ is a hydrogen atom, at least one of the rest $R_b$ is a cyclopropyl group or an 1-alkoxyalkyl group, n represents an integer of 0 to 2,
m represents an integer of 1 to 3, and
n+m=3.

41. The actinic-ray-sensitive or radiation-sensitive resin composition according to claim 23, further comprising:

a compound represented by following General Formula (F):

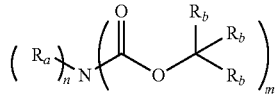

(F)

in General Formula (F), $R_a$s, each independently, represents a hydrogen atom, an alkyl group, a cycloalkyl group, an aryl group, or an aralkyl group, $R_b$s, each independently, represents a hydrogen atom, an alkyl group, a cycloalkyl group, an aryl group or an aralkyl group, however, in $C(R_b)(R_b)(R_b)$, when one or more of $R_b$ is a hydrogen atom, at least one of the rest $R_b$ is a cyclopropyl group or an 1-alkoxyalkyl group, n represents an integer of 0 to 2,
m represents an integer of 1 to 3, and
n+m=3.

42. The actinic-ray-sensitive or radiation-sensitive resin composition according to claim 31, further comprising:

a compound represented by following General Formula (F):

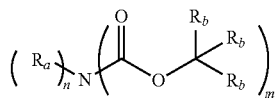

(F)

in General Formula (F), $R_a$s, each independently, represents a hydrogen atom, an alkyl group, a cycloalkyl group, an aryl group, or an aralkyl group, $R_b$s, each independently, represents a hydrogen atom, an alkyl group, a cycloalkyl group, an aryl group or an aralkyl group, however, in $C(R_b)(R_b)(R_b)$, when one or more of $R_b$ is a hydrogen atom, at least one of the rest $R_b$ is a cyclopropyl group or an 1-alkoxyalkyl group, n represents an integer of 0 to 2,
m represents an integer of 1 to 3, and
n+m=3.

* * * * *